United States Patent
Moingeon et al.

(10) Patent No.: US 10,190,166 B2
(45) Date of Patent: Jan. 29, 2019

(54) METHODS FOR IDENTIFYING DENDRITIC CELL SUBSETS, FOR DETERMINING IF A PATIENT IS DEVELOPING A REGULATORY OR AN EFFECTOR IMMUNE RESPONSE, AND FOR DETERMINING RESPONSE TO IMMUNOTHERAPY

(75) Inventors: Philippe Moingeon, Verrières-le-Buisson (FR); Aline Zimmer, Gross Genau (DE); Julien Bouley, Montrouge (FR); Laurent Mascarell, Paris (FR); Emmanuel Nony, Antony (FR)

(73) Assignee: STALLERGENES, Antony (FR)

( * ) Notice: Subject to any disclaimer, the term of this patent is extended or adjusted under 35 U.S.C. 154(b) by 623 days.

(21) Appl. No.: 14/343,480

(22) PCT Filed: Sep. 5, 2012

(86) PCT No.: PCT/EP2012/067261
§ 371 (c)(1),
(2), (4) Date: Jun. 23, 2014

(87) PCT Pub. No.: WO2013/034569
PCT Pub. Date: Mar. 14, 2013

(65) Prior Publication Data
US 2014/0377761 A1    Dec. 25, 2014

(30) Foreign Application Priority Data

Sep. 7, 2011 (EP) .................... 11306113

(51) Int. Cl.
*A61K 39/35* (2006.01)
*A61K 39/36* (2006.01)
*C12Q 1/68* (2018.01)
*G01N 33/53* (2006.01)
*C12Q 1/6881* (2018.01)

(52) U.S. Cl.
CPC ..... *C12Q 1/6881* (2013.01); *C12Q 2600/136* (2013.01); *C12Q 2600/158* (2013.01)

(58) Field of Classification Search
None
See application file for complete search history.

(56) References Cited

FOREIGN PATENT DOCUMENTS

| WO | WO-2008008846 A2 * | 1/2008 | ........... C12Q 1/6883 |
| WO | 2009026660 A1 | 3/2009 | |
| WO | 2010006414 A1 | 1/2010 | |

OTHER PUBLICATIONS

Castellano et al., 2004, Blood, vol. 103: 3813-3820.*
Rutella et al., 2006, Blood vol. 108: 218-227.*
Baruah et al., 2010, Eur. J. Immunol. vol. 40: 1758-1767.*
Passalacqua et la., All. Asthma, Clin. Immunol. vol. 2: 117-123.*
Onyemelukwe et al., 1989, Annals of ALlergy, vol. 63: 309-312.*
Hata et al., 2009, Innnnunol. Letters, vol. 126: 29-36.*
Constantine L et al: "Use of genechip high-density oligonucleotide arrays for gene expression monitoring", Life Science News, Amersham Life Science, pp. 11-14, (Jan. 1998).
Alexey Popov et al: "IDO-expressing regulatory dendritic cells in cancer and chronic infection", Journal of Molecular Medicine, pp. 145-160, vol. 86, No. 2, (Sep. 2007).
Van Vliet S J et al: "Differential regulation of C-type lectin expression on to 1 erogenic dendritic ce 11 subsets", Immunobiology, pp. 577-585, vol. 211, No. 6-8, (Sep. 2006).
"Human Genome U95Av2", XP002215481, URL:http:www.affymetrix. com, (Oct. 2002).
"GeneChip Human Genome U133 Set", XP002232760, URL:http:ffwww.affymetrix.com/support/ technicalfdatasheetshgu133 datasheet.pdf, (Feb. 2003).

\* cited by examiner

*Primary Examiner* — Amy E Juedes
(74) *Attorney, Agent, or Firm* — Browdy and Neimark, PLLC

(57) ABSTRACT

The present invention concerns methods for determining if a dendritic cell belongs to a tolerogenic dendritic cell subset or to an effector dendritic cell subset, and methods for determining if a patient undergoing immunotherapy, and/or who has been administered with a vaccine, is developing an immune response oriented either towards a regulatory T cell response or towards an effector T cell response, and methods of determining response to immunotherapy.

4 Claims, 16 Drawing Sheets

Specification includes a Sequence Listing.

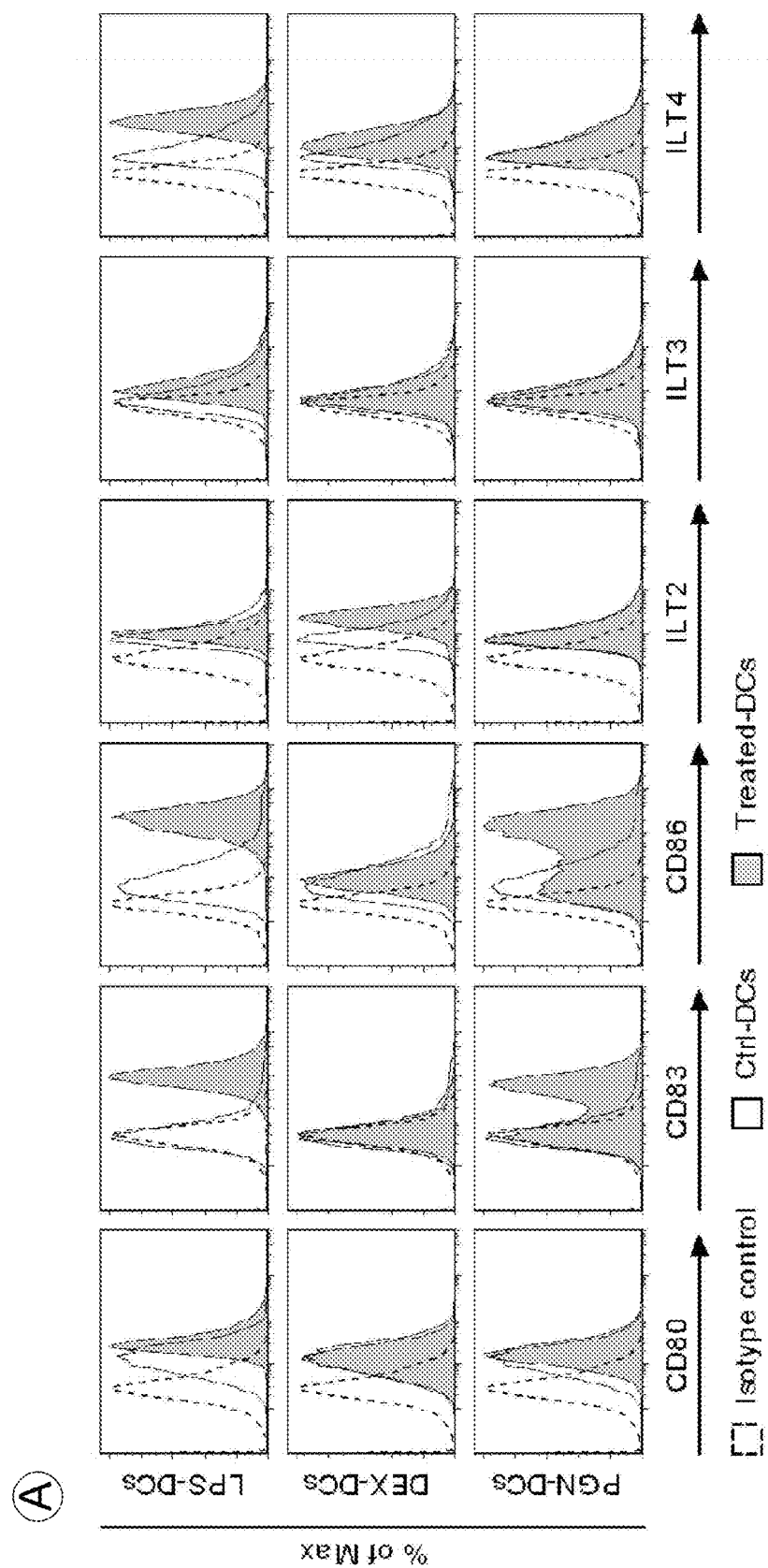
FIG.2 (Beginning)

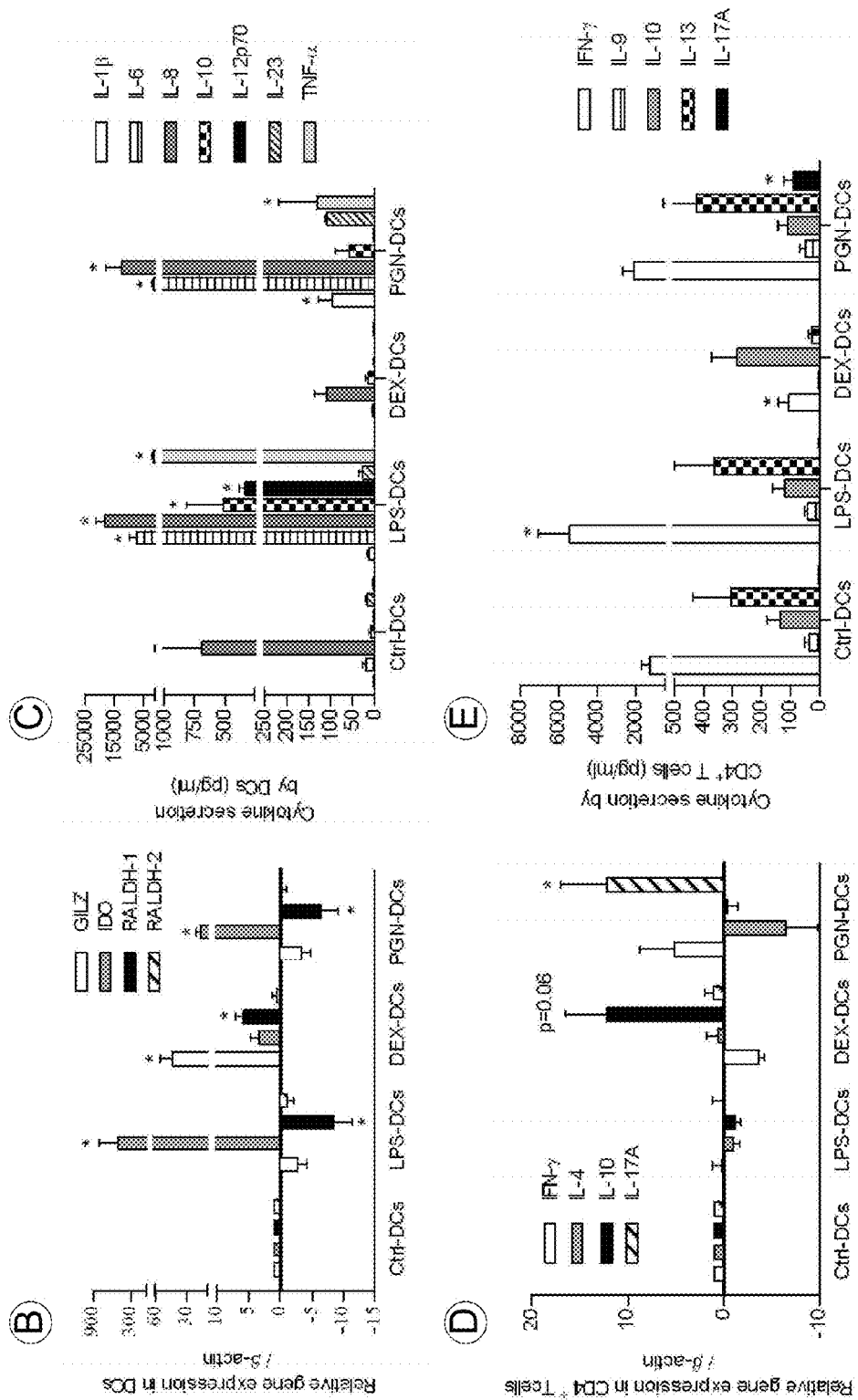
FIG. 2 (End)

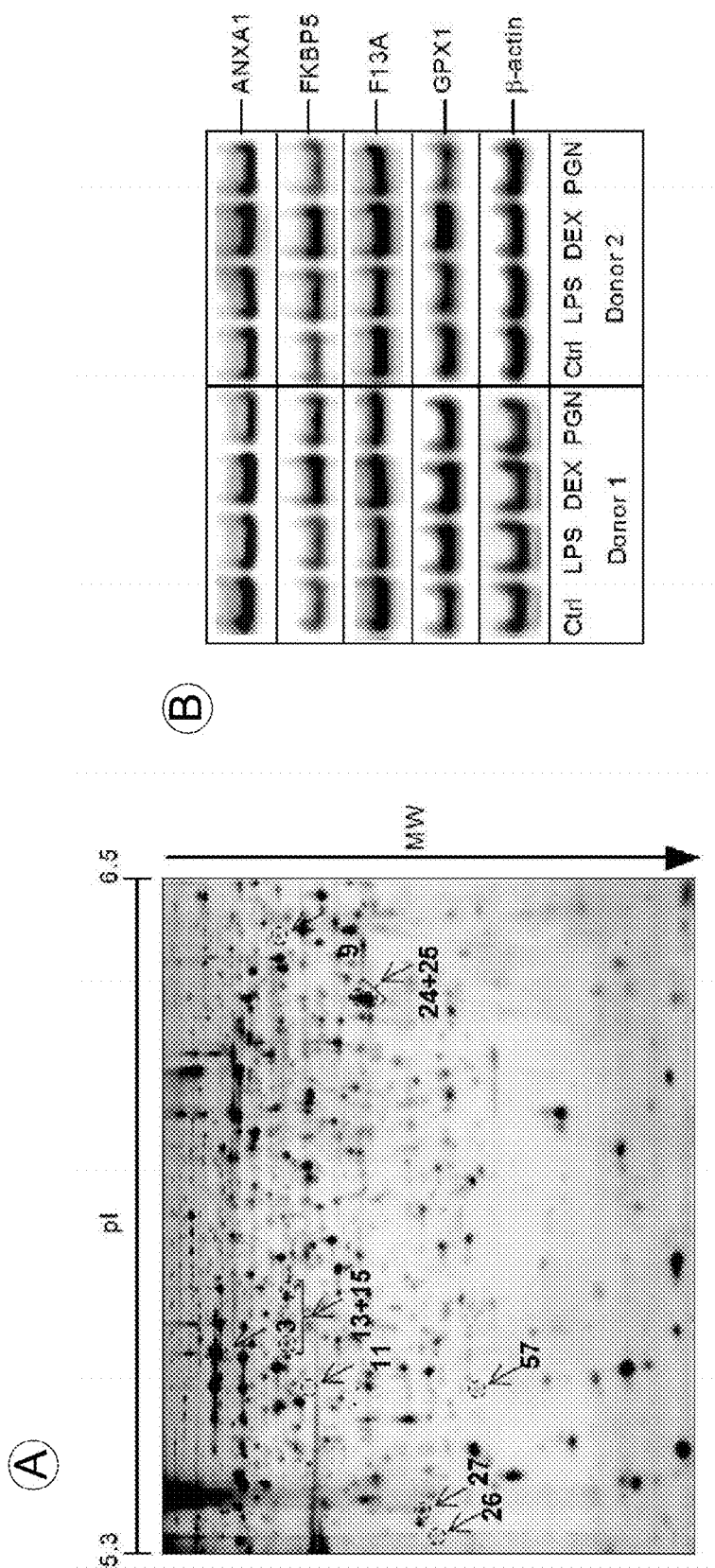
FIG. 3 (Beginning)

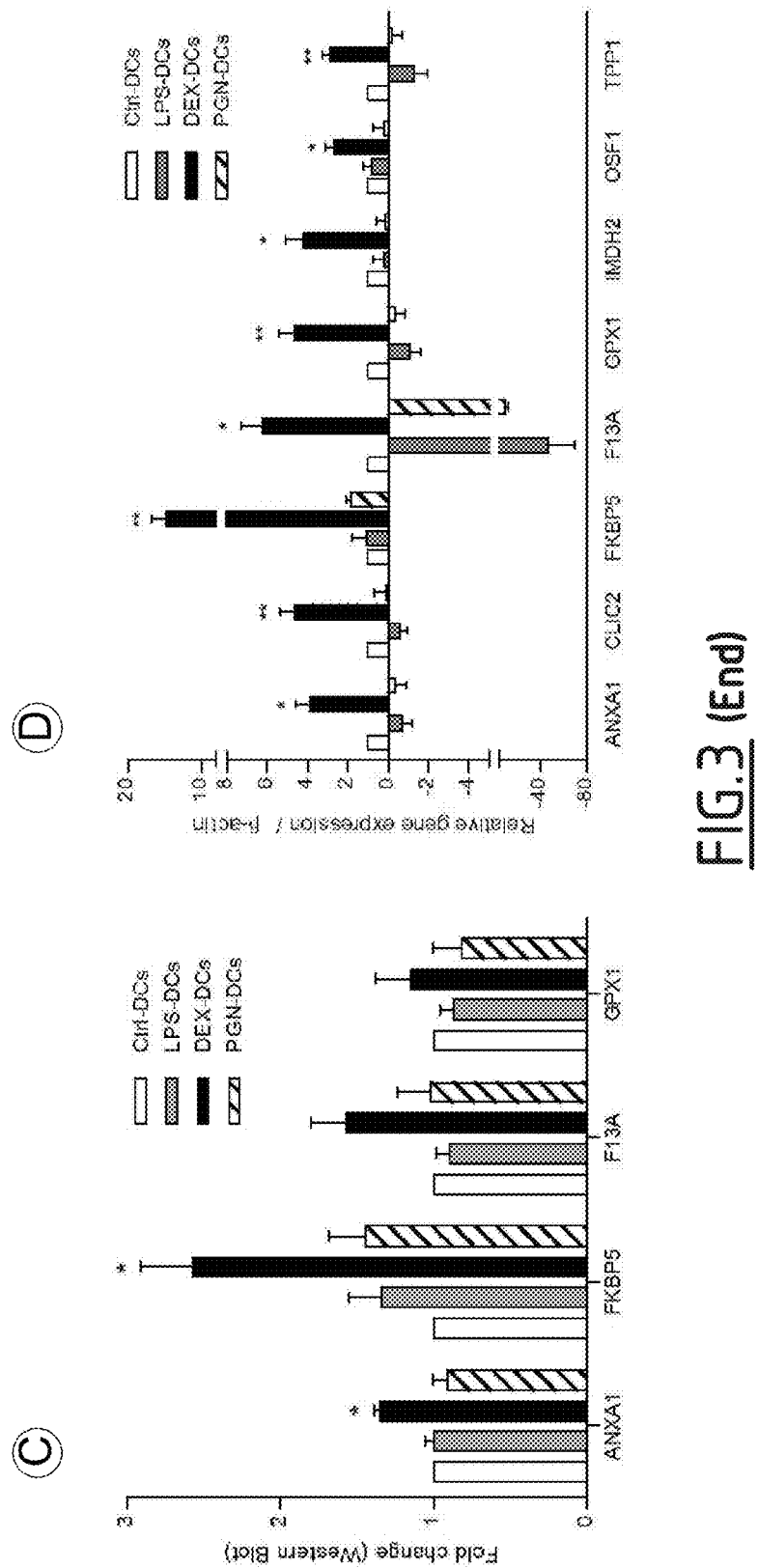
FIG.3 (End)

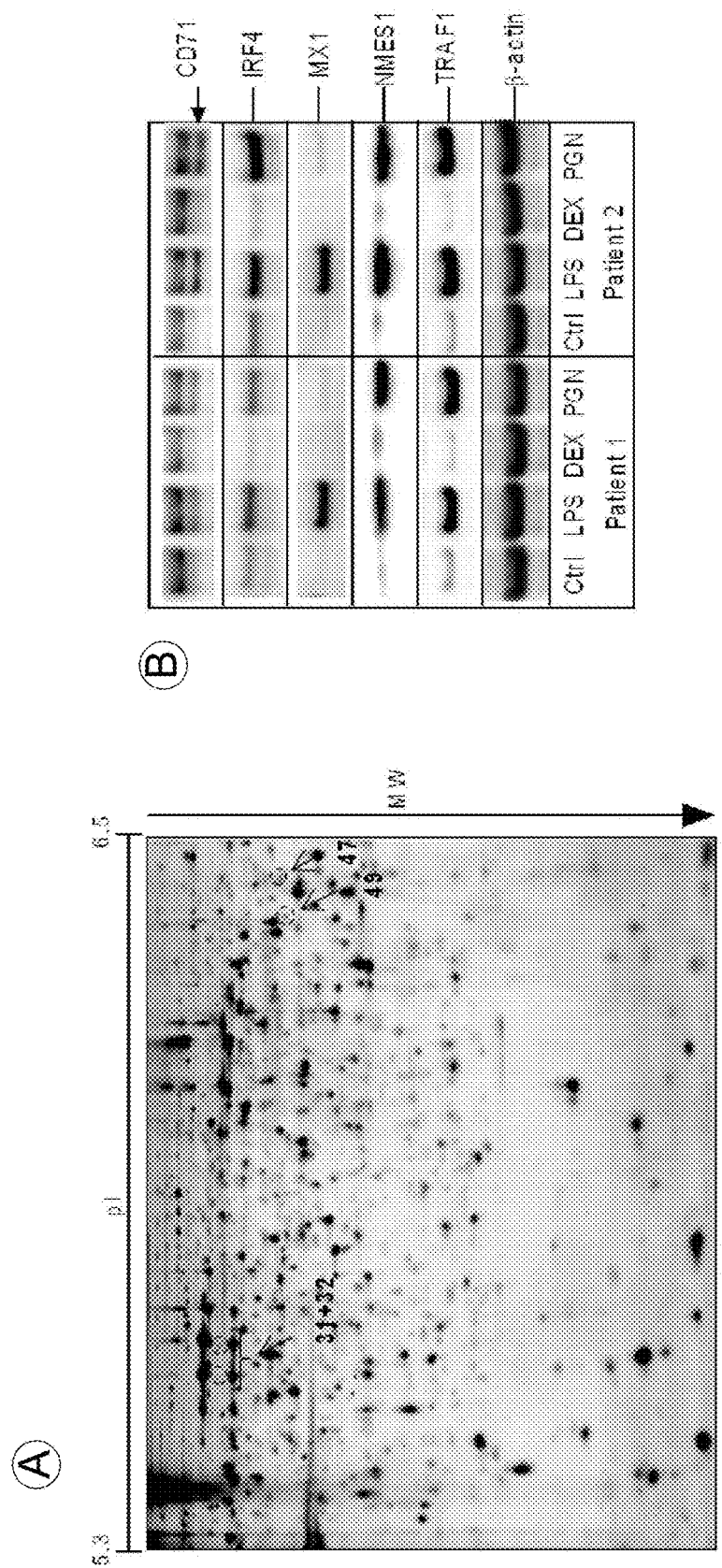
FIG.4 (Beginning)

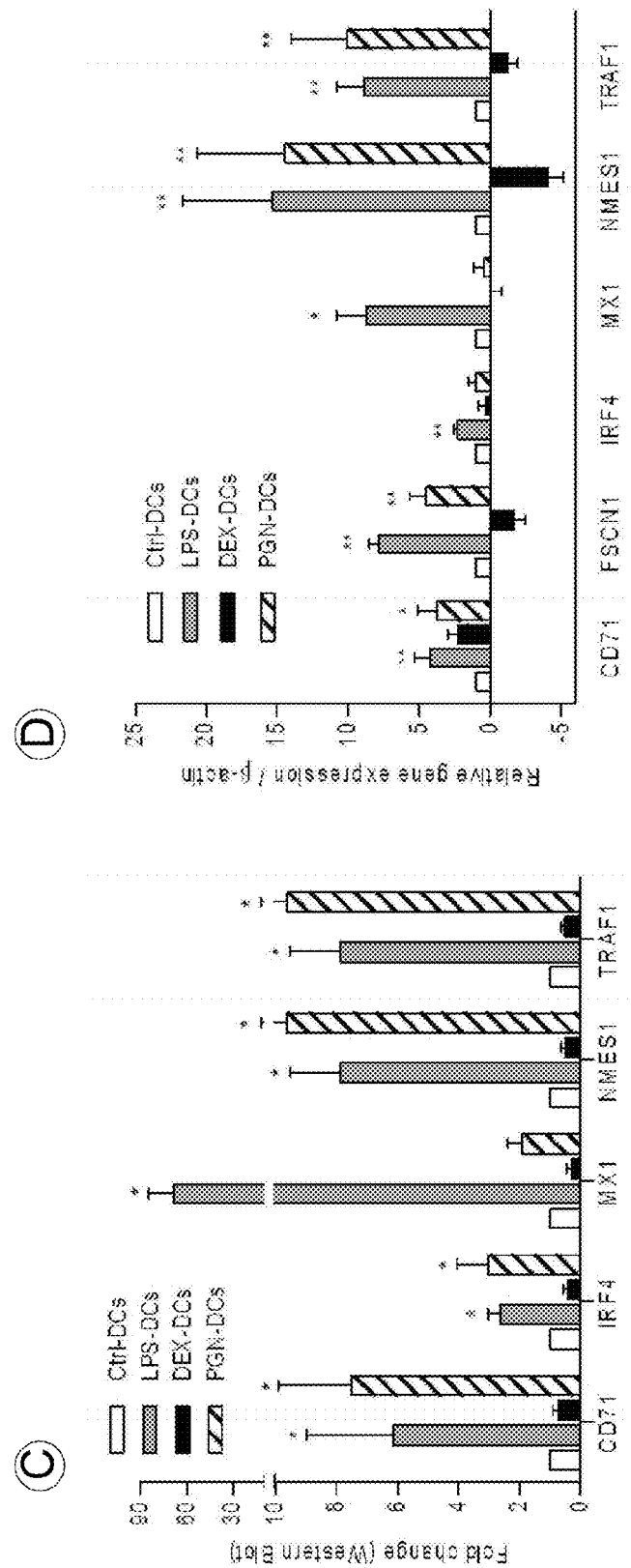
FIG.4 (End)

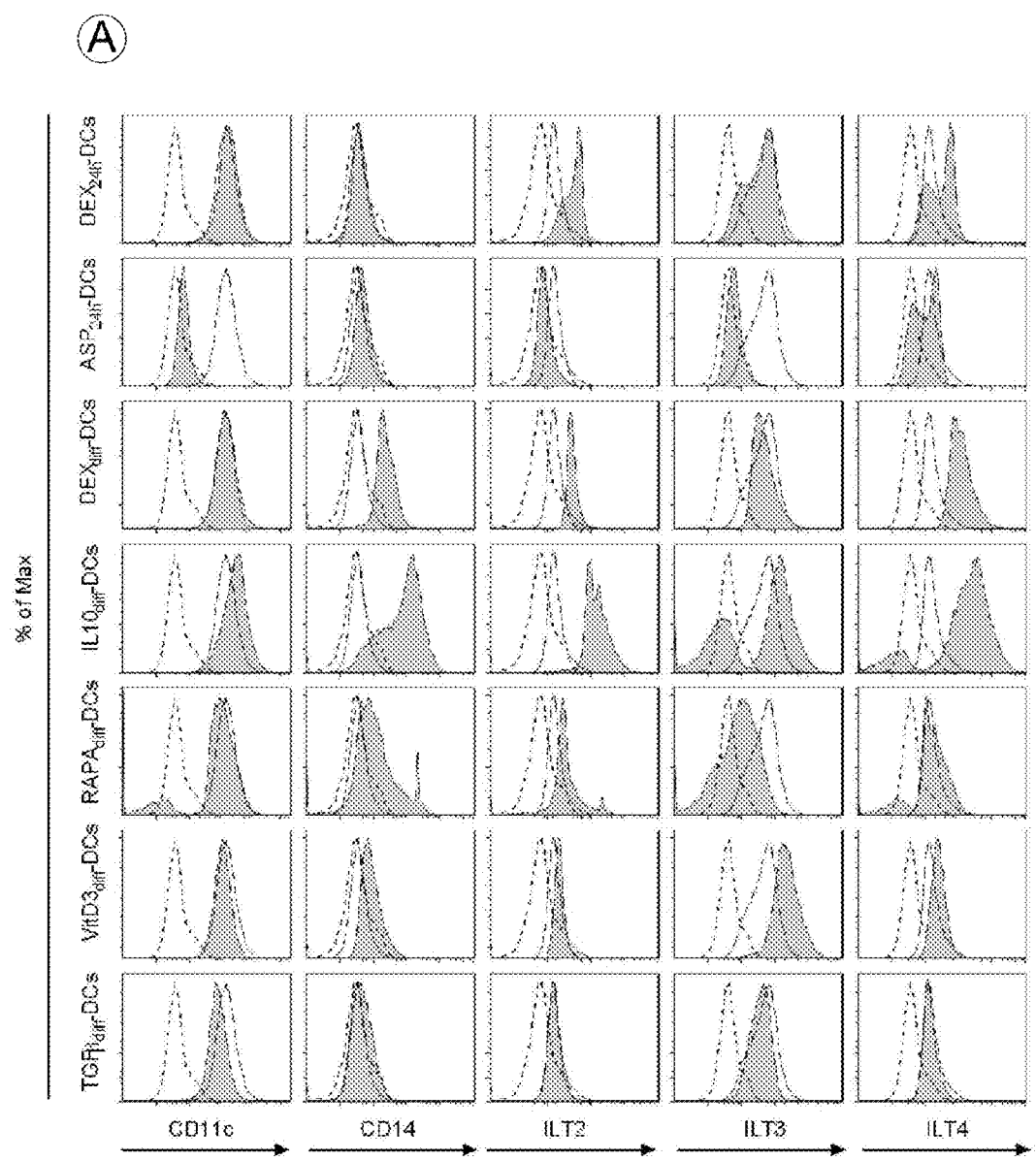
FIG.6 (Beginning)

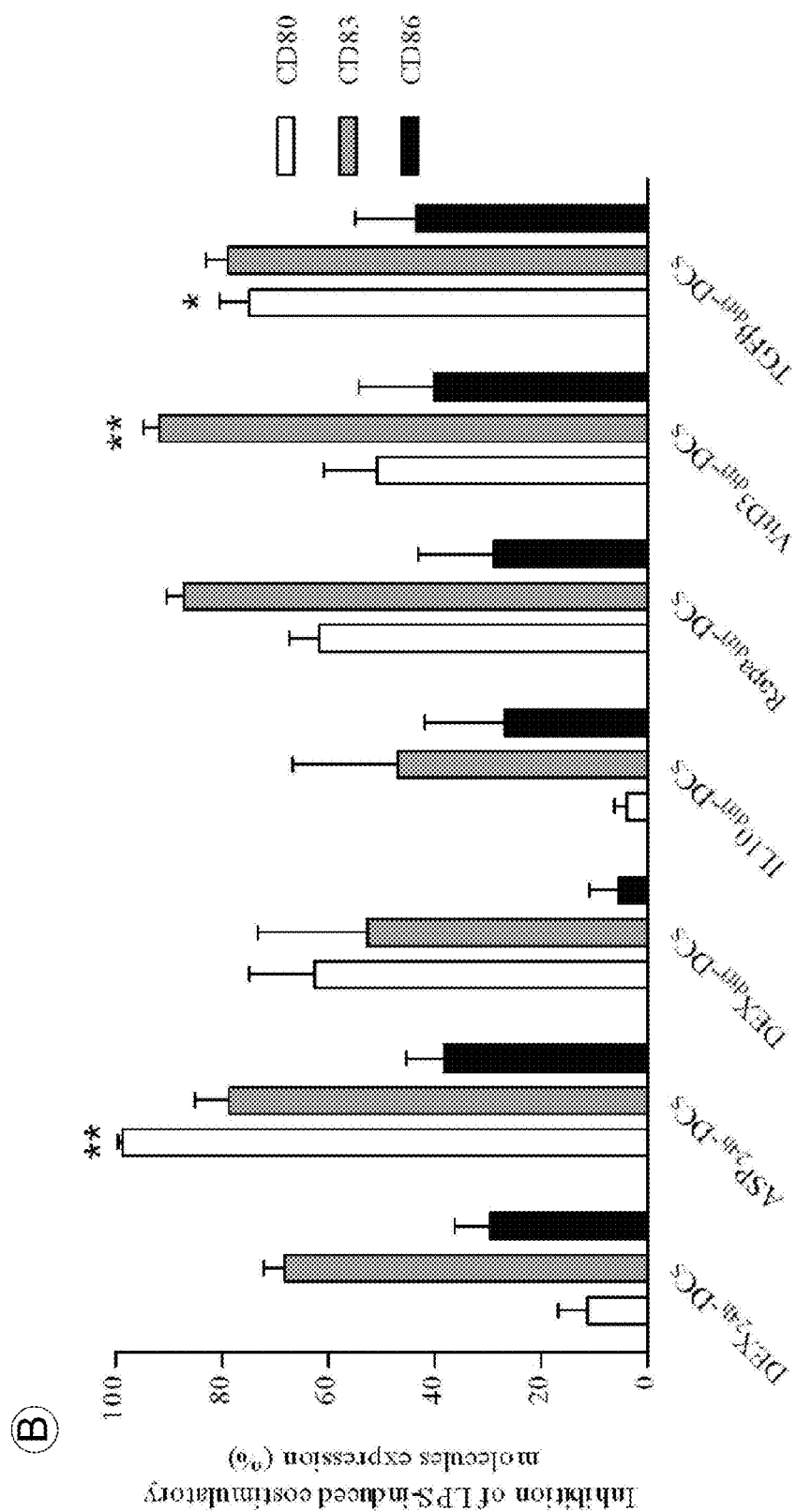
FIG.6 (Continuation)

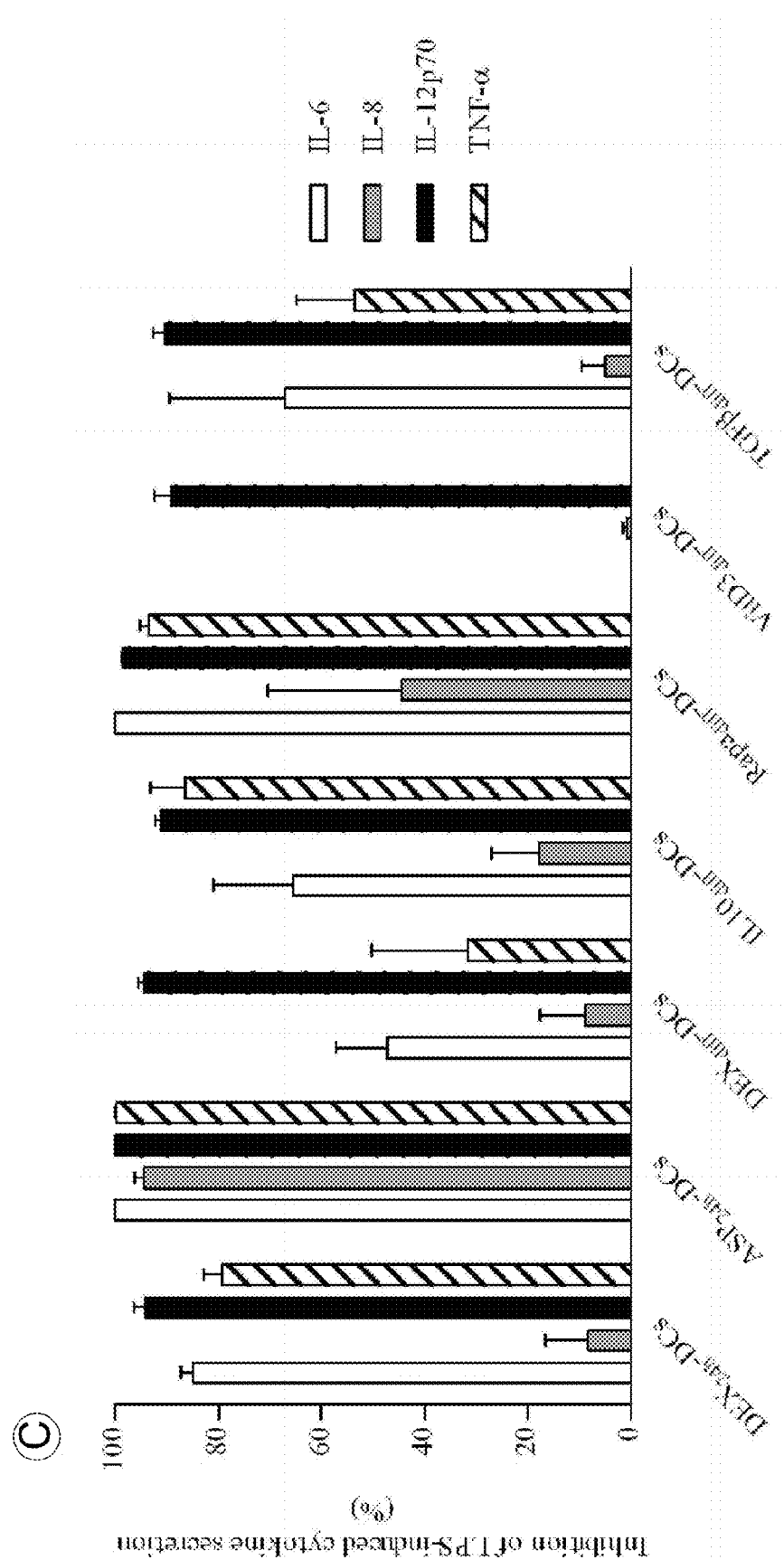
FIG.6 (End)

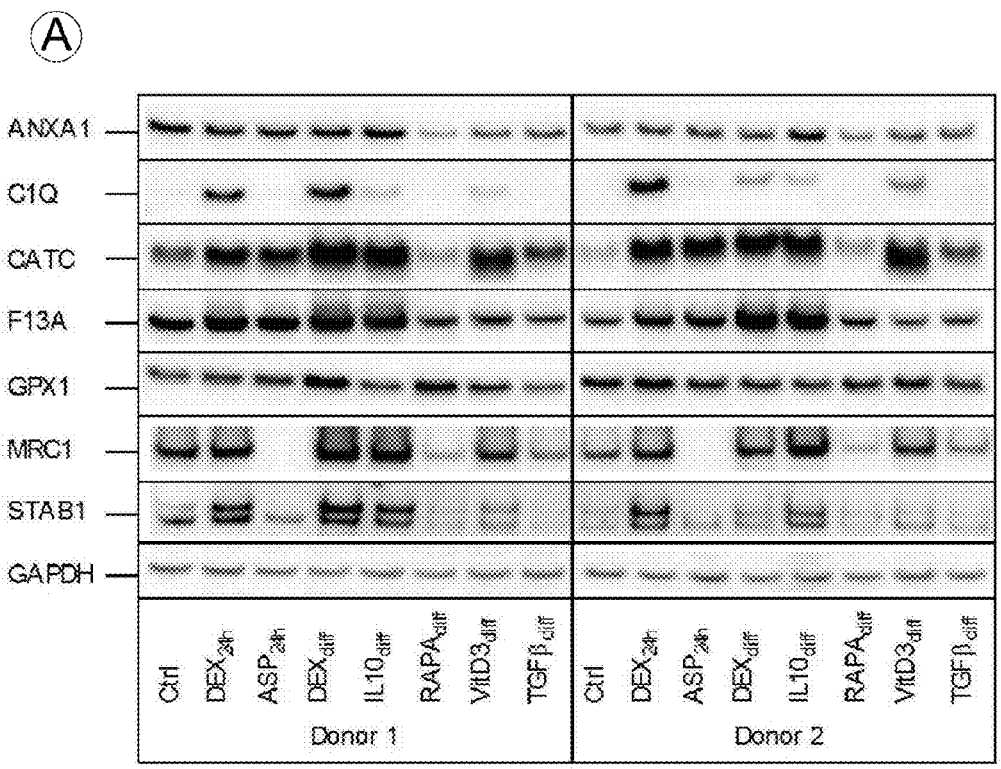
FIG.7 (Beginning)

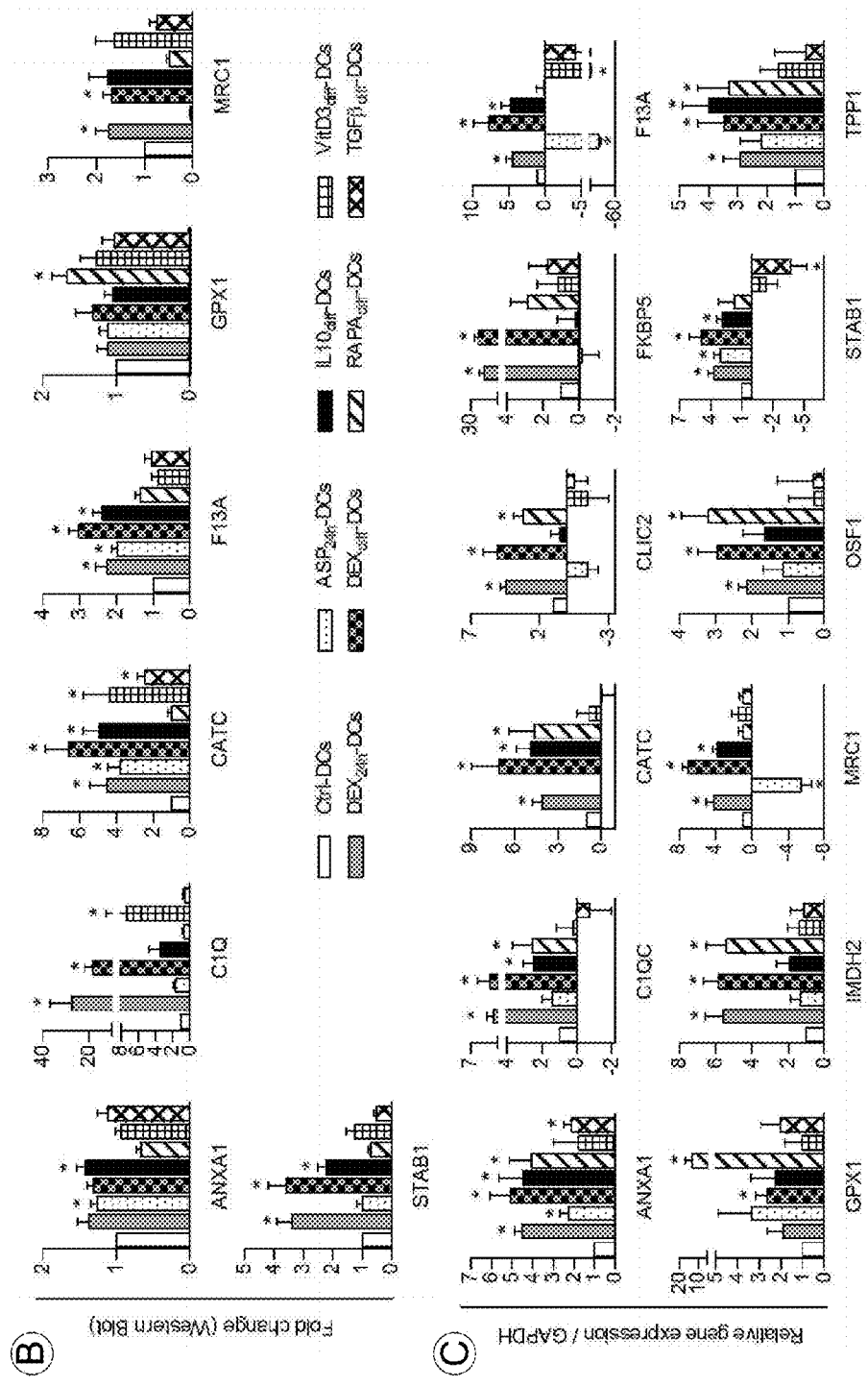
FIG. 7 (Continuation)

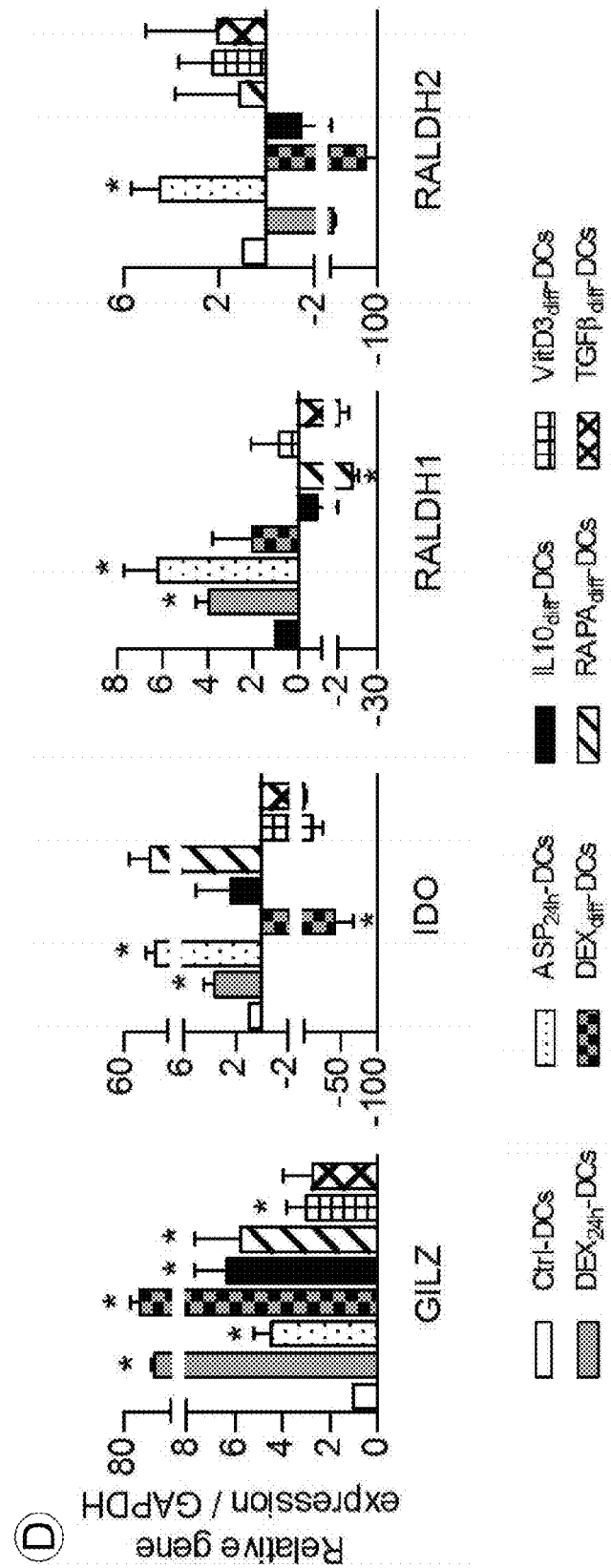
FIG. 7 (End)

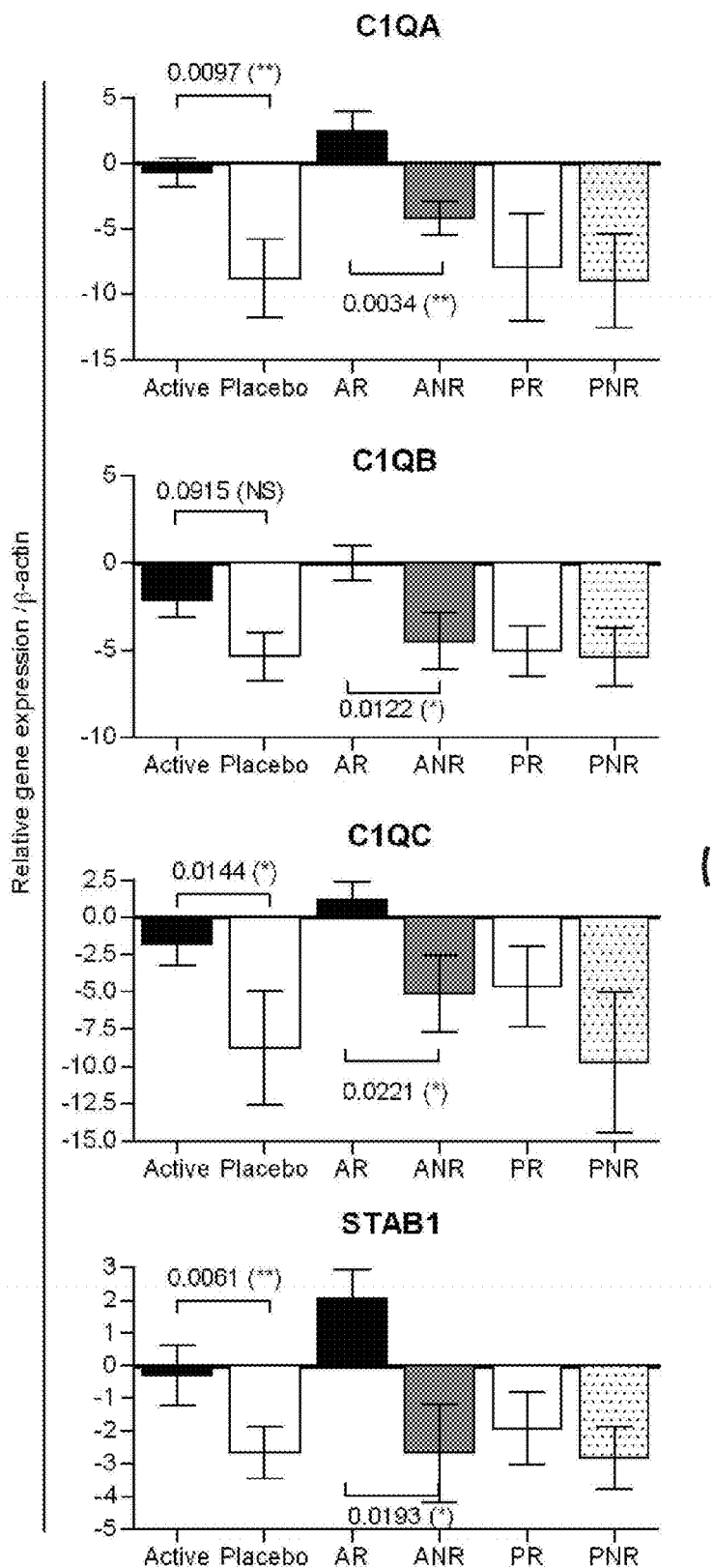
FIG. 8 (Beginning)

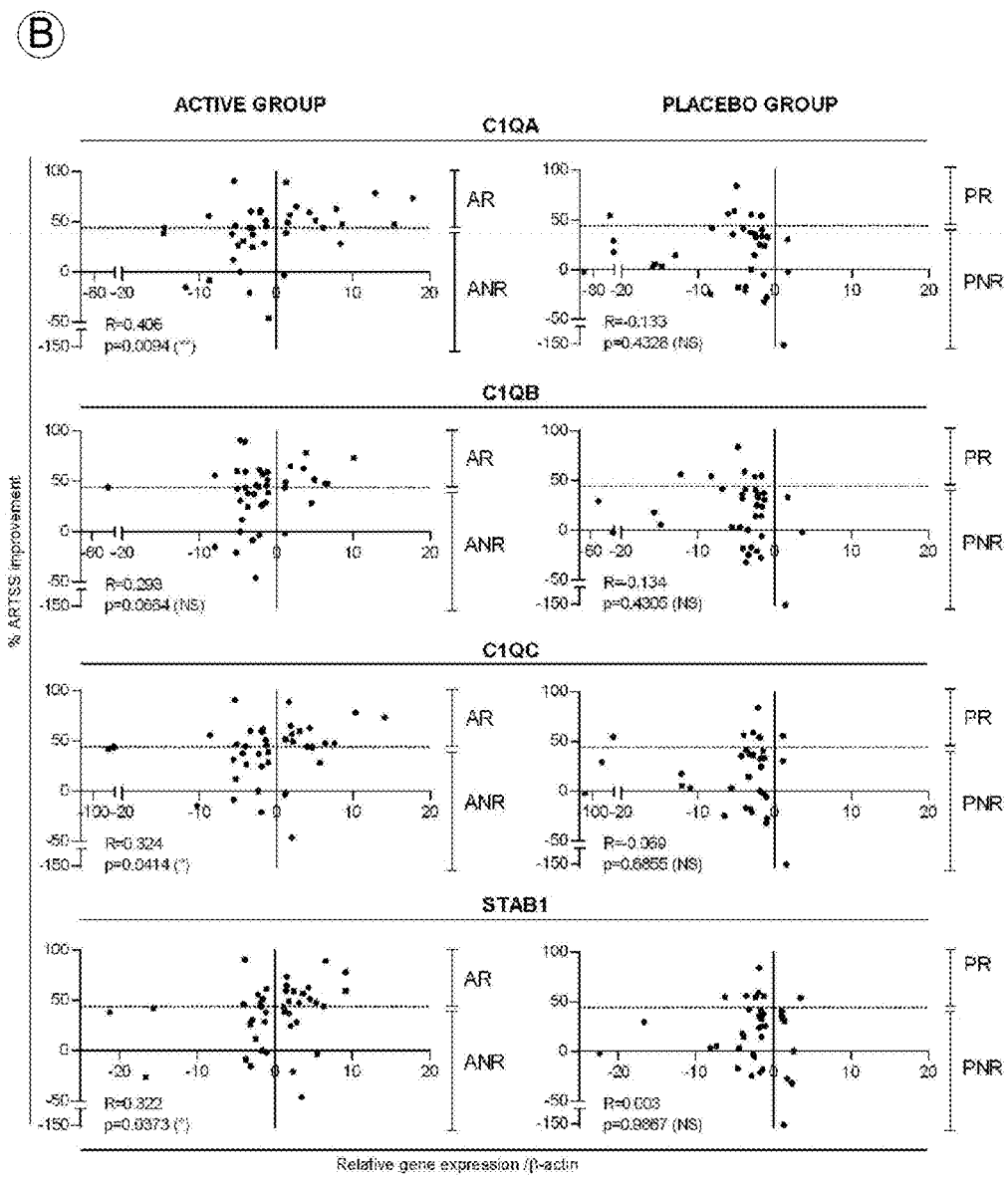
FIG.8 (End)

SEQUENCE LISTING

```
<160> NUMBER OF SEQ ID NOS: 115

<210> SEQ ID NO 1
<211> LENGTH: 214
<212> TYPE: PRT
<213> ORGANISM: Homo sapiens

<400> SEQUENCE: 1

Met Ser Lys Pro Pro Pro Lys Pro Val Lys Pro Gly Gln Val Lys Val
1               5                   10                  15

Phe Arg Ala Leu Tyr Thr Phe Glu Pro Arg Thr Pro Asp Glu Leu Tyr
            20                  25                  30

Phe Glu Glu Gly Asp Ile Ile Tyr Ile Thr Asp Met Ser Asp Thr Asn
```

```
                    35                  40                  45
Trp Trp Lys Gly Thr Ser Lys Gly Arg Thr Gly Leu Ile Pro Ser Asn
 50                  55                  60

Tyr Val Ala Glu Gln Ala Glu Ser Ile Asp Asn Pro Leu His Glu Ala
 65                  70                  75                  80

Ala Lys Arg Gly Asn Leu Ser Trp Leu Arg Glu Cys Leu Asp Asn Arg
                 85                  90                  95

Val Gly Val Asn Gly Leu Asp Lys Ala Gly Ser Thr Ala Leu Tyr Trp
                100                 105                 110

Ala Cys His Gly Gly His Lys Asp Ile Val Glu Met Leu Phe Thr Gln
            115                 120                 125

Pro Asn Ile Glu Leu Asn Gln Gln Asn Lys Leu Gly Asp Thr Ala Leu
    130                 135                 140

His Ala Ala Ala Trp Lys Gly Tyr Ala Asp Ile Val Gln Leu Leu Leu
145                 150                 155                 160

Ala Lys Gly Ala Arg Thr Asp Leu Arg Asn Ile Glu Lys Lys Leu Ala
                165                 170                 175

Phe Asp Met Ala Thr Asn Ala Ala Cys Ala Ser Leu Leu Lys Lys Lys
            180                 185                 190

Gln Gly Thr Asp Ala Val Arg Thr Leu Ser Asn Ala Glu Asp Tyr Leu
        195                 200                 205

Asp Asp Glu Asp Ser Asp
    210

<210> SEQ ID NO 2
<211> LENGTH: 858
<212> TYPE: PRT
<213> ORGANISM: Homo sapiens

<400> SEQUENCE: 2

Met Val Asn Phe Thr Val Asp Gln Ile Arg Ala Ile Met Asp Lys Lys
 1               5                  10                  15

Ala Asn Ile Arg Asn Met Ser Val Ile Ala His Val Asp His Gly Lys
                20                  25                  30

Ser Thr Leu Thr Asp Ser Leu Val Cys Lys Ala Gly Ile Ile Ala Ser
            35                  40                  45

Ala Arg Ala Gly Glu Thr Arg Phe Thr Asp Thr Arg Lys Asp Glu Gln
 50                  55                  60

Glu Arg Cys Ile Thr Ile Lys Ser Thr Ala Ile Ser Leu Phe Tyr Glu
 65                  70                  75                  80

Leu Ser Glu Asn Asp Leu Asn Phe Ile Lys Gln Ser Lys Asp Gly Ala
                85                  90                  95

Gly Phe Leu Ile Asn Leu Ile Asp Ser Pro Gly His Val Asp Phe Ser
                100                 105                 110

Ser Glu Val Thr Ala Ala Leu Arg Val Thr Asp Gly Ala Leu Val Val
            115                 120                 125

Val Asp Cys Val Ser Gly Val Cys Val Gln Thr Glu Thr Val Leu Arg
    130                 135                 140

Gln Ala Ile Ala Glu Arg Ile Lys Pro Val Leu Met Met Asn Lys Met
145                 150                 155                 160

Asp Arg Ala Leu Leu Glu Leu Gln Leu Glu Pro Glu Glu Leu Tyr Gln
                165                 170                 175

Thr Phe Gln Arg Ile Val Glu Asn Val Asn Val Ile Ile Ser Thr Tyr
            180                 185                 190
```

```
Gly Glu Gly Glu Ser Gly Pro Met Gly Asn Ile Met Ile Asp Pro Val
            195                 200                 205
Leu Gly Thr Val Gly Phe Gly Ser Gly Leu His Gly Trp Ala Phe Thr
        210                 215                 220
Leu Lys Gln Phe Ala Glu Met Tyr Val Ala Lys Phe Ala Ala Lys Gly
225                 230                 235                 240
Glu Gly Gln Leu Gly Pro Ala Glu Arg Ala Lys Lys Val Glu Asp Met
                245                 250                 255
Met Lys Lys Leu Trp Gly Asp Arg Tyr Phe Asp Pro Ala Asn Gly Lys
            260                 265                 270
Phe Ser Lys Ser Ala Thr Ser Pro Glu Gly Lys Lys Leu Pro Arg Thr
        275                 280                 285
Phe Cys Gln Leu Ile Leu Asp Pro Ile Phe Lys Val Phe Asp Ala Ile
290                 295                 300
Met Asn Phe Lys Lys Glu Glu Thr Ala Lys Leu Ile Glu Lys Leu Asp
305                 310                 315                 320
Ile Lys Leu Asp Ser Glu Asp Lys Asp Lys Glu Gly Lys Pro Leu Leu
                325                 330                 335
Lys Ala Val Met Arg Arg Trp Leu Pro Ala Gly Asp Ala Leu Leu Gln
            340                 345                 350
Met Ile Thr Ile His Leu Pro Ser Pro Val Thr Ala Gln Lys Tyr Arg
        355                 360                 365
Cys Glu Leu Leu Tyr Glu Gly Pro Pro Asp Asp Glu Ala Ala Met Gly
        370                 375                 380
Ile Lys Ser Cys Asp Pro Lys Gly Pro Leu Met Met Tyr Ile Ser Lys
385                 390                 395                 400
Met Val Pro Thr Ser Asp Lys Gly Arg Phe Tyr Ala Phe Gly Arg Val
                405                 410                 415
Phe Ser Gly Leu Val Ser Thr Gly Leu Lys Val Arg Ile Met Gly Pro
            420                 425                 430
Asn Tyr Thr Pro Gly Lys Lys Glu Asp Leu Tyr Leu Lys Pro Ile Gln
        435                 440                 445
Arg Thr Ile Leu Met Met Gly Arg Tyr Val Glu Pro Ile Glu Asp Val
        450                 455                 460
Pro Cys Gly Asn Ile Val Gly Leu Val Gly Val Asp Gln Phe Leu Val
465                 470                 475                 480
Lys Thr Gly Thr Ile Thr Thr Phe Glu His Ala His Asn Met Arg Val
                485                 490                 495
Met Lys Phe Ser Val Ser Pro Val Val Arg Val Ala Val Glu Ala Lys
            500                 505                 510
Asn Pro Ala Asp Leu Pro Lys Leu Val Glu Gly Leu Lys Arg Leu Ala
        515                 520                 525
Lys Ser Asp Pro Met Val Gln Cys Ile Ile Glu Ser Gly Glu His
        530                 535                 540
Ile Ile Ala Gly Ala Gly Glu Leu His Leu Glu Ile Cys Leu Lys Asp
545                 550                 555                 560
Leu Glu Glu Asp His Ala Cys Ile Pro Ile Lys Lys Ser Asp Pro Val
                565                 570                 575
Val Ser Tyr Arg Glu Thr Val Ser Glu Ser Asn Val Leu Cys Leu
            580                 585                 590
Ser Lys Ser Pro Asn Lys His Asn Arg Leu Tyr Met Lys Ala Arg Pro
        595                 600                 605
Phe Pro Asp Gly Leu Ala Glu Asp Ile Asp Lys Gly Glu Val Ser Ala
```

|     |     |     |     |     |     |     |     |     |     |     |     |
|---|---|---|---|---|---|---|---|---|---|---|---|
|     |     | 610 |     |     |     | 615 |     |     |     | 620 |     |

Arg Gln Glu Leu Lys Gln Arg Ala Arg Tyr Leu Ala Glu Lys Tyr Glu
625                 630                 635                 640

Trp Asp Val Ala Glu Ala Arg Lys Ile Trp Cys Phe Gly Pro Asp Gly
                    645                 650                 655

Thr Gly Pro Asn Ile Leu Thr Asp Ile Thr Lys Gly Val Gln Tyr Leu
                660                 665                 670

Asn Glu Ile Lys Asp Ser Val Val Ala Gly Phe Gln Trp Ala Thr Lys
                675                 680                 685

Glu Gly Ala Leu Cys Glu Glu Asn Met Arg Gly Val Arg Phe Asp Val
690                 695                 700

His Asp Val Thr Leu His Ala Asp Ala Ile His Arg Gly Gly Gly Gln
705                 710                 715                 720

Ile Ile Pro Thr Ala Arg Arg Cys Leu Tyr Ala Ser Val Leu Thr Ala
                725                 730                 735

Gln Pro Arg Leu Met Glu Pro Ile Tyr Leu Val Glu Ile Gln Cys Pro
                740                 745                 750

Glu Gln Val Val Gly Gly Ile Tyr Gly Val Leu Asn Arg Lys Arg Gly
                755                 760                 765

His Val Phe Glu Glu Ser Gln Val Ala Gly Thr Pro Met Phe Val Val
770                 775                 780

Lys Ala Tyr Leu Pro Val Asn Glu Ser Phe Gly Phe Thr Ala Asp Leu
785                 790                 795                 800

Arg Ser Asn Thr Gly Gly Gln Ala Phe Pro Gln Cys Val Phe Asp His
                805                 810                 815

Trp Gln Ile Leu Pro Gly Asp Pro Phe Asp Asn Ser Ser Arg Pro Ser
                820                 825                 830

Gln Val Val Ala Glu Thr Arg Lys Arg Lys Gly Leu Lys Glu Gly Ile
                835                 840                 845

Pro Ala Leu Asp Asn Phe Leu Asp Lys Leu
            850                 855

<210> SEQ ID NO 3
<211> LENGTH: 732
<212> TYPE: PRT
<213> ORGANISM: Homo sapiens

<400> SEQUENCE: 3

Met Ser Glu Thr Ser Arg Thr Ala Phe Gly Gly Arg Arg Ala Val Pro
1               5                   10                  15

Pro Asn Asn Ser Asn Ala Ala Glu Asp Asp Leu Pro Thr Val Glu Leu
                20                  25                  30

Gln Gly Val Val Pro Arg Gly Val Asn Leu Gln Glu Phe Leu Asn Val
            35                  40                  45

Thr Ser Val His Leu Phe Lys Glu Arg Trp Asp Thr Asn Lys Val Asp
        50                  55                  60

His His Thr Asp Lys Tyr Glu Asn Asn Lys Leu Ile Val Arg Arg Gly
65                  70                  75                  80

Gln Ser Phe Tyr Val Gln Ile Asp Phe Ser Arg Pro Tyr Asp Pro Arg
                85                  90                  95

Arg Asp Leu Phe Arg Val Glu Tyr Val Ile Gly Arg Tyr Pro Gln Glu
                100                 105                 110

Asn Lys Gly Thr Tyr Ile Pro Val Pro Ile Val Ser Glu Leu Gln Ser
            115                 120                 125

```
Gly Lys Trp Gly Ala Lys Ile Val Met Arg Glu Asp Arg Ser Val Arg
130                 135                 140

Leu Ser Ile Gln Ser Ser Pro Lys Cys Ile Val Gly Lys Phe Arg Met
145                 150                 155                 160

Tyr Val Ala Val Trp Thr Pro Tyr Gly Val Leu Arg Thr Ser Arg Asn
                165                 170                 175

Pro Glu Thr Asp Thr Tyr Ile Leu Phe Asn Pro Trp Cys Glu Asp Asp
                180                 185                 190

Ala Val Tyr Leu Asp Asn Glu Lys Glu Arg Glu Tyr Val Leu Asn
                195                 200                 205

Asp Ile Gly Val Ile Phe Tyr Gly Val Asn Asp Ile Lys Thr Arg
210                 215                 220

Ser Trp Ser Tyr Gly Gln Phe Glu Asp Gly Ile Leu Asp Thr Cys Leu
225                 230                 235                 240

Tyr Val Met Asp Arg Ala Gln Met Asp Leu Ser Gly Arg Gly Asn Pro
                245                 250                 255

Ile Lys Val Ser Arg Val Gly Ser Ala Met Val Asn Ala Lys Asp Asp
                260                 265                 270

Glu Gly Val Leu Val Gly Ser Trp Asp Asn Ile Tyr Ala Tyr Gly Val
                275                 280                 285

Pro Pro Ser Ala Trp Thr Gly Ser Val Asp Ile Leu Leu Glu Tyr Arg
290                 295                 300

Ser Ser Glu Asn Pro Val Arg Tyr Gly Gln Cys Trp Val Phe Ala Gly
305                 310                 315                 320

Val Phe Asn Thr Phe Leu Arg Cys Leu Gly Ile Pro Ala Arg Ile Val
                325                 330                 335

Thr Asn Tyr Phe Ser Ala His Asp Asn Asp Ala Asn Leu Gln Met Asp
                340                 345                 350

Ile Phe Leu Glu Glu Asp Gly Asn Val Asn Ser Lys Leu Thr Lys Asp
                355                 360                 365

Ser Val Trp Asn Tyr His Cys Trp Asn Glu Ala Trp Met Thr Arg Pro
370                 375                 380

Asp Leu Pro Val Gly Phe Gly Gly Trp Gln Ala Val Asp Ser Thr Pro
385                 390                 395                 400

Gln Glu Asn Ser Asp Gly Met Tyr Arg Cys Gly Pro Ala Ser Val Gln
                405                 410                 415

Ala Ile Lys His Gly His Val Cys Phe Gln Phe Asp Ala Pro Phe Val
                420                 425                 430

Phe Ala Glu Val Asn Ser Asp Leu Ile Tyr Ile Thr Ala Lys Lys Asp
                435                 440                 445

Gly Thr His Val Val Glu Asn Val Asp Ala Thr His Ile Gly Lys Leu
450                 455                 460

Ile Val Thr Lys Gln Ile Gly Gly Asp Gly Met Met Asp Ile Thr Asp
465                 470                 475                 480

Thr Tyr Lys Phe Gln Glu Gly Gln Glu Glu Arg Leu Ala Leu Glu
                485                 490                 495

Thr Ala Leu Met Tyr Gly Ala Lys Lys Pro Leu Asn Thr Glu Gly Val
                500                 505                 510

Met Lys Ser Arg Ser Asn Val Asp Met Asp Phe Glu Val Glu Asn Ala
                515                 520                 525

Val Leu Gly Lys Asp Phe Lys Leu Ser Ile Thr Phe Arg Asn Asn Ser
530                 535                 540

His Asn Arg Tyr Thr Ile Thr Ala Tyr Leu Ser Ala Asn Ile Thr Phe
```

```
            545                 550                 555                 560
        Tyr Thr Gly Val Pro Lys Ala Glu Phe Lys Lys Glu Thr Phe Asp Val
                        565                 570                 575

Thr Leu Glu Pro Leu Ser Phe Lys Lys Glu Ala Val Leu Ile Gln Ala
                        580                 585                 590

Gly Glu Tyr Met Gly Gln Leu Leu Glu Gln Ala Ser Leu His Phe Phe
                        595                 600                 605

Val Thr Ala Arg Ile Asn Glu Thr Arg Asp Val Leu Ala Lys Gln Lys
                        610                 615                 620

Ser Thr Val Leu Thr Ile Pro Glu Ile Ile Lys Val Arg Gly Thr
        625                 630                 635                 640

Gln Val Val Gly Ser Asp Met Thr Val Thr Val Gln Phe Thr Asn Pro
                        645                 650                 655

Leu Lys Glu Thr Leu Arg Asn Val Trp Val His Leu Asp Gly Pro Gly
                        660                 665                 670

Val Thr Arg Pro Met Lys Lys Met Phe Arg Glu Ile Arg Pro Asn Ser
                        675                 680                 685

Thr Val Gln Trp Glu Glu Val Cys Arg Pro Trp Val Ser Gly His Arg
                        690                 695                 700

Lys Leu Ile Ala Ser Met Ser Ser Asp Ser Leu Arg His Val Tyr Gly
        705                 710                 715                 720

Glu Leu Asp Val Gln Ile Gln Arg Arg Pro Ser Met
                        725                 730

<210> SEQ ID NO 4
<211> LENGTH: 346
<212> TYPE: PRT
<213> ORGANISM: Homo sapiens

<400> SEQUENCE: 4

Met Ala Met Val Ser Glu Phe Leu Lys Gln Ala Trp Phe Ile Glu Asn
        1               5                   10                  15

Glu Glu Gln Glu Tyr Val Gln Thr Val Lys Ser Ser Lys Gly Gly Pro
                        20                  25                  30

Gly Ser Ala Val Ser Pro Tyr Pro Thr Phe Asn Pro Ser Ser Asp Val
                        35                  40                  45

Ala Ala Leu His Lys Ala Ile Met Val Lys Gly Val Asp Glu Ala Thr
        50                  55                  60

Ile Ile Asp Ile Leu Thr Lys Arg Asn Asn Ala Gln Arg Gln Gln Ile
        65                  70                  75                  80

Lys Ala Ala Tyr Leu Gln Glu Thr Gly Lys Pro Leu Asp Glu Thr Leu
                        85                  90                  95

Lys Lys Ala Leu Thr Gly His Leu Glu Glu Val Val Leu Ala Leu Leu
                        100                 105                 110

Lys Thr Pro Ala Gln Phe Asp Ala Asp Glu Leu Arg Ala Ala Met Lys
                        115                 120                 125

Gly Leu Gly Thr Asp Glu Asp Thr Leu Ile Glu Ile Leu Ala Ser Arg
                        130                 135                 140

Thr Asn Lys Glu Ile Arg Asp Ile Asn Arg Val Tyr Arg Glu Glu Leu
        145                 150                 155                 160

Lys Arg Asp Leu Ala Lys Asp Ile Thr Ser Asp Thr Ser Gly Asp Phe
                        165                 170                 175

Arg Asn Ala Leu Leu Ser Leu Ala Lys Gly Asp Arg Ser Glu Asp Phe
                        180                 185                 190
```

```
Gly Val Asn Glu Asp Leu Ala Asp Ser Asp Ala Arg Ala Leu Tyr Glu
            195                 200                 205

Ala Gly Glu Arg Arg Lys Gly Thr Asp Val Asn Val Phe Asn Thr Ile
        210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345

<210> SEQ ID NO 5
<211> LENGTH: 563
<212> TYPE: PRT
<213> ORGANISM: Homo sapiens

<400> SEQUENCE: 5

Met Gly Leu Gln Ala Cys Leu Leu Gly Leu Phe Ala Leu Ile Leu Ser
1               5                   10                  15

Gly Lys Cys Ser Tyr Ser Pro Glu Pro Asp Gln Arg Arg Thr Leu Pro
            20                  25                  30

Pro Gly Trp Val Ser Leu Gly Arg Ala Asp Pro Glu Glu Glu Leu Ser
        35                  40                  45

Leu Thr Phe Ala Leu Arg Gln Gln Asn Val Glu Arg Leu Ser Glu Leu
    50                  55                  60

Val Gln Ala Val Ser Asp Pro Ser Ser Pro Gln Tyr Gly Lys Tyr Leu
65                  70                  75                  80

Thr Leu Glu Asn Val Ala Asp Leu Val Arg Pro Ser Pro Leu Thr Leu
                85                  90                  95

His Thr Val Gln Lys Trp Leu Leu Ala Ala Gly Ala Gln Lys Cys His
            100                 105                 110

Ser Val Ile Thr Gln Asp Phe Leu Thr Cys Trp Leu Ser Ile Arg Gln
        115                 120                 125

Ala Glu Leu Leu Leu Pro Gly Ala Glu Phe His His Tyr Val Gly Gly
    130                 135                 140

Pro Thr Glu Thr His Val Val Arg Ser Pro His Pro Tyr Gln Leu Pro
145                 150                 155                 160

Gln Ala Leu Ala Pro His Val Asp Phe Val Gly Gly Leu His Arg Phe
                165                 170                 175

Pro Pro Thr Ser Ser Leu Arg Gln Arg Pro Glu Pro Val Thr Gly
            180                 185                 190

Thr Val Gly Leu His Leu Gly Val Thr Pro Ser Val Ile Arg Lys Arg
        195                 200                 205

Tyr Asn Leu Thr Ser Gln Asp Val Gly Ser Gly Thr Ser Asn Asn Ser
    210                 215                 220
```

Gln Ala Cys Ala Gln Phe Leu Glu Gln Tyr Phe His Asp Ser Asp Leu
225                 230                 235                 240

Ala Gln Phe Met Arg Leu Phe Gly Gly Asn Phe Ala His Gln Ala Ser
            245                 250                 255

Val Ala Arg Val Val Gly Gln Gln Gly Arg Gly Arg Ala Gly Ile Glu
        260                 265                 270

Ala Ser Leu Asp Val Gln Tyr Leu Met Ser Ala Gly Ala Asn Ile Ser
    275                 280                 285

Thr Trp Val Tyr Ser Ser Pro Gly Arg His Glu Gly Gln Glu Pro Phe
290                 295                 300

Leu Gln Trp Leu Met Leu Leu Ser Asn Glu Ser Ala Leu Pro His Val
305                 310                 315                 320

His Thr Val Ser Tyr Gly Asp Asp Glu Asp Ser Leu Ser Ser Ala Tyr
                325                 330                 335

Ile Gln Arg Val Asn Thr Glu Leu Met Lys Ala Ala Arg Gly Leu
        340                 345                 350

Thr Leu Leu Phe Ala Ser Gly Asp Ser Gly Ala Gly Cys Trp Ser Val
    355                 360                 365

Ser Gly Arg His Gln Phe Arg Pro Thr Phe Pro Ala Ser Ser Pro Tyr
370                 375                 380

Val Thr Thr Val Gly Gly Thr Ser Phe Gln Glu Pro Phe Leu Ile Thr
385                 390                 395                 400

Asn Glu Ile Val Asp Tyr Ile Ser Gly Gly Gly Phe Ser Asn Val Phe
                405                 410                 415

Pro Arg Pro Ser Tyr Gln Glu Glu Ala Val Thr Lys Phe Leu Ser Ser
            420                 425                 430

Ser Pro His Leu Pro Pro Ser Ser Tyr Phe Asn Ala Ser Gly Arg Ala
        435                 440                 445

Tyr Pro Asp Val Ala Ala Leu Ser Asp Gly Tyr Trp Val Val Ser Asn
    450                 455                 460

Arg Val Pro Ile Pro Trp Val Ser Gly Thr Ser Ala Ser Thr Pro Val
465                 470                 475                 480

Phe Gly Gly Ile Leu Ser Leu Ile Asn Glu His Arg Ile Leu Ser Gly
                485                 490                 495

Arg Pro Pro Leu Gly Phe Leu Asn Pro Arg Leu Tyr Gln Gln His Gly
            500                 505                 510

Ala Gly Leu Phe Asp Val Thr Arg Gly Cys His Glu Ser Cys Leu Asp
        515                 520                 525

Glu Glu Val Glu Gly Gln Gly Phe Cys Ser Gly Pro Gly Trp Asp Pro
    530                 535                 540

Val Thr Gly Trp Gly Thr Pro Asn Phe Pro Ala Leu Leu Lys Thr Leu
545                 550                 555                 560

Leu Asn Pro

<210> SEQ ID NO 6
<211> LENGTH: 247
<212> TYPE: PRT
<213> ORGANISM: Homo sapiens

<400> SEQUENCE: 6

Met Ser Gly Leu Arg Pro Gly Thr Gln Val Asp Pro Glu Ile Glu Leu
1               5                   10                  15

Phe Val Lys Ala Gly Ser Asp Gly Glu Ser Ile Gly Asn Cys Pro Phe
            20                  25                  30

Cys Gln Arg Leu Phe Met Ile Leu Trp Leu Lys Gly Val Lys Phe Asn
                35                  40                  45

Val Thr Thr Val Asp Met Thr Arg Lys Pro Glu Glu Leu Lys Asp Leu
         50                  55                  60

Ala Pro Gly Thr Asn Pro Pro Phe Leu Val Tyr Asn Lys Glu Leu Lys
 65                  70                  75                  80

Thr Asp Phe Ile Lys Ile Glu Glu Phe Leu Glu Gln Thr Leu Ala Pro
             85                  90                  95

Pro Arg Tyr Pro His Leu Ser Pro Lys Tyr Lys Glu Ser Phe Asp Val
            100                 105                 110

Gly Cys Asn Leu Phe Ala Lys Ser Ala Tyr Ile Lys Asn Thr Gln
            115                 120                 125

Lys Glu Ala Asn Lys Asn Phe Glu Lys Ser Leu Leu Lys Glu Phe Lys
        130                 135                 140

Arg Leu Asp Asp Tyr Leu Asn Thr Pro Leu Leu Asp Glu Ile Asp Pro
145                 150                 155                 160

Asp Ser Ala Glu Glu Pro Pro Val Ser Arg Leu Phe Leu Asp Gly
                165                 170                 175

Asp Gln Leu Thr Leu Ala Asp Cys Ser Leu Leu Pro Lys Leu Asn Ile
            180                 185                 190

Ile Lys Val Ala Ala Lys Lys Tyr Arg Asp Phe Asp Ile Pro Ala Glu
            195                 200                 205

Phe Ser Gly Val Trp Arg Tyr Leu His Asn Tyr Ala Arg Glu Glu
        210                 215                 220

Phe Thr His Thr Cys Pro Glu Asp Lys Glu Ile Glu Asn Thr Tyr Ala
225                 230                 235                 240

Asn Val Ala Lys Gln Lys Ser
                245

<210> SEQ ID NO 7
<211> LENGTH: 203
<212> TYPE: PRT
<213> ORGANISM: Homo sapiens
<220> FEATURE:
<221> NAME/KEY: MISC_FEATURE
<222> LOCATION: (49)..(49)
<223> OTHER INFORMATION: Xaa is Selenocysteine.

<400> SEQUENCE: 7

Met Cys Ala Ala Arg Leu Ala Ala Ala Ala Ala Gln Ser Val
 1               5                  10                  15

Tyr Ala Phe Ser Ala Arg Pro Leu Ala Gly Gly Glu Pro Val Ser Leu
             20                  25                  30

Gly Ser Leu Arg Gly Lys Val Leu Leu Ile Glu Asn Val Ala Ser Leu
         35                  40                  45

Xaa Gly Thr Thr Val Arg Asp Tyr Thr Gln Met Asn Glu Leu Gln Arg
 50                  55                  60

Arg Leu Gly Pro Arg Gly Leu Val Val Leu Gly Phe Pro Cys Asn Gln
 65                  70                  75                  80

Phe Gly His Gln Glu Asn Ala Lys Asn Glu Glu Ile Leu Asn Ser Leu
             85                  90                  95

Lys Tyr Val Arg Pro Gly Gly Gly Phe Glu Pro Asn Phe Met Leu Phe
            100                 105                 110

Glu Lys Cys Glu Val Asn Gly Ala Gly Ala His Pro Leu Phe Ala Phe
        115                 120                 125

```
Leu Arg Glu Ala Leu Pro Ala Pro Ser Asp Asp Ala Thr Ala Leu Met
    130                 135                 140

Thr Asp Pro Lys Leu Ile Thr Trp Ser Pro Val Cys Arg Asn Asp Val
145                 150                 155                 160

Ala Trp Asn Phe Glu Lys Phe Leu Val Gly Pro Asp Gly Val Pro Leu
                165                 170                 175

Arg Arg Tyr Ser Arg Arg Phe Gln Thr Ile Asp Ile Glu Pro Asp Ile
                180                 185                 190

Glu Ala Leu Leu Ser Gln Gly Pro Ser Cys Ala
            195                 200

<210> SEQ ID NO 8
<211> LENGTH: 514
<212> TYPE: PRT
<213> ORGANISM: Homo sapiens

<400> SEQUENCE: 8

Met Ala Asp Tyr Leu Ile Ser Gly Gly Thr Ser Tyr Val Pro Asp Asp
1               5                   10                  15

Gly Leu Thr Ala Gln Gln Leu Phe Asn Cys Gly Asp Gly Leu Thr Tyr
            20                  25                  30

Asn Asp Phe Leu Ile Leu Pro Gly Tyr Ile Asp Phe Thr Ala Asp Gln
            35                  40                  45

Val Asp Leu Thr Ser Ala Leu Thr Lys Lys Ile Thr Leu Lys Thr Pro
50                  55                  60

Leu Val Ser Ser Pro Met Asp Thr Val Thr Glu Ala Gly Met Ala Ile
65                  70                  75                  80

Ala Met Ala Leu Thr Gly Gly Ile Gly Phe Ile His His Asn Cys Thr
                85                  90                  95

Pro Glu Phe Gln Ala Asn Glu Val Arg Lys Val Lys Lys Tyr Glu Gln
                100                 105                 110

Gly Phe Ile Thr Asp Pro Val Val Leu Ser Pro Lys Asp Arg Val Arg
            115                 120                 125

Asp Val Phe Glu Ala Lys Ala Arg His Gly Phe Cys Gly Ile Pro Ile
130                 135                 140

Thr Asp Thr Gly Arg Met Gly Ser Arg Leu Val Gly Ile Ile Ser Ser
145                 150                 155                 160

Arg Asp Ile Asp Phe Leu Lys Glu Glu His Asp Cys Phe Leu Glu
                165                 170                 175

Glu Ile Met Thr Lys Arg Glu Asp Leu Val Val Ala Pro Ala Gly Ile
                180                 185                 190

Thr Leu Lys Glu Ala Asn Glu Ile Leu Gln Arg Ser Lys Lys Gly Lys
            195                 200                 205

Leu Pro Ile Val Asn Glu Asp Asp Glu Leu Val Ala Ile Ile Ala Arg
            210                 215                 220

Thr Asp Leu Lys Lys Asn Arg Asp Tyr Pro Leu Ala Ser Lys Asp Ala
225                 230                 235                 240

Lys Lys Gln Leu Leu Cys Gly Ala Ala Ile Gly Thr His Glu Asp Asp
                245                 250                 255

Lys Tyr Arg Leu Asp Leu Leu Ala Gln Ala Gly Val Asp Val Val Val
            260                 265                 270

Leu Asp Ser Ser Gln Gly Asn Ser Ile Phe Gln Ile Asn Met Ile Lys
            275                 280                 285

Tyr Ile Lys Asp Lys Tyr Pro Asn Leu Gln Val Ile Gly Gly Asn Val
            290                 295                 300
```

```
Val Thr Ala Ala Gln Ala Lys Asn Leu Ile Asp Ala Gly Val Asp Ala
305                 310                 315                 320

Leu Arg Val Gly Met Gly Ser Gly Ser Ile Cys Ile Thr Gln Glu Val
            325                 330                 335

Leu Ala Cys Gly Arg Pro Gln Ala Thr Ala Val Tyr Lys Val Ser Glu
            340                 345                 350

Tyr Ala Arg Arg Phe Gly Val Pro Val Ile Ala Asp Gly Gly Ile Gln
            355                 360                 365

Asn Val Gly His Ile Ala Lys Ala Leu Ala Leu Gly Ala Ser Thr Val
            370                 375                 380

Met Met Gly Ser Leu Leu Ala Ala Thr Thr Glu Ala Pro Gly Glu Tyr
385                 390                 395                 400

Phe Phe Ser Asp Gly Ile Arg Leu Lys Lys Tyr Arg Gly Met Gly Ser
            405                 410                 415

Leu Asp Ala Met Asp Lys His Leu Ser Ser Gln Asn Arg Tyr Phe Ser
            420                 425                 430

Glu Ala Asp Lys Ile Lys Val Ala Gln Gly Val Ser Gly Ala Val Gln
            435                 440                 445

Asp Lys Gly Ser Ile His Lys Phe Val Pro Tyr Leu Ile Ala Gly Ile
450                 455                 460

Gln His Ser Cys Gln Asp Ile Gly Ala Lys Ser Leu Thr Gln Val Arg
465                 470                 475                 480

Ala Met Met Tyr Ser Gly Glu Leu Lys Phe Glu Lys Arg Thr Ser Ser
            485                 490                 495

Ala Gln Val Glu Gly Gly Val His Ser Leu His Ser Tyr Glu Lys Arg
            500                 505                 510

Leu Phe

<210> SEQ ID NO 9
<211> LENGTH: 340
<212> TYPE: PRT
<213> ORGANISM: Homo sapiens

<400> SEQUENCE: 9

Met Ser Glu Leu Glu Gln Leu Arg Gln Glu Ala Glu Gln Leu Arg Asn
1               5                   10                  15

Gln Ile Arg Asp Ala Arg Lys Ala Cys Gly Asp Ser Thr Leu Thr Gln
            20                  25                  30

Ile Thr Ala Gly Leu Asp Pro Val Gly Arg Ile Gln Met Arg Thr Arg
            35                  40                  45

Arg Thr Leu Arg Gly His Leu Ala Lys Ile Tyr Ala Met His Trp Gly
    50                  55                  60

Thr Asp Ser Arg Leu Leu Val Ser Ala Ser Gln Asp Gly Lys Leu Ile
65                  70                  75                  80

Ile Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Phe Val
            100                 105                 110

Ala Cys Gly Gly Leu Asp Asn Ile Cys Ser Ile Tyr Ser Leu Lys Thr
            115                 120                 125

Arg Glu Gly Asn Val Arg Val Ser Arg Glu Leu Pro Gly His Thr Gly
    130                 135                 140

Tyr Leu Ser Cys Cys Arg Phe Leu Asp Asp Asn Gln Ile Ile Thr Ser
145                 150                 155                 160
```

```
Ser Gly Asp Thr Thr Cys Ala Leu Trp Asp Ile Glu Thr Gly Gln Gln
            165                 170                 175

Thr Val Gly Phe Ala Gly His Ser Gly Asp Val Met Ser Leu Ser Leu
        180                 185                 190

Ala Pro Asp Gly Arg Thr Phe Val Ser Gly Ala Cys Asp Ala Ser Ile
            195                 200                 205

Lys Leu Trp Asp Val Arg Asp Ser Met Cys Arg Gln Thr Phe Ile Gly
210                 215                 220

His Glu Ser Asp Ile Asn Ala Val Ala Phe Phe Pro Asn Gly Tyr Ala
225                 230                 235                 240

Phe Thr Thr Gly Ser Asp Asp Ala Thr Cys Arg Leu Phe Asp Leu Arg
            245                 250                 255

Ala Asp Gln Glu Leu Leu Met Tyr Ser His Asp Asn Ile Ile Cys Gly
            260                 265                 270

Ile Thr Ser Val Ala Phe Ser Arg Ser Gly Arg Leu Leu Leu Ala Gly
        275                 280                 285

Tyr Asp Asp Phe Asn Cys Asn Ile Trp Asp Ala Met Lys Gly Asp Arg
        290                 295                 300

Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
            325                 330                 335

Lys Ile Trp Asn
            340

<210> SEQ ID NO 10
<211> LENGTH: 340
<212> TYPE: PRT
<213> ORGANISM: Homo sapiens

<400> SEQUENCE: 10

Met Ser Glu Leu Asp Gln Leu Arg Gln Glu Ala Glu Gln Leu Lys Asn
1               5                   10                  15

Gln Ile Arg Asp Ala Arg Lys Ala Cys Ala Asp Ala Thr Leu Ser Gln
            20                  25                  30

Ile Thr Asn Asn Ile Asp Pro Val Gly Arg Ile Gln Met Arg Thr Arg
        35                  40                  45

Arg Thr Leu Arg Gly His Leu Ala Lys Ile Tyr Ala Met His Trp Gly
    50                  55                  60

Thr Asp Ser Arg Leu Leu Val Ser Ala Ser Gln Asp Gly Lys Leu Ile
65                  70                  75                  80

Ile Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Tyr Val
            100                 105                 110

Ala Cys Gly Gly Leu Asp Asn Ile Cys Ser Ile Tyr Asn Leu Lys Thr
        115                 120                 125

Arg Glu Gly Asn Val Arg Val Ser Arg Glu Leu Ala Gly His Thr Gly
    130                 135                 140

Tyr Leu Ser Cys Cys Arg Phe Leu Asp Asp Asn Gln Ile Val Thr Ser
145                 150                 155                 160

Ser Gly Asp Thr Thr Cys Ala Leu Trp Asp Ile Glu Thr Gly Gln Gln
                165                 170                 175

Thr Thr Thr Phe Thr Gly His Thr Gly Asp Val Met Ser Leu Ser Leu
```

```
                    180                 185                 190
Ala Pro Asp Thr Arg Leu Phe Val Ser Gly Ala Cys Asp Ala Ser Ala
                195                 200                 205

Lys Leu Trp Asp Val Arg Glu Gly Met Cys Arg Gln Thr Phe Thr Gly
            210                 215                 220

His Glu Ser Asp Ile Asn Ala Ile Cys Phe Phe Pro Asn Gly Asn Ala
225                 230                 235                 240

Phe Ala Thr Gly Ser Asp Asp Ala Thr Cys Arg Leu Phe Asp Leu Arg
                245                 250                 255

Ala Asp Gln Glu Leu Met Thr Tyr Ser His Asp Asn Ile Ile Cys Gly
            260                 265                 270

Ile Thr Ser Val Ser Phe Ser Lys Ser Gly Arg Leu Leu Leu Ala Gly
                275                 280                 285

Tyr Asp Asp Phe Asn Cys Asn Val Trp Asp Ala Leu Lys Ala Asp Arg
            290                 295                 300

Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                325                 330                 335

Lys Ile Trp Asn
            340

<210> SEQ ID NO 11
<211> LENGTH: 411
<212> TYPE: PRT
<213> ORGANISM: Homo sapiens

<400> SEQUENCE: 11

Met Ala Thr Thr Ala Thr Met Ala Thr Ser Gly Ser Ala Arg Lys Arg
1               5                   10                  15

Leu Leu Lys Glu Glu Asp Met Thr Lys Val Glu Phe Glu Thr Ser Glu
                20                  25                  30

Glu Val Asp Val Thr Pro Thr Phe Asp Thr Met Gly Leu Arg Glu Asp
            35                  40                  45

Leu Leu Arg Gly Ile Tyr Ala Tyr Gly Phe Glu Lys Pro Ser Ala Ile
        50                  55                  60

Gln Gln Arg Ala Ile Lys Gln Ile Ile Lys Gly Arg Asp Val Ile Ala
65              70                  75                  80

Gln Ser Gln Ser Gly Thr Gly Lys Thr Ala Thr Phe Ser Ile Ser Val
                85                  90                  95

Leu Gln Cys Leu Asp Ile Gln Val Arg Glu Thr Gln Ala Leu Ile Leu
            100                 105                 110

Ala Pro Thr Arg Glu Leu Ala Val Gln Ile Gln Lys Gly Leu Leu Ala
        115                 120                 125

Leu Gly Asp Tyr Met Asn Val Gln Cys His Ala Cys Ile Gly Gly Thr
130             135                 140

Asn Val Gly Glu Asp Ile Arg Lys Leu Asp Tyr Gly Gln His Val Val
145                 150                 155                 160

Ala Gly Thr Pro Gly Arg Val Phe Asp Met Ile Arg Arg Arg Ser Leu
                165                 170                 175

Arg Thr Arg Ala Ile Lys Met Leu Val Leu Asp Glu Ala Asp Glu Met
            180                 185                 190

Leu Asn Lys Gly Phe Lys Glu Gln Ile Tyr Asp Val Tyr Arg Tyr Leu
        195                 200                 205
```

```
Pro Pro Ala Thr Gln Val Val Leu Ile Ser Ala Thr Leu Pro His Glu
    210                 215                 220
Ile Leu Glu Met Thr Asn Lys Phe Met Thr Asp Pro Ile Arg Ile Leu
225                 230                 235                 240
Val Lys Arg Asp Glu Leu Thr Leu Glu Gly Ile Lys Gln Phe Phe Val
                245                 250                 255
Ala Val Glu Arg Glu Glu Trp Lys Phe Asp Thr Leu Cys Asp Leu Tyr
            260                 265                 270
Asp Thr Leu Thr Ile Thr Gln Ala Val Ile Phe Cys Asn Thr Lys Arg
        275                 280                 285
Lys Val Asp Trp Leu Thr Glu Lys Met Arg Glu Ala Asn Phe Thr Val
290                 295                 300
Ser Ser Met His Gly Asp Met Pro Gln Lys Glu Arg Glu Ser Ile Met
305                 310                 315                 320
Lys Glu Phe Arg Ser Gly Ala Ser Arg Val Leu Ile Ser Thr Asp Val
                325                 330                 335
Trp Ala Arg Gly Leu Asp Val Pro Gln Val Ser Leu Ile Ile Asn Tyr
            340                 345                 350
Asp Leu Pro Asn Asn Arg Glu Leu Tyr Ile His Arg Ile Gly Arg Ser
        355                 360                 365
Gly Arg Tyr Gly Arg Lys Gly Val Ala Ile Asn Phe Val Lys Asn Asp
370                 375                 380
Asp Ile Arg Ile Leu Arg Asp Ile Glu Gln Tyr Tyr Ser Thr Gln Ile
385                 390                 395                 400
Asp Glu Met Pro Met Asn Val Ala Asp Leu Ile
                405                 410

<210> SEQ ID NO 12
<211> LENGTH: 166
<212> TYPE: PRT
<213> ORGANISM: Homo sapiens

<400> SEQUENCE: 12

Met Ala Ser Gly Val Ala Val Ser Asp Gly Val Ile Lys Val Phe Asn
1               5                   10                  15
Asp Met Lys Val Arg Lys Ser Ser Thr Pro Glu Glu Val Lys Lys Arg
                20                  25                  30
Lys Lys Ala Val Leu Phe Cys Leu Ser Glu Asp Lys Lys Asn Ile Ile
            35                  40                  45
Leu Glu Glu Gly Lys Glu Ile Leu Val Gly Asp Val Gly Gln Thr Val
        50                  55                  60
Asp Asp Pro Tyr Ala Thr Phe Val Lys Met Leu Pro Asp Lys Asp Cys
65                  70                  75                  80
Arg Tyr Ala Leu Tyr Asp Ala Thr Tyr Glu Thr Lys Glu Ser Lys Lys
                85                  90                  95
Glu Asp Leu Val Phe Ile Phe Trp Ala Pro Glu Ser Ala Pro Leu Lys
            100                 105                 110
Ser Lys Met Ile Tyr Ala Ser Ser Lys Asp Ala Ile Lys Lys Lys Leu
        115                 120                 125
Thr Gly Ile Lys His Glu Leu Gln Ala Asn Cys Tyr Glu Glu Val Lys
    130                 135                 140
Asp Arg Cys Thr Leu Ala Glu Lys Leu Gly Gly Ser Ala Val Ile Ser
145                 150                 155                 160
Leu Glu Gly Lys Pro Leu
                165
```

<210> SEQ ID NO 13
<211> LENGTH: 360
<212> TYPE: PRT
<213> ORGANISM: Homo sapiens

<400> SEQUENCE: 13

```
Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His
    50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
    130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
    210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala
    290                 295                 300

His Ala Tyr Phe Ala Gln Tyr His Asp Pro Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
            340                 345                 350

Leu Asp Gln Glu Glu Met Glu Ser
    355                 360
```

```
<210> SEQ ID NO 14
<211> LENGTH: 626
<212> TYPE: PRT
<213> ORGANISM: Homo sapiens

<400> SEQUENCE: 14

Met Gln Arg Ala Asp Ser Glu Gln Pro Ser Lys Arg Pro Arg Cys Asp
1               5                   10                  15

Asp Ser Pro Arg Thr Pro Ser Asn Thr Pro Ser Ala Glu Ala Asp Trp
            20                  25                  30

Ser Pro Gly Leu Glu Leu His Pro Asp Tyr Lys Thr Trp Gly Pro Glu
        35                  40                  45

Gln Val Cys Ser Phe Leu Arg Arg Gly Gly Phe Glu Glu Pro Val Leu
    50                  55                  60

Leu Lys Asn Ile Arg Glu Asn Glu Ile Thr Gly Ala Leu Leu Pro Cys
65                  70                  75                  80

Leu Asp Glu Ser Arg Phe Glu Asn Leu Gly Val Ser Ser Leu Gly Glu
                85                  90                  95

Arg Lys Lys Leu Leu Ser Tyr Ile Gln Arg Leu Val Gln Ile His Val
            100                 105                 110

Asp Thr Met Lys Val Ile Asn Asp Pro Ile His Gly His Ile Glu Leu
        115                 120                 125

His Pro Leu Leu Val Arg Ile Ile Asp Thr Pro Gln Phe Gln Arg Leu
    130                 135                 140

Arg Tyr Ile Lys Gln Leu Gly Gly Gly Tyr Tyr Val Phe Pro Gly Ala
145                 150                 155                 160

Ser His Asn Arg Phe Glu His Ser Leu Gly Val Gly Tyr Leu Ala Gly
                165                 170                 175

Cys Leu Val His Ala Leu Gly Glu Lys Gln Pro Glu Leu Gln Ile Ser
            180                 185                 190

Glu Arg Asp Val Leu Cys Val Gln Ile Ala Gly Leu Cys His Asp Leu
        195                 200                 205

Gly His Gly Pro Phe Ser His Met Phe Asp Gly Arg Phe Ile Pro Leu
    210                 215                 220

Ala Arg Pro Glu Val Lys Trp Thr His Glu Gln Gly Ser Val Met Met
225                 230                 235                 240

Phe Glu His Leu Ile Asn Ser Asn Gly Ile Lys Pro Val Met Glu Gln
                245                 250                 255

Tyr Gly Leu Ile Pro Glu Glu Asp Ile Cys Phe Ile Lys Glu Gln Ile
            260                 265                 270

Val Gly Pro Leu Glu Ser Pro Val Glu Asp Ser Leu Trp Pro Tyr Lys
        275                 280                 285

Gly Arg Pro Glu Asn Lys Ser Phe Leu Tyr Glu Ile Val Ser Asn Lys
    290                 295                 300

Arg Asn Gly Ile Asp Val Asp Lys Trp Asp Tyr Phe Ala Arg Asp Cys
305                 310                 315                 320

His His Leu Gly Ile Gln Asn Asn Phe Asp Tyr Lys Arg Phe Ile Lys
                325                 330                 335

Phe Ala Arg Val Cys Glu Val Asp Asn Glu Leu Arg Ile Cys Ala Arg
            340                 345                 350

Asp Lys Glu Val Gly Asn Leu Tyr Asp Met Phe His Thr Arg Asn Ser
        355                 360                 365

Leu His Arg Arg Ala Tyr Gln His Lys Val Gly Asn Ile Ile Asp Thr
    370                 375                 380
```

Met Ile Thr Asp Ala Phe Leu Lys Ala Asp Asp Tyr Ile Glu Ile Thr
385                 390                 395                 400

Gly Ala Gly Gly Lys Lys Tyr Arg Ile Ser Thr Ala Ile Asp Asp Met
            405                 410                 415

Glu Ala Tyr Thr Lys Leu Thr Asp Asn Ile Phe Leu Glu Ile Leu Tyr
        420                 425                 430

Ser Thr Asp Pro Lys Leu Lys Asp Ala Arg Glu Ile Leu Lys Gln Ile
        435                 440                 445

Glu Tyr Arg Asn Leu Phe Lys Tyr Val Gly Glu Thr Gln Pro Thr Gly
    450                 455                 460

Gln Ile Lys Ile Lys Arg Glu Asp Tyr Glu Ser Leu Pro Lys Glu Val
465                 470                 475                 480

Ala Ser Ala Lys Pro Lys Val Leu Leu Asp Val Lys Leu Lys Ala Glu
                485                 490                 495

Asp Phe Ile Val Asp Val Ile Asn Met Asp Tyr Gly Met Gln Glu Lys
            500                 505                 510

Asn Pro Ile Asp His Val Ser Phe Tyr Cys Lys Thr Ala Pro Asn Arg
        515                 520                 525

Ala Ile Arg Ile Thr Lys Asn Gln Val Ser Gln Leu Leu Pro Glu Lys
    530                 535                 540

Phe Ala Glu Gln Leu Ile Arg Val Tyr Cys Lys Lys Val Asp Arg Lys
545                 550                 555                 560

Ser Leu Tyr Ala Ala Arg Gln Tyr Phe Val Gln Trp Cys Ala Asp Arg
                565                 570                 575

Asn Phe Thr Lys Pro Gln Asp Gly Asp Val Ile Ala Pro Leu Ile Thr
            580                 585                 590

Pro Gln Lys Lys Glu Trp Asn Asp Ser Thr Ser Val Gln Asn Pro Thr
        595                 600                 605

Arg Leu Arg Glu Ala Ser Lys Ser Arg Val Gln Leu Phe Lys Asp Asp
    610                 615                 620

Pro Met
625

<210> SEQ ID NO 15
<211> LENGTH: 1152
<212> TYPE: PRT
<213> ORGANISM: Homo sapiens

<400> SEQUENCE: 15

Met Ala Leu Arg Val Leu Leu Thr Ala Leu Thr Leu Cys His Gly
1               5                   10                  15

Phe Asn Leu Asp Thr Glu Asn Ala Met Thr Phe Gln Glu Asn Ala Arg
            20                  25                  30

Gly Phe Gly Gln Ser Val Val Gln Leu Gln Gly Ser Arg Val Val Val
        35                  40                  45

Gly Ala Pro Gln Glu Ile Val Ala Ala Asn Gln Arg Gly Ser Leu Tyr
    50                  55                  60

Gln Cys Asp Tyr Ser Thr Gly Ser Cys Glu Pro Ile Arg Leu Gln Val
65                  70                  75                  80

Pro Val Glu Ala Val Asn Met Ser Leu Gly Leu Ser Leu Ala Ala Thr
                85                  90                  95

Thr Ser Pro Pro Gln Leu Leu Ala Cys Gly Pro Thr Val His Gln Thr
            100                 105                 110

Cys Ser Glu Asn Thr Tyr Val Lys Gly Leu Cys Phe Leu Phe Gly Ser
        115                 120                 125

```
Asn Leu Arg Gln Gln Pro Gln Lys Phe Pro Glu Ala Leu Arg Gly Cys
    130                 135                 140

Pro Gln Glu Asp Ser Asp Ile Ala Phe Leu Ile Asp Gly Ser Gly Ser
145                 150                 155                 160

Ile Ile Pro His Asp Phe Arg Arg Met Lys Glu Phe Val Ser Thr Val
                165                 170                 175

Met Glu Gln Leu Lys Lys Ser Lys Thr Leu Phe Ser Leu Met Gln Tyr
                180                 185                 190

Ser Glu Glu Phe Arg Ile His Phe Thr Phe Lys Glu Phe Gln Asn Asn
            195                 200                 205

Pro Asn Pro Arg Ser Leu Val Lys Pro Ile Thr Gln Leu Leu Gly Arg
    210                 215                 220

Thr His Thr Ala Thr Gly Ile Arg Lys Val Val Arg Glu Leu Phe Asn
225                 230                 235                 240

Ile Thr Asn Gly Ala Arg Lys Asn Ala Phe Lys Ile Leu Val Val Ile
                245                 250                 255

Thr Asp Gly Glu Lys Phe Gly Asp Pro Leu Gly Tyr Glu Asp Val Ile
                260                 265                 270

Pro Glu Ala Asp Arg Glu Gly Val Ile Arg Tyr Val Ile Gly Val Gly
            275                 280                 285

Asp Ala Phe Arg Ser Glu Lys Ser Arg Gln Glu Leu Asn Thr Ile Ala
    290                 295                 300

Ser Lys Pro Pro Arg Asp His Val Phe Gln Val Asn Asn Phe Glu Ala
305                 310                 315                 320

Leu Lys Thr Ile Gln Asn Gln Leu Arg Glu Lys Ile Phe Ala Ile Glu
                325                 330                 335

Gly Thr Gln Thr Gly Ser Ser Ser Phe Glu His Glu Met Ser Gln
                340                 345                 350

Glu Gly Phe Ser Ala Ala Ile Thr Ser Asn Gly Pro Leu Leu Ser Thr
            355                 360                 365

Val Gly Ser Tyr Asp Trp Ala Gly Gly Val Phe Leu Tyr Thr Ser Lys
    370                 375                 380

Glu Lys Ser Thr Phe Ile Asn Met Thr Arg Val Asp Ser Asp Met Asn
385                 390                 395                 400

Asp Ala Tyr Leu Gly Tyr Ala Ala Ala Ile Ile Leu Arg Asn Arg Val
                405                 410                 415

Gln Ser Leu Val Leu Gly Ala Pro Arg Tyr Gln His Ile Gly Leu Val
            420                 425                 430

Ala Met Phe Arg Gln Asn Thr Gly Met Trp Glu Ser Asn Ala Asn Val
    435                 440                 445

Lys Gly Thr Gln Ile Gly Ala Tyr Phe Gly Ala Ser Leu Cys Ser Val
450                 455                 460

Asp Val Asp Ser Asn Gly Ser Thr Asp Leu Val Leu Ile Gly Ala Pro
465                 470                 475                 480

His Tyr Tyr Glu Gln Thr Arg Gly Gly Gln Val Ser Val Cys Pro Leu
                485                 490                 495

Pro Arg Gly Arg Ala Arg Trp Gln Cys Asp Ala Val Leu Tyr Gly Glu
            500                 505                 510

Gln Gly Gln Pro Trp Gly Arg Phe Gly Ala Ala Leu Thr Val Leu Gly
    515                 520                 525

Asp Val Asn Gly Asp Lys Leu Thr Asp Val Ala Ile Gly Ala Pro Gly
530                 535                 540
```

-continued

Glu Glu Asp Asn Arg Gly Ala Val Tyr Leu Phe His Gly Thr Ser Gly
545                 550                 555                 560

Ser Gly Ile Ser Pro Ser His Ser Gln Arg Ile Ala Gly Ser Lys Leu
            565                 570                 575

Ser Pro Arg Leu Gln Tyr Phe Gly Gln Ser Leu Ser Gly Gly Gln Asp
        580                 585                 590

Leu Thr Met Asp Gly Leu Val Asp Leu Thr Val Gly Ala Gln Gly His
    595                 600                 605

Val Leu Leu Leu Arg Ser Gln Pro Val Leu Arg Val Lys Ala Ile Met
610                 615                 620

Glu Phe Asn Pro Arg Glu Val Ala Arg Asn Val Phe Glu Cys Asn Asp
625                 630                 635                 640

Gln Val Val Lys Gly Lys Glu Ala Gly Glu Val Arg Val Cys Leu His
                645                 650                 655

Val Gln Lys Ser Thr Arg Asp Arg Leu Arg Glu Gly Gln Ile Gln Ser
            660                 665                 670

Val Val Thr Tyr Asp Leu Ala Leu Asp Ser Gly Arg Pro His Ser Arg
        675                 680                 685

Ala Val Phe Asn Glu Thr Lys Asn Ser Thr Arg Arg Gln Thr Gln Val
    690                 695                 700

Leu Gly Leu Thr Gln Thr Cys Glu Thr Leu Lys Leu Gln Leu Pro Asn
705                 710                 715                 720

Cys Ile Glu Asp Pro Val Ser Pro Ile Val Leu Arg Leu Asn Phe Ser
                725                 730                 735

Leu Val Gly Thr Pro Leu Ser Ala Phe Gly Asn Leu Arg Pro Val Leu
            740                 745                 750

Ala Glu Asp Ala Gln Arg Leu Phe Thr Ala Leu Phe Pro Phe Glu Lys
        755                 760                 765

Asn Cys Gly Asn Asp Asn Ile Cys Gln Asp Asp Leu Ser Ile Thr Phe
    770                 775                 780

Ser Phe Met Ser Leu Asp Cys Leu Val Val Gly Gly Pro Arg Glu Phe
785                 790                 795                 800

Asn Val Thr Val Thr Val Arg Asn Asp Gly Glu Asp Ser Tyr Arg Thr
                805                 810                 815

Gln Val Thr Phe Phe Phe Pro Leu Asp Leu Ser Tyr Arg Lys Val Ser
            820                 825                 830

Thr Leu Gln Asn Gln Arg Ser Gln Arg Ser Trp Arg Leu Ala Cys Glu
        835                 840                 845

Ser Ala Ser Ser Thr Glu Val Ser Gly Ala Leu Lys Ser Thr Ser Cys
    850                 855                 860

Ser Ile Asn His Pro Ile Phe Pro Glu Asn Ser Glu Val Thr Phe Asn
865                 870                 875                 880

Ile Thr Phe Asp Val Asp Ser Lys Ala Ser Leu Gly Asn Lys Leu Leu
                885                 890                 895

Leu Lys Ala Asn Val Thr Ser Glu Asn Asn Met Pro Arg Thr Asn Lys
            900                 905                 910

Thr Glu Phe Gln Leu Glu Leu Pro Val Lys Tyr Ala Val Tyr Met Val
        915                 920                 925

Val Thr Ser His Gly Val Ser Thr Lys Tyr Leu Asn Phe Thr Ala Ser
    930                 935                 940

Glu Asn Thr Ser Arg Val Met Gln His Gln Tyr Gln Val Ser Asn Leu
945                 950                 955                 960

Gly Gln Arg Ser Leu Pro Ile Ser Leu Val Phe Leu Val Pro Val Arg

```
              965                 970                 975
Leu Asn Gln Thr Val Ile Trp Asp Arg Pro Gln Val Thr Phe Ser Glu
            980                 985                 990

Asn Leu Ser Ser Thr Cys His Thr Lys Glu Arg Leu Pro Ser His Ser
            995                 1000                1005

Asp Phe Leu Ala Glu Leu Arg Lys Ala Pro Val Val Asn Cys Ser
    1010                1015                1020

Ile Ala Val Cys Gln Arg Ile Gln Cys Asp Ile Pro Phe Phe Gly
    1025                1030                1035

Ile Gln Glu Glu Phe Asn Ala Thr Leu Lys Gly Asn Leu Ser Phe
    1040                1045                1050

Asp Trp Tyr Ile Lys Thr Ser His Asn His Leu Leu Ile Val Ser
    1055                1060                1065

Thr Ala Glu Ile Leu Phe Asn Asp Ser Val Phe Thr Leu Leu Pro
    1070                1075                1080

Gly Gln Gly Ala Phe Val Arg Ser Gln Thr Glu Thr Lys Val Glu
    1085                1090                1095

Pro Phe Glu Val Pro Asn Pro Leu Pro Leu Ile Val Gly Ser Ser
    1100                1105                1110

Val Gly Gly Leu Leu Leu Leu Ala Leu Ile Thr Ala Ala Leu Tyr
    1115                1120                1125

Lys Leu Gly Phe Phe Lys Arg Gln Tyr Lys Asp Met Met Ser Glu
    1130                1135                1140

Gly Gly Pro Pro Gly Ala Glu Pro Gln
    1145                1150

<210> SEQ ID NO 16
<211> LENGTH: 466
<212> TYPE: PRT
<213> ORGANISM: Homo sapiens

<400> SEQUENCE: 16

Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
            20                  25                  30

Thr Ser Thr Arg Thr Tyr Ser Leu Gly Ser Ala Leu Arg Pro Ser Thr
        35                  40                  45

Ser Arg Ser Leu Tyr Ala Ser Ser Pro Gly Gly Val Tyr Ala Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175
```

```
Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
    260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
        435                 440                 445

Thr Arg Asp Gly Gln Val Ile Asn Glu Thr Ser Gln His His Asp Asp
    450                 455                 460

Leu Glu
465

<210> SEQ ID NO 17
<211> LENGTH: 439
<212> TYPE: PRT
<213> ORGANISM: Homo sapiens

<400> SEQUENCE: 17

Met Asp Pro Leu Ser Glu Leu Gln Asp Leu Thr Leu Asp Asp Thr
1               5                   10                  15

Ser Glu Ala Leu Asn Gln Leu Lys Leu Ala Ser Ile Asp Glu Lys Asn
            20                  25                  30

Trp Pro Ser Asp Glu Met Pro Asp Phe Pro Lys Ser Asp Ser Lys
            35                  40                  45

Ser Ser Ser Pro Glu Leu Val Thr His Leu Lys Trp Asp Asp Pro Tyr
    50                  55                  60

Tyr Asp Ile Ala Arg His Gln Ile Val Glu Val Ala Gly Asp Asp Lys
65                  70                  75                  80
```

```
Tyr Gly Arg Lys Ile Ile Val Phe Ser Ala Cys Arg Met Pro Pro Ser
                85                  90                  95

His Gln Leu Asp His Ser Lys Leu Leu Gly Tyr Leu Lys His Thr Leu
            100                 105                 110

Asp Gln Tyr Val Glu Ser Asp Tyr Thr Leu Leu Tyr Leu His His Gly
        115                 120                 125

Leu Thr Ser Asp Asn Lys Pro Ser Leu Ser Trp Leu Arg Asp Ala Tyr
    130                 135                 140

Arg Glu Phe Asp Arg Lys Tyr Lys Asn Ile Lys Ala Leu Tyr Ile
145                 150                 155                 160

Val His Pro Thr Met Phe Ile Lys Thr Leu Leu Ile Leu Phe Lys Pro
                165                 170                 175

Leu Ile Ser Phe Lys Phe Gly Gln Lys Ile Phe Tyr Val Asn Tyr Leu
            180                 185                 190

Ser Glu Leu Ser Glu His Val Lys Leu Glu Gln Leu Gly Ile Pro Arg
        195                 200                 205

Gln Val Leu Lys Tyr Asp Asp Phe Leu Lys Ser Thr Gln Lys Ser Pro
    210                 215                 220

Ala Thr Ala Pro Lys Pro Met Pro Pro Arg Pro Pro Leu Pro Asn Gln
225                 230                 235                 240

Gln Phe Gly Val Ser Leu Gln His Leu Gln Glu Lys Asn Pro Glu Gln
                245                 250                 255

Glu Pro Ile Pro Ile Val Leu Arg Glu Thr Val Ala Tyr Leu Gln Ala
            260                 265                 270

His Ala Leu Thr Thr Glu Gly Ile Phe Arg Arg Ser Ala Asn Thr Gln
        275                 280                 285

Val Val Arg Glu Val Gln Gln Lys Tyr Asn Met Gly Leu Pro Val Asp
    290                 295                 300

Phe Asp Gln Tyr Asn Glu Leu His Leu Pro Ala Val Ile Leu Lys Thr
305                 310                 315                 320

Phe Leu Arg Glu Leu Pro Glu Pro Leu Leu Thr Phe Asp Leu Tyr Pro
                325                 330                 335

His Val Val Gly Phe Leu Asn Ile Asp Glu Ser Gln Arg Val Pro Ala
            340                 345                 350

Thr Leu Gln Val Leu Gln Thr Leu Pro Glu Glu Asn Tyr Gln Val Leu
        355                 360                 365

Arg Phe Leu Thr Ala Phe Leu Val Gln Ile Ser Ala His Ser Asp Gln
    370                 375                 380

Asn Lys Met Thr Asn Thr Asn Leu Ala Val Val Phe Gly Pro Asn Leu
385                 390                 395                 400

Leu Trp Ala Lys Asp Ala Ala Ile Thr Leu Lys Ala Ile Asn Pro Ile
                405                 410                 415

Asn Thr Phe Thr Lys Phe Leu Leu Asp His Gln Gly Glu Leu Phe Pro
            420                 425                 430

Ser Pro Asp Pro Ser Gly Leu
        435
```

<210> SEQ ID NO 18
<211> LENGTH: 457
<212> TYPE: PRT
<213> ORGANISM: Homo sapiens

<400> SEQUENCE: 18

Met Thr Thr Asp Glu Gly Ala Lys Asn Asn Glu Glu Ser Pro Thr Ala

-continued

```
1               5                   10                  15
Thr Val Ala Glu Gln Gly Glu Asp Ile Thr Ser Lys Lys Asp Arg Gly
                20                  25                  30

Val Leu Lys Ile Val Lys Arg Val Gly Asn Gly Glu Glu Thr Pro Met
                35                  40                  45

Ile Gly Asp Lys Val Tyr Val His Tyr Lys Gly Lys Leu Ser Asn Gly
                50                  55                  60

Lys Lys Phe Asp Ser Ser His Asp Arg Asn Glu Pro Phe Val Phe Ser
65                  70                  75                  80

Leu Gly Lys Gly Gln Val Ile Lys Ala Trp Asp Ile Gly Val Ala Thr
                85                  90                  95

Met Lys Lys Gly Glu Ile Cys His Leu Leu Cys Lys Pro Glu Tyr Ala
                100                 105                 110

Tyr Gly Ser Ala Gly Ser Leu Pro Lys Ile Pro Ser Asn Ala Thr Leu
                115                 120                 125

Phe Phe Glu Ile Glu Leu Leu Asp Phe Lys Gly Glu Asp Leu Phe Glu
                130                 135                 140

Asp Gly Gly Ile Ile Arg Arg Thr Lys Arg Lys Gly Glu Gly Tyr Ser
145                 150                 155                 160

Asn Pro Asn Glu Gly Ala Thr Val Glu Ile His Leu Glu Gly Arg Cys
                165                 170                 175

Gly Gly Arg Met Phe Asp Cys Arg Asp Val Ala Phe Thr Val Gly Glu
                180                 185                 190

Gly Glu Asp His Asp Ile Pro Ile Gly Ile Asp Lys Ala Leu Glu Lys
                195                 200                 205

Met Gln Arg Glu Glu Gln Cys Ile Leu Tyr Leu Gly Pro Arg Tyr Gly
                210                 215                 220

Phe Gly Glu Ala Gly Lys Pro Lys Phe Gly Ile Glu Pro Asn Ala Glu
225                 230                 235                 240

Leu Ile Tyr Glu Val Thr Leu Lys Ser Phe Glu Lys Ala Lys Glu Ser
                245                 250                 255

Trp Glu Met Asp Thr Lys Glu Lys Leu Glu Gln Ala Ala Ile Val Lys
                260                 265                 270

Glu Lys Gly Thr Val Tyr Phe Lys Gly Gly Lys Tyr Met Gln Ala Val
                275                 280                 285

Ile Gln Tyr Gly Lys Ile Val Ser Trp Leu Glu Met Glu Tyr Gly Leu
                290                 295                 300

Ser Glu Lys Glu Ser Lys Ala Ser Glu Ser Phe Leu Leu Ala Ala Phe
305                 310                 315                 320

Leu Asn Leu Ala Met Cys Tyr Leu Lys Leu Arg Glu Tyr Thr Lys Ala
                325                 330                 335

Val Glu Cys Cys Asp Lys Ala Leu Gly Leu Asp Ser Ala Asn Glu Lys
                340                 345                 350

Gly Leu Tyr Arg Arg Gly Glu Ala Gln Leu Leu Met Asn Glu Phe Glu
                355                 360                 365

Ser Ala Lys Gly Asp Phe Glu Lys Val Leu Glu Val Asn Pro Gln Asn
                370                 375                 380

Lys Ala Ala Arg Leu Gln Ile Ser Met Cys Gln Lys Ala Lys Glu
385                 390                 395                 400

His Asn Glu Arg Asp Arg Arg Ile Tyr Ala Asn Met Phe Lys Lys Phe
                405                 410                 415

Ala Glu Gln Asp Ala Lys Glu Glu Ala Asn Lys Ala Met Gly Lys Lys
                420                 425                 430
```

```
Thr Ser Glu Gly Val Thr Asn Glu Lys Gly Thr Asp Ser Gln Ala Met
        435                 440                 445

Glu Glu Glu Lys Pro Glu Gly His Val
    450                 455
```

<210> SEQ ID NO 19
<211> LENGTH: 266
<212> TYPE: PRT
<213> ORGANISM: Homo sapiens

<400> SEQUENCE: 19

```
Met Val Cys Leu Lys Leu Pro Gly Gly Ser Cys Met Thr Ala Leu Thr
1               5                   10                  15

Val Thr Leu Met Val Leu Ser Ser Pro Leu Ala Leu Ala Gly Asp Thr
            20                  25                  30

Arg Pro Arg Phe Leu Trp Gln Leu Lys Phe Glu Cys His Phe Phe Asn
        35                  40                  45

Gly Thr Glu Arg Val Arg Leu Leu Glu Arg Cys Ile Tyr Asn Gln Glu
    50                  55                  60

Glu Ser Val Arg Phe Asp Ser Asp Val Gly Glu Tyr Arg Ala Val Thr
65                  70                  75                  80

Glu Leu Gly Arg Pro Asp Ala Glu Tyr Trp Asn Ser Gln Lys Asp Leu
                85                  90                  95

Leu Glu Gln Arg Arg Ala Ala Val Asp Thr Tyr Cys Arg His Asn Tyr
            100                 105                 110

Gly Val Gly Glu Ser Phe Thr Val Gln Arg Arg Val Glu Pro Lys Val
        115                 120                 125

Thr Val Tyr Pro Ser Lys Thr Gln Pro Leu Gln His His Asn Leu Leu
    130                 135                 140

Val Cys Ser Val Ser Gly Phe Tyr Pro Gly Ser Ile Glu Val Arg Trp
145                 150                 155                 160

Phe Arg Asn Gly Gln Glu Glu Lys Ala Gly Val Val Ser Thr Gly Leu
                165                 170                 175

Ile Gln Asn Gly Asp Trp Thr Phe Gln Thr Leu Val Met Leu Glu Thr
            180                 185                 190

Val Pro Arg Ser Gly Glu Val Tyr Thr Cys Gln Val Glu His Pro Ser
        195                 200                 205

Val Thr Ser Pro Leu Thr Val Glu Trp Arg Ala Arg Ser Glu Ser Ala
    210                 215                 220

Gln Ser Lys Met Leu Ser Gly Val Gly Gly Phe Val Leu Gly Leu Leu
225                 230                 235                 240

Phe Leu Gly Ala Gly Leu Phe Ile Tyr Phe Arg Asn Gln Lys Gly His
                245                 250                 255

Ser Gly Leu Gln Pro Thr Gly Phe Leu Ser
            260                 265
```

<210> SEQ ID NO 20
<211> LENGTH: 266
<212> TYPE: PRT
<213> ORGANISM: Homo sapiens

<400> SEQUENCE: 20

```
Met Val Cys Leu Lys Leu Pro Gly Gly Ser Cys Met Thr Ala Leu Thr
1               5                   10                  15

Val Thr Leu Met Val Leu Ser Ser Pro Leu Ala Leu Ala Gly Asp Thr
            20                  25                  30
```

```
Arg Pro Arg Phe Leu Trp Gln Pro Lys Arg Glu Cys His Phe Phe Asn
        35                  40                  45

Gly Thr Glu Arg Val Arg Phe Leu Asp Arg Tyr Phe Tyr Asn Gln Glu
 50                  55                  60

Glu Ser Val Arg Phe Asp Ser Asp Val Gly Glu Tyr Arg Ala Val Thr
 65                  70                  75                  80

Glu Leu Gly Arg Pro Asp Ala Glu Tyr Trp Asn Ser Gln Lys Asp Phe
                 85                  90                  95

Leu Glu Asp Arg Arg Ala Ala Val Asp Thr Tyr Cys Arg His Asn Tyr
                100                 105                 110

Gly Val Gly Glu Ser Phe Thr Val Gln Arg Arg Val Gln Pro Lys Val
            115                 120                 125

Thr Val Tyr Pro Ser Lys Thr Gln Pro Leu Gln His His Asn Leu Leu
130                 135                 140

Val Cys Ser Val Ser Gly Phe Tyr Pro Gly Ser Ile Glu Val Arg Trp
145                 150                 155                 160

Phe Leu Asn Gly Gln Glu Lys Ala Gly Met Val Ser Thr Gly Leu
                165                 170                 175

Ile Gln Asn Gly Asp Trp Thr Phe Gln Thr Leu Val Met Leu Glu Thr
                180                 185                 190

Val Pro Arg Ser Gly Glu Val Tyr Thr Cys Gln Val Glu His Pro Ser
            195                 200                 205

Val Thr Ser Pro Leu Thr Val Glu Trp Arg Ala Arg Ser Glu Ser Ala
            210                 215                 220

Gln Ser Lys Met Leu Ser Gly Val Gly Gly Phe Val Leu Gly Leu Leu
225                 230                 235                 240

Phe Leu Gly Ala Gly Leu Phe Ile Tyr Phe Arg Asn Gln Lys Gly His
                245                 250                 255

Ser Gly Leu Gln Pro Thr Gly Phe Leu Ser
                260                 265

<210> SEQ ID NO 21
<211> LENGTH: 103
<212> TYPE: PRT
<213> ORGANISM: Homo sapiens

<400> SEQUENCE: 21

Met Ser Gly Arg Gly Lys Gly Gly Lys Gly Leu Gly Lys Gly Gly Ala
 1               5                  10                  15

Lys Arg His Arg Lys Val Leu Arg Asp Asn Ile Gln Gly Ile Thr Lys
                20                  25                  30

Pro Ala Ile Arg Arg Leu Ala Arg Arg Gly Gly Val Lys Arg Ile Ser
            35                  40                  45

Gly Leu Ile Tyr Glu Glu Thr Arg Gly Val Leu Lys Val Phe Leu Glu
 50                  55                  60

Asn Val Ile Arg Asp Ala Val Thr Tyr Thr Glu His Ala Lys Arg Lys
 65                  70                  75                  80

Thr Val Thr Ala Met Asp Val Val Tyr Ala Leu Lys Arg Gln Gly Arg
                 85                  90                  95

Thr Leu Tyr Gly Phe Gly Gly
                100

<210> SEQ ID NO 22
<211> LENGTH: 205
<212> TYPE: PRT
```

<213> ORGANISM: Homo sapiens

<400> SEQUENCE: 22

Met Thr Glu Arg Arg Val Pro Phe Ser Leu Leu Arg Gly Pro Ser Trp
1               5                   10                  15

Asp Pro Phe Arg Asp Trp Tyr Pro His Ser Arg Leu Phe Asp Gln Ala
            20                  25                  30

Phe Gly Leu Pro Arg Leu Pro Glu Glu Trp Ser Gln Trp Leu Gly Gly
        35                  40                  45

Ser Ser Trp Pro Gly Tyr Val Arg Pro Leu Pro Pro Ala Ala Ile Glu
    50                  55                  60

Ser Pro Ala Val Ala Ala Pro Ala Tyr Ser Arg Ala Leu Ser Arg Gln
65                  70                  75                  80

Leu Ser Ser Gly Val Ser Glu Ile Arg His Thr Ala Asp Arg Trp Arg
                85                  90                  95

Val Ser Leu Asp Val Asn His Phe Ala Pro Asp Glu Leu Thr Val Lys
            100                 105                 110

Thr Lys Asp Gly Val Val Glu Ile Thr Gly Lys His Glu Glu Arg Gln
        115                 120                 125

Asp Glu His Gly Tyr Ile Ser Arg Cys Phe Thr Arg Lys Tyr Thr Leu
    130                 135                 140

Pro Pro Gly Val Asp Pro Thr Gln Val Ser Ser Leu Ser Pro Glu
145                 150                 155                 160

Gly Thr Leu Thr Val Glu Ala Pro Met Pro Lys Leu Ala Thr Gln Ser
                165                 170                 175

Asn Glu Ile Thr Ile Pro Val Thr Phe Glu Ser Arg Ala Gln Leu Gly
            180                 185                 190

Gly Pro Glu Ala Ala Lys Ser Asp Glu Thr Ala Ala Lys
        195                 200                 205

<210> SEQ ID NO 23
<211> LENGTH: 493
<212> TYPE: PRT
<213> ORGANISM: Homo sapiens

<400> SEQUENCE: 23

Met Thr Ala Asn Gly Thr Ala Glu Ala Val Gln Ile Gln Phe Gly Leu
1               5                   10                  15

Ile Asn Cys Gly Asn Lys Tyr Leu Thr Ala Glu Ala Phe Gly Phe Lys
            20                  25                  30

Val Asn Ala Ser Ala Ser Ser Leu Lys Lys Lys Gln Ile Trp Thr Leu
        35                  40                  45

Glu Gln Pro Pro Asp Glu Ala Gly Ser Ala Ala Val Cys Leu Arg Ser
    50                  55                  60

His Leu Gly Arg Tyr Leu Ala Ala Asp Lys Asp Gly Asn Val Thr Cys
65                  70                  75                  80

Glu Arg Glu Val Pro Gly Pro Asp Cys Arg Phe Leu Ile Val Ala His
                85                  90                  95

Asp Asp Gly Arg Trp Ser Leu Gln Ser Glu Ala His Arg Arg Tyr Phe
            100                 105                 110

Gly Gly Thr Glu Asp Arg Leu Ser Cys Phe Ala Gln Thr Val Ser Pro
        115                 120                 125

Ala Glu Lys Trp Ser Val His Ile Ala Met His Pro Gln Val Asn Ile
    130                 135                 140

Tyr Ser Val Thr Arg Lys Arg Tyr Ala His Leu Ser Ala Arg Pro Ala

```
                145                 150                 155                 160
Asp Glu Ile Ala Val Asp Arg Asp Val Pro Trp Gly Val Asp Ser Leu
                165                 170                 175

Ile Thr Leu Ala Phe Gln Asp Gln Arg Tyr Ser Val Gln Thr Ala Asp
                180                 185                 190

His Arg Phe Leu Arg His Asp Gly Arg Leu Val Ala Arg Pro Glu Pro
                195                 200                 205

Ala Thr Gly Tyr Thr Leu Glu Phe Arg Ser Gly Lys Val Ala Phe Arg
                210                 215                 220

Asp Cys Glu Gly Arg Tyr Leu Ala Pro Ser Gly Pro Ser Gly Thr Leu
225                 230                 235                 240

Lys Ala Gly Lys Ala Thr Lys Val Gly Lys Asp Glu Leu Phe Ala Leu
                    245                 250                 255

Glu Gln Ser Cys Ala Gln Val Val Leu Gln Ala Ala Asn Glu Arg Asn
                260                 265                 270

Val Ser Thr Arg Gln Gly Met Asp Leu Ser Ala Asn Gln Asp Glu Glu
                275                 280                 285

Thr Asp Gln Glu Thr Phe Gln Leu Glu Ile Asp Arg Asp Thr Lys Lys
                290                 295                 300

Cys Ala Phe Arg Thr His Thr Gly Lys Tyr Trp Thr Leu Thr Ala Thr
305                 310                 315                 320

Gly Gly Val Gln Ser Thr Ala Ser Ser Lys Asn Ala Ser Cys Tyr Phe
                    325                 330                 335

Asp Ile Glu Trp Arg Asp Arg Arg Ile Thr Leu Arg Ala Ser Asn Gly
                340                 345                 350

Lys Phe Val Thr Ser Lys Lys Asn Gly Gln Leu Ala Ala Ser Val Glu
                355                 360                 365

Thr Ala Gly Asp Ser Glu Leu Phe Leu Met Lys Leu Ile Asn Arg Pro
                370                 375                 380

Ile Ile Val Phe Arg Gly Glu His Gly Phe Ile Gly Cys Arg Lys Val
385                 390                 395                 400

Thr Gly Thr Leu Asp Ala Asn Arg Ser Ser Tyr Asp Val Phe Gln Leu
                    405                 410                 415

Glu Phe Asn Asp Gly Ala Tyr Asn Ile Lys Asp Ser Thr Gly Lys Tyr
                420                 425                 430

Trp Thr Val Gly Ser Asp Ser Ala Val Thr Ser Ser Gly Asp Thr Pro
                435                 440                 445

Val Asp Phe Phe Phe Glu Phe Cys Asp Tyr Asn Lys Val Ala Ile Lys
                450                 455                 460

Val Gly Gly Arg Tyr Leu Lys Gly Asp His Ala Gly Val Leu Lys Ala
465                 470                 475                 480

Ser Ala Glu Thr Val Asp Pro Ala Ser Leu Trp Glu Tyr
                    485                 490

<210> SEQ ID NO 24
<211> LENGTH: 534
<212> TYPE: PRT
<213> ORGANISM: Homo sapiens

<400> SEQUENCE: 24

Met Phe Ser Trp Val Ser Lys Asp Ala Arg Arg Lys Lys Glu Pro Glu
1               5                   10                  15

Leu Phe Gln Thr Val Ala Glu Gly Leu Arg Gln Leu Tyr Ala Gln Lys
                20                  25                  30
```

-continued

```
Leu Leu Pro Leu Glu Glu His Tyr Arg Phe His Glu Phe His Ser Pro
         35                  40                  45

Ala Leu Glu Asp Ala Asp Phe Asp Asn Lys Pro Met Val Leu Leu Val
 50                  55                  60

Gly Gln Tyr Ser Thr Gly Lys Thr Thr Phe Ile Arg His Leu Ile Glu
 65                  70                  75                  80

Gln Asp Phe Pro Gly Met Arg Ile Gly Pro Glu Pro Thr Thr Asp Ser
                 85                  90                  95

Phe Ile Ala Val Met His Gly Pro Thr Glu Gly Val Val Pro Gly Asn
             100                 105                 110

Ala Leu Val Val Asp Pro Arg Arg Pro Phe Arg Lys Leu Asn Ala Phe
         115                 120                 125

Gly Asn Ala Phe Leu Asn Arg Phe Met Cys Ala Gln Leu Pro Asn Pro
130                 135                 140

Val Leu Asp Ser Ile Ser Ile Ile Asp Thr Pro Gly Ile Leu Ser Gly
145                 150                 155                 160

Glu Lys Gln Arg Ile Ser Arg Gly Tyr Asp Phe Ala Ala Val Leu Glu
                 165                 170                 175

Trp Phe Ala Glu Arg Val Asp Arg Ile Ile Leu Leu Phe Asp Ala His
             180                 185                 190

Lys Leu Asp Ile Ser Asp Glu Phe Ser Glu Val Ile Lys Ala Leu Lys
         195                 200                 205

Asn His Glu Asp Lys Ile Arg Val Val Leu Asn Lys Ala Asp Gln Ile
210                 215                 220

Glu Thr Gln Gln Leu Met Arg Val Tyr Gly Ala Leu Met Trp Ser Leu
225                 230                 235                 240

Gly Lys Ile Ile Asn Thr Pro Glu Val Val Arg Val Tyr Ile Gly Ser
                 245                 250                 255

Phe Trp Ser His Pro Leu Leu Ile Pro Asp Asn Arg Lys Leu Phe Glu
             260                 265                 270

Ala Glu Glu Gln Asp Leu Phe Lys Asp Ile Gln Ser Leu Pro Arg Asn
         275                 280                 285

Ala Ala Leu Arg Lys Leu Asn Asp Leu Ile Lys Arg Ala Arg Leu Ala
290                 295                 300

Lys Val His Ala Tyr Ile Ile Ser Ser Leu Lys Lys Glu Met Pro Asn
305                 310                 315                 320

Val Phe Gly Lys Glu Ser Lys Lys Lys Glu Leu Val Asn Asn Leu Gly
                 325                 330                 335

Glu Ile Tyr Gln Lys Ile Glu Arg Glu His Gln Ile Ser Pro Gly Asp
             340                 345                 350

Phe Pro Ser Leu Arg Lys Met Gln Glu Leu Leu Gln Thr Gln Asp Phe
         355                 360                 365

Ser Lys Phe Gln Ala Leu Lys Pro Lys Leu Leu Asp Thr Val Asp Asp
370                 375                 380

Met Leu Ala Asn Asp Ile Ala Arg Leu Met Val Met Val Arg Gln Glu
385                 390                 395                 400

Glu Ser Leu Met Pro Ser Gln Val Val Lys Gly Gly Ala Phe Asp Gly
                 405                 410                 415

Thr Met Asn Gly Pro Phe Gly His Gly Tyr Gly Glu Gly Ala Gly Glu
             420                 425                 430

Gly Ile Asp Asp Val Glu Trp Val Val Gly Lys Asp Lys Pro Thr Tyr
         435                 440                 445

Asp Glu Ile Phe Tyr Thr Leu Ser Pro Val Asn Gly Lys Ile Thr Gly
```

```
                450                 455                 460
Ala Asn Ala Lys Lys Glu Met Val Lys Ser Lys Leu Pro Asn Thr Val
465                 470                 475                 480

Leu Gly Lys Ile Trp Lys Leu Ala Asp Val Asp Lys Asp Gly Leu Leu
                485                 490                 495

Asp Asp Glu Glu Phe Ala Leu Ala Asn His Leu Ile Lys Val Lys Leu
                500                 505                 510

Glu Gly His Glu Leu Pro Ala Asp Leu Pro Pro His Leu Val Pro Pro
                515                 520                 525

Ser Lys Arg Arg His Glu
        530

<210> SEQ ID NO 25
<211> LENGTH: 699
<212> TYPE: PRT
<213> ORGANISM: Homo sapiens

<400> SEQUENCE: 25

Met Cys Gly Ile Phe Ala Tyr Leu Asn Tyr His Val Pro Arg Thr Arg
1               5                   10                  15

Arg Glu Ile Leu Glu Thr Leu Ile Lys Gly Leu Gln Arg Leu Glu Tyr
                20                  25                  30

Arg Gly Tyr Asp Ser Ala Gly Val Gly Phe Asp Gly Gly Asn Asp Lys
            35                  40                  45

Asp Trp Glu Ala Asn Ala Cys Lys Ile Gln Leu Ile Lys Lys Lys Gly
        50                  55                  60

Lys Val Lys Ala Leu Asp Glu Glu Val His Lys Gln Gln Asp Met Asp
65                  70                  75                  80

Leu Asp Ile Glu Phe Asp Val His Leu Gly Ile Ala His Thr Arg Trp
                85                  90                  95

Ala Thr His Gly Glu Pro Ser Pro Val Asn Ser His Pro Gln Arg Ser
                100                 105                 110

Asp Lys Asn Asn Glu Phe Ile Val Ile His Asn Gly Ile Ile Thr Asn
                115                 120                 125

Tyr Lys Asp Leu Lys Lys Phe Leu Glu Ser Lys Gly Tyr Asp Phe Glu
                130                 135                 140

Ser Glu Thr Asp Thr Glu Thr Ile Ala Lys Leu Val Lys Tyr Met Tyr
145                 150                 155                 160

Asp Asn Arg Glu Ser Gln Asp Thr Ser Phe Thr Thr Leu Val Glu Arg
                165                 170                 175

Val Ile Gln Gln Leu Glu Gly Ala Phe Ala Leu Val Phe Lys Ser Val
                180                 185                 190

His Phe Pro Gly Gln Ala Val Gly Thr Arg Arg Gly Ser Pro Leu Leu
                195                 200                 205

Ile Gly Val Arg Ser Glu His Lys Leu Ser Thr Asp His Ile Pro Ile
                210                 215                 220

Leu Tyr Arg Thr Ala Arg Thr Gln Ile Gly Ser Lys Phe Thr Arg Trp
225                 230                 235                 240

Gly Ser Gln Gly Glu Arg Gly Lys Asp Lys Lys Gly Ser Cys Asn Leu
                245                 250                 255

Ser Arg Val Asp Ser Thr Thr Cys Leu Phe Pro Val Glu Glu Lys Ala
                260                 265                 270

Val Glu Tyr Tyr Phe Ala Ser Asp Ala Ser Ala Val Ile Glu His Thr
                275                 280                 285
```

-continued

```
Asn Arg Val Ile Phe Leu Glu Asp Asp Val Ala Val Val Asp
    290                 295                 300
Gly Arg Leu Ser Ile His Arg Ile Lys Arg Thr Ala Gly Asp His Pro
305                 310                 315                 320
Gly Arg Ala Val Gln Thr Leu Gln Met Glu Leu Gln Gln Ile Met Lys
                325                 330                 335
Gly Asn Phe Ser Ser Phe Met Gln Lys Glu Ile Phe Glu Gln Pro Glu
                340                 345                 350
Ser Val Val Asn Thr Met Arg Gly Arg Val Asn Phe Asp Asp Tyr Thr
                355                 360                 365
Val Asn Leu Gly Gly Leu Lys Asp His Ile Lys Glu Ile Gln Arg Cys
    370                 375                 380
Arg Arg Leu Ile Leu Ile Ala Cys Gly Thr Ser Tyr His Ala Gly Val
385                 390                 395                 400
Ala Thr Arg Gln Val Leu Glu Glu Leu Thr Glu Leu Pro Val Met Val
                405                 410                 415
Glu Leu Ala Ser Asp Phe Leu Asp Arg Asn Thr Pro Val Phe Arg Asp
                420                 425                 430
Asp Val Cys Phe Phe Leu Ser Gln Ser Gly Glu Thr Ala Asp Thr Leu
                435                 440                 445
Met Gly Leu Arg Tyr Cys Lys Glu Arg Gly Ala Leu Thr Val Gly Ile
    450                 455                 460
Thr Asn Thr Val Gly Ser Ser Ile Ser Arg Glu Thr Asp Cys Gly Val
465                 470                 475                 480
His Ile Asn Ala Gly Pro Glu Ile Gly Val Ala Ser Thr Lys Ala Tyr
                485                 490                 495
Thr Ser Gln Phe Val Ser Leu Val Met Phe Ala Leu Met Met Cys Asp
                500                 505                 510
Asp Arg Ile Ser Met Gln Glu Arg Arg Lys Glu Ile Met Leu Gly Leu
                515                 520                 525
Lys Arg Leu Pro Asp Leu Ile Lys Glu Val Leu Ser Met Asp Asp Glu
    530                 535                 540
Ile Gln Lys Leu Ala Thr Glu Leu Tyr His Gln Lys Ser Val Leu Ile
545                 550                 555                 560
Met Gly Arg Gly Tyr His Tyr Ala Thr Cys Leu Glu Gly Ala Leu Lys
                565                 570                 575
Ile Lys Glu Ile Thr Tyr Met His Ser Glu Gly Ile Leu Ala Gly Glu
                580                 585                 590
Leu Lys His Gly Pro Leu Ala Leu Val Asp Lys Leu Met Pro Val Ile
    595                 600                 605
Met Ile Ile Met Arg Asp His Thr Tyr Ala Lys Cys Gln Asn Ala Leu
610                 615                 620
Gln Gln Val Val Ala Arg Gln Gly Arg Pro Val Val Ile Cys Asp Lys
625                 630                 635                 640
Glu Asp Thr Glu Thr Ile Lys Asn Thr Lys Arg Thr Ile Lys Val Pro
                645                 650                 655
His Ser Val Asp Cys Leu Gln Gly Ile Leu Ser Val Ile Pro Leu Gln
                660                 665                 670
Leu Leu Ala Phe His Leu Ala Val Leu Arg Gly Tyr Asp Val Asp Phe
                675                 680                 685
Pro Arg Asn Leu Ala Lys Ser Val Thr Val Glu
    690                 695
```

-continued

```
<210> SEQ ID NO 26
<211> LENGTH: 133
<212> TYPE: PRT
<213> ORGANISM: Homo sapiens

<400> SEQUENCE: 26
```

Met Val Asp Ala Phe Leu Gly Thr Trp Lys Leu Val Asp Ser Lys Asn
1               5                   10                  15

Phe Asp Asp Tyr Met Lys Ser Leu Gly Val Gly Phe Ala Thr Arg Gln
                20                  25                  30

Val Ala Ser Met Thr Lys Pro Thr Thr Ile Ile Glu Lys Asn Gly Asp
            35                  40                  45

Ile Leu Thr Leu Lys Thr His Ser Thr Phe Lys Asn Thr Glu Ile Ser
    50                  55                  60

Phe Lys Leu Gly Val Glu Phe Asp Glu Thr Thr Ala Asp Asp Arg Lys
65                  70                  75                  80

Val Lys Ser Ile Val Thr Leu Asp Gly Gly Lys Leu Val His Leu Gln
                85                  90                  95

Lys Trp Asp Gly Gln Glu Thr Thr Leu Val Arg Glu Leu Ile Asp Gly
                100                 105                 110

Lys Leu Ile Leu Thr Leu Thr His Gly Thr Ala Val Cys Thr Arg Thr
            115                 120                 125

Tyr Glu Lys Glu Ala
    130

```
<210> SEQ ID NO 27
<211> LENGTH: 526
<212> TYPE: PRT
<213> ORGANISM: Homo sapiens

<400> SEQUENCE: 27
```

Met Gly Gly Arg Ser Ser Cys Glu Asp Pro Gly Cys Pro Arg Asp Glu
1               5                   10                  15

Glu Arg Ala Pro Arg Met Gly Cys Met Lys Ser Lys Phe Leu Gln Val
                20                  25                  30

Gly Gly Asn Thr Phe Ser Lys Thr Glu Thr Ser Ala Ser Pro His Cys
            35                  40                  45

Pro Val Tyr Val Pro Asp Pro Thr Ser Thr Ile Lys Pro Gly Pro Asn
    50                  55                  60

Ser His Asn Ser Asn Thr Pro Gly Ile Arg Glu Ala Gly Ser Glu Asp
65                  70                  75                  80

Ile Ile Val Val Ala Leu Tyr Asp Tyr Glu Ala Ile His His Glu Asp
                85                  90                  95

Leu Ser Phe Gln Lys Gly Asp Gln Met Val Val Leu Glu Glu Ser Gly
                100                 105                 110

Glu Trp Trp Lys Ala Arg Ser Leu Ala Thr Arg Lys Glu Gly Tyr Ile
            115                 120                 125

Pro Ser Asn Tyr Val Ala Arg Val Asp Ser Leu Glu Thr Glu Glu Trp
    130                 135                 140

Phe Phe Lys Gly Ile Ser Arg Lys Asp Ala Glu Arg Gln Leu Leu Ala
145                 150                 155                 160

Pro Gly Asn Met Leu Gly Ser Phe Met Ile Arg Asp Ser Glu Thr Thr
                165                 170                 175

Lys Gly Ser Tyr Ser Leu Ser Val Arg Asp Tyr Asp Pro Arg Gln Gly
            180                 185                 190

Asp Thr Val Lys His Tyr Lys Ile Arg Thr Leu Asp Asn Gly Gly Phe

```
            195                 200                 205
Tyr Ile Ser Pro Arg Ser Thr Phe Ser Thr Leu Gln Glu Leu Val Asp
            210                 215                 220
His Tyr Lys Lys Gly Asn Asp Gly Leu Cys Gln Lys Leu Ser Val Pro
225                 230                 235                 240
Cys Met Ser Ser Lys Pro Gln Lys Pro Trp Glu Lys Asp Ala Trp Glu
                245                 250                 255
Ile Pro Arg Glu Ser Leu Lys Leu Glu Lys Lys Leu Gly Ala Gly Gln
            260                 265                 270
Phe Gly Glu Val Trp Met Ala Thr Tyr Asn Lys His Thr Lys Val Ala
            275                 280                 285
Val Lys Thr Met Lys Pro Gly Ser Met Ser Val Glu Ala Phe Leu Ala
290                 295                 300
Glu Ala Asn Val Met Lys Thr Leu Gln His Asp Lys Leu Val Lys Leu
305                 310                 315                 320
His Ala Val Val Thr Lys Glu Pro Ile Tyr Ile Ile Thr Glu Phe Met
                325                 330                 335
Ala Lys Gly Ser Leu Leu Asp Phe Leu Lys Ser Asp Glu Gly Ser Lys
            340                 345                 350
Gln Pro Leu Pro Lys Leu Ile Asp Phe Ser Ala Gln Ile Ala Glu Gly
            355                 360                 365
Met Ala Phe Ile Glu Gln Arg Asn Tyr Ile His Arg Asp Leu Arg Ala
370                 375                 380
Ala Asn Ile Leu Val Ser Ala Ser Leu Val Cys Lys Ile Ala Asp Phe
385                 390                 395                 400
Gly Leu Ala Arg Val Ile Glu Asp Asn Glu Tyr Thr Ala Arg Glu Gly
                405                 410                 415
Ala Lys Phe Pro Ile Lys Trp Thr Ala Pro Glu Ala Ile Asn Phe Gly
            420                 425                 430
Ser Phe Thr Ile Lys Ser Asp Val Trp Ser Phe Gly Ile Leu Leu Met
            435                 440                 445
Glu Ile Val Thr Tyr Gly Arg Ile Pro Tyr Pro Gly Met Ser Asn Pro
450                 455                 460
Glu Val Ile Arg Ala Leu Glu Arg Gly Tyr Arg Met Pro Arg Pro Glu
465                 470                 475                 480
Asn Cys Pro Glu Glu Leu Tyr Asn Ile Met Met Arg Cys Trp Lys Asn
                485                 490                 495
Arg Pro Glu Glu Arg Pro Thr Phe Glu Tyr Ile Gln Ser Val Leu Asp
            500                 505                 510
Asp Phe Tyr Thr Ala Thr Glu Ser Gln Tyr Gln Gln Pro
            515                 520                 525

<210> SEQ ID NO 28
<211> LENGTH: 523
<212> TYPE: PRT
<213> ORGANISM: Homo sapiens

<400> SEQUENCE: 28

Met Ala Ala Val Gly Arg Val Gly Ser Phe Gly Ser Ser Pro Pro Gly
1               5                   10                  15
Leu Ser Ser Thr Tyr Thr Gly Gly Pro Leu Gly Asn Glu Ile Ala Ser
            20                  25                  30
Gly Asn Gly Gly Ala Ala Ala Gly Asp Asp Glu Asp Gly Gln Asn Leu
        35                  40                  45
```

-continued

Trp Ser Cys Ile Leu Ser Glu Val Ser Thr Arg Ser Arg Lys Leu
     50              55                  60

Pro Ala Gly Lys Asn Val Leu Leu Gly Glu Asp Gly Ala Gly Lys
 65              70                  75                  80

Thr Ser Leu Ile Arg Lys Ile Gln Gly Ile Glu Glu Tyr Lys Lys Gly
                 85              90                  95

Arg Gly Leu Glu Tyr Leu Tyr Leu Asn Val His Asp Glu Asp Arg Asp
            100             105                 110

Asp Gln Thr Arg Cys Asn Val Trp Ile Leu Asp Gly Asp Leu Tyr His
            115                 120                 125

Lys Gly Leu Leu Lys Phe Ser Leu Asp Ala Val Ser Leu Lys Asp Thr
130                 135                 140

Leu Val Met Leu Val Val Asp Met Ser Lys Pro Trp Thr Ala Leu Asp
145                 150                 155                 160

Ser Leu Gln Lys Trp Ala Ser Val Val Arg Glu His Val Asp Lys Leu
                165                 170                 175

Lys Ile Pro Pro Glu Glu Met Lys Gln Met Gln Lys Leu Ile Arg
                180                 185                 190

Asp Phe Gln Glu Tyr Val Glu Pro Gly Glu Asp Phe Pro Ala Ser Pro
            195                 200                 205

Gln Arg Arg Asn Thr Ala Ser Gln Glu Asp Lys Asp Asp Ser Val Val
            210                 215                 220

Leu Pro Leu Gly Ala Asp Thr Leu Thr His Asn Leu Gly Ile Pro Val
225                 230                 235                 240

Leu Val Val Cys Thr Lys Cys Asp Ala Ile Ser Val Leu Glu Lys Glu
                245                 250                 255

His Asp Tyr Arg Asp Glu His Phe Asp Phe Ile Gln Ser His Ile Arg
            260                 265                 270

Lys Phe Cys Leu Gln Tyr Gly Ala Ala Leu Ile Tyr Thr Ser Val Lys
            275                 280                 285

Glu Asn Lys Asn Ile Asp Leu Val Tyr Lys Tyr Ile Val Gln Lys Leu
            290                 295                 300

Tyr Gly Phe Pro Tyr Lys Ile Pro Ala Val Val Val Glu Lys Asp Ala
305                 310                 315                 320

Val Phe Ile Pro Ala Gly Trp Asp Asn Asp Lys Lys Ile Gly Ile Leu
                325                 330                 335

His Glu Asn Phe Gln Thr Leu Lys Ala Glu Asp Asn Phe Glu Asp Ile
            340                 345                 350

Ile Thr Lys Pro Pro Val Arg Lys Phe Val His Glu Lys Glu Ile Met
            355                 360                 365

Ala Glu Asp Asp Gln Val Phe Leu Met Lys Leu Gln Ser Leu Leu Ala
            370                 375                 380

Lys Gln Pro Pro Thr Ala Ala Gly Arg Pro Val Asp Ala Ser Pro Arg
385                 390                 395                 400

Val Pro Gly Gly Ser Pro Arg Thr Pro Asn Arg Ser Val Ser Ser Asn
                405                 410                 415

Val Ala Ser Val Ser Pro Ile Pro Ala Gly Ser Lys Lys Ile Asp Pro
            420                 425                 430

Asn Met Lys Ala Gly Ala Thr Ser Glu Gly Val Leu Ala Asn Phe Phe
            435                 440                 445

Asn Ser Leu Leu Ser Lys Lys Thr Gly Ser Pro Gly Gly Pro Gly Val
450                 455                 460

Ser Gly Gly Ser Pro Ala Gly Gly Ala Gly Gly Ser Ser Gly Leu

```
                465                 470                 475                 480

Pro Pro Ser Thr Lys Lys Ser Gly Gln Lys Pro Val Leu Asp Val His
                        485                 490                 495

Ala Glu Leu Asp Arg Ile Thr Arg Lys Pro Val Thr Val Ser Pro Thr
                    500                 505                 510

Thr Pro Thr Ser Pro Thr Glu Gly Glu Ala Ser
                    515                 520

<210> SEQ ID NO 29
<211> LENGTH: 577
<212> TYPE: PRT
<213> ORGANISM: Homo sapiens

<400> SEQUENCE: 29

Met Pro Lys Thr Ile Ser Val Arg Val Thr Thr Met Asp Ala Glu Leu
1               5                   10                  15

Glu Phe Ala Ile Gln Pro Asn Thr Thr Gly Lys Gln Leu Phe Asp Gln
                20                  25                  30

Val Val Lys Thr Ile Gly Leu Arg Glu Val Trp Phe Phe Gly Leu Gln
            35                  40                  45

Tyr Gln Asp Thr Lys Gly Phe Ser Thr Trp Leu Lys Leu Asn Lys Lys
        50                  55                  60

Val Thr Ala Gln Asp Val Arg Lys Glu Ser Pro Leu Leu Phe Lys Phe
65                  70                  75                  80

Arg Ala Lys Phe Tyr Pro Glu Asp Val Ser Glu Glu Leu Ile Gln Asp
                85                  90                  95

Ile Thr Gln Arg Leu Phe Phe Leu Gln Val Lys Glu Gly Ile Leu Asn
            100                 105                 110

Asp Asp Ile Tyr Cys Pro Pro Glu Thr Ala Val Leu Leu Ala Ser Tyr
        115                 120                 125

Ala Val Gln Ser Lys Tyr Gly Asp Phe Asn Lys Glu Val His Lys Ser
    130                 135                 140

Gly Tyr Leu Ala Gly Asp Lys Leu Leu Pro Gln Arg Val Leu Glu Gln
145                 150                 155                 160

His Lys Leu Asn Lys Asp Gln Trp Glu Glu Arg Ile Gln Val Trp His
                165                 170                 175

Glu Glu His Arg Gly Met Leu Arg Glu Asp Ala Val Leu Glu Tyr Leu
            180                 185                 190

Lys Ile Ala Gln Asp Leu Glu Met Tyr Gly Val Asn Tyr Phe Ser Ile
        195                 200                 205

Lys Asn Lys Lys Gly Ser Glu Leu Trp Leu Gly Val Asp Ala Leu Gly
    210                 215                 220

Leu Asn Ile Tyr Glu Gln Asn Asp Arg Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
            260                 265                 270

Arg Leu Arg Ile Asn Lys Arg Ile Leu Ala Leu Cys Met Gly Asn His
        275                 280                 285

Glu Leu Tyr Met Arg Arg Arg Lys Pro Asp Thr Ile Glu Val Gln Gln
    290                 295                 300

Met Lys Ala Gln Ala Arg Glu Glu Lys His Gln Lys Gln Met Glu Arg
305                 310                 315                 320
```

Ala Met Leu Glu Asn Glu Lys Lys Arg Glu Met Ala Glu Lys Glu
            325                 330                 335

Lys Glu Lys Ile Glu Arg Glu Leu Glu Glu Leu Met Glu Arg Leu Lys
            340                 345                 350

Gln Ile Glu Glu Gln Thr Lys Lys Ala Gln Gln Glu Leu Glu Glu Gln
            355                 360                 365

Thr Arg Arg Ala Leu Glu Leu Glu Gln Glu Arg Lys Arg Ala Gln Ser
370                 375                 380

Glu Ala Glu Lys Leu Ala Lys Glu Arg Gln Ala Glu Glu Ala Lys
385                 390                 395                 400

Glu Ala Leu Leu Gln Ala Ser Arg Asp Gln Lys Lys Thr Gln Glu Gln
            405                 410                 415

Leu Ala Leu Glu Met Ala Glu Leu Thr Ala Arg Ile Ser Gln Leu Glu
            420                 425                 430

Met Ala Arg Gln Lys Lys Glu Ser Glu Ala Val Glu Trp Gln Gln Lys
            435                 440                 445

Ala Gln Met Val Gln Glu Asp Leu Glu Lys Thr Arg Ala Glu Leu Lys
            450                 455                 460

Thr Ala Met Ser Thr Pro His Val Ala Glu Pro Ala Glu Asn Glu Gln
465                 470                 475                 480

Asp Glu Gln Asp Glu Asn Gly Ala Glu Ala Ser Ala Asp Leu Arg Ala
            485                 490                 495

Asp Ala Met Ala Lys Asp Arg Ser Glu Glu Arg Thr Thr Glu Ala
            500                 505                 510

Glu Lys Asn Glu Arg Val Gln Lys His Leu Lys Ala Leu Thr Ser Glu
            515                 520                 525

Leu Ala Asn Ala Arg Asp Glu Ser Lys Lys Thr Ala Asn Asp Met Ile
            530                 535                 540

His Ala Glu Asn Met Arg Leu Gly Arg Asp Lys Tyr Lys Thr Leu Arg
545                 550                 555                 560

Gln Ile Arg Gln Gly Asn Thr Lys Gln Arg Ile Asp Glu Phe Glu Ser
            565                 570                 575

Met

<210> SEQ ID NO 30
<211> LENGTH: 430
<212> TYPE: PRT
<213> ORGANISM: Homo sapiens

<400> SEQUENCE: 30

Met Leu Val Ser Leu Lys Met Ser Tyr Lys Ala Ala Gly Glu Asp
1               5                   10                  15

Tyr Lys Ala Asp Cys Pro Pro Gly Asn Pro Ala Pro Thr Ser Asn His
            20                  25                  30

Gly Pro Asp Ala Thr Glu Ala Glu Asp Phe Val Asp Pro Trp Thr
            35                  40                  45

Val Gln Thr Ser Ser Ala Lys Gly Ile Asp Tyr Asp Lys Leu Ile Val
        50                  55                  60

Arg Phe Gly Ser Ser Lys Ile Asp Lys Glu Leu Ile Asn Arg Ile Glu
65                  70                  75                  80

Arg Ala Thr Gly Gln Arg Pro His His Phe Leu Arg Arg Gly Ile Phe
            85                  90                  95

Phe Ser His Arg Asp Met Asn Gln Val Leu Asp Ala Tyr Glu Asn Lys
            100                 105                 110

Lys Pro Phe Tyr Leu Tyr Thr Gly Arg Gly Pro Ser Glu Ala Met
115                 120                 125

His Val Gly His Leu Ile Pro Phe Ile Phe Thr Lys Trp Leu Gln Asp
130                 135                 140

Val Phe Asn Val Pro Leu Val Ile Gln Met Thr Asp Asp Glu Lys Tyr
145                 150                 155                 160

Leu Trp Lys Asp Leu Thr Leu Asp Gln Ala Tyr Ser Tyr Ala Val Glu
                165                 170                 175

Asn Ala Lys Asp Ile Ile Ala Cys Gly Phe Asp Ile Asn Lys Thr Phe
            180                 185                 190

Ile Phe Ser Asp Leu Asp Tyr Met Gly Met Ser Ser Gly Phe Tyr Lys
        195                 200                 205

Asn Val Val Lys Ile Gln Lys His Val Thr Phe Asn Gln Val Lys Gly
    210                 215                 220

Ile Phe Gly Phe Thr Asp Ser Asp Cys Ile Gly Lys Ile Ser Phe Pro
225                 230                 235                 240

Ala Ile Gln Ala Ala Pro Ser Phe Ser Asn Ser Phe Pro Gln Ile Phe
                245                 250                 255

Arg Asp Arg Thr Asp Ile Gln Cys Leu Ile Pro Cys Ala Ile Asp Gln
            260                 265                 270

Asp Pro Tyr Phe Arg Met Thr Arg Asp Val Ala Pro Arg Ile Gly Tyr
        275                 280                 285

Pro Lys Pro Ala Leu Leu His Ser Thr Phe Phe Pro Ala Leu Gln Gly
    290                 295                 300

Ala Gln Thr Lys Met Ser Ala Ser Asp Pro Asn Ser Ser Ile Phe Leu
305                 310                 315                 320

Thr Asp Thr Ala Lys Gln Ile Lys Thr Lys Val Asn Lys His Ala Phe
                325                 330                 335

Ser Gly Gly Arg Asp Thr Ile Glu Glu His Arg Gln Phe Gly Gly Asn
            340                 345                 350

Cys Asp Val Asp Val Ser Phe Met Tyr Leu Thr Phe Phe Leu Glu Asp
        355                 360                 365

Asp Asp Lys Leu Glu Gln Ile Arg Lys Asp Tyr Thr Ser Gly Ala Met
    370                 375                 380

Leu Thr Gly Glu Leu Lys Lys Ala Leu Ile Glu Val Leu Gln Pro Leu
385                 390                 395                 400

Ile Ala Glu His Gln Ala Arg Arg Lys Glu Val Thr Asp Glu Ile Val
                405                 410                 415

Lys Glu Phe Met Thr Pro Arg Lys Leu Ser Phe Asp Phe Gln
            420                 425                 430

<210> SEQ ID NO 31
<211> LENGTH: 794
<212> TYPE: PRT
<213> ORGANISM: Homo sapiens

<400> SEQUENCE: 31

Met Ala Asp Ala Trp Glu Glu Ile Arg Arg Leu Ala Ala Asp Phe Gln
1               5                   10                  15

Arg Ala Gln Phe Ala Glu Ala Thr Gln Arg Leu Ser Glu Arg Asn Cys
                20                  25                  30

Ile Glu Ile Val Asn Lys Leu Ile Ala Gln Lys Gln Leu Glu Val Val
            35                  40                  45

His Thr Leu Asp Gly Lys Glu Tyr Ile Thr Pro Ala Gln Ile Ser Lys
        50                  55                  60

-continued

```
Glu Met Arg Asp Glu Leu His Val Arg Gly Arg Val Asn Ile Val
 65              70                  75                  80

Asp Leu Gln Gln Val Ile Asn Val Asp Leu Ile His Ile Glu Asn Arg
                 85                  90                  95

Ile Gly Asp Ile Ile Lys Ser Glu Lys His Val Gln Leu Val Leu Gly
                100                 105                 110

Gln Leu Ile Asp Glu Asn Tyr Leu Asp Arg Leu Ala Glu Glu Val Asn
            115                 120                 125

Asp Lys Leu Gln Glu Ser Gly Gln Val Thr Ile Ser Glu Leu Cys Lys
130                 135                 140

Thr Tyr Asp Leu Pro Gly Asn Phe Leu Thr Gln Ala Leu Thr Gln Arg
145                 150                 155                 160

Leu Gly Arg Ile Ile Ser Gly His Ile Asp Leu Asp Asn Arg Gly Val
                165                 170                 175

Ile Phe Thr Glu Ala Phe Val Ala Arg His Lys Ala Arg Ile Arg Gly
                180                 185                 190

Leu Phe Ser Ala Ile Thr Arg Pro Thr Ala Val Asn Ser Leu Ile Ser
            195                 200                 205

Lys Tyr Gly Phe Gln Glu Gln Leu Leu Tyr Ser Val Leu Glu Glu Leu
210                 215                 220

Val Asn Ser Gly Arg Leu Arg Gly Thr Val Val Gly Gly Arg Gln Asp
225                 230                 235                 240

Lys Ala Val Phe Val Pro Asp Ile Tyr Ser Arg Thr Gln Ser Thr Trp
                245                 250                 255

Val Asp Ser Phe Phe Arg Gln Asn Gly Tyr Leu Glu Phe Asp Ala Leu
            260                 265                 270

Ser Arg Leu Gly Ile Pro Asp Ala Val Ser Tyr Ile Lys Lys Arg Tyr
            275                 280                 285

Lys Thr Thr Gln Leu Leu Phe Leu Lys Ala Ala Cys Val Gly Gln Gly
            290                 295                 300

Leu Val Asp Gln Val Glu Ala Ser Val Glu Glu Ala Ile Ser Ser Gly
305                 310                 315                 320

Thr Trp Val Asp Ile Ala Pro Leu Leu Pro Thr Ser Leu Ser Val Glu
                325                 330                 335

Asp Ala Ala Ile Leu Leu Gln Gln Val Met Arg Ala Phe Ser Lys Gln
            340                 345                 350

Ala Ser Thr Val Val Phe Ser Asp Thr Val Val Ser Glu Lys Phe
            355                 360                 365

Ile Asn Asp Cys Thr Glu Leu Phe Arg Glu Leu Met His Gln Lys Ala
            370                 375                 380

Glu Lys Glu Met Lys Asn Asn Pro Val His Leu Ile Thr Glu Glu Asp
385                 390                 395                 400

Leu Lys Gln Ile Ser Thr Leu Glu Ser Val Ser Thr Ser Lys Lys Asp
                405                 410                 415

Lys Lys Asp Glu Arg Arg Lys Ala Thr Glu Gly Ser Gly Ser Met
                420                 425                 430

Arg Gly Gly Gly Gly Asn Ala Arg Glu Tyr Lys Ile Lys Lys Val
            435                 440                 445

Lys Lys Lys Gly Arg Lys Asp Asp Ser Asp Asp Glu Ser Gln Ser
            450                 455                 460

Ser His Thr Gly Lys Lys Lys Pro Glu Ile Ser Phe Met Phe Gln Asp
465                 470                 475                 480
```

-continued

```
Glu Ile Glu Asp Phe Leu Arg Lys His Ile Gln Asp Ala Pro Glu
            485                 490                 495

Phe Ile Ser Glu Leu Ala Glu Tyr Leu Ile Lys Pro Leu Asn Lys Thr
            500                 505                 510

Tyr Leu Glu Val Val Arg Ser Val Phe Met Ser Ser Thr Thr Ser Ala
            515                 520                 525

Ser Gly Thr Gly Arg Lys Arg Thr Ile Lys Asp Leu Gln Glu Glu Val
            530                 535                 540

Ser Asn Leu Tyr Asn Asn Ile Arg Leu Phe Glu Lys Gly Met Lys Phe
545                 550                 555                 560

Phe Ala Asp Asp Thr Gln Ala Ala Leu Thr Lys His Leu Leu Lys Ser
                565                 570                 575

Val Cys Thr Asp Ile Thr Asn Leu Ile Phe Asn Phe Leu Ala Ser Asp
                580                 585                 590

Leu Met Met Ala Val Asp Asp Pro Ala Ala Ile Thr Ser Glu Ile Arg
                595                 600                 605

Lys Lys Ile Leu Ser Lys Leu Ser Glu Glu Thr Lys Val Ala Leu Thr
            610                 615                 620

Lys Leu His Asn Ser Leu Asn Glu Lys Ser Ile Glu Asp Phe Ile Ser
625                 630                 635                 640

Cys Leu Asp Ser Ala Ala Glu Ala Cys Asp Ile Met Val Lys Arg Gly
                645                 650                 655

Asp Lys Lys Arg Glu Arg Gln Ile Leu Phe Gln His Arg Gln Ala Leu
                660                 665                 670

Ala Glu Gln Leu Lys Val Thr Glu Asp Pro Ala Leu Ile Leu His Leu
                675                 680                 685

Thr Ser Val Leu Leu Phe Gln Phe Ser Thr His Ser Met Leu His Ala
            690                 695                 700

Pro Gly Arg Cys Val Pro Gln Ile Ile Ala Phe Leu Asn Ser Lys Ile
705                 710                 715                 720

Pro Glu Asp Gln His Ala Leu Leu Val Lys Tyr Gln Gly Leu Val Val
                725                 730                 735

Lys Gln Leu Val Ser Gln Ser Lys Lys Thr Gly Gln Gly Asp Tyr Pro
                740                 745                 750

Leu Asn Asn Glu Leu Asp Lys Glu Gln Glu Asp Val Ala Ser Thr Thr
            755                 760                 765

Arg Lys Glu Leu Gln Glu Leu Ser Ser Ser Ile Lys Asp Leu Val Leu
                770                 775                 780

Lys Ser Arg Lys Ser Ser Val Thr Glu Glu
785                 790

<210> SEQ ID NO 32
<211> LENGTH: 664
<212> TYPE: PRT
<213> ORGANISM: Homo sapiens

<400> SEQUENCE: 32

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
                35                  40                  45

Val Arg Ser Leu Glu Thr Glu Asn Ala Gly Leu Arg Leu Arg Ile Thr
            50                  55                  60
```

```
Glu Ser Glu Glu Val Val Ser Arg Glu Val Ser Gly Ile Lys Ala Ala
 65                  70                  75                  80

Tyr Glu Ala Glu Leu Gly Asp Ala Arg Lys Thr Leu Asp Ser Val Ala
                 85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
        290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365

Leu Asp Met Glu Ile His Ala Tyr Arg Lys Leu Leu Glu Gly Glu Glu
        370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
        435                 440                 445

Gly Lys Phe Val Arg Leu Arg Asn Lys Ser Asn Glu Asp Gln Ser Met
        450                 455                 460

Gly Asn Trp Gln Ile Lys Arg Gln Asn Gly Asp Asp Pro Leu Leu Thr
465                 470                 475                 480
```

```
Tyr Arg Phe Pro Pro Lys Phe Thr Leu Lys Ala Gly Gln Val Val Thr
            485                 490                 495

Ile Trp Ala Ala Gly Ala Gly Thr His Ser Pro Pro Thr Asp Leu
        500                 505                 510

Val Trp Lys Ala Gln Asn Thr Trp Gly Cys Gly Asn Ser Leu Arg Thr
        515                 520                 525

Ala Leu Ile Asn Ser Thr Gly Glu Glu Val Ala Met Arg Lys Leu Val
    530                 535                 540

Arg Ser Val Thr Val Val Glu Asp Glu Asp Glu Asp Gly Asp Asp
545                 550                 555                 560

Leu Leu His His His His Gly Ser His Cys Ser Ser Ser Gly Asp Pro
                565                 570                 575

Ala Glu Tyr Asn Leu Arg Ser Arg Thr Val Leu Cys Gly Thr Cys Gly
            580                 585                 590

Gln Pro Ala Asp Lys Ala Ser Ala Ser Gly Ser Gly Ala Gln Val Gly
        595                 600                 605

Gly Pro Ile Ser Ser Gly Ser Ser Ala Ser Ser Val Thr Val Thr Arg
    610                 615                 620

Ser Tyr Arg Ser Val Gly Gly Ser Gly Gly Ser Phe Gly Asp Asn
625                 630                 635                 640

Leu Val Thr Arg Ser Tyr Leu Leu Gly Asn Ser Ser Pro Arg Thr Gln
                645                 650                 655

Ser Pro Gln Asn Cys Ser Ile Met
            660

<210> SEQ ID NO 33
<211> LENGTH: 471
<212> TYPE: PRT
<213> ORGANISM: Homo sapiens

<400> SEQUENCE: 33

Met Pro Asn Ser Glu Pro Ala Ser Leu Leu Glu Leu Phe Asn Ser Ile
1               5                   10                  15

Ala Thr Gln Gly Glu Leu Val Arg Ser Leu Lys Ala Gly Asn Ala Ser
            20                  25                  30

Lys Asp Glu Ile Asp Ser Ala Val Lys Met Leu Val Ser Leu Lys Met
        35                  40                  45

Ser Tyr Lys Ala Ala Gly Glu Asp Tyr Lys Ala Asp Cys Pro Pro
    50                  55                  60

Gly Asn Pro Ala Pro Thr Ser Asn His Gly Pro Asp Ala Thr Glu Ala
65                  70                  75                  80

Glu Glu Asp Phe Val Asp Pro Trp Thr Val Gln Thr Ser Ser Ala Lys
                85                  90                  95

Gly Ile Asp Tyr Asp Lys Leu Ile Val Arg Phe Gly Ser Ser Lys Ile
            100                 105                 110

Asp Lys Glu Leu Ile Asn Arg Ile Glu Arg Ala Thr Gly Gln Arg Pro
        115                 120                 125

His His Phe Leu Arg Arg Gly Ile Phe Phe Ser His Arg Asp Met Asn
    130                 135                 140

Gln Val Leu Asp Ala Tyr Glu Asn Lys Lys Pro Phe Tyr Leu Tyr Thr
145                 150                 155                 160

Gly Arg Gly Pro Ser Ser Glu Ala Met His Val Gly His Leu Ile Pro
                165                 170                 175

Phe Ile Phe Thr Lys Trp Leu Gln Asp Val Phe Asn Val Pro Leu Val
            180                 185                 190
```

-continued

Ile Gln Met Thr Asp Asp Glu Lys Tyr Leu Trp Lys Asp Leu Thr Leu
        195                 200                 205

Asp Gln Ala Tyr Ser Tyr Ala Val Glu Asn Ala Lys Asp Ile Ile Ala
    210                 215                 220

Cys Gly Phe Asp Ile Asn Lys Thr Phe Ile Phe Ser Asp Leu Asp Tyr
225                 230                 235                 240

Met Gly Met Ser Ser Gly Phe Tyr Lys Asn Val Val Lys Ile Gln Lys
                245                 250                 255

His Val Thr Phe Asn Gln Val Lys Gly Ile Phe Gly Phe Thr Asp Ser
            260                 265                 270

Asp Cys Ile Gly Lys Ile Ser Phe Pro Ala Ile Gln Ala Pro Ser
        275                 280                 285

Phe Ser Asn Ser Phe Pro Gln Ile Phe Arg Asp Arg Thr Asp Ile Gln
    290                 295                 300

Cys Leu Ile Pro Cys Ala Ile Asp Gln Asp Pro Tyr Phe Arg Met Thr
305                 310                 315                 320

Arg Asp Val Ala Pro Arg Ile Gly Tyr Pro Lys Pro Ala Leu Leu His
                325                 330                 335

Ser Thr Phe Phe Pro Ala Leu Gln Gly Ala Gln Thr Lys Met Ser Ala
            340                 345                 350

Ser Asp Pro Asn Ser Ser Ile Phe Leu Thr Asp Thr Ala Lys Gln Ile
        355                 360                 365

Lys Thr Lys Val Asn Lys His Ala Phe Ser Gly Arg Asp Thr Ile
    370                 375                 380

Glu Glu His Arg Gln Phe Gly Gly Asn Cys Asp Val Asp Val Ser Phe
385                 390                 395                 400

Met Tyr Leu Thr Phe Phe Leu Glu Asp Asp Lys Leu Glu Gln Ile
                405                 410                 415

Arg Lys Asp Tyr Thr Ser Gly Ala Met Leu Thr Gly Glu Leu Lys Lys
            420                 425                 430

Ala Leu Ile Glu Val Leu Gln Pro Leu Ile Ala Glu His Gln Ala Arg
        435                 440                 445

Arg Lys Glu Val Thr Asp Glu Ile Val Lys Glu Phe Met Thr Pro Arg
    450                 455                 460

Lys Leu Ser Phe Asp Phe Gln
465                 470

<210> SEQ ID NO 34
<211> LENGTH: 685
<212> TYPE: PRT
<213> ORGANISM: Homo sapiens

<400> SEQUENCE: 34

Met Asp Gly Ala Gly Ala Glu Glu Val Leu Ala Pro Leu Arg Leu Ala
1               5                   10                  15

Val Arg Gln Gln Gly Asp Leu Val Arg Lys Leu Lys Glu Asp Lys Ala
            20                  25                  30

Pro Gln Val Asp Val Asp Lys Ala Val Ala Glu Leu Lys Ala Arg Lys
        35                  40                  45

Arg Val Leu Glu Ala Lys Glu Leu Ala Leu Gln Pro Lys Asp Asp Ile
    50                  55                  60

Val Asp Arg Ala Lys Met Glu Asp Thr Leu Lys Arg Arg Phe Phe Tyr
65                  70                  75                  80

Asp Gln Ala Phe Ala Ile Tyr Gly Gly Val Ser Gly Leu Tyr Asp Phe

-continued

```
                        85                  90                  95
Gly Pro Val Gly Cys Ala Leu Lys Asn Asn Ile Ile Gln Thr Trp Arg
                100                 105                 110

Gln His Phe Ile Gln Glu Glu Gln Ile Leu Glu Ile Asp Cys Thr Met
            115                 120                 125

Leu Thr Pro Glu Pro Val Leu Lys Thr Ser Gly His Val Asp Lys Phe
        130                 135                 140

Ala Asp Phe Met Val Lys Asp Val Lys Asn Gly Glu Cys Phe Arg Ala
145                 150                 155                 160

Asp His Leu Leu Lys Ala His Leu Gln Lys Leu Met Ser Asp Lys Lys
                165                 170                 175

Cys Ser Val Glu Lys Lys Ser Glu Met Glu Ser Val Leu Ala Gln Leu
            180                 185                 190

Asp Asn Tyr Gly Gln Gln Glu Leu Ala Asp Leu Phe Val Asn Tyr Asn
        195                 200                 205

Val Lys Ser Pro Ile Thr Gly Asn Asp Leu Ser Pro Pro Val Ser Phe
    210                 215                 220

Asn Leu Met Phe Lys Thr Phe Ile Gly Pro Gly Gly Asn Met Pro Gly
225                 230                 235                 240

Tyr Leu Arg Pro Glu Thr Ala Gln Gly Ile Phe Leu Asn Phe Lys Arg
                245                 250                 255

Leu Leu Glu Phe Asn Gln Gly Lys Leu Pro Phe Ala Ala Ala Gln Ile
            260                 265                 270

Gly Asn Ser Phe Arg Asn Glu Ile Ser Pro Arg Ser Gly Leu Ile Arg
        275                 280                 285

Val Arg Glu Phe Thr Met Ala Glu Ile Glu His Phe Val Asp Pro Ser
    290                 295                 300

Glu Lys Asp His Pro Lys Phe Gln Asn Val Ala Asp Leu His Leu Tyr
305                 310                 315                 320

Leu Tyr Ser Ala Lys Ala Gln Val Ser Gly Gln Ser Ala Arg Lys Met
                325                 330                 335

Arg Leu Gly Asp Ala Val Glu Gln Gly Val Ile Asn Asn Thr Val Leu
            340                 345                 350

Gly Tyr Phe Ile Gly Arg Ile Tyr Leu Tyr Leu Thr Lys Val Gly Ile
        355                 360                 365

Ser Pro Asp Lys Leu Arg Phe Arg Gln His Met Glu Asn Glu Met Ala
    370                 375                 380

His Tyr Ala Cys Asp Cys Trp Asp Ala Glu Ser Lys Thr Ser Tyr Gly
385                 390                 395                 400

Trp Ile Glu Ile Val Gly Cys Ala Asp Arg Ser Cys Tyr Asp Leu Ser
                405                 410                 415

Cys His Ala Arg Ala Thr Lys Val Pro Leu Val Ala Glu Lys Pro Leu
            420                 425                 430

Lys Glu Pro Lys Thr Val Asn Val Val Gln Phe Glu Pro Ser Lys Gly
        435                 440                 445

Ala Ile Gly Lys Ala Tyr Lys Lys Asp Ala Lys Leu Val Met Glu Tyr
    450                 455                 460

Leu Ala Ile Cys Asp Glu Cys Tyr Ile Thr Glu Ile Glu Met Leu Leu
465                 470                 475                 480

Asn Glu Lys Gly Glu Phe Thr Ile Glu Thr Glu Gly Lys Thr Phe Gln
                485                 490                 495

Leu Thr Lys Asp Met Ile Asn Val Lys Arg Phe Gln Lys Thr Leu Tyr
            500                 505                 510
```

```
Val Glu Glu Val Val Pro Asn Val Ile Glu Pro Ser Phe Gly Leu Gly
            515                 520                 525

Arg Ile Met Tyr Thr Val Phe Glu His Thr Phe His Val Arg Glu Gly
        530                 535                 540

Asp Glu Gln Arg Thr Phe Phe Ser Phe Pro Ala Val Val Ala Pro Phe
545                 550                 555                 560

Lys Cys Ser Val Leu Pro Leu Ser Gln Asn Gln Glu Phe Met Pro Phe
                565                 570                 575

Val Lys Glu Leu Ser Glu Ala Leu Thr Arg His Gly Val Ser His Lys
                580                 585                 590

Val Asp Asp Ser Ser Gly Ser Ile Gly Arg Arg Tyr Ala Arg Thr Asp
                595                 600                 605

Glu Ile Gly Val Ala Phe Gly Val Thr Ile Asp Phe Asp Thr Val Asn
        610                 615                 620

Lys Thr Pro His Thr Ala Thr Leu Arg Asp Arg Asp Ser Met Arg Gln
625                 630                 635                 640

Ile Arg Ala Glu Ile Ser Glu Leu Pro Ser Ile Val Gln Asp Leu Ala
                645                 650                 655

Asn Gly Asn Ile Thr Trp Ala Asp Val Glu Ala Arg Tyr Pro Leu Phe
                660                 665                 670

Glu Gly Gln Glu Thr Gly Lys Lys Glu Thr Ile Glu Glu
                675                 680                 685

<210> SEQ ID NO 35
<211> LENGTH: 451
<212> TYPE: PRT
<213> ORGANISM: Homo sapiens

<400> SEQUENCE: 35

Met Asn Leu Glu Gly Gly Gly Arg Gly Gly Glu Phe Gly Met Ser Ala
1               5                   10                  15

Val Ser Cys Gly Asn Gly Lys Leu Arg Gln Trp Leu Ile Asp Gln Ile
            20                  25                  30

Asp Ser Gly Lys Tyr Pro Gly Leu Val Trp Glu Asn Glu Glu Lys Ser
            35                  40                  45

Ile Phe Arg Ile Pro Trp Lys His Ala Gly Lys Gln Asp Tyr Asn Arg
    50                  55                  60

Glu Glu Asp Ala Ala Leu Phe Lys Ala Trp Ala Leu Phe Lys Gly Lys
65                  70                  75                  80

Phe Arg Glu Gly Ile Asp Lys Pro Asp Pro Thr Trp Lys Thr Arg
                85                  90                  95

Leu Arg Cys Ala Leu Asn Lys Ser Asn Asp Phe Glu Glu Leu Val Glu
                100                 105                 110

Arg Ser Gln Leu Asp Ile Ser Asp Pro Tyr Lys Val Tyr Arg Ile Val
            115                 120                 125

Pro Glu Gly Ala Lys Lys Gly Ala Lys Gln Leu Thr Leu Glu Asp Pro
        130                 135                 140

Gln Met Ser Met Ser His Pro Tyr Thr Met Thr Thr Pro Tyr Pro Ser
145                 150                 155                 160

Leu Pro Ala Gln Gln Val His Asn Tyr Met Met Pro Pro Leu Asp Arg
                165                 170                 175

Ser Trp Arg Asp Tyr Val Pro Asp Gln Pro His Pro Glu Ile Pro Tyr
                180                 185                 190

Gln Cys Pro Met Thr Phe Gly Pro Arg Gly His His Trp Gln Gly Pro
```

```
                195                 200                 205
Ala Cys Glu Asn Gly Cys Gln Val Thr Gly Thr Phe Tyr Ala Cys Ala
    210                 215                 220

Pro Pro Glu Ser Gln Ala Pro Gly Val Pro Thr Glu Pro Ser Ile Arg
225                 230                 235                 240

Ser Ala Glu Ala Leu Ala Phe Ser Asp Cys Arg Leu His Ile Cys Leu
                245                 250                 255

Tyr Tyr Arg Glu Ile Leu Val Lys Glu Leu Thr Thr Ser Ser Pro Glu
            260                 265                 270

Gly Cys Arg Ile Ser His Gly His Thr Tyr Asp Ala Ser Asn Leu Asp
        275                 280                 285

Gln Val Leu Phe Pro Tyr Pro Glu Asp Asn Gly Gln Arg Lys Asn Ile
    290                 295                 300

Glu Lys Leu Leu Ser His Leu Glu Arg Gly Val Val Leu Trp Met Ala
305                 310                 315                 320

Pro Asp Gly Leu Tyr Ala Lys Arg Leu Cys Gln Ser Arg Ile Tyr Trp
                325                 330                 335

Asp Gly Pro Leu Ala Leu Cys Asn Asp Arg Pro Asn Lys Leu Glu Arg
            340                 345                 350

Asp Gln Thr Cys Lys Leu Phe Asp Thr Gln Gln Phe Leu Ser Glu Leu
        355                 360                 365

Gln Ala Phe Ala His His Gly Arg Ser Leu Pro Arg Phe Gln Val Thr
    370                 375                 380

Leu Cys Phe Gly Glu Glu Phe Pro Asp Pro Gln Arg Gln Arg Lys Leu
385                 390                 395                 400

Ile Thr Ala His Val Glu Pro Leu Leu Ala Arg Gln Leu Tyr Tyr Phe
                405                 410                 415

Ala Gln Gln Asn Ser Gly His Phe Leu Arg Gly Tyr Asp Leu Pro Glu
            420                 425                 430

His Ile Ser Asn Pro Glu Asp Tyr His Arg Ser Ile Arg His Ser Ser
        435                 440                 445

Ile Gln Glu
    450

<210> SEQ ID NO 36
<211> LENGTH: 1134
<212> TYPE: PRT
<213> ORGANISM: Homo sapiens

<400> SEQUENCE: 36

Met Pro Val Phe His Thr Arg Thr Ile Glu Ser Ile Leu Glu Pro Val
1               5                   10                  15

Ala Gln Gln Ile Ser His Leu Val Ile Met His Glu Glu Gly Glu Val
            20                  25                  30

Asp Gly Lys Ala Ile Pro Asp Leu Thr Ala Pro Val Ala Ala Val Gln
        35                  40                  45

Ala Ala Val Ser Asn Leu Val Arg Val Gly Lys Glu Thr Val Gln Thr
    50                  55                  60

Thr Glu Asp Gln Ile Leu Lys Arg Asp Met Pro Pro Ala Phe Ile Lys
65                  70                  75                  80

Val Glu Asn Ala Cys Thr Lys Leu Val Gln Ala Ala Gln Met Leu Gln
                85                  90                  95

Ser Asp Pro Tyr Ser Val Pro Ala Arg Asp Tyr Leu Ile Asp Gly Ser
            100                 105                 110
```

```
Arg Gly Ile Leu Ser Gly Thr Ser Asp Leu Leu Thr Phe Asp Glu
            115                 120                 125
Ala Glu Val Arg Lys Ile Ile Arg Val Cys Lys Gly Ile Leu Glu Tyr
        130                 135                 140
Leu Thr Val Ala Glu Val Val Glu Thr Met Glu Asp Leu Val Thr Tyr
145                 150                 155                 160
Thr Lys Asn Leu Gly Pro Gly Met Thr Lys Met Ala Lys Met Ile Asp
                165                 170                 175
Glu Arg Gln Gln Glu Leu Thr His Gln Glu His Arg Val Met Leu Val
            180                 185                 190
Asn Ser Met Asn Thr Val Lys Glu Leu Leu Pro Val Leu Ile Ser Ala
        195                 200                 205
Met Lys Ile Phe Val Thr Thr Lys Asn Ser Lys Asn Gln Gly Ile Glu
210                 215                 220
Glu Ala Leu Lys Asn Arg Asn Phe Thr Val Glu Lys Met Ser Ala Glu
225                 230                 235                 240
Ile Asn Glu Ile Ile Arg Val Leu Gln Leu Thr Ser Trp Asp Glu Asp
                245                 250                 255
Ala Trp Ala Ser Lys Asp Thr Glu Ala Met Lys Arg Ala Leu Ala Ser
            260                 265                 270
Ile Asp Ser Lys Leu Asn Gln Ala Lys Gly Trp Leu Arg Asp Pro Ser
        275                 280                 285
Ala Ser Pro Gly Asp Ala Gly Glu Gln Ala Ile Arg Gln Ile Leu Asp
        290                 295                 300
Glu Ala Gly Lys Val Gly Glu Leu Cys Ala Gly Lys Glu Arg Arg Glu
305                 310                 315                 320
Ile Leu Gly Thr Cys Lys Met Leu Gly Gln Met Thr Asp Gln Val Ala
                325                 330                 335
Asp Leu Arg Ala Arg Gly Gln Gly Ser Ser Pro Val Ala Met Gln Lys
            340                 345                 350
Ala Gln Gln Val Ser Gln Gly Leu Asp Val Leu Thr Ala Lys Val Glu
        355                 360                 365
Asn Ala Ala Arg Lys Leu Glu Ala Met Thr Asn Ser Lys Gln Ser Ile
370                 375                 380
Ala Lys Lys Ile Asp Ala Ala Gln Asn Trp Leu Ala Asp Pro Asn Gly
385                 390                 395                 400
Gly Pro Glu Gly Glu Glu Gln Ile Arg Gly Ala Leu Ala Glu Ala Arg
                405                 410                 415
Lys Ile Ala Glu Leu Cys Asp Asp Pro Lys Glu Arg Asp Asp Ile Leu
            420                 425                 430
Arg Ser Leu Gly Glu Ile Ser Ala Leu Thr Ser Lys Leu Ala Asp Leu
        435                 440                 445
Arg Arg Gln Gly Lys Gly Asp Ser Pro Glu Ala Arg Ala Leu Ala Lys
        450                 455                 460
Gln Val Ala Thr Ala Leu Gln Asn Leu Gln Thr Lys Thr Asn Arg Ala
465                 470                 475                 480
Val Ala Asn Ser Arg Pro Ala Lys Ala Ala Val His Leu Glu Gly Lys
                485                 490                 495
Ile Glu Gln Ala Gln Arg Trp Ile Asp Asn Pro Thr Val Asp Asp Arg
            500                 505                 510
Gly Val Gly Gln Ala Ala Ile Arg Gly Leu Val Ala Glu Gly His Arg
        515                 520                 525
Leu Ala Asn Val Met Met Gly Pro Tyr Arg Gln Asp Leu Leu Ala Lys
```

```
                530                 535                 540
Cys Asp Arg Val Asp Gln Leu Thr Ala Gln Leu Ala Asp Leu Ala Ala
545                 550                 555                 560

Arg Gly Glu Gly Glu Ser Pro Gln Ala Arg Ala Leu Ala Ser Gln Leu
                565                 570                 575

Gln Asp Ser Leu Lys Asp Leu Lys Ala Arg Met Gln Glu Ala Met Thr
                580                 585                 590

Gln Glu Val Ser Asp Val Phe Ser Asp Thr Thr Pro Ile Lys Leu
                595                 600                 605

Leu Ala Val Ala Ala Thr Ala Pro Pro Asp Ala Pro Asn Arg Glu Glu
610                 615                 620

Val Phe Asp Glu Arg Ala Ala Asn Phe Glu Asn His Ser Gly Lys Leu
625                 630                 635                 640

Gly Ala Thr Ala Glu Lys Ala Ala Ala Val Gly Thr Ala Asn Lys Ser
                645                 650                 655

Thr Val Glu Gly Ile Gln Ala Ser Val Lys Thr Ala Arg Glu Leu Thr
                660                 665                 670

Pro Gln Val Val Ser Ala Ala Arg Ile Leu Leu Arg Asn Pro Gly Asn
                675                 680                 685

Gln Ala Ala Tyr Glu His Phe Glu Thr Met Lys Asn Gln Trp Ile Asp
690                 695                 700

Asn Val Glu Lys Met Thr Gly Leu Val Asp Glu Ala Ile Asp Thr Lys
705                 710                 715                 720

Ser Leu Leu Asp Ala Ser Glu Glu Ala Ile Lys Lys Asp Leu Asp Lys
                725                 730                 735

Cys Lys Val Ala Met Ala Asn Ile Gln Pro Gln Met Leu Val Ala Gly
                740                 745                 750

Ala Thr Ser Ile Ala Arg Arg Ala Asn Arg Ile Leu Leu Val Ala Lys
                755                 760                 765

Arg Glu Val Glu Asn Ser Glu Asp Pro Lys Phe Arg Glu Ala Val Lys
                770                 775                 780

Ala Ala Ser Asp Glu Leu Ser Lys Thr Ile Ser Pro Met Val Met Asp
785                 790                 795                 800

Ala Lys Ala Val Ala Gly Asn Ile Ser Asp Pro Gly Leu Gln Lys Ser
                805                 810                 815

Phe Leu Asp Ser Gly Tyr Arg Ile Leu Gly Ala Val Ala Lys Val Arg
                820                 825                 830

Glu Ala Phe Gln Pro Gln Glu Pro Asp Phe Pro Pro Pro Pro Asp
                835                 840                 845

Leu Glu Gln Leu Arg Leu Thr Asp Glu Leu Ala Pro Pro Lys Pro Pro
850                 855                 860

Leu Pro Glu Gly Glu Val Pro Pro Arg Pro Pro Pro Glu Glu
865                 870                 875                 880

Lys Asp Glu Glu Phe Pro Glu Gln Lys Ala Gly Glu Val Ile Asn Gln
                885                 890                 895

Pro Met Met Met Ala Ala Arg Gln Leu His Asp Glu Ala Arg Lys Trp
                900                 905                 910

Ser Ser Lys Pro Gly Ile Pro Ala Ala Glu Val Gly Ile Gly Val Val
                915                 920                 925

Ala Glu Ala Asp Ala Ala Asp Ala Ala Gly Phe Pro Val Pro Pro Asp
930                 935                 940

Met Glu Asp Asp Tyr Glu Pro Glu Leu Leu Leu Met Pro Ser Asn Gln
945                 950                 955                 960
```

Pro Val Asn Gln Pro Ile Leu Ala Ala Ala Gln Ser Leu His Arg Glu
            965                 970                 975

Ala Thr Lys Trp Ser Ser Lys Gly Asn Asp Ile Ile Ala Ala Ala Lys
        980                 985                 990

Arg Met Ala Leu Leu Met Ala Glu Met Ser Arg Leu Val Arg Gly Gly
    995                1000                1005

Ser Gly Thr Lys Arg Ala Leu Ile Gln Cys Ala Lys Asp Ile Ala
   1010                1015                1020

Lys Ala Ser Asp Glu Val Thr Arg Leu Ala Lys Glu Val Ala Lys
   1025                1030                1035

Gln Cys Thr Asp Lys Arg Ile Arg Thr Asn Leu Leu Gln Val Cys
   1040                1045                1050

Glu Arg Ile Pro Thr Ile Ser Thr Gln Leu Lys Ile Leu Ser Thr
   1055                1060                1065

Val Lys Ala Thr Met Leu Gly Arg Thr Asn Ile Ser Asp Glu Glu
   1070                1075                1080

Ser Glu Gln Ala Thr Glu Met Leu Val His Asn Ala Gln Asn Leu
   1085                1090                1095

Met Gln Ser Val Lys Glu Thr Val Arg Glu Ala Glu Ala Ala Ser
   1100                1105                1110

Ile Lys Ile Arg Thr Asp Ala Gly Phe Thr Leu Arg Trp Val Arg
   1115                1120                1125

Lys Thr Pro Trp Tyr Gln
   1130

<210> SEQ ID NO 37
<211> LENGTH: 525
<212> TYPE: PRT
<213> ORGANISM: Homo sapiens

<400> SEQUENCE: 37

Met Ser Asp Asn Gly Glu Leu Glu Asp Lys Pro Pro Ala Pro Pro Val
1               5                  10                  15

Arg Met Ser Ser Thr Ile Phe Ser Thr Gly Gly Lys Asp Pro Leu Ser
            20                  25                  30

Ala Asn His Ser Leu Lys Pro Leu Pro Ser Val Pro Glu Glu Lys Lys
        35                  40                  45

Pro Arg His Lys Ile Ile Ser Ile Phe Ser Gly Thr Glu Lys Gly Ser
    50                  55                  60

Lys Lys Lys Glu Lys Glu Arg Pro Glu Ile Ser Pro Pro Ser Asp Phe
65                  70                  75                  80

Glu His Thr Ile His Val Gly Phe Asp Ala Val Thr Gly Glu Phe Thr
                85                  90                  95

Gly Met Pro Glu Gln Trp Ala Arg Leu Leu Gln Thr Ser Asn Ile Thr
            100                 105                 110

Lys Leu Glu Gln Lys Lys Asn Pro Gln Ala Val Leu Asp Val Leu Lys
        115                 120                 125

Phe Tyr Asp Ser Asn Thr Val Lys Gln Lys Tyr Leu Ser Phe Thr Pro
    130                 135                 140

Pro Glu Lys Asp Gly Leu Pro Ser Gly Thr Pro Ala Leu Asn Ala Lys
145                 150                 155                 160

Gly Thr Glu Ala Pro Ala Val Val Thr Glu Glu Asp Asp Asp Glu
                165                 170                 175

Glu Thr Ala Pro Pro Val Ile Ala Pro Arg Pro Asp His Thr Lys Ser

```
            180                 185                 190
Ile Tyr Thr Arg Ser Val Ile Asp Pro Val Pro Ala Pro Val Gly Asp
            195                 200                 205

Ser His Val Asp Gly Ala Ala Lys Ser Leu Asp Lys Gln Lys Lys Lys
        210                 215                 220

Pro Lys Met Thr Asp Glu Ile Met Glu Lys Leu Arg Thr Ile Val
225                 230                 235                 240

Ser Ile Gly Asp Pro Lys Lys Tyr Thr Arg Tyr Glu Lys Ile Gly
                245                 250                 255

Gln Gly Ala Ser Gly Thr Val Phe Thr Ala Thr Asp Val Ala Leu Gly
            260                 265                 270

Gln Glu Val Ala Ile Lys Gln Ile Asn Leu Gln Lys Gln Pro Lys Lys
        275                 280                 285

Glu Leu Ile Ile Asn Glu Ile Leu Val Met Lys Glu Leu Lys Asn Pro
            290                 295                 300

Asn Ile Val Asn Phe Leu Asp Ser Tyr Leu Val Gly Asp Glu Leu Phe
305                 310                 315                 320

Val Val Met Glu Tyr Leu Ala Gly Gly Ser Leu Thr Asp Val Val Thr
                325                 330                 335

Glu Thr Ala Cys Met Asp Glu Ala Gln Ile Ala Ala Val Cys Arg Glu
            340                 345                 350

Cys Leu Gln Ala Leu Glu Phe Leu His Ala Asn Gln Val Ile His Arg
        355                 360                 365

Asp Ile Lys Ser Asp Asn Val Leu Leu Gly Met Glu Gly Ser Val Lys
370                 375                 380

Leu Thr Asp Phe Gly Phe Cys Ala Gln Ile Thr Pro Glu Gln Ser Lys
385                 390                 395                 400

Arg Ser Thr Met Val Gly Thr Pro Tyr Trp Met Ala Pro Glu Val Val
                405                 410                 415

Thr Arg Lys Ala Tyr Gly Pro Lys Val Asp Ile Trp Ser Leu Gly Ile
            420                 425                 430

Met Ala Ile Glu Met Val Glu Gly Glu Pro Pro Tyr Leu Asn Glu Asn
        435                 440                 445

Pro Leu Arg Ala Leu Tyr Leu Ile Ala Thr Asn Gly Thr Pro Glu Leu
450                 455                 460

Gln Asn Pro Glu Lys Leu Ser Pro Ile Phe Arg Asp Phe Leu Asn Arg
465                 470                 475                 480

Cys Leu Glu Met Asp Val Glu Lys Arg Gly Ser Ala Lys Glu Leu Leu
                485                 490                 495

Gln His Pro Phe Leu Lys Leu Ala Lys Pro Leu Ser Ser Leu Thr Pro
            500                 505                 510

Leu Ile Met Ala Ala Lys Glu Ala Met Lys Ser Asn Arg
        515                 520                 525

<210> SEQ ID NO 38
<211> LENGTH: 216
<212> TYPE: PRT
<213> ORGANISM: Homo sapiens

<400> SEQUENCE: 38

Met Ser Phe Leu Phe Gly Ser Arg Ser Ser Lys Thr Phe Lys Pro Lys
1               5                   10                  15

Lys Asn Ile Pro Glu Gly Ser His Gln Tyr Glu Leu Leu Lys His Ala
            20                  25                  30
```

```
Glu Ala Thr Leu Gly Ser Gly Asn Leu Arg Met Ala Val Met Leu Pro
             35                  40                  45

Glu Gly Glu Asp Leu Asn Glu Trp Val Ala Val Asn Thr Val Asp Phe
 50                  55                  60

Phe Asn Gln Ile Asn Met Leu Tyr Gly Thr Ile Thr Asp Phe Cys Thr
 65                  70                  75                  80

Glu Glu Ser Cys Pro Val Met Ser Ala Gly Pro Lys Tyr Glu Tyr His
                 85                  90                  95

Trp Ala Asp Gly Thr Asn Ile Lys Lys Pro Ile Lys Cys Ser Ala Pro
                100                 105                 110

Lys Tyr Ile Asp Tyr Leu Met Thr Trp Val Gln Asp Gln Leu Asp Asp
            115                 120                 125

Glu Thr Leu Phe Pro Ser Lys Ile Gly Val Pro Phe Pro Lys Asn Phe
130                 135                 140

Met Ser Val Ala Lys Thr Ile Leu Lys Arg Leu Phe Arg Val Tyr Ala
145                 150                 155                 160

His Ile Tyr His Gln His Phe Asp Pro Val Ile Gln Leu Gln Glu Glu
                165                 170                 175

Ala His Leu Asn Thr Ser Phe Lys His Phe Ile Phe Phe Val Gln Glu
            180                 185                 190

Phe Asn Leu Ile Asp Arg Arg Glu Leu Ala Pro Leu Gln Glu Leu Ile
        195                 200                 205

Glu Lys Leu Thr Ser Lys Asp Arg
    210                 215

<210> SEQ ID NO 39
<211> LENGTH: 327
<212> TYPE: PRT
<213> ORGANISM: Homo sapiens

<400> SEQUENCE: 39

Met Ala Asp Gly Glu Leu Asn Val Asp Ser Leu Ile Thr Arg Leu Leu
 1               5                  10                  15

Glu Val Arg Gly Cys Arg Pro Gly Lys Ile Val Gln Met Thr Glu Ala
                20                  25                  30

Glu Val Arg Gly Leu Cys Ile Lys Ser Arg Glu Ile Phe Leu Ser Gln
            35                  40                  45

Pro Ile Leu Leu Glu Leu Glu Ala Pro Leu Lys Ile Cys Gly Asp Ile
 50                  55                  60

His Gly Gln Tyr Thr Asp Leu Leu Arg Leu Phe Glu Tyr Gly Gly Phe
 65                  70                  75                  80

Pro Pro Glu Ala Asn Tyr Leu Phe Leu Gly Asp Tyr Val Asp Arg Gly
                 85                  90                  95

Lys Gln Ser Leu Glu Thr Ile Cys Leu Leu Ala Tyr Lys Ile Lys
                100                 105                 110

Tyr Pro Glu Asn Phe Phe Leu Leu Arg Gly Asn His Glu Cys Ala Ser
            115                 120                 125

Ile Asn Arg Ile Tyr Gly Phe Tyr Asp Glu Cys Lys Arg Arg Phe Asn
130                 135                 140

Ile Lys Leu Trp Lys Thr Phe Thr Asp Cys Phe Asn Cys Leu Pro Ile
145                 150                 155                 160

Ala Ala Ile Val Asp Glu Lys Ile Phe Cys Cys His Gly Gly Leu Ser
                165                 170                 175

Pro Asp Leu Gln Ser Met Glu Gln Ile Arg Arg Ile Met Arg Pro Thr
            180                 185                 190
```

```
Asp Val Pro Asp Thr Gly Leu Leu Cys Asp Leu Leu Trp Ser Asp Pro
            195                 200                 205

Asp Lys Asp Val Gln Gly Trp Gly Glu Asn Asp Arg Gly Val Ser Phe
210                 215                 220

Thr Phe Gly Ala Asp Val Val Ser Lys Phe Leu Asn Arg His Asp Leu
225                 230                 235                 240

Asp Leu Ile Cys Arg Ala His Gln Val Val Glu Asp Gly Tyr Glu Phe
                245                 250                 255

Phe Ala Lys Arg Gln Leu Val Thr Leu Phe Ser Ala Pro Asn Tyr Cys
                260                 265                 270

Gly Glu Phe Asp Asn Ala Gly Gly Met Met Ser Val Asp Glu Thr Leu
            275                 280                 285

Met Cys Ser Phe Gln Ile Leu Lys Pro Ser Glu Lys Lys Ala Lys Tyr
        290                 295                 300

Gln Tyr Gly Gly Leu Asn Ser Gly Arg Pro Val Thr Pro Pro Arg Thr
305                 310                 315                 320

Ala Asn Pro Pro Lys Lys Arg
                325

<210> SEQ ID NO 40
<211> LENGTH: 434
<212> TYPE: PRT
<213> ORGANISM: Homo sapiens

<400> SEQUENCE: 40

Met Ser Ile Leu Lys Ile His Ala Arg Glu Ile Phe Asp Ser Arg Gly
1               5                   10                  15

Asn Pro Thr Val Glu Val Asp Leu Phe Thr Ser Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Asn Asp Lys Thr Arg Tyr Met Gly Lys Gly Val Ser Lys
    50                  55                  60

Ala Val Glu His Ile Asn Lys Thr Ile Ala Pro Ala Leu Val Ser Lys
65                  70                  75                  80

Lys Leu Asn Val Thr Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
        115                 120                 125

Pro Leu Tyr Arg His Ile Ala Asp Leu Ala Gly Asn Ser Glu Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ala
                165                 170                 175

Asn Phe Arg Glu Ala Met Arg Ile Gly Ala Glu Val Tyr His Asn Leu
            180                 185                 190

Lys Asn Val Ile Lys Glu Lys Tyr Gly Lys Asp Ala Thr Asn Val Gly
        195                 200                 205

Asp Glu Gly Gly Phe Ala Pro Asn Ile Leu Glu Asn Lys Glu Gly Leu
    210                 215                 220

Glu Leu Leu Lys Thr Ala Ile Gly Lys Ala Gly Tyr Thr Asp Lys Val
```

```
                225                 230                 235                 240
        Val Ile Gly Met Asp Val Ala Ala Ser Glu Phe Phe Arg Ser Gly Lys
                        245                 250                 255

Tyr Asp Leu Asp Phe Lys Ser Pro Asp Pro Ser Arg Tyr Ile Ser
                        260                 265                 270

Pro Asp Gln Leu Ala Asp Leu Tyr Lys Ser Phe Ile Lys Asp Tyr Pro
                        275                 280                 285

Val Val Ser Ile Glu Asp Pro Phe Asp Gln Asp Trp Gly Ala Trp
                290                 295                 300

Gln Lys Phe Thr Ala Ser Ala Gly Ile Gln Val Val Gly Asp Asp Leu
        305                 310                 315                 320

Thr Val Thr Asn Pro Lys Arg Ile Ala Lys Ala Val Asn Glu Lys Ser
                        325                 330                 335

Cys Asn Cys Leu Leu Leu Lys Val Asn Gln Ile Gly Ser Val Thr Glu
                        340                 345                 350

Ser Leu Gln Ala Cys Lys Leu Ala Gln Ala Asn Gly Trp Gly Val Met
                        355                 360                 365

Val Ser His Arg Ser Gly Glu Thr Glu Asp Thr Phe Ile Ala Asp Leu
                370                 375                 380

Val Val Gly Leu Cys Thr Gly Gln Ile Lys Thr Gly Ala Pro Cys Arg
        385                 390                 395                 400

Ser Glu Arg Leu Ala Lys Tyr Asn Gln Leu Leu Arg Ile Glu Glu Glu
                        405                 410                 415

Leu Gly Ser Lys Ala Lys Phe Ala Gly Arg Asn Phe Arg Asn Pro Leu
                        420                 425                 430

Ala Lys

<210> SEQ ID NO 41
<211> LENGTH: 662
<212> TYPE: PRT
<213> ORGANISM: Homo sapiens

<400> SEQUENCE: 41

Met Val Val Ser Glu Val Asp Ile Ala Lys Ala Asp Pro Ala Ala Ala
        1               5                   10                  15

Ser His Pro Leu Leu Asn Gly Asp Ala Thr Val Ala Gln Lys Asn
                        20                  25                  30

Pro Gly Ser Val Ala Glu Asn Asn Leu Cys Ser Gln Tyr Glu Glu Lys
                        35                  40                  45

Val Arg Pro Cys Ile Asp Leu Ile Asp Ser Leu Arg Ala Leu Gly Val
                50                  55                  60

Glu Gln Asp Leu Ala Leu Pro Ala Ile Ala Val Ile Gly Asp Gln Ser
        65                  70                  75                  80

Ser Gly Lys Ser Ser Val Leu Glu Ala Leu Ser Gly Val Ala Leu Pro
                        85                  90                  95

Arg Gly Ser Gly Ile Val Thr Arg Cys Pro Leu Val Leu Lys Leu Lys
                        100                 105                 110

Lys Leu Val Asn Glu Asp Lys Trp Arg Gly Lys Val Ser Tyr Gln Asp
                        115                 120                 125

Tyr Glu Ile Glu Ile Ser Asp Ala Ser Glu Val Glu Lys Glu Ile Asn
                        130                 135                 140

Lys Ala Gln Asn Ala Ile Ala Gly Glu Gly Met Gly Ile Ser His Glu
        145                 150                 155                 160

Leu Ile Thr Leu Glu Ile Ser Ser Arg Asp Val Pro Asp Leu Thr Leu
```

```
              165                 170                 175
Ile Asp Leu Pro Gly Ile Thr Arg Val Ala Val Gly Asn Gln Pro Ala
            180                 185                 190
Asp Ile Gly Tyr Lys Ile Lys Thr Leu Ile Lys Lys Tyr Ile Gln Arg
            195                 200                 205
Gln Glu Thr Ile Ser Leu Val Val Pro Ser Asn Val Asp Ile Ala
            210                 215                 220
Thr Thr Glu Ala Leu Ser Met Ala Gln Glu Val Asp Pro Glu Gly Asp
225                 230                 235                 240
Arg Thr Ile Gly Ile Leu Thr Lys Pro Asp Leu Val Asp Lys Gly Thr
                245                 250                 255
Glu Asp Lys Val Val Asp Val Val Arg Asn Leu Val Phe His Leu Lys
                260                 265                 270
Lys Gly Tyr Met Ile Val Lys Cys Arg Gly Gln Gln Glu Ile Gln Asp
                275                 280                 285
Gln Leu Ser Leu Ser Glu Ala Leu Gln Arg Glu Lys Ile Phe Phe Glu
            290                 295                 300
Asn His Pro Tyr Phe Arg Asp Leu Leu Glu Glu Gly Lys Ala Thr Val
305                 310                 315                 320
Pro Cys Leu Ala Glu Lys Leu Thr Ser Glu Leu Ile Thr His Ile Cys
                325                 330                 335
Lys Ser Leu Pro Leu Leu Glu Asn Gln Ile Lys Glu Thr His Gln Arg
                340                 345                 350
Ile Thr Glu Glu Leu Gln Lys Tyr Gly Val Asp Ile Pro Glu Asp Glu
                355                 360                 365
Asn Glu Lys Met Phe Phe Leu Ile Asp Lys Ile Asn Ala Phe Asn Gln
            370                 375                 380
Asp Ile Thr Ala Leu Met Gln Gly Glu Glu Thr Val Gly Glu Glu Asp
385                 390                 395                 400
Ile Arg Leu Phe Thr Arg Leu Arg His Glu Phe His Lys Trp Ser Thr
                405                 410                 415
Ile Ile Glu Asn Asn Phe Gln Glu Gly His Lys Ile Leu Ser Arg Lys
                420                 425                 430
Ile Gln Lys Phe Glu Asn Gln Tyr Arg Gly Arg Glu Leu Pro Gly Phe
            435                 440                 445
Val Asn Tyr Arg Thr Phe Glu Thr Ile Val Lys Gln Gln Ile Lys Ala
450                 455                 460
Leu Glu Glu Pro Ala Val Asp Met Leu His Thr Val Thr Asp Met Val
465                 470                 475                 480
Arg Leu Ala Phe Thr Asp Val Ser Ile Lys Asn Phe Glu Glu Phe Phe
                485                 490                 495
Asn Leu His Arg Thr Ala Lys Ser Lys Ile Glu Asp Ile Arg Ala Glu
                500                 505                 510
Gln Glu Arg Glu Gly Glu Lys Leu Ile Arg Leu His Phe Gln Met Glu
            515                 520                 525
Gln Ile Val Tyr Cys Gln Asp Gln Val Tyr Arg Gly Ala Leu Gln Lys
            530                 535                 540
Val Arg Glu Lys Glu Leu Glu Glu Lys Lys Lys Ser Trp Asp
545                 550                 555                 560
Phe Gly Ala Phe Gln Ser Ser Ser Ala Thr Asp Ser Ser Met Glu Glu
                565                 570                 575
Ile Phe Gln His Leu Met Ala Tyr His Gln Glu Ala Ser Lys Arg Ile
            580                 585                 590
```

```
Ser Ser His Ile Pro Leu Ile Ile Gln Phe Phe Met Leu Gln Thr Tyr
        595                 600                 605

Gly Gln Gln Leu Gln Lys Ala Met Leu Gln Leu Leu Gln Asp Lys Asp
        610                 615                 620

Thr Tyr Ser Trp Leu Leu Lys Glu Arg Ser Asp Thr Ser Asp Lys Arg
625                 630                 635                 640

Lys Phe Leu Lys Glu Arg Leu Ala Arg Leu Thr Gln Ala Arg Arg Arg
                645                 650                 655

Leu Ala Gln Phe Pro Gly
            660

<210> SEQ ID NO 42
<211> LENGTH: 662
<212> TYPE: PRT
<213> ORGANISM: Homo sapiens

<400> SEQUENCE: 42

Met Val Val Ser Glu Val Asp Ile Ala Lys Ala Asp Pro Ala Ala Ala
1               5                   10                  15

Ser His Pro Leu Leu Leu Asn Gly Asp Ala Thr Val Ala Gln Lys Asn
                20                  25                  30

Pro Gly Ser Val Ala Glu Asn Asn Leu Cys Ser Gln Tyr Glu Glu Lys
            35                  40                  45

Val Arg Pro Cys Ile Asp Leu Ile Asp Ser Leu Arg Ala Leu Gly Val
        50                  55                  60

Glu Gln Asp Leu Ala Leu Pro Ala Ile Ala Val Ile Gly Asp Gln Ser
65                  70                  75                  80

Ser Gly Lys Ser Ser Val Leu Glu Ala Leu Ser Gly Val Ala Leu Pro
                85                  90                  95

Arg Gly Ser Gly Ile Val Thr Arg Cys Pro Leu Val Leu Lys Leu Lys
            100                 105                 110

Lys Leu Val Asn Glu Asp Lys Trp Arg Gly Lys Val Ser Tyr Gln Asp
        115                 120                 125

Tyr Glu Ile Glu Ile Ser Asp Ala Ser Glu Val Glu Lys Glu Ile Asn
130                 135                 140

Lys Ala Gln Asn Ala Ile Ala Gly Glu Gly Met Gly Ile Ser His Glu
145                 150                 155                 160

Leu Ile Thr Arg Glu Ile Ser Ser Arg Asp Val Pro Asp Leu Thr Leu
                165                 170                 175

Ile Asp Leu Pro Gly Ile Thr Arg Val Ala Val Gly Asn Gln Pro Ala
            180                 185                 190

Asp Ile Gly Tyr Lys Ile Lys Thr Leu Ile Lys Lys Tyr Ile Gln Arg
        195                 200                 205

Gln Glu Thr Ile Ser Leu Val Val Val Pro Ser Asn Val Asp Ile Ala
    210                 215                 220

Thr Thr Glu Ala Leu Ser Met Ala Gln Glu Val Asp Pro Glu Gly Asp
225                 230                 235                 240

Arg Thr Ile Gly Ile Leu Thr Lys Pro Asp Leu Val Asp Lys Gly Thr
                245                 250                 255

Glu Asp Lys Val Val Asp Val Val Arg Asn Leu Val Phe His Leu Lys
            260                 265                 270

Lys Gly Tyr Met Ile Val Lys Cys Arg Gly Gln Gln Glu Ile Gln Asp
        275                 280                 285

Gln Leu Ser Leu Ser Glu Ala Leu Gln Arg Glu Lys Ile Phe Phe Glu
```

```
                    290                 295                 300

Asn His Pro Tyr Phe Arg Asp Leu Leu Glu Glu Gly Lys Ala Thr Val
305                 310                 315                 320

Pro Cys Leu Ala Glu Lys Leu Thr Ser Glu Leu Ile Thr His Ile Cys
                    325                 330                 335

Lys Ser Leu Pro Leu Leu Glu Asn Gln Ile Lys Glu Thr His Gln Arg
                340                 345                 350

Ile Thr Glu Glu Leu Gln Lys Tyr Gly Val Asp Ile Pro Glu Asp Glu
            355                 360                 365

Asn Glu Lys Met Phe Phe Leu Ile Asp Lys Ile Asn Ala Phe Asn Gln
370                 375                 380

Asp Ile Thr Ala Leu Met Gln Gly Glu Glu Thr Val Gly Glu Glu Asp
385                 390                 395                 400

Ile Arg Leu Phe Thr Arg Leu Arg His Glu Phe His Lys Trp Ser Thr
                    405                 410                 415

Ile Ile Glu Asn Asn Phe Gln Glu Gly His Lys Ile Leu Ser Arg Lys
                420                 425                 430

Ile Gln Lys Phe Glu Asn Gln Tyr Arg Gly Arg Glu Leu Pro Gly Phe
            435                 440                 445

Val Asn Tyr Arg Thr Phe Glu Thr Ile Val Lys Gln Gln Ile Lys Ala
450                 455                 460

Leu Glu Glu Pro Ala Val Asp Met Leu His Thr Val Thr Asp Met Val
465                 470                 475                 480

Arg Leu Ala Phe Thr Asp Val Ser Ile Lys Asn Phe Glu Glu Phe Phe
                    485                 490                 495

Asn Leu His Arg Thr Ala Lys Ser Lys Ile Glu Asp Ile Arg Ala Glu
                500                 505                 510

Gln Glu Arg Glu Gly Glu Lys Leu Ile Arg Leu His Phe Gln Met Glu
            515                 520                 525

Gln Ile Val Tyr Cys Gln Asp Gln Val Tyr Arg Gly Ala Leu Gln Lys
530                 535                 540

Val Arg Glu Lys Glu Leu Glu Glu Lys Lys Lys Ser Trp Asp
545                 550                 555                 560

Phe Gly Ala Phe Gln Ser Ser Ala Thr Asp Ser Ser Met Glu Glu
                    565                 570                 575

Ile Phe Gln His Leu Met Ala Tyr His Gln Glu Ala Ser Lys Arg Ile
                580                 585                 590

Ser Ser His Ile Pro Leu Ile Ile Gln Phe Phe Met Leu Gln Thr Tyr
            595                 600                 605

Gly Gln Gln Leu Gln Lys Ala Met Leu Gln Leu Leu Gln Asp Lys Asp
610                 615                 620

Thr Tyr Ser Trp Leu Leu Lys Glu Arg Ser Asp Thr Ser Asp Lys Arg
625                 630                 635                 640

Lys Phe Leu Lys Glu Arg Leu Ala Arg Leu Thr Gln Ala Arg Arg Arg
                    645                 650                 655

Leu Ala Gln Phe Pro Gly
                660

<210> SEQ ID NO 43
<211> LENGTH: 303
<212> TYPE: PRT
<213> ORGANISM: Homo sapiens

<400> SEQUENCE: 43
```

```
Met Ala Asp Asp Gln Gly Cys Ile Glu Glu Gln Gly Val Glu Asp Ser
1               5                   10                  15

Ala Asn Glu Asp Ser Val Asp Ala Lys Pro Arg Ser Ser Phe Val
            20                  25                  30

Pro Ser Leu Phe Ser Lys Lys Lys Asn Val Thr Met Arg Ser Ile
        35                  40                  45

Lys Thr Thr Arg Asp Arg Val Pro Thr Tyr Gln Tyr Asn Met Asn Phe
50                  55                  60

Glu Lys Leu Gly Lys Cys Ile Ile Ile Asn Asn Lys Asn Phe Asp Lys
65                  70                  75                  80

Val Thr Gly Met Gly Val Arg Asn Gly Thr Asp Lys Asp Ala Glu Ala
                85                  90                  95

Leu Phe Lys Cys Phe Arg Ser Leu Gly Phe Asp Val Ile Val Tyr Asn
                100                 105                 110

Asp Cys Ser Cys Ala Lys Met Gln Asp Leu Leu Lys Lys Ala Ser Glu
            115                 120                 125

Glu Asp His Thr Asn Ala Ala Cys Phe Ala Cys Ile Leu Leu Ser His
        130                 135                 140

Gly Glu Glu Asn Val Ile Tyr Gly Lys Asp Gly Val Thr Pro Ile Lys
145                 150                 155                 160

Asp Leu Thr Ala His Phe Arg Gly Asp Arg Cys Lys Thr Leu Leu Glu
                165                 170                 175

Lys Pro Lys Leu Phe Phe Ile Gln Ala Cys Arg Gly Thr Glu Leu Asp
                180                 185                 190

Asp Gly Ile Gln Ala Asp Ser Gly Pro Ile Asn Asp Thr Asp Ala Asn
            195                 200                 205

Pro Arg Tyr Lys Ile Pro Val Glu Ala Asp Phe Leu Phe Ala Tyr Ser
210                 215                 220

Thr Val Pro Gly Tyr Tyr Ser Trp Arg Ser Pro Gly Arg Gly Ser Trp
225                 230                 235                 240

Phe Val Gln Ala Leu Cys Ser Ile Leu Glu Glu His Gly Lys Asp Leu
                245                 250                 255

Glu Ile Met Gln Ile Leu Thr Arg Val Asn Asp Arg Val Ala Arg His
                260                 265                 270

Phe Glu Ser Gln Ser Asp Asp Pro His Phe His Glu Lys Lys Gln Ile
                275                 280                 285

Pro Cys Val Val Ser Met Leu Thr Lys Glu Leu Tyr Phe Ser Gln
                290                 295                 300
```

<210> SEQ ID NO 44
<211> LENGTH: 239
<212> TYPE: PRT
<213> ORGANISM: Homo sapiens

<400> SEQUENCE: 44

```
Met Ala Lys Pro Cys Gly Val Arg Leu Ser Gly Glu Ala Arg Lys Gln
1               5                   10                  15

Val Glu Val Phe Arg Gln Asn Leu Phe Gln Glu Ala Glu Glu Phe Leu
            20                  25                  30

Tyr Arg Phe Leu Pro Gln Lys Ile Ile Tyr Leu Asn Gln Leu Leu Gln
        35                  40                  45

Glu Asp Ser Leu Asn Val Ala Asp Leu Thr Ser Leu Arg Ala Pro Leu
50                  55                  60

Asp Ile Pro Ile Pro Asp Pro Pro Lys Asp Asp Glu Met Glu Thr
65                  70                  75                  80
```

Asp Lys Gln Glu Lys Lys Glu Val His Lys Cys Gly Phe Leu Pro Gly
                85                  90                  95

Asn Glu Lys Val Leu Ser Leu Leu Ala Leu Val Lys Pro Glu Val Trp
            100                 105                 110

Thr Leu Lys Glu Lys Cys Ile Leu Val Ile Thr Trp Ile Gln His Leu
        115                 120                 125

Ile Pro Lys Ile Glu Asp Gly Asn Asp Phe Gly Val Ala Ile Gln Glu
    130                 135                 140

Lys Val Leu Glu Arg Val Asn Ala Val Lys Thr Lys Val Glu Ala Phe
145                 150                 155                 160

Gln Thr Thr Ile Ser Lys Tyr Phe Ser Glu Arg Gly Asp Ala Val Ala
                165                 170                 175

Lys Ala Ser Lys Glu Thr His Val Met Asp Tyr Arg Ala Leu Val His
            180                 185                 190

Glu Arg Asp Glu Ala Ala Tyr Gly Glu Leu Arg Ala Met Val Leu Asp
        195                 200                 205

Leu Arg Ala Phe Tyr Ala Glu Leu Tyr His Ile Ile Ser Ser Asn Leu
    210                 215                 220

Glu Lys Ile Val Asn Pro Lys Gly Glu Glu Lys Pro Ser Met Tyr
225                 230                 235

<210> SEQ ID NO 45
<211> LENGTH: 245
<212> TYPE: PRT
<213> ORGANISM: Homo sapiens

<400> SEQUENCE: 45

Met Glu Gly Pro Arg Gly Trp Leu Val Leu Cys Val Leu Ala Ile Ser
1               5                   10                  15

Leu Ala Ser Met Val Thr Glu Asp Leu Cys Arg Ala Pro Asp Gly Lys
            20                  25                  30

Lys Gly Glu Ala Gly Arg Pro Gly Arg Arg Gly Arg Pro Gly Leu Lys
        35                  40                  45

Gly Glu Gln Gly Glu Pro Gly Ala Pro Gly Ile Arg Thr Gly Ile Gln
    50                  55                  60

Gly Leu Lys Gly Asp Gln Gly Glu Pro Gly Pro Ser Gly Asn Pro Gly
65                  70                  75                  80

Lys Val Gly Tyr Pro Gly Pro Ser Gly Pro Leu Gly Ala Arg Gly Ile
                85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
    130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly

His Ile Tyr Gln Gly Ser Glu Ala Asp Ser Val Phe Ser Gly Phe Leu
225                 230                 235                 240

Ile Phe Pro Ser Ala
                245

<210> SEQ ID NO 46
<211> LENGTH: 253
<212> TYPE: PRT
<213> ORGANISM: Homo sapiens

<400> SEQUENCE: 46

Met Met Met Lys Ile Pro Trp Gly Ser Ile Pro Val Leu Met Leu Leu
1               5                   10                  15

Leu Leu Leu Gly Leu Ile Asp Ile Ser Gln Ala Gln Leu Ser Cys Thr
                20                  25                  30

Gly Pro Pro Ala Ile Pro Gly Ile Pro Gly Ile Pro Gly Thr Pro Gly
            35                  40                  45

Pro Asp Gly Gln Pro Gly Thr Pro Gly Ile Lys Gly Glu Lys Gly Leu
    50                  55                  60

Pro Gly Leu Ala Gly Asp His Gly Glu Phe Gly Glu Lys Gly Asp Pro
65                  70                  75                  80

Gly Ile Pro Gly Asn Pro Gly Lys Val Gly Pro Lys Gly Pro Met Gly
                85                  90                  95

Pro Lys Gly Gly Pro Gly Ala Pro Gly Ala Pro Gly Pro Lys Gly Glu
            100                 105                 110

Ser Gly Asp Tyr Lys Ala Thr Gln Lys Ile Ala Phe Ser Ala Thr Arg
        115                 120                 125

Thr Ile Asn Val Pro Leu Arg Arg Asp Gln Thr Ile Arg Phe Asp His
    130                 135                 140

Val Ile Thr Asn Met Asn Asn Asn Tyr Glu Pro Arg Ser Gly Lys Phe
145                 150                 155                 160

Thr Cys Lys Val Pro Gly Leu Tyr Tyr Phe Thr Tyr His Ala Ser Ser
                165                 170                 175

Arg Gly Asn Leu Cys Val Asn Leu Met Arg Gly Arg Glu Arg Ala Gln
            180                 185                 190

Lys Val Val Thr Phe Cys Asp Tyr Ala Tyr Asn Thr Phe Gln Val Thr
        195                 200                 205

Thr Gly Gly Met Val Leu Lys Leu Glu Gln Gly Glu Asn Val Phe Leu
    210                 215                 220

Gln Ala Thr Asp Lys Asn Ser Leu Leu Gly Met Glu Gly Ala Asn Ser
225                 230                 235                 240

Ile Phe Ser Gly Phe Leu Leu Phe Pro Asp Met Glu Ala
                245                 250

<210> SEQ ID NO 47
<211> LENGTH: 245
<212> TYPE: PRT
<213> ORGANISM: Homo sapiens

<400> SEQUENCE: 47

Met Asp Val Gly Pro Ser Ser Leu Pro His Leu Gly Leu Lys Leu Leu
1               5                   10                  15

Leu Leu Leu Leu Leu Leu Pro Leu Arg Gly Gln Ala Asn Thr Gly Cys
                20                  25                  30

Tyr Gly Ile Pro Gly Met Pro Gly Leu Pro Gly Ala Pro Gly Lys Asp

```
                    35                  40                  45
Gly Tyr Asp Gly Leu Pro Gly Lys Gly Glu Pro Gly Ile Pro Ala
 50                  55                  60

Ile Pro Gly Ile Arg Gly Pro Lys Gly Gln Lys Gly Glu Pro Gly Leu
 65                  70                  75                  80

Pro Gly His Pro Gly Lys Asn Gly Pro Met Gly Pro Pro Gly Met Pro
                 85                  90                  95

Gly Val Pro Gly Pro Met Gly Ile Pro Gly Glu Pro Gly Glu Glu Gly
                100                 105                 110

Arg Tyr Lys Gln Lys Phe Gln Ser Val Phe Thr Val Thr Arg Gln Thr
                115                 120                 125

His Gln Pro Pro Ala Pro Asn Ser Leu Ile Arg Phe Asn Ala Val Leu
                130                 135                 140

Thr Asn Pro Gln Gly Asp Tyr Asp Thr Ser Thr Gly Lys Phe Thr Cys
145                 150                 155                 160

Lys Val Pro Gly Leu Tyr Tyr Phe Val Tyr His Ala Ser His Thr Ala
                165                 170                 175

Asn Leu Cys Val Leu Leu Tyr Arg Ser Gly Val Lys Val Val Thr Phe
                180                 185                 190

Cys Gly His Thr Ser Lys Thr Asn Gln Val Asn Ser Gly Gly Val Leu
                195                 200                 205

Leu Arg Leu Gln Val Gly Glu Glu Val Trp Leu Ala Val Asn Asp Tyr
                210                 215                 220

Tyr Asp Met Val Gly Ile Gln Gly Ser Asp Ser Val Phe Ser Gly Phe
225                 230                 235                 240

Leu Leu Phe Pro Asp
                245

<210> SEQ ID NO 48
<211> LENGTH: 463
<212> TYPE: PRT
<213> ORGANISM: Homo sapiens

<400> SEQUENCE: 48

Met Gly Ala Gly Pro Ser Leu Leu Leu Ala Ala Leu Leu Leu Leu Leu
  1               5                  10                  15

Ser Gly Asp Gly Ala Val Arg Cys Asp Thr Pro Ala Asn Cys Thr Tyr
                 20                  25                  30

Leu Asp Leu Leu Gly Thr Trp Val Phe Gln Val Gly Ser Ser Gly Ser
                 35                  40                  45

Gln Arg Asp Val Asn Cys Ser Val Met Gly Pro Gln Glu Lys Lys Val
 50                  55                  60

Val Val Tyr Leu Gln Lys Leu Asp Thr Ala Tyr Asp Asp Leu Gly Asn
 65                  70                  75                  80

Ser Gly His Phe Thr Ile Ile Tyr Asn Gln Gly Phe Glu Ile Val Leu
                 85                  90                  95

Asn Asp Tyr Lys Trp Phe Ala Phe Phe Lys Tyr Lys Glu Glu Gly Ser
                100                 105                 110

Lys Val Thr Thr Tyr Cys Asn Glu Thr Met Thr Gly Trp Val His Asp
                115                 120                 125

Val Leu Gly Arg Asn Trp Ala Cys Phe Thr Gly Lys Lys Val Gly Thr
                130                 135                 140

Ala Ser Glu Asn Val Tyr Val Asn Ile Ala His Leu Lys Asn Ser Gln
145                 150                 155                 160
```

-continued

Glu Lys Tyr Ser Asn Arg Leu Tyr Lys Tyr Asp His Asn Phe Val Lys
            165                 170                 175

Ala Ile Asn Ala Ile Gln Lys Ser Trp Thr Ala Thr Thr Tyr Met Glu
        180                 185                 190

Tyr Glu Thr Leu Thr Leu Gly Asp Met Ile Arg Arg Ser Gly Gly His
            195                 200                 205

Ser Arg Lys Ile Pro Arg Pro Lys Pro Ala Pro Leu Thr Ala Glu Ile
        210                 215                 220

Gln Gln Lys Ile Leu His Leu Pro Thr Ser Trp Asp Trp Arg Asn Val
225                 230                 235                 240

His Gly Ile Asn Phe Val Ser Pro Val Arg Asn Gln Ala Ser Cys Gly
                245                 250                 255

Ser Cys Tyr Ser Phe Ala Ser Met Gly Met Leu Glu Ala Arg Ile Arg
            260                 265                 270

Ile Leu Thr Asn Asn Ser Gln Thr Pro Ile Leu Ser Pro Gln Glu Val
        275                 280                 285

Val Ser Cys Ser Gln Tyr Ala Gln Gly Cys Glu Gly Gly Phe Pro Tyr
    290                 295                 300

Leu Ile Ala Gly Lys Tyr Ala Gln Asp Phe Gly Leu Val Glu Glu Ala
305                 310                 315                 320

Cys Phe Pro Tyr Thr Gly Thr Asp Ser Pro Cys Lys Met Lys Glu Asp
                325                 330                 335

Cys Phe Arg Tyr Tyr Ser Ser Glu Tyr His Tyr Val Gly Gly Phe Tyr
            340                 345                 350

Gly Gly Cys Asn Glu Ala Leu Met Lys Leu Glu Leu Val His His Gly
        355                 360                 365

Pro Met Ala Val Ala Phe Glu Val Tyr Asp Asp Phe Leu His Tyr Lys
    370                 375                 380

Lys Gly Ile Tyr His His Thr Gly Leu Arg Asp Pro Phe Asn Pro Phe
385                 390                 395                 400

Glu Leu Thr Asn His Ala Val Leu Leu Val Gly Tyr Gly Thr Asp Ser
                405                 410                 415

Ala Ser Gly Met Asp Tyr Trp Ile Val Lys Asn Ser Trp Gly Thr Gly
            420                 425                 430

Trp Gly Glu Asn Gly Tyr Phe Arg Ile Arg Arg Gly Thr Asp Glu Cys
        435                 440                 445

Ala Ile Glu Ser Ile Ala Val Ala Ala Thr Pro Ile Pro Lys Leu
    450                 455                 460

<210> SEQ ID NO 49
<211> LENGTH: 457
<212> TYPE: PRT
<213> ORGANISM: Homo sapiens

<400> SEQUENCE: 49

Met Thr Thr Asp Glu Gly Ala Lys Asn Asn Glu Glu Ser Pro Thr Ala
1               5                   10                  15

Thr Val Ala Glu Gln Gly Glu Asp Ile Thr Ser Lys Lys Asp Arg Gly
            20                  25                  30

Val Leu Lys Ile Val Lys Arg Val Gly Asn Gly Glu Glu Thr Pro Met
        35                  40                  45

Ile Gly Asp Lys Val Tyr Val His Tyr Lys Gly Lys Leu Ser Asn Gly
    50                  55                  60

Lys Lys Phe Asp Ser Ser His Asp Arg Asn Glu Pro Phe Val Phe Ser
65                  70                  75                  80

Leu Gly Lys Gly Gln Val Ile Lys Ala Trp Asp Ile Gly Val Ala Thr
            85                  90                  95

Met Lys Lys Gly Glu Ile Cys His Leu Leu Cys Lys Pro Glu Tyr Ala
        100                 105                 110

Tyr Gly Ser Ala Gly Ser Leu Pro Lys Ile Pro Ser Asn Ala Thr Leu
    115                 120                 125

Phe Phe Glu Ile Glu Leu Leu Asp Phe Lys Gly Glu Asp Leu Phe Glu
130                 135                 140

Asp Gly Gly Ile Ile Arg Arg Thr Lys Arg Lys Gly Glu Gly Tyr Ser
145                 150                 155                 160

Asn Pro Asn Glu Gly Ala Thr Val Glu Ile His Leu Glu Gly Arg Cys
                165                 170                 175

Gly Gly Arg Met Phe Asp Cys Arg Asp Val Ala Phe Thr Val Gly Glu
            180                 185                 190

Gly Glu Asp His Asp Ile Pro Ile Gly Ile Asp Lys Ala Leu Glu Lys
        195                 200                 205

Met Gln Arg Glu Glu Gln Cys Ile Leu Tyr Leu Gly Pro Arg Tyr Gly
    210                 215                 220

Phe Gly Glu Ala Gly Lys Pro Lys Phe Gly Ile Glu Pro Asn Ala Glu
225                 230                 235                 240

Leu Ile Tyr Glu Val Thr Leu Lys Ser Phe Glu Lys Ala Lys Glu Ser
                245                 250                 255

Trp Glu Met Asp Thr Lys Glu Lys Leu Glu Gln Ala Ala Ile Val Lys
            260                 265                 270

Glu Lys Gly Thr Val Tyr Phe Lys Gly Gly Lys Tyr Met Gln Ala Val
        275                 280                 285

Ile Gln Tyr Gly Lys Ile Val Ser Trp Leu Glu Met Glu Tyr Gly Leu
    290                 295                 300

Ser Glu Lys Glu Ser Lys Ala Ser Glu Ser Phe Leu Leu Ala Ala Phe
305                 310                 315                 320

Leu Asn Leu Ala Met Cys Tyr Leu Lys Leu Arg Glu Tyr Thr Lys Ala
                325                 330                 335

Val Glu Cys Cys Asp Lys Ala Leu Gly Leu Asp Ser Ala Asn Glu Lys
            340                 345                 350

Gly Leu Tyr Arg Arg Gly Glu Ala Gln Leu Leu Met Asn Glu Phe Glu
        355                 360                 365

Ser Ala Lys Gly Asp Phe Glu Lys Val Leu Glu Val Asn Pro Gln Asn
    370                 375                 380

Lys Ala Ala Arg Leu Gln Ile Ser Met Cys Gln Lys Lys Ala Lys Glu
385                 390                 395                 400

His Asn Glu Arg Asp Arg Arg Ile Tyr Ala Asn Met Phe Lys Lys Phe
                405                 410                 415

Ala Glu Gln Asp Ala Lys Glu Glu Ala Asn Lys Ala Met Gly Lys Lys
            420                 425                 430

Thr Ser Glu Gly Val Thr Asn Glu Lys Gly Thr Asp Ser Gln Ala Met
        435                 440                 445

Glu Glu Glu Lys Pro Glu Gly His Val
    450                 455

<210> SEQ ID NO 50
<211> LENGTH: 1456
<212> TYPE: PRT
<213> ORGANISM: Homo sapiens -continued

```
<400> SEQUENCE: 50

Met Arg Leu Pro Leu Leu Val Phe Ala Ser Val Ile Pro Gly Ala
1               5                   10                  15

Val Leu Leu Leu Asp Thr Arg Gln Phe Leu Ile Tyr Asn Glu Asp His
            20                  25                  30

Lys Arg Cys Val Asp Ala Val Ser Pro Ser Ala Val Gln Thr Ala Ala
        35                  40                  45

Cys Asn Gln Asp Ala Glu Ser Gln Lys Phe Arg Trp Val Ser Glu Ser
    50                  55                  60

Gln Ile Met Ser Val Ala Phe Lys Leu Cys Leu Gly Val Pro Ser Lys
65                  70                  75                  80

Thr Asp Trp Val Ala Ile Thr Leu Tyr Ala Cys Asp Ser Lys Ser Glu
                85                  90                  95

Phe Gln Lys Trp Glu Cys Lys Asn Asp Thr Leu Leu Gly Ile Lys Gly
            100                 105                 110

Glu Asp Leu Phe Phe Asn Tyr Gly Asn Arg Gln Glu Lys Asn Ile Met
        115                 120                 125

Leu Tyr Lys Gly Ser Gly Leu Trp Ser Arg Trp Lys Ile Tyr Gly Thr
130                 135                 140

Thr Asp Asn Leu Cys Ser Arg Gly Tyr Glu Ala Met Tyr Thr Leu Leu
145                 150                 155                 160

Gly Asn Ala Asn Gly Ala Thr Cys Ala Phe Pro Phe Lys Phe Glu Asn
                165                 170                 175

Lys Trp Tyr Ala Asp Cys Thr Ser Ala Gly Arg Ser Asp Gly Trp Leu
            180                 185                 190

Trp Cys Gly Thr Thr Thr Asp Tyr Asp Thr Asp Lys Leu Phe Gly Tyr
        195                 200                 205

Cys Pro Leu Lys Phe Glu Gly Ser Glu Ser Leu Trp Asn Lys Asp Pro
210                 215                 220

Leu Thr Ser Val Ser Tyr Gln Ile Asn Ser Lys Ser Ala Leu Thr Trp
225                 230                 235                 240

His Gln Ala Arg Lys Ser Cys Gln Gln Gln Asn Ala Glu Leu Leu Ser
                245                 250                 255

Ile Thr Glu Ile His Glu Gln Thr Tyr Leu Thr Gly Leu Thr Ser Ser
            260                 265                 270

Leu Thr Ser Gly Leu Trp Ile Gly Leu Asn Ser Leu Ser Phe Asn Ser
        275                 280                 285

Gly Trp Gln Trp Ser Asp Arg Ser Pro Phe Arg Tyr Leu Asn Trp Leu
290                 295                 300

Pro Gly Ser Pro Ser Ala Glu Pro Gly Lys Ser Cys Val Ser Leu Asn
305                 310                 315                 320

Pro Gly Lys Asn Ala Lys Trp Glu Asn Leu Glu Cys Val Gln Lys Leu
                325                 330                 335

Gly Tyr Ile Cys Lys Lys Gly Asn Thr Thr Leu Asn Ser Phe Val Ile
            340                 345                 350

Pro Ser Glu Ser Asp Val Pro Thr His Cys Pro Ser Gln Trp Trp Pro
        355                 360                 365

Tyr Ala Gly His Cys Tyr Lys Ile His Arg Asp Glu Lys Lys Ile Gln
370                 375                 380

Arg Asp Ala Leu Thr Thr Cys Arg Lys Glu Gly Gly Asp Leu Thr Ser
385                 390                 395                 400

Ile His Thr Ile Glu Glu Leu Asp Phe Ile Ile Ser Gln Leu Gly Tyr
            405                 410                 415
```

```
Glu Pro Asn Asp Glu Leu Trp Ile Gly Leu Asn Asp Ile Lys Ile Gln
            420                 425                 430

Met Tyr Phe Glu Trp Ser Asp Gly Thr Pro Val Thr Phe Thr Lys Trp
            435                 440                 445

Leu Arg Gly Glu Pro Ser His Glu Asn Asn Arg Gln Glu Asp Cys Val
            450                 455                 460

Val Met Lys Gly Lys Asp Gly Tyr Trp Ala Asp Arg Gly Cys Glu Trp
465                 470                 475                 480

Pro Leu Gly Tyr Ile Cys Lys Met Lys Ser Arg Ser Gln Gly Pro Glu
                485                 490                 495

Ile Val Glu Val Glu Lys Gly Cys Arg Lys Gly Trp Lys Lys His His
            500                 505                 510

Phe Tyr Cys Tyr Met Ile Gly His Thr Leu Ser Thr Phe Ala Glu Ala
            515                 520                 525

Asn Gln Thr Cys Asn Asn Glu Asn Ala Tyr Leu Thr Thr Ile Glu Asp
            530                 535                 540

Arg Tyr Glu Gln Ala Phe Leu Thr Ser Phe Val Gly Leu Arg Pro Glu
545                 550                 555                 560

Lys Tyr Phe Trp Thr Gly Leu Ser Asp Ile Gln Thr Lys Gly Thr Phe
                565                 570                 575

Gln Trp Thr Ile Glu Glu Val Arg Phe Thr His Trp Asn Ser Asp
            580                 585                 590

Met Pro Gly Arg Lys Pro Gly Cys Val Ala Met Arg Thr Gly Ile Ala
            595                 600                 605

Gly Gly Leu Trp Asp Val Leu Lys Cys Asp Glu Lys Ala Lys Phe Val
            610                 615                 620

Cys Lys His Trp Ala Glu Gly Val Thr His Pro Pro Lys Pro Thr Thr
625                 630                 635                 640

Thr Pro Glu Pro Lys Cys Pro Glu Asp Trp Gly Ala Ser Ser Arg Thr
                645                 650                 655

Ser Leu Cys Phe Lys Leu Tyr Ala Lys Gly Lys His Glu Lys Lys Thr
            660                 665                 670

Trp Phe Glu Ser Arg Asp Phe Cys Arg Ala Leu Gly Gly Asp Leu Ala
            675                 680                 685

Ser Ile Asn Asn Lys Glu Glu Gln Gln Thr Ile Trp Arg Leu Ile Thr
690                 695                 700

Ala Ser Gly Ser Tyr His Lys Leu Phe Trp Leu Gly Leu Thr Tyr Gly
705                 710                 715                 720

Ser Pro Ser Glu Gly Phe Thr Trp Ser Asp Gly Ser Pro Val Ser Tyr
                725                 730                 735

Glu Asn Trp Ala Tyr Gly Glu Pro Asn Asn Tyr Gln Asn Val Glu Tyr
            740                 745                 750

Cys Gly Glu Leu Lys Gly Asp Pro Thr Met Ser Trp Asn Asp Ile Asn
            755                 760                 765

Cys Glu His Leu Asn Asn Trp Ile Cys Gln Ile Gln Lys Gly Gln Thr
            770                 775                 780

Pro Lys Pro Glu Pro Thr Pro Ala Pro Gln Asp Asn Pro Pro Val Thr
785                 790                 795                 800

Glu Asp Gly Trp Val Ile Tyr Lys Asp Tyr Gln Tyr Tyr Phe Ser Lys
                805                 810                 815

Glu Lys Glu Thr Met Asp Asn Ala Arg Ala Phe Cys Lys Arg Asn Phe
            820                 825                 830
```

```
Gly Asp Leu Val Ser Ile Gln Ser Glu Ser Lys Lys Phe Leu Trp
        835                 840                 845

Lys Tyr Val Asn Arg Asn Asp Ala Gln Ser Ala Tyr Phe Ile Gly Leu
850                 855                 860

Leu Ile Ser Leu Asp Lys Lys Phe Ala Trp Met Asp Gly Ser Lys Val
865                 870                 875                 880

Asp Tyr Val Ser Trp Ala Thr Gly Glu Pro Asn Phe Ala Asn Glu Asp
                885                 890                 895

Glu Asn Cys Val Thr Met Tyr Ser Asn Ser Gly Phe Trp Asn Asp Ile
            900                 905                 910

Asn Cys Gly Tyr Pro Asn Ala Phe Ile Cys Gln Arg His Asn Ser Ser
            915                 920                 925

Ile Asn Ala Thr Thr Val Met Pro Thr Met Pro Ser Val Pro Ser Gly
            930                 935                 940

Cys Lys Glu Gly Trp Asn Phe Tyr Ser Asn Lys Cys Phe Lys Ile Phe
945                 950                 955                 960

Gly Phe Met Glu Glu Arg Lys Asn Trp Gln Glu Ala Arg Lys Ala
                965                 970                 975

Cys Ile Gly Phe Gly Gly Asn Leu Val Ser Ile Gln Asn Glu Lys Glu
            980                 985                 990

Gln Ala Phe Leu Thr Tyr His Met Lys Asp Ser Thr Phe Ser Ala Trp
        995                 1000                1005

Thr Gly Leu Asn Asp Val Asn Ser Glu His Thr Phe Leu Trp Thr
        1010                1015                1020

Asp Gly Arg Gly Val His Tyr Thr Asn Trp Gly Lys Gly Tyr Pro
        1025                1030                1035

Gly Gly Arg Arg Ser Ser Leu Ser Tyr Glu Asp Ala Asp Cys Val
        1040                1045                1050

Val Ile Ile Gly Gly Ala Ser Asn Glu Ala Gly Lys Trp Met Asp
        1055                1060                1065

Asp Thr Cys Asp Ser Lys Arg Gly Tyr Ile Cys Gln Thr Arg Ser
        1070                1075                1080

Asp Pro Ser Leu Thr Asn Pro Ala Thr Ile Gln Thr Asp Gly
        1085                1090                1095

Phe Val Lys Tyr Gly Lys Ser Ser Tyr Ser Leu Met Arg Gln Lys
        1100                1105                1110

Phe Gln Trp His Glu Ala Glu Thr Tyr Cys Lys Leu His Asn Ser
        1115                1120                1125

Leu Ile Ala Ser Ile Leu Asp Pro Tyr Ser Asn Ala Phe Ala Trp
        1130                1135                1140

Leu Gln Met Glu Thr Ser Asn Glu Arg Val Trp Ile Ala Leu Asn
        1145                1150                1155

Ser Asn Leu Thr Asp Asn Gln Tyr Thr Trp Thr Asp Lys Trp Arg
        1160                1165                1170

Val Arg Tyr Thr Asn Trp Ala Ala Asp Glu Pro Lys Leu Lys Ser
        1175                1180                1185

Ala Cys Val Tyr Leu Asp Leu Asp Gly Tyr Trp Lys Thr Ala His
        1190                1195                1200

Cys Asn Glu Ser Phe Tyr Phe Leu Cys Lys Arg Ser Asp Glu Ile
        1205                1210                1215

Pro Ala Thr Glu Pro Pro Gln Leu Pro Gly Arg Cys Pro Glu Ser
        1220                1225                1230

Asp His Thr Ala Trp Ile Pro Phe His Gly His Cys Tyr Tyr Ile
```

```
                    1235               1240                1245

Glu Ser Ser Tyr Thr Arg Asn Trp Gly Gln Ala Ser Leu Glu Cys
    1250                1255                1260

Leu Arg Met Gly Ser Ser Leu Val Ser Ile Glu Ser Ala Ala Glu
    1265                1270                1275

Ser Ser Phe Leu Ser Tyr Arg Val Glu Pro Leu Lys Ser Lys Thr
    1280                1285                1290

Asn Phe Trp Ile Gly Leu Phe Arg Asn Val Glu Gly Thr Trp Leu
    1295                1300                1305

Trp Ile Asn Asn Ser Pro Val Ser Phe Val Asn Trp Asn Thr Gly
    1310                1315                1320

Asp Pro Ser Gly Glu Arg Asn Asp Cys Val Ala Leu His Ala Ser
    1325                1330                1335

Ser Gly Phe Trp Ser Asn Ile His Cys Ser Ser Tyr Lys Gly Tyr
    1340                1345                1350

Ile Cys Lys Arg Pro Lys Ile Ile Asp Ala Lys Pro Thr His Glu
    1355                1360                1365

Leu Leu Thr Thr Lys Ala Asp Thr Arg Lys Met Asp Pro Ser Lys
    1370                1375                1380

Pro Ser Ser Asn Val Ala Gly Val Val Ile Val Ile Leu Leu
    1385                1390                1395

Ile Leu Thr Gly Ala Gly Leu Ala Ala Tyr Phe Phe Tyr Lys Lys
    1400                1405                1410

Arg Arg Val His Leu Pro Gln Glu Gly Ala Phe Glu Asn Thr Leu
    1415                1420                1425

Tyr Phe Asn Ser Gln Ser Ser Pro Gly Thr Ser Asp Met Lys Asp
    1430                1435                1440

Leu Val Gly Asn Ile Glu Gln Asn Glu His Ser Val Ile
    1445                1450                1455

<210> SEQ ID NO 51
<211> LENGTH: 2570
<212> TYPE: PRT
<213> ORGANISM: Homo sapiens

<400> SEQUENCE: 51

Met Ala Gly Pro Arg Gly Leu Leu Pro Leu Cys Leu Leu Ala Phe Cys
1               5                   10                  15

Leu Ala Gly Phe Ser Phe Val Arg Gly Gln Val Leu Phe Lys Gly Cys
                20                  25                  30

Asp Val Lys Thr Thr Phe Val Thr His Val Pro Cys Thr Ser Cys Ala
            35                  40                  45

Ala Ile Lys Lys Gln Thr Cys Pro Ser Gly Trp Leu Arg Glu Leu Pro
        50                  55                  60

Asp Gln Ile Thr Gln Asp Cys Arg Tyr Glu Val Gln Leu Gly Gly Ser
65                  70                  75                  80

Met Val Ser Met Ser Gly Cys Arg Arg Lys Cys Arg Lys Gln Val Val
                85                  90                  95

Gln Lys Ala Cys Cys Pro Gly Tyr Trp Gly Ser Arg Cys His Glu Cys
            100                 105                 110

Pro Gly Gly Ala Glu Thr Pro Cys Asn Gly His Gly Thr Cys Leu Asp
        115                 120                 125

Gly Met Asp Arg Asn Gly Thr Cys Val Cys Gln Glu Asn Phe Arg Gly
    130                 135                 140
```

```
Ser Ala Cys Gln Glu Cys Gln Asp Pro Asn Arg Phe Gly Pro Asp Cys
145                 150                 155                 160

Gln Ser Val Cys Ser Cys Val His Gly Val Cys Asn His Gly Pro Arg
            165                 170                 175

Gly Asp Gly Ser Cys Leu Cys Phe Ala Gly Tyr Thr Gly Pro His Cys
        180                 185                 190

Asp Gln Glu Leu Pro Val Cys Gln Glu Leu Arg Cys Pro Gln Asn Thr
    195                 200                 205

Gln Cys Ser Ala Glu Ala Pro Ser Cys Arg Cys Leu Pro Gly Tyr Thr
210                 215                 220

Gln Gln Gly Ser Glu Cys Arg Ala Pro Asn Pro Cys Trp Pro Ser Pro
225                 230                 235                 240

Cys Ser Leu Leu Ala Gln Cys Ser Val Ser Pro Lys Gly Gln Ala Gln
            245                 250                 255

Cys His Cys Pro Glu Asn Tyr His Gly Asp Gly Met Val Cys Leu Pro
            260                 265                 270

Lys Asp Pro Cys Thr Asp Asn Leu Gly Gly Cys Pro Ser Asn Ser Thr
        275                 280                 285

Leu Cys Val Tyr Gln Lys Pro Gly Gln Ala Phe Cys Thr Cys Arg Pro
    290                 295                 300

Gly Leu Val Ser Ile Asn Ser Asn Ala Ser Ala Gly Cys Phe Ala Phe
305                 310                 315                 320

Cys Ser Pro Phe Ser Cys Asp Arg Ser Ala Thr Cys Gln Val Thr Ala
                325                 330                 335

Asp Gly Lys Thr Ser Cys Val Cys Arg Glu Ser Glu Val Gly Asp Gly
            340                 345                 350

Arg Ala Cys Tyr Gly His Leu Leu His Glu Val Gln Lys Ala Thr Gln
        355                 360                 365

Thr Gly Arg Val Phe Leu Gln Leu Arg Val Ala Val Ala Met Met Asp
    370                 375                 380

Gln Gly Cys Arg Glu Ile Leu Thr Thr Ala Gly Pro Phe Thr Val Leu
385                 390                 395                 400

Val Pro Ser Val Ser Ser Phe Ser Ser Arg Thr Met Asn Ala Ser Leu
                405                 410                 415

Ala Gln Gln Leu Cys Arg Gln His Ile Ile Ala Gly Gln His Ile Leu
            420                 425                 430

Glu Asp Thr Arg Thr Gln Thr Arg Arg Trp Trp Thr Leu Ala Gly
        435                 440                 445

Gln Glu Ile Thr Val Thr Phe Asn Gln Phe Thr Lys Tyr Ser Tyr Lys
    450                 455                 460

Tyr Lys Asp Gln Pro Gln Gln Thr Phe Asn Ile Tyr Lys Ala Asn Asn
465                 470                 475                 480

Ile Ala Ala Asn Gly Val Phe His Val Thr Gly Leu Arg Trp Gln
                485                 490                 495

Ala Pro Ser Gly Thr Pro Gly Asp Pro Lys Arg Thr Ile Gly Gln Ile
            500                 505                 510

Leu Ala Ser Thr Glu Ala Phe Ser Arg Phe Glu Thr Ile Leu Glu Asn
        515                 520                 525

Cys Gly Leu Pro Ser Ile Leu Asp Gly Pro Gly Pro Phe Thr Val Phe
    530                 535                 540

Ala Pro Ser Asn Glu Ala Val Asp Ser Leu Arg Asp Gly Arg Leu Ile
545                 550                 555                 560

Tyr Leu Phe Thr Ala Gly Leu Ser Lys Leu Gln Glu Leu Val Arg Tyr
```

-continued

```
            565                 570                 575
His Ile Tyr Asn His Gly Gln Leu Thr Val Glu Lys Leu Ile Ser Lys
            580                 585                 590

Gly Arg Ile Leu Thr Met Ala Asn Gln Val Leu Ala Val Asn Ile Ser
            595                 600                 605

Glu Glu Gly Arg Ile Leu Leu Gly Pro Glu Gly Val Pro Leu Gln Arg
            610                 615                 620

Val Asp Val Met Ala Ala Asn Gly Val Ile His Met Leu Asp Gly Ile
625                 630                 635                 640

Leu Leu Pro Pro Thr Ile Leu Pro Ile Leu Pro Lys His Cys Ser Glu
            645                 650                 655

Glu Gln His Lys Ile Val Ala Gly Ser Cys Val Asp Cys Gln Ala Leu
            660                 665                 670

Asn Thr Ser Thr Cys Pro Pro Asn Ser Val Lys Leu Asp Ile Phe Pro
            675                 680                 685

Lys Glu Cys Val Tyr Ile His Asp Pro Thr Gly Leu Asn Val Leu Lys
            690                 695                 700

Lys Gly Cys Ala Ser Tyr Cys Asn Gln Thr Ile Met Glu Gln Gly Cys
705                 710                 715                 720

Cys Lys Gly Phe Phe Gly Pro Asp Cys Thr Gln Cys Pro Gly Gly Phe
            725                 730                 735

Ser Asn Pro Cys Tyr Lys Gly Asn Cys Ser Asp Gly Ile Gln Gly
            740                 745                 750

Asn Gly Ala Cys Leu Cys Phe Pro Asp Tyr Lys Gly Ile Ala Cys His
            755                 760                 765

Ile Cys Ser Asn Pro Asn Lys His Gly Glu Gln Cys Gln Glu Asp Cys
770                 775                 780

Gly Cys Val His Gly Leu Cys Asp Asn Arg Pro Gly Ser Gly Gly Val
785                 790                 795                 800

Cys Gln Gln Gly Thr Cys Ala Pro Gly Phe Ser Gly Arg Phe Cys Asn
            805                 810                 815

Glu Ser Met Gly Asp Cys Gly Pro Thr Gly Leu Ala Gln His Cys His
            820                 825                 830

Leu His Ala Arg Cys Val Ser Gln Glu Gly Val Ala Arg Cys Arg Cys
            835                 840                 845

Leu Asp Gly Phe Glu Gly Asp Gly Phe Ser Cys Thr Pro Ser Asn Pro
850                 855                 860

Cys Ser His Pro Asp Arg Gly Gly Cys Ser Glu Asn Ala Glu Cys Val
865                 870                 875                 880

Pro Gly Ser Leu Gly Thr His His Cys Thr Cys His Lys Gly Trp Ser
            885                 890                 895

Gly Asp Gly Arg Val Cys Val Ala Ile Asp Glu Cys Glu Leu Asp Met
            900                 905                 910

Arg Gly Gly Cys His Thr Asp Ala Leu Cys Ser Tyr Val Gly Pro Gly
            915                 920                 925

Gln Ser Arg Cys Thr Cys Lys Leu Gly Phe Ala Gly Asp Gly Tyr Gln
            930                 935                 940

Cys Ser Pro Ile Asp Pro Cys Arg Ala Gly Asn Gly Gly Cys His Gly
945                 950                 955                 960

Leu Ala Thr Cys Arg Ala Val Gly Gly Gly Gln Arg Val Cys Thr Cys
            965                 970                 975

Pro Pro Gly Phe Gly Gly Asp Gly Phe Ser Cys Tyr Gly Asp Ile Phe
            980                 985                 990
```

-continued

```
Arg Glu Leu Glu Ala Asn Ala His Phe Ser Ile Phe Tyr Gln Trp Leu
        995                 1000                1005
Lys Ser Ala Gly Ile Thr Leu Pro Ala Asp Arg Val Thr Ala
    1010                1015                1020
Leu Val Pro Ser Glu Ala Ala Val Arg Gln Leu Ser Pro Glu Asp
    1025                1030                1035
Arg Ala Phe Trp Leu Gln Pro Arg Thr Leu Pro Asn Leu Val Arg
    1040                1045                1050
Ala His Phe Leu Gln Gly Ala Leu Phe Glu Glu Leu Ala Arg
    1055                1060                1065
Leu Gly Gly Gln Glu Val Ala Thr Leu Asn Pro Thr Thr Arg Trp
    1070                1075                1080
Glu Ile Arg Asn Ile Ser Gly Arg Val Trp Val Gln Asn Ala Ser
    1085                1090                1095
Val Asp Val Ala Asp Leu Leu Ala Thr Asn Gly Val Leu His Ile
    1100                1105                1110
Leu Ser Gln Val Leu Leu Pro Pro Arg Gly Asp Val Pro Gly Gly
    1115                1120                1125
Gln Gly Leu Leu Gln Gln Leu Asp Leu Val Pro Ala Phe Ser Leu
    1130                1135                1140
Phe Arg Glu Leu Leu Gln His His Gly Leu Val Pro Gln Ile Glu
    1145                1150                1155
Ala Ala Thr Ala Tyr Thr Ile Phe Val Pro Thr Asn Arg Ser Leu
    1160                1165                1170
Glu Ala Gln Gly Asn Ser Ser His Leu Asp Ala Asp Thr Val Arg
    1175                1180                1185
His His Val Val Leu Gly Glu Ala Leu Ser Met Glu Thr Leu Arg
    1190                1195                1200
Lys Gly Gly His Arg Asn Ser Leu Leu Gly Pro Ala His Trp Ile
    1205                1210                1215
Val Phe Tyr Asn His Ser Gly Gln Pro Glu Val Asn His Val Pro
    1220                1225                1230
Leu Glu Gly Pro Met Leu Glu Ala Pro Gly Arg Ser Leu Ile Gly
    1235                1240                1245
Leu Ser Gly Val Leu Thr Val Gly Ser Ser Arg Cys Leu His Ser
    1250                1255                1260
His Ala Glu Ala Leu Arg Glu Lys Cys Val Asn Cys Thr Arg Arg
    1265                1270                1275
Phe Arg Cys Thr Gln Gly Phe Gln Leu Gln Asp Thr Pro Arg Lys
    1280                1285                1290
Ser Cys Val Tyr Arg Ser Gly Phe Ser Phe Ser Arg Gly Cys Ser
    1295                1300                1305
Tyr Thr Cys Ala Lys Lys Ile Gln Val Pro Asp Cys Cys Pro Gly
    1310                1315                1320
Phe Phe Gly Thr Leu Cys Glu Pro Cys Pro Gly Gly Leu Gly Gly
    1325                1330                1335
Val Cys Ser Gly His Gly Gln Cys Gln Asp Arg Phe Leu Gly Ser
    1340                1345                1350
Gly Glu Cys His Cys His Glu Gly Phe His Gly Thr Ala Cys Glu
    1355                1360                1365
Val Cys Glu Leu Gly Arg Tyr Gly Pro Asn Cys Thr Gly Val Cys
    1370                1375                1380
```

-continued

Asp Cys Ala His Gly Leu Cys Gln Glu Gly Leu Gln Gly Asp Gly
1385                 1390                 1395

Ser Cys Val Cys Asn Val Gly Trp Gln Gly Leu Arg Cys Asp Gln
1400                 1405                 1410

Lys Ile Thr Ser Pro Gln Cys Pro Arg Lys Cys Asp Pro Asn Ala
1415                 1420                 1425

Asn Cys Val Gln Asp Ser Ala Gly Ala Ser Thr Cys Ala Cys Ala
1430                 1435                 1440

Ala Gly Tyr Ser Gly Asn Gly Ile Phe Cys Ser Glu Val Asp Pro
1445                 1450                 1455

Cys Ala His Gly His Gly Gly Cys Ser Pro His Ala Asn Cys Thr
1460                 1465                 1470

Lys Val Ala Pro Gly Gln Arg Thr Cys Thr Cys Gln Asp Gly Tyr
1475                 1480                 1485

Met Gly Asp Gly Glu Leu Cys Gln Glu Ile Asn Ser Cys Leu Ile
1490                 1495                 1500

His His Gly Gly Cys His Ile His Ala Glu Cys Ile Pro Thr Gly
1505                 1510                 1515

Pro Gln Gln Val Ser Cys Ser Cys Arg Glu Gly Tyr Ser Gly Asp
1520                 1525                 1530

Gly Ile Arg Thr Cys Glu Leu Leu Asp Pro Cys Ser Lys Asn Asn
1535                 1540                 1545

Gly Gly Cys Ser Pro Tyr Ala Thr Cys Lys Ser Thr Gly Asp Gly
1550                 1555                 1560

Gln Arg Thr Cys Thr Cys Asp Thr Ala His Thr Val Gly Asp Gly
1565                 1570                 1575

Leu Thr Cys Arg Ala Arg Val Gly Leu Glu Leu Arg Asp Lys
1580                 1585                 1590

His Ala Ser Phe Phe Ser Leu Arg Leu Leu Glu Tyr Lys Glu Leu
1595                 1600                 1605

Lys Gly Asp Gly Pro Phe Thr Ile Phe Val Pro His Ala Asp Leu
1610                 1615                 1620

Met Ser Asn Leu Ser Gln Asp Glu Leu Ala Arg Ile Arg Ala His
1625                 1630                 1635

Arg Gln Leu Val Phe Arg Tyr His Val Val Gly Cys Arg Arg Leu
1640                 1645                 1650

Arg Ser Glu Asp Leu Leu Glu Gln Gly Tyr Ala Thr Ala Leu Ser
1655                 1660                 1665

Gly His Pro Leu Arg Phe Ser Glu Arg Glu Gly Ser Ile Tyr Leu
1670                 1675                 1680

Asn Asp Phe Ala Arg Val Val Ser Ser Asp His Glu Ala Val Asn
1685                 1690                 1695

Gly Ile Leu His Phe Ile Asp Arg Val Leu Leu Pro Pro Glu Ala
1700                 1705                 1710

Leu His Trp Glu Pro Asp Asp Ala Pro Ile Pro Arg Arg Asn Val
1715                 1720                 1725

Thr Ala Ala Ala Gln Gly Phe Gly Tyr Lys Ile Phe Ser Gly Leu
1730                 1735                 1740

Leu Lys Val Ala Gly Leu Leu Pro Leu Leu Arg Glu Ala Ser His
1745                 1750                 1755

Arg Pro Phe Thr Met Leu Trp Pro Thr Asp Ala Ala Phe Arg Ala
1760                 1765                 1770

Leu Pro Pro Asp Arg Gln Ala Trp Leu Tyr His Glu Asp His Arg

-continued

```
                1775                1780                1785

Asp Lys Leu Ala Ala Ile Leu Arg Gly His Met Ile Arg Asn Val
        1790                1795                1800

Glu Ala Leu Ala Ser Asp Leu Pro Asn Leu Gly Pro Leu Arg Thr
        1805                1810                1815

Met His Gly Thr Pro Ile Ser Phe Ser Cys Ser Arg Thr Arg Ala
        1820                1825                1830

Gly Glu Leu Met Val Gly Glu Asp Asp Ala Arg Ile Val Gln Arg
        1835                1840                1845

His Leu Pro Phe Glu Gly Gly Leu Ala Tyr Gly Ile Asp Gln Leu
        1850                1855                1860

Leu Glu Pro Pro Gly Leu Gly Ala Arg Cys Asp His Phe Glu Thr
        1865                1870                1875

Arg Pro Leu Arg Leu Asn Thr Cys Ser Ile Cys Gly Leu Glu Pro
        1880                1885                1890

Pro Cys Pro Glu Gly Ser Gln Glu Gln Gly Ser Pro Glu Ala Cys
        1895                1900                1905

Trp Arg Phe Tyr Pro Lys Phe Trp Thr Ser Pro Pro Leu His Ser
        1910                1915                1920

Leu Gly Leu Arg Ser Val Trp Val His Pro Ser Leu Trp Gly Arg
        1925                1930                1935

Pro Gln Gly Leu Gly Arg Gly Cys His Arg Asn Cys Val Thr Thr
        1940                1945                1950

Thr Trp Lys Pro Ser Cys Cys Pro Gly His Tyr Gly Ser Glu Cys
        1955                1960                1965

Gln Ala Cys Pro Gly Gly Pro Ser Ser Pro Cys Ser Asp Arg Gly
        1970                1975                1980

Val Cys Met Asp Gly Met Ser Gly Ser Gly Gln Cys Leu Cys Arg
        1985                1990                1995

Ser Gly Phe Ala Gly Thr Ala Cys Glu Leu Cys Ala Pro Gly Ala
        2000                2005                2010

Phe Gly Pro His Cys Gln Ala Cys Arg Cys Thr Val His Gly Arg
        2015                2020                2025

Cys Asp Glu Gly Leu Gly Gly Ser Gly Ser Cys Phe Cys Asp Glu
        2030                2035                2040

Gly Trp Thr Gly Pro Arg Cys Glu Val Gln Leu Glu Leu Gln Pro
        2045                2050                2055

Val Cys Thr Pro Pro Cys Ala Pro Glu Ala Val Cys Arg Ala Gly
        2060                2065                2070

Asn Ser Cys Glu Cys Ser Leu Gly Tyr Glu Gly Asp Gly Arg Val
        2075                2080                2085

Cys Thr Val Ala Asp Leu Cys Gln Asp Gly His Gly Gly Cys Ser
        2090                2095                2100

Glu His Ala Asn Cys Ser Gln Val Gly Thr Met Val Thr Cys Thr
        2105                2110                2115

Cys Leu Pro Asp Tyr Glu Gly Asp Gly Trp Ser Cys Arg Ala Arg
        2120                2125                2130

Asn Pro Cys Thr Asp Gly His Arg Gly Gly Cys Ser Glu His Ala
        2135                2140                2145

Asn Cys Leu Ser Thr Gly Leu Asn Thr Arg Arg Cys Glu Cys His
        2150                2155                2160

Ala Gly Tyr Val Gly Asp Gly Leu Gln Cys Leu Glu Glu Ser Glu
        2165                2170                2175
```

```
Pro Pro Val Asp Arg Cys Leu Gly Gln Pro Pro Cys His Ser
    2180             2185             2190

Asp Ala Met Cys Thr Asp Leu His Phe Gln Glu Lys Arg Ala Gly
    2195             2200             2205

Val Phe His Leu Gln Ala Thr Ser Gly Pro Tyr Gly Leu Asn Phe
    2210             2215             2220

Ser Glu Ala Glu Ala Ala Cys Glu Ala Gln Gly Ala Val Leu Ala
    2225             2230             2235

Ser Phe Pro Gln Leu Ser Ala Ala Gln Gln Leu Gly Phe His Leu
    2240             2245             2250

Cys Leu Met Gly Trp Leu Ala Asn Gly Ser Thr Ala His Pro Val
    2255             2260             2265

Val Phe Pro Val Ala Asp Cys Gly Asn Gly Arg Val Gly Ile Val
    2270             2275             2280

Ser Leu Gly Ala Arg Lys Asn Leu Ser Glu Arg Trp Asp Ala Tyr
    2285             2290             2295

Cys Phe Arg Val Gln Asp Val Ala Cys Arg Cys Arg Asn Gly Phe
    2300             2305             2310

Val Gly Asp Gly Ile Ser Thr Cys Asn Gly Lys Leu Leu Asp Val
    2315             2320             2325

Leu Ala Ala Thr Ala Asn Phe Ser Thr Phe Tyr Gly Met Leu Leu
    2330             2335             2340

Gly Tyr Ala Asn Ala Thr Gln Arg Gly Leu Asp Phe Leu Asp Phe
    2345             2350             2355

Leu Asp Asp Glu Leu Thr Tyr Lys Thr Leu Phe Val Pro Val Asn
    2360             2365             2370

Glu Gly Phe Val Asp Asn Met Thr Leu Ser Gly Pro Asp Leu Glu
    2375             2380             2385

Leu His Ala Ser Asn Ala Thr Leu Leu Ser Ala Asn Ala Ser Gln
    2390             2395             2400

Gly Lys Leu Leu Pro Ala His Ser Gly Leu Ser Leu Ile Ile Ser
    2405             2410             2415

Asp Ala Gly Pro Asp Asn Ser Ser Trp Ala Pro Val Ala Pro Gly
    2420             2425             2430

Thr Val Val Val Ser Arg Ile Ile Val Trp Asp Ile Met Ala Phe
    2435             2440             2445

Asn Gly Ile Ile His Ala Leu Ala Ser Pro Leu Leu Ala Pro Pro
    2450             2455             2460

Gln Pro Gln Ala Val Leu Ala Pro Glu Ala Pro Val Ala Ala
    2465             2470             2475

Gly Val Gly Ala Val Leu Ala Ala Gly Ala Leu Leu Gly Leu Val
    2480             2485             2490

Ala Gly Ala Leu Tyr Leu Arg Ala Arg Gly Lys Pro Met Gly Phe
    2495             2500             2505

Gly Phe Ser Ala Phe Gln Ala Glu Asp Asp Ala Asp Asp Asp Phe
    2510             2515             2520

Ser Pro Trp Gln Glu Gly Thr Asn Pro Thr Leu Val Ser Val Pro
    2525             2530             2535

Asn Pro Val Phe Gly Ser Asp Thr Phe Cys Glu Pro Phe Asp Asp
    2540             2545             2550

Ser Leu Leu Glu Glu Asp Phe Pro Asp Thr Gln Arg Ile Leu Thr
    2555             2560             2565
```

Val Lys
    2570

<210> SEQ ID NO 52
<211> LENGTH: 146
<212> TYPE: PRT
<213> ORGANISM: Homo sapiens

<400> SEQUENCE: 52

Met Ala Gly Pro Leu Arg Ala Pro Leu Leu Leu Ala Ile Leu Ala
1               5                   10                  15

Val Ala Leu Ala Val Ser Pro Ala Ala Gly Ser Ser Pro Gly Lys Pro
            20                  25                  30

Pro Arg Leu Val Gly Gly Pro Met Asp Ala Ser Val Glu Glu Glu Gly
            35                  40                  45

Val Arg Arg Ala Leu Asp Phe Ala Val Gly Glu Tyr Asn Lys Ala Ser
50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg
                85                  90                  95

Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
            115                 120                 125

Ala Val Pro Trp Gln Gly Thr Met Thr Leu Ser Lys Ser Thr Cys Gln
            130                 135                 140

Asp Ala
145

<210> SEQ ID NO 53
<211> LENGTH: 782
<212> TYPE: PRT
<213> ORGANISM: Homo sapiens

<400> SEQUENCE: 53

Met Ala Pro His Arg Pro Ala Pro Ala Leu Leu Cys Ala Leu Ser Leu
1               5                   10                  15

Ala Leu Cys Ala Leu Ser Leu Pro Val Arg Ala Ala Thr Ala Ser Arg
            20                  25                  30

Gly Ala Ser Gln Ala Gly Ala Pro Gln Gly Arg Val Pro Glu Ala Arg
            35                  40                  45

Pro Asn Ser Met Val Val Glu His Pro Glu Phe Leu Lys Ala Gly Lys
50                  55                  60

Glu Pro Gly Leu Gln Ile Trp Arg Val Glu Lys Phe Asp Leu Val Pro
65                  70                  75                  80

Val Pro Thr Asn Leu Tyr Gly Asp Phe Phe Thr Gly Asp Ala Tyr Val
            85                  90                  95

Ile Leu Lys Thr Val Gln Leu Arg Asn Gly Asn Leu Gln Tyr Asp Leu
            100                 105                 110

His Tyr Trp Leu Gly Asn Glu Cys Ser Gln Asp Glu Ser Gly Ala Ala
            115                 120                 125

Ala Ile Phe Thr Val Gln Leu Asp Asp Tyr Leu Asn Gly Arg Ala Val
            130                 135                 140

Gln His Arg Glu Val Gln Gly Phe Glu Ser Ala Thr Phe Leu Gly Tyr
145                 150                 155                 160

-continued

```
Phe Lys Ser Gly Leu Lys Tyr Lys Lys Gly Val Ala Ser Gly Phe
            165                 170                 175

Lys His Val Val Pro Asn Glu Val Val Gln Arg Leu Phe Gln Val
            180                 185                 190

Lys Gly Arg Arg Val Val Arg Ala Thr Glu Val Pro Val Ser Trp Glu
            195                 200                 205

Ser Phe Asn Asn Gly Asp Cys Phe Ile Leu Asp Leu Gly Asn Asn Ile
    210                 215                 220

His Gln Trp Cys Gly Ser Asn Ser Asn Arg Tyr Glu Arg Leu Lys Ala
225                 230                 235                 240

Thr Gln Val Ser Lys Gly Ile Arg Asp Asn Glu Arg Ser Gly Arg Ala
                245                 250                 255

Arg Val His Val Ser Glu Glu Gly Thr Glu Pro Glu Ala Met Leu Gln
                260                 265                 270

Val Leu Gly Pro Lys Pro Ala Leu Pro Ala Gly Thr Glu Asp Thr Ala
            275                 280                 285

Lys Glu Asp Ala Ala Asn Arg Lys Leu Ala Lys Leu Tyr Lys Val Ser
    290                 295                 300

Asn Gly Ala Gly Thr Met Ser Val Ser Leu Val Ala Asp Glu Asn Pro
305                 310                 315                 320

Phe Ala Gln Gly Ala Leu Lys Ser Glu Asp Cys Phe Ile Leu Asp His
                325                 330                 335

Gly Lys Asp Gly Lys Ile Phe Val Trp Lys Gly Lys Gln Ala Asn Thr
            340                 345                 350

Glu Glu Arg Lys Ala Ala Leu Lys Thr Ala Ser Asp Phe Ile Thr Lys
        355                 360                 365

Met Asp Tyr Pro Lys Gln Thr Gln Val Ser Val Leu Pro Glu Gly Gly
    370                 375                 380

Glu Thr Pro Leu Phe Lys Gln Phe Phe Lys Asn Trp Arg Asp Pro Asp
385                 390                 395                 400

Gln Thr Asp Gly Leu Gly Leu Ser Tyr Leu Ser Ser His Ile Ala Asn
                405                 410                 415

Val Glu Arg Val Pro Phe Asp Ala Ala Thr Leu His Thr Ser Thr Ala
            420                 425                 430

Met Ala Ala Gln His Gly Met Asp Asp Gly Thr Gly Gln Lys Gln
        435                 440                 445

Ile Trp Arg Ile Glu Gly Ser Asn Lys Val Pro Val Asp Pro Ala Thr
    450                 455                 460

Tyr Gly Gln Phe Tyr Gly Gly Asp Ser Tyr Ile Ile Leu Tyr Asn Tyr
465                 470                 475                 480

Arg His Gly Gly Arg Gln Gly Gln Ile Ile Tyr Asn Trp Gln Gly Ala
                485                 490                 495

Gln Ser Thr Gln Asp Glu Val Ala Ala Ser Ala Ile Leu Thr Ala Gln
            500                 505                 510

Leu Asp Glu Glu Leu Gly Gly Thr Pro Val Gln Ser Arg Val Val Gln
        515                 520                 525

Gly Lys Glu Pro Ala His Leu Met Ser Leu Phe Gly Gly Lys Pro Met
    530                 535                 540

Ile Ile Tyr Lys Gly Gly Thr Ser Arg Glu Gly Gly Gln Thr Ala Pro
545                 550                 555                 560

Ala Ser Thr Arg Leu Phe Gln Val Arg Ala Asn Ser Ala Gly Ala Thr
                565                 570                 575

Arg Ala Val Glu Val Leu Pro Lys Ala Gly Ala Leu Asn Ser Asn Asp
```

```
                    580                 585                 590
Ala Phe Val Leu Lys Thr Pro Ser Ala Ala Tyr Leu Trp Val Gly Thr
                595                 600                 605
Gly Ala Ser Glu Ala Glu Lys Thr Gly Ala Gln Glu Leu Leu Arg Val
            610                 615                 620
Leu Arg Ala Gln Pro Val Gln Val Ala Glu Gly Ser Glu Pro Asp Gly
625                 630                 635                 640
Phe Trp Glu Ala Leu Gly Gly Lys Ala Ala Tyr Arg Thr Ser Pro Arg
                645                 650                 655
Leu Lys Asp Lys Lys Met Asp Ala His Pro Pro Arg Leu Phe Ala Cys
            660                 665                 670
Ser Asn Lys Ile Gly Arg Phe Val Ile Glu Glu Val Pro Gly Glu Leu
        675                 680                 685
Met Gln Glu Asp Leu Ala Thr Asp Asp Val Met Leu Leu Asp Thr Trp
    690                 695                 700
Asp Gln Val Phe Val Trp Val Gly Lys Asp Ser Gln Glu Glu Glu Lys
705                 710                 715                 720
Thr Glu Ala Leu Thr Ser Ala Lys Arg Tyr Ile Glu Thr Asp Pro Ala
                725                 730                 735
Asn Arg Asp Arg Arg Thr Pro Ile Thr Val Val Lys Gln Gly Phe Glu
            740                 745                 750
Pro Pro Ser Phe Val Gly Trp Phe Leu Gly Trp Asp Asp Asp Tyr Trp
        755                 760                 765
Ser Val Asp Pro Leu Asp Arg Ala Met Ala Glu Leu Ala Ala
    770                 775                 780

<210> SEQ ID NO 54
<211> LENGTH: 5890
<212> TYPE: PRT
<213> ORGANISM: Homo sapiens

<400> SEQUENCE: 54

Met Glu Lys Glu Glu Thr Thr Arg Glu Leu Leu Pro Asn Trp Gln
1                   5                   10                  15
Gly Ser Gly Ser His Gly Leu Thr Ile Ala Gln Arg Asp Asp Gly Val
                20                  25                  30
Phe Val Gln Glu Val Thr Gln Asn Ser Pro Ala Ala Arg Thr Gly Val
            35                  40                  45
Val Lys Glu Gly Asp Gln Ile Val Gly Ala Thr Ile Tyr Phe Asp Asn
        50                  55                  60
Leu Gln Ser Gly Glu Val Thr Gln Leu Leu Asn Thr Met Gly His His
65                  70                  75                  80
Thr Val Gly Leu Lys Leu His Arg Lys Gly Asp Arg Ser Pro Glu Pro
                85                  90                  95
Gly Gln Thr Trp Thr Arg Glu Val Phe Ser Ser Cys Ser Ser Glu Val
            100                 105                 110
Val Leu Ser Gly Asp Asp Glu Glu Tyr Gln Arg Ile Tyr Thr Thr Lys
        115                 120                 125
Ile Lys Pro Arg Leu Lys Ser Glu Asp Gly Val Glu Gly Asp Leu Gly
    130                 135                 140
Glu Thr Gln Ser Arg Thr Ile Thr Val Thr Arg Arg Val Thr Ala Tyr
145                 150                 155                 160
Thr Val Asp Val Thr Gly Arg Glu Gly Ala Lys Asp Ile Asp Ile Ser
                165                 170                 175
```

```
Ser Pro Glu Phe Lys Ile Lys Ile Pro Arg His Glu Leu Thr Glu Ile
            180                 185                 190

Ser Asn Val Asp Val Glu Thr Gln Ser Gly Lys Thr Val Ile Arg Leu
        195                 200                 205

Pro Ser Gly Ser Gly Ala Ala Ser Pro Thr Gly Ser Ala Val Asp Ile
    210                 215                 220

Arg Ala Gly Ala Ile Ser Ala Ser Gly Pro Glu Leu Gln Gly Ala Gly
225                 230                 235                 240

His Ser Lys Leu Gln Val Thr Met Pro Gly Ile Lys Val Gly Gly Ser
                245                 250                 255

Gly Val Asn Val Asn Ala Lys Gly Leu Asp Leu Gly Gly Arg Gly Gly
            260                 265                 270

Val Gln Val Pro Ala Val Asp Ile Ser Ser Leu Gly Gly Arg Ala
        275                 280                 285

Val Glu Val Gln Gly Pro Ser Leu Glu Ser Gly Asp His Gly Lys Ile
    290                 295                 300

Lys Phe Pro Thr Met Lys Val Pro Lys Phe Gly Val Ser Thr Gly Arg
305                 310                 315                 320

Glu Gly Gln Thr Pro Lys Ala Gly Leu Arg Val Ser Ala Pro Glu Val
                325                 330                 335

Ser Val Gly His Lys Gly Lys Pro Gly Leu Thr Ile Gln Ala Pro
            340                 345                 350

Gln Leu Glu Val Ser Val Pro Ser Ala Asn Ile Glu Gly Leu Glu Gly
        355                 360                 365

Lys Leu Lys Gly Pro Gln Ile Thr Gly Pro Ser Leu Glu Gly Asp Leu
370                 375                 380

Gly Leu Lys Gly Ala Lys Pro Gln Gly His Ile Gly Val Asp Ala Ser
385                 390                 395                 400

Ala Pro Gln Ile Gly Gly Ser Ile Thr Gly Pro Ser Val Glu Val Gln
                405                 410                 415

Ala Pro Asp Ile Asp Val Gln Gly Pro Gly Ser Lys Leu Asn Val Pro
            420                 425                 430

Lys Met Lys Val Pro Lys Phe Ser Val Ser Gly Ala Lys Gly Glu Glu
        435                 440                 445

Thr Gly Ile Asp Val Thr Leu Pro Thr Gly Glu Val Thr Val Pro Gly
    450                 455                 460

Val Ser Gly Asp Val Ser Leu Pro Glu Ile Ala Thr Gly Gly Leu Glu
465                 470                 475                 480

Gly Lys Met Lys Gly Thr Lys Val Lys Thr Pro Glu Met Ile Ile Gln
                485                 490                 495

Lys Pro Lys Ile Ser Met Gln Asp Val Asp Leu Ser Leu Gly Ser Pro
            500                 505                 510

Lys Leu Lys Gly Asp Ile Lys Val Ser Ala Pro Gly Val Gln Gly Asp
        515                 520                 525

Val Lys Gly Pro Gln Val Ala Leu Lys Gly Ser Arg Val Asp Ile Glu
    530                 535                 540

Thr Pro Asn Leu Glu Gly Thr Leu Thr Gly Pro Arg Leu Gly Ser Pro
545                 550                 555                 560

Ser Gly Lys Thr Gly Thr Cys Arg Ile Ser Met Ser Glu Val Asp Leu
                565                 570                 575

Asn Val Ala Ala Pro Lys Val Lys Gly Val Asp Val Thr Leu Pro
            580                 585                 590

Arg Val Glu Gly Lys Val Lys Val Pro Glu Val Asp Val Arg Gly Pro
```

```
            595                 600                 605
Lys Val Asp Val Ser Ala Pro Asp Val Glu Ala His Gly Pro Glu Trp
610                 615                 620

Asn Leu Lys Met Pro Lys Met Lys Met Pro Thr Phe Ser Thr Pro Gly
625                 630                 635                 640

Ala Lys Gly Glu Gly Pro Asp Val His Met Thr Leu Pro Lys Gly Asp
                645                 650                 655

Ile Ser Ile Ser Gly Pro Lys Val Asn Val Glu Ala Pro Asp Val Asn
                660                 665                 670

Leu Glu Gly Leu Gly Gly Lys Leu Lys Gly Pro Asp Val Lys Leu Pro
                675                 680                 685

Asp Met Ser Val Lys Thr Pro Lys Ile Ser Met Pro Asp Val Asp Leu
                690                 695                 700

His Val Lys Gly Thr Lys Val Lys Gly Glu Tyr Asp Val Thr Val Pro
705                 710                 715                 720

Lys Leu Glu Gly Glu Leu Lys Gly Pro Lys Val Asp Ile Asp Ala Pro
                725                 730                 735

Asp Val Asp Val His Gly Pro Asp Trp His Leu Lys Met Pro Lys Met
                740                 745                 750

Lys Met Pro Lys Phe Ser Val Pro Gly Phe Lys Ala Glu Gly Pro Glu
                755                 760                 765

Val Asp Val Asn Leu Pro Lys Ala Asp Val Asp Ile Ser Gly Pro Lys
770                 775                 780

Ile Asp Val Thr Ala Pro Asp Val Ser Ile Glu Glu Pro Glu Gly Lys
785                 790                 795                 800

Leu Lys Gly Pro Lys Phe Lys Met Pro Glu Met Asn Ile Lys Val Pro
                805                 810                 815

Lys Ile Ser Met Pro Asp Val Asp Leu His Leu Lys Gly Pro Asn Val
                820                 825                 830

Lys Gly Glu Tyr Asp Val Thr Met Pro Lys Val Glu Ser Glu Ile Lys
                835                 840                 845

Val Pro Asp Val Glu Leu Lys Ser Ala Lys Met Asp Ile Asp Val Pro
850                 855                 860

Asp Val Glu Val Gln Gly Pro Asp Trp His Leu Lys Met Pro Lys Met
865                 870                 875                 880

Lys Met Pro Lys Phe Ser Met Pro Gly Phe Lys Ala Glu Gly Pro Glu
                885                 890                 895

Val Asp Val Asn Leu Pro Lys Ala Asp Val Asp Ile Ser Gly Pro Lys
                900                 905                 910

Val Gly Val Glu Val Pro Asp Val Asn Ile Glu Gly Pro Glu Gly Lys
                915                 920                 925

Leu Lys Gly Pro Lys Phe Lys Met Pro Glu Met Asn Ile Lys Ala Pro
                930                 935                 940

Lys Ile Ser Met Pro Asp Val Asp Leu His Met Lys Gly Pro Lys Val
945                 950                 955                 960

Lys Gly Glu Tyr Asp Met Thr Val Pro Lys Leu Glu Gly Asp Leu Lys
                965                 970                 975

Gly Pro Lys Val Asp Val Ser Ala Pro Asp Val Glu Met Gln Gly Pro
                980                 985                 990

Asp Trp Asn Leu Lys Met Pro Lys Ile Lys Met Pro Lys Phe Ser Met
                995                 1000                1005

Pro Ser Leu Lys Gly Glu Gly Pro Glu Phe Asp Val Asn Leu Ser
      1010                1015                1020
```

-continued

```
Lys Ala Asn Val Asp Ile Ser Ala Pro Lys Val Asp Thr Asn Ala
    1025                1030                1035
Pro Asp Leu Ser Leu Glu Gly Pro Glu Gly Lys Leu Lys Gly Pro
    1040                1045                1050
Lys Phe Lys Met Pro Glu Met His Phe Arg Ala Pro Lys Met Ser
    1055                1060                1065
Leu Pro Asp Val Asp Leu Asp Leu Lys Gly Pro Lys Met Lys Gly
    1070                1075                1080
Asn Val Asp Ile Ser Ala Pro Lys Ile Glu Gly Glu Met Gln Val
    1085                1090                1095
Pro Asp Val Asp Ile Arg Gly Pro Lys Val Asp Ile Lys Ala Pro
    1100                1105                1110
Asp Val Glu Gly Gln Gly Leu Asp Trp Ser Leu Lys Ile Pro Lys
    1115                1120                1125
Met Lys Met Pro Lys Phe Ser Met Pro Ser Leu Lys Gly Glu Gly
    1130                1135                1140
Pro Glu Val Asp Val Asn Leu Pro Lys Ala Asp Val Val Val Ser
    1145                1150                1155
Gly Pro Lys Val Asp Ile Glu Ala Pro Asp Val Ser Leu Glu Gly
    1160                1165                1170
Pro Glu Gly Lys Leu Lys Gly Pro Lys Phe Lys Met Pro Glu Met
    1175                1180                1185
His Phe Lys Thr Pro Lys Ile Ser Met Pro Asp Val Asp Leu His
    1190                1195                1200
Leu Lys Gly Pro Lys Val Lys Gly Asp Val Asp Val Ser Val Pro
    1205                1210                1215
Lys Val Glu Gly Glu Met Lys Val Pro Asp Val Glu Ile Lys Gly
    1220                1225                1230
Pro Lys Met Asp Ile Asp Ala Pro Asp Val Glu Val Gln Gly Pro
    1235                1240                1245
Asp Trp His Leu Lys Met Pro Lys Met Lys Met Pro Lys Phe Ser
    1250                1255                1260
Met Pro Gly Phe Lys Gly Glu Gly Arg Glu Val Asp Val Asn Leu
    1265                1270                1275
Pro Lys Ala Asp Ile Asp Val Ser Gly Pro Lys Val Asp Val Glu
    1280                1285                1290
Val Pro Asp Val Ser Leu Glu Gly Pro Glu Gly Lys Leu Lys Gly
    1295                1300                1305
Pro Lys Phe Lys Met Pro Glu Met His Phe Lys Ala Pro Lys Ile
    1310                1315                1320
Ser Met Pro Asp Val Asp Leu Asn Leu Lys Gly Pro Lys Leu Lys
    1325                1330                1335
Gly Asp Val Asp Val Ser Leu Pro Glu Val Glu Gly Glu Met Lys
    1340                1345                1350
Val Pro Asp Val Asp Ile Lys Gly Pro Lys Val Asp Ile Ser Ala
    1355                1360                1365
Pro Asp Val Asp Val His Gly Pro Asp Trp His Leu Lys Met Pro
    1370                1375                1380
Lys Val Lys Met Pro Lys Phe Ser Met Pro Gly Phe Lys Gly Glu
    1385                1390                1395
Gly Pro Glu Val Asp Val Lys Leu Pro Lys Ala Asp Val Asp Val
    1400                1405                1410
```

```
Ser Gly Pro Lys Met Asp Ala Glu Val Pro Asp Val Asn Ile Glu
    1415                1420                1425

Gly Pro Asp Ala Lys Leu Lys Gly Pro Lys Phe Lys Met Pro Glu
    1430                1435                1440

Met Ser Ile Lys Pro Gln Lys Ile Ser Ile Pro Asp Val Gly Leu
    1445                1450                1455

His Leu Lys Gly Pro Lys Met Lys Gly Asp Tyr Asp Val Thr Val
    1460                1465                1470

Pro Lys Val Glu Gly Glu Ile Lys Ala Pro Asp Val Asp Ile Lys
    1475                1480                1485

Gly Pro Lys Val Asp Ile Asn Ala Pro Asp Val Glu Val His Gly
    1490                1495                1500

Pro Asp Trp His Leu Lys Met Pro Lys Val Lys Met Pro Lys Phe
    1505                1510                1515

Ser Met Pro Gly Phe Lys Gly Glu Gly Pro Glu Val Asp Met Asn
    1520                1525                1530

Leu Pro Lys Ala Asp Leu Gly Val Ser Gly Pro Lys Val Asp Ile
    1535                1540                1545

Asp Val Pro Asp Val Asn Leu Glu Ala Pro Glu Gly Lys Leu Lys
    1550                1555                1560

Gly Pro Lys Phe Lys Met Pro Ser Met Asn Ile Gln Thr His Lys
    1565                1570                1575

Ile Ser Met Pro Asp Val Gly Leu Asn Leu Lys Ala Pro Lys Leu
    1580                1585                1590

Lys Thr Asp Val Asp Val Ser Leu Pro Lys Val Glu Gly Asp Leu
    1595                1600                1605

Lys Gly Pro Glu Ile Asp Val Lys Ala Pro Lys Met Asp Val Asn
    1610                1615                1620

Val Gly Asp Ile Asp Ile Glu Gly Pro Glu Gly Lys Leu Lys Gly
    1625                1630                1635

Pro Lys Phe Lys Met Pro Glu Met His Phe Lys Ala Pro Lys Ile
    1640                1645                1650

Ser Met Pro Asp Val Asp Leu His Leu Lys Gly Pro Lys Val Lys
    1655                1660                1665

Gly Asp Met Asp Val Ser Val Pro Lys Val Glu Gly Glu Met Lys
    1670                1675                1680

Val Pro Asp Val Asp Ile Lys Gly Pro Lys Val Asp Ile Asp Ala
    1685                1690                1695

Pro Asp Val Glu Val His Asp Pro Asp Trp His Leu Lys Met Pro
    1700                1705                1710

Lys Met Lys Met Pro Lys Phe Ser Met Pro Gly Phe Lys Ala Glu
    1715                1720                1725

Gly Pro Glu Val Asp Val Asn Leu Pro Lys Ala Asp Ile Asp Val
    1730                1735                1740

Ser Gly Pro Ser Val Asp Thr Asp Ala Pro Asp Leu Asp Ile Glu
    1745                1750                1755

Gly Pro Glu Gly Lys Leu Lys Gly Ser Lys Phe Lys Met Pro Lys
    1760                1765                1770

Leu Asn Ile Lys Ala Pro Lys Val Ser Met Pro Asp Val Asp Leu
    1775                1780                1785

Asn Leu Lys Gly Pro Lys Leu Lys Gly Glu Ile Asp Ala Ser Val
    1790                1795                1800

Pro Glu Leu Glu Gly Asp Leu Arg Gly Pro Gln Val Asp Val Lys
```

-continued

```
            1805                1810                1815
Gly Pro Phe Val Glu Ala Glu Val Pro Asp Val Asp Leu Glu Cys
            1820                1825                1830
Pro Asp Ala Lys Leu Lys Gly Pro Lys Phe Lys Met Pro Glu Met
            1835                1840                1845
His Phe Lys Ala Pro Lys Ile Ser Met Pro Asp Val Asp Leu His
            1850                1855                1860
Leu Lys Gly Pro Lys Val Lys Gly Asp Ala Asp Val Ser Val Pro
            1865                1870                1875
Lys Leu Glu Gly Asp Leu Thr Gly Pro Ser Val Gly Val Glu Val
            1880                1885                1890
Pro Asp Val Glu Leu Glu Cys Pro Asp Ala Lys Leu Lys Gly Pro
            1895                1900                1905
Lys Phe Lys Met Pro Asp Met His Phe Lys Ala Pro Lys Ile Ser
            1910                1915                1920
Met Pro Asp Val Asp Leu His Leu Lys Gly Pro Lys Val Lys Gly
            1925                1930                1935
Asp Val Asp Val Ser Val Pro Lys Leu Glu Gly Asp Leu Thr Gly
            1940                1945                1950
Pro Ser Val Gly Val Glu Val Pro Asp Val Glu Leu Glu Cys Pro
            1955                1960                1965
Asp Ala Lys Leu Lys Gly Pro Lys Phe Lys Met Pro Glu Met His
            1970                1975                1980
Phe Lys Thr Pro Lys Ile Ser Met Pro Asp Val Asp Leu His Leu
            1985                1990                1995
Lys Gly Pro Lys Val Lys Gly Asp Met Asp Val Ser Val Pro Lys
            2000                2005                2010
Val Glu Gly Glu Met Lys Val Pro Asp Val Asp Ile Lys Gly Pro
            2015                2020                2025
Lys Met Asp Ile Asp Ala Pro Asp Val Asp Val His Gly Pro Asp
            2030                2035                2040
Trp His Leu Lys Met Pro Lys Met Lys Met Pro Lys Phe Ser Met
            2045                2050                2055
Pro Gly Phe Lys Ala Glu Gly Pro Glu Val Asp Val Asn Leu Pro
            2060                2065                2070
Lys Ala Asp Val Val Val Ser Gly Pro Lys Val Asp Val Glu Val
            2075                2080                2085
Pro Asp Val Ser Leu Glu Gly Pro Glu Gly Lys Leu Lys Gly Pro
            2090                2095                2100
Lys Leu Lys Met Pro Glu Met His Phe Lys Ala Pro Lys Ile Ser
            2105                2110                2115
Met Pro Asp Val Asp Leu His Leu Lys Gly Pro Lys Val Lys Gly
            2120                2125                2130
Asp Val Asp Val Ser Leu Pro Lys Leu Glu Gly Asp Leu Thr Gly
            2135                2140                2145
Pro Ser Val Asp Val Glu Val Pro Asp Val Glu Leu Glu Cys Pro
            2150                2155                2160
Asp Ala Lys Leu Lys Gly Pro Lys Phe Lys Met Pro Glu Met His
            2165                2170                2175
Phe Lys Thr Pro Lys Ile Ser Met Pro Asp Val Asn Leu Asn Leu
            2180                2185                2190
Lys Gly Pro Lys Val Lys Gly Asp Met Asp Val Ser Val Pro Lys
            2195                2200                2205
```

-continued

```
Val Glu Gly Glu Met Lys Val Pro Asp Val Asp Ile Arg Gly Pro
    2210            2215                2220
Lys Val Asp Ile Asp Ala Pro Asp Val Asp Val His Gly Pro Asp
    2225            2230                2235
Trp His Leu Lys Met Pro Lys Met Lys Met Pro Lys Phe Ser Met
    2240            2245                2250
Pro Gly Phe Lys Gly Glu Gly Pro Glu Val Asp Val Asn Leu Pro
    2255            2260                2265
Lys Ala Asp Val Asp Val Ser Gly Pro Lys Val Asp Val Glu Val
    2270            2275                2280
Pro Asp Val Ser Leu Glu Gly Pro Glu Gly Lys Leu Lys Gly Pro
    2285            2290                2295
Lys Phe Lys Met Pro Glu Met His Phe Lys Thr Pro Lys Ile Ser
    2300            2305                2310
Met Pro Asp Val Asp Phe Asn Leu Lys Gly Pro Lys Ile Lys Gly
    2315            2320                2325
Asp Val Asp Val Ser Ala Pro Lys Leu Glu Gly Glu Leu Lys Gly
    2330            2335                2340
Pro Glu Leu Asp Val Lys Gly Pro Lys Leu Asp Ala Asp Met Pro
    2345            2350                2355
Glu Val Ala Val Glu Gly Pro Asn Gly Lys Trp Lys Thr Pro Lys
    2360            2365                2370
Phe Lys Met Pro Asp Met His Phe Lys Ala Pro Lys Ile Ser Met
    2375            2380                2385
Pro Asp Leu Asp Leu His Leu Lys Ser Pro Lys Ala Lys Gly Glu
    2390            2395                2400
Val Asp Val Asp Val Pro Lys Leu Glu Gly Asp Leu Lys Gly Pro
    2405            2410                2415
His Val Asp Val Ser Gly Pro Asp Ile Asp Ile Glu Gly Pro Glu
    2420            2425                2430
Gly Lys Leu Lys Gly Pro Lys Phe Lys Met Pro Asp Met His Phe
    2435            2440                2445
Lys Ala Pro Asn Ile Ser Met Pro Asp Val Asp Leu Asn Leu Lys
    2450            2455                2460
Gly Pro Lys Ile Lys Gly Asp Val Asp Val Ser Val Pro Glu Val
    2465            2470                2475
Glu Gly Lys Leu Glu Val Pro Asp Met Asn Ile Arg Gly Pro Lys
    2480            2485                2490
Val Asp Val Asn Ala Pro Asp Val Gln Ala Pro Asp Trp His Leu
    2495            2500                2505
Lys Met Pro Lys Met Lys Met Pro Lys Phe Ser Met Pro Gly Phe
    2510            2515                2520
Lys Ala Glu Gly Pro Glu Val Asp Val Asn Leu Pro Lys Ala Asp
    2525            2530                2535
Val Asp Ile Ser Gly Pro Lys Val Asp Ile Glu Gly Pro Asp Val
    2540            2545                2550
Asn Ile Glu Gly Pro Glu Gly Lys Leu Lys Gly Pro Lys Leu Lys
    2555            2560                2565
Met Pro Glu Met Asn Ile Lys Ala Pro Lys Ile Ser Met Pro Asp
    2570            2575                2580
Phe Asp Leu His Leu Lys Gly Pro Lys Val Lys Gly Asp Val Asp
    2585            2590                2595
```

-continued

Val Ser Leu Pro Lys Val Glu Gly Asp Leu Lys Gly Pro Glu Val
2600            2605                2610

Asp Ile Lys Gly Pro Lys Val Asp Ile Asn Ala Pro Asp Val Gly
2615            2620                2625

Val Gln Gly Pro Asp Trp His Leu Lys Met Pro Lys Val Lys Met
2630            2635                2640

Pro Lys Phe Ser Met Pro Gly Phe Lys Gly Glu Gly Pro Asp Gly
2645            2650                2655

Asp Val Lys Leu Pro Lys Ala Asp Ile Asp Val Ser Gly Pro Lys
2660            2665                2670

Val Asp Ile Glu Gly Pro Asp Val Asn Ile Glu Gly Pro Glu Gly
2675            2680                2685

Lys Leu Lys Gly Pro Lys Phe Lys Met Pro Glu Met Asn Ile Lys
2690            2695                2700

Ala Pro Lys Ile Ser Met Pro Asp Ile Asp Leu Asn Leu Lys Gly
2705            2710                2715

Pro Lys Val Lys Gly Asp Val Asp Val Ser Leu Pro Lys Val Glu
2720            2725                2730

Gly Asp Leu Lys Gly Pro Glu Val Asp Ile Lys Gly Pro Lys Val
2735            2740                2745

Asp Ile Asp Ala Pro Asp Val Asp Val His Gly Pro Asp Trp His
2750            2755                2760

Leu Lys Met Pro Lys Ile Lys Met Pro Lys Ile Ser Met Pro Gly
2765            2770                2775

Phe Lys Gly Glu Gly Pro Asp Val Asp Val Asn Leu Pro Lys Ala
2780            2785                2790

Asp Ile Asp Val Ser Gly Pro Lys Val Asp Val Glu Cys Pro Asp
2795            2800                2805

Val Asn Ile Glu Gly Pro Glu Gly Lys Trp Lys Ser Pro Lys Phe
2810            2815                2820

Lys Met Pro Glu Met His Phe Lys Thr Pro Lys Ile Ser Met Pro
2825            2830                2835

Asp Ile Asp Leu Asn Leu Thr Gly Pro Lys Ile Lys Gly Asp Val
2840            2845                2850

Asp Val Thr Gly Pro Lys Val Glu Gly Asp Leu Lys Gly Pro Glu
2855            2860                2865

Val Asp Leu Lys Gly Pro Lys Val Asp Ile Asp Val Pro Asp Val
2870            2875                2880

Asn Val Gln Gly Pro Asp Trp His Leu Lys Met Pro Lys Met Lys
2885            2890                2895

Met Pro Lys Phe Ser Met Pro Gly Phe Lys Ala Glu Gly Pro Glu
2900            2905                2910

Val Asp Val Asn Leu Pro Lys Ala Asp Val Asp Val Ser Gly Pro
2915            2920                2925

Lys Val Asp Val Glu Gly Pro Asp Val Asn Ile Glu Gly Pro Glu
2930            2935                2940

Gly Lys Leu Lys Gly Pro Lys Phe Lys Met Pro Glu Met Asn Ile
2945            2950                2955

Lys Ala Pro Lys Ile Pro Met Pro Asp Phe Asp Leu His Leu Lys
2960            2965                2970

Gly Pro Lys Val Lys Gly Asp Val Asp Ile Ser Leu Pro Lys Val
2975            2980                2985

Glu Gly Asp Leu Lys Gly Pro Glu Val Asp Ile Arg Gly Pro Gln

```
                 2990                2995                3000
Val Asp Ile Asp Val Pro Asp Val Gly Val Gln Gly Pro Asp Trp
    3005                3010                3015
His Leu Lys Met Pro Lys Val Lys Met Pro Lys Phe Ser Met Pro
    3020                3025                3030
Gly Phe Lys Gly Glu Gly Pro Asp Val Asp Val Asn Leu Pro Lys
    3035                3040                3045
Ala Asp Leu Asp Val Ser Gly Pro Lys Val Asp Ile Asp Val Pro
    3050                3055                3060
Asp Val Asn Ile Glu Gly Pro Glu Gly Lys Leu Lys Gly Pro Lys
    3065                3070                3075
Phe Lys Met Pro Glu Met Asn Ile Lys Ala Pro Lys Ile Ser Met
    3080                3085                3090
Pro Asp Ile Asp Leu Asn Leu Lys Gly Pro Lys Val Lys Gly Asp
    3095                3100                3105
Met Asp Val Ser Leu Pro Lys Val Glu Gly Asp Met Lys Val Pro
    3110                3115                3120
Asp Val Asp Ile Lys Gly Pro Lys Val Asp Ile Asn Ala Pro Asp
    3125                3130                3135
Val Asp Val Gln Gly Pro Asp Trp His Leu Lys Met Pro Lys Ile
    3140                3145                3150
Lys Met Pro Lys Ile Ser Met Pro Gly Phe Lys Gly Glu Gly Pro
    3155                3160                3165
Glu Val Asp Val Asn Leu Pro Lys Ala Asp Leu Asp Val Ser Gly
    3170                3175                3180
Pro Lys Val Asp Val Asp Val Pro Asp Val Asn Ile Glu Gly Pro
    3185                3190                3195
Asp Ala Lys Leu Lys Gly Pro Lys Phe Lys Met Pro Glu Met Asn
    3200                3205                3210
Ile Lys Ala Pro Lys Ile Ser Met Pro Asp Leu Asp Leu Asn Leu
    3215                3220                3225
Lys Gly Pro Lys Met Lys Gly Glu Val Asp Val Ser Leu Ala Asn
    3230                3235                3240
Val Glu Gly Asp Leu Lys Gly Pro Ala Leu Asp Ile Lys Gly Pro
    3245                3250                3255
Lys Ile Asp Val Asp Ala Pro Asp Ile Asp Ile His Gly Pro Asp
    3260                3265                3270
Ala Lys Leu Lys Gly Pro Lys Leu Lys Met Pro Asp Met His Val
    3275                3280                3285
Asn Met Pro Lys Ile Ser Met Pro Glu Ile Asp Leu Asn Leu Lys
    3290                3295                3300
Gly Ser Lys Leu Lys Gly Asp Val Asp Val Ser Gly Pro Lys Leu
    3305                3310                3315
Glu Gly Asp Ile Lys Ala Pro Ser Leu Asp Ile Lys Gly Pro Glu
    3320                3325                3330
Val Asp Val Ser Gly Pro Lys Leu Asn Ile Glu Gly Lys Ser Lys
    3335                3340                3345
Lys Ser Arg Phe Lys Leu Pro Lys Phe Asn Phe Ser Gly Ser Lys
    3350                3355                3360
Val Gln Thr Pro Glu Val Asp Val Lys Gly Lys Lys Pro Asp Ile
    3365                3370                3375
Asp Ile Thr Gly Pro Lys Val Asp Ile Asn Ala Pro Asp Val Glu
    3380                3385                3390
```

-continued

```
Val Gln Gly Lys Val Lys Gly Ser Lys Phe Lys Met Pro Phe Leu
    3395            3400            3405

Ser Ile Ser Ser Pro Lys Val Ser Met Pro Asp Val Glu Leu Asn
    3410            3415            3420

Leu Lys Ser Pro Lys Val Lys Gly Asp Leu Asp Ile Ala Gly Pro
    3425            3430            3435

Asn Leu Glu Gly Asp Phe Lys Gly Pro Lys Val Asp Ile Lys Ala
    3440            3445            3450

Pro Glu Val Asn Leu Asn Ala Pro Asp Val Asp Val His Gly Pro
    3455            3460            3465

Asp Trp Asn Leu Lys Met Pro Lys Met Lys Met Pro Lys Phe Ser
    3470            3475            3480

Val Ser Gly Leu Lys Ala Glu Gly Pro Asp Val Ala Val Asp Leu
    3485            3490            3495

Pro Lys Gly Asp Ile Asn Ile Glu Gly Pro Ser Met Asn Ile Glu
    3500            3505            3510

Gly Pro Asp Leu Asn Val Glu Gly Pro Glu Gly Gly Leu Lys Gly
    3515            3520            3525

Pro Lys Phe Lys Met Pro Asp Met Asn Ile Lys Ala Pro Lys Ile
    3530            3535            3540

Ser Met Pro Asp Ile Asp Leu Asn Leu Lys Gly Pro Lys Val Lys
    3545            3550            3555

Gly Asp Val Asp Ile Ser Leu Pro Lys Leu Glu Gly Asp Leu Lys
    3560            3565            3570

Gly Pro Glu Val Asp Ile Lys Gly Pro Lys Val Asp Ile Asn Ala
    3575            3580            3585

Pro Asp Val Asp Val His Gly Pro Asp Trp His Leu Lys Met Pro
    3590            3595            3600

Lys Val Lys Met Pro Lys Phe Ser Met Pro Gly Phe Lys Gly Glu
    3605            3610            3615

Gly Pro Glu Val Asp Val Thr Leu Pro Lys Ala Asp Ile Asp Ile
    3620            3625            3630

Ser Gly Pro Asn Val Asp Val Asp Val Pro Asp Val Asn Ile Glu
    3635            3640            3645

Gly Pro Asp Ala Lys Leu Lys Gly Pro Lys Phe Lys Met Pro Glu
    3650            3655            3660

Met Asn Ile Lys Ala Pro Lys Ile Ser Met Pro Asp Phe Asp Leu
    3665            3670            3675

Asn Leu Lys Gly Pro Lys Met Lys Gly Asp Val Val Val Ser Leu
    3680            3685            3690

Pro Lys Val Glu Gly Asp Leu Lys Gly Pro Glu Val Asp Ile Lys
    3695            3700            3705

Gly Pro Lys Val Asp Ile Asp Thr Pro Asp Ile Asn Ile Glu Gly
    3710            3715            3720

Ser Glu Gly Lys Phe Lys Gly Pro Lys Phe Lys Ile Pro Glu Met
    3725            3730            3735

His Leu Lys Ala Pro Lys Ile Ser Met Pro Asp Ile Asp Leu Asn
    3740            3745            3750

Leu Lys Gly Pro Lys Val Lys Gly Asp Val Asp Val Ser Leu Pro
    3755            3760            3765

Lys Met Glu Gly Asp Leu Lys Gly Pro Glu Val Asp Ile Lys Gly
    3770            3775            3780
```

```
Pro Lys Val Asp Ile Asn Ala Pro Asp Val Asp Val Gln Gly Pro
    3785                3790                3795

Asp Trp His Leu Lys Met Pro Lys Val Lys Met Pro Lys Phe Ser
    3800                3805                3810

Met Pro Gly Phe Lys Gly Glu Gly Pro Asp Val Asp Val Asn Leu
    3815                3820                3825

Pro Lys Ala Asp Leu Asp Val Ser Gly Pro Lys Val Asp Ile Asp
    3830                3835                3840

Val Pro Asp Val Asn Ile Glu Gly Pro Glu Gly Lys Leu Lys Gly
    3845                3850                3855

Pro Lys Phe Lys Met Pro Glu Met Asn Ile Lys Ala Pro Lys Ile
    3860                3865                3870

Ser Met Pro Asp Ile Asp Leu Asn Leu Lys Gly Pro Lys Val Lys
    3875                3880                3885

Gly Asp Met Asp Val Ser Leu Pro Lys Val Glu Gly Asp Met Gln
    3890                3895                3900

Val Pro Asp Leu Asp Ile Lys Gly Pro Lys Val Asp Ile Asn Ala
    3905                3910                3915

Pro Asp Val Asp Val Arg Gly Pro Asp Trp His Leu Lys Met Pro
    3920                3925                3930

Lys Ile Lys Met Pro Lys Ile Ser Met Pro Gly Phe Lys Gly Glu
    3935                3940                3945

Gly Pro Glu Val Asp Val Asn Leu Pro Lys Ala Asp Leu Asp Val
    3950                3955                3960

Ser Gly Pro Lys Val Asp Val Asp Val Pro Asp Val Asn Ile Glu
    3965                3970                3975

Gly Pro Asp Ala Lys Leu Lys Gly Pro Lys Phe Lys Met Pro Glu
    3980                3985                3990

Met Asn Ile Lys Ala Pro Lys Ile Ser Met Pro Asp Phe Asp Leu
    3995                4000                4005

His Leu Lys Gly Pro Lys Val Lys Gly Asp Val Asp Val Ser Leu
    4010                4015                4020

Pro Lys Met Glu Gly Asp Leu Lys Ala Pro Glu Val Asp Ile Lys
    4025                4030                4035

Gly Pro Lys Val Asp Ile Asp Ala Pro Asp Val Asp Val His Gly
    4040                4045                4050

Pro Asp Trp His Leu Lys Met Pro Lys Val Lys Met Pro Lys Phe
    4055                4060                4065

Ser Met Pro Gly Phe Lys Gly Glu Gly Pro Glu Val Asp Val Asn
    4070                4075                4080

Leu Pro Lys Ala Asp Ile Asp Val Ser Gly Pro Lys Val Asp Ile
    4085                4090                4095

Asp Thr Pro Asp Ile Asp Ile His Gly Pro Glu Gly Lys Leu Lys
    4100                4105                4110

Gly Pro Lys Phe Lys Met Pro Asp Leu His Leu Lys Ala Pro Lys
    4115                4120                4125

Ile Ser Met Pro Glu Val Asp Leu Asn Leu Lys Gly Pro Lys Met
    4130                4135                4140

Lys Gly Asp Val Asp Val Ser Leu Pro Lys Val Glu Gly Asp Leu
    4145                4150                4155

Lys Gly Pro Glu Val Asp Ile Lys Gly Pro Lys Val Asp Ile Asp
    4160                4165                4170

Val Pro Asp Val Asp Val Gln Gly Pro Asp Trp His Leu Lys Met
```

-continued

```
                    4175                4180                4185

Pro Lys Val Lys Met Pro Lys Phe Ser Met Pro Gly Phe Lys Gly
        4190                4195                4200

Glu Gly Pro Asp Val Asp Val Asn Leu Pro Lys Ala Asp Leu Asp
        4205                4210                4215

Val Ser Gly Pro Lys Val Asp Ile Asp Val Pro Asp Val Asn Ile
        4220                4225                4230

Glu Gly Pro Asp Ala Lys Leu Lys Gly Pro Lys Phe Lys Met Pro
        4235                4240                4245

Glu Met Asn Ile Lys Ala Pro Lys Ile Ser Met Pro Asp Phe Asp
        4250                4255                4260

Leu His Leu Lys Gly Pro Lys Val Lys Gly Asp Val Asp Val Ser
        4265                4270                4275

Leu Pro Lys Val Glu Gly Asp Leu Lys Gly Pro Glu Val Asp Ile
        4280                4285                4290

Lys Gly Pro Lys Val Asp Ile Asp Ala Pro Asp Val Asp Val His
        4295                4300                4305

Gly Pro Asp Trp His Leu Lys Met Pro Lys Val Lys Met Pro Lys
        4310                4315                4320

Phe Ser Met Pro Gly Phe Lys Gly Glu Gly Pro Asp Val Asp Val
        4325                4330                4335

Thr Leu Pro Lys Ala Asp Ile Glu Ile Ser Gly Pro Lys Val Asp
        4340                4345                4350

Ile Asp Ala Pro Asp Val Ser Ile Glu Gly Pro Asp Ala Lys Leu
        4355                4360                4365

Lys Gly Pro Lys Phe Lys Met Pro Glu Met Asn Ile Lys Ala Pro
        4370                4375                4380

Lys Ile Ser Met Pro Asp Ile Asp Phe Asn Leu Lys Gly Pro Lys
        4385                4390                4395

Val Lys Gly Asp Val Asp Val Ser Leu Pro Lys Val Glu Gly Asp
        4400                4405                4410

Leu Lys Gly Pro Glu Ile Asp Ile Lys Gly Pro Ser Leu Asp Ile
        4415                4420                4425

Asp Thr Pro Asp Val Asn Ile Glu Gly Pro Glu Gly Lys Leu Lys
        4430                4435                4440

Gly Pro Lys Phe Lys Met Pro Glu Met Asn Ile Lys Ala Pro Lys
        4445                4450                4455

Ile Ser Met Pro Asp Phe Asp Leu His Leu Lys Gly Pro Lys Val
        4460                4465                4470

Lys Gly Asp Val Asp Val Ser Leu Pro Lys Val Glu Ser Asp Leu
        4475                4480                4485

Lys Gly Pro Glu Val Asp Ile Glu Gly Pro Glu Gly Lys Leu Lys
        4490                4495                4500

Gly Pro Lys Phe Lys Met Pro Asp Val His Phe Lys Ser Pro Gln
        4505                4510                4515

Ile Ser Met Ser Asp Ile Asp Leu Asn Leu Lys Gly Pro Lys Ile
        4520                4525                4530

Lys Gly Asp Met Asp Ile Ser Val Pro Lys Leu Glu Gly Asp Leu
        4535                4540                4545

Lys Gly Pro Lys Val Asp Val Lys Gly Pro Lys Val Gly Ile Asp
        4550                4555                4560

Thr Pro Asp Ile Asp Ile His Gly Pro Glu Gly Lys Leu Lys Gly
        4565                4570                4575
```

```
Pro Lys Phe Lys Met Pro Asp Leu His Leu Lys Ala Pro Lys Ile
    4580            4585                4590

Ser Met Pro Glu Val Asp Leu Asn Leu Lys Gly Pro Lys Val Lys
    4595            4600                4605

Gly Asp Met Asp Ile Ser Leu Pro Lys Val Glu Gly Asp Leu Lys
    4610            4615                4620

Gly Pro Glu Val Asp Ile Arg Asp Pro Lys Val Asp Ile Asp Val
    4625            4630                4635

Pro Asp Val Asp Val Gln Gly Pro Asp Trp His Leu Lys Met Pro
    4640            4645                4650

Lys Val Lys Met Pro Lys Phe Ser Met Pro Gly Phe Lys Gly Glu
    4655            4660                4665

Gly Pro Asp Val Asp Val Asn Leu Pro Lys Ala Asp Ile Asp Val
    4670            4675                4680

Ser Gly Pro Lys Val Asp Val Asp Val Pro Asp Val Asn Ile Glu
    4685            4690                4695

Gly Pro Asp Ala Lys Leu Lys Gly Pro Lys Phe Lys Met Pro Glu
    4700            4705                4710

Met Ser Ile Lys Ala Pro Lys Ile Ser Met Pro Asp Ile Asp Leu
    4715            4720                4725

Asn Leu Lys Gly Pro Lys Val Lys Gly Asp Val Asp Val Thr Leu
    4730            4735                4740

Pro Lys Val Glu Gly Asp Leu Lys Gly Pro Glu Ala Asp Ile Lys
    4745            4750                4755

Gly Pro Lys Val Asp Ile Asn Thr Pro Asp Val Asp Val His Gly
    4760            4765                4770

Pro Asp Trp His Leu Lys Met Pro Lys Val Lys Met Pro Lys Phe
    4775            4780                4785

Ser Met Pro Gly Phe Lys Gly Glu Gly Pro Asp Val Asp Val Ser
    4790            4795                4800

Leu Pro Lys Ala Asp Ile Asp Val Ser Gly Pro Lys Val Asp Val
    4805            4810                4815

Asp Ile Pro Asp Val Asn Ile Glu Gly Pro Asp Ala Lys Leu Lys
    4820            4825                4830

Gly Pro Lys Phe Lys Met Pro Glu Ile Asn Ile Lys Ala Pro Lys
    4835            4840                4845

Ile Ser Ile Pro Asp Val Asp Leu Asp Leu Lys Gly Pro Lys Val
    4850            4855                4860

Lys Gly Asp Phe Asp Val Ser Val Pro Lys Val Glu Gly Thr Leu
    4865            4870                4875

Lys Gly Pro Glu Val Asp Leu Lys Gly Pro Arg Leu Asp Phe Glu
    4880            4885                4890

Gly Pro Asp Ala Lys Leu Ser Gly Pro Ser Leu Lys Met Pro Ser
    4895            4900                4905

Leu Glu Ile Ser Ala Pro Lys Val Thr Ala Pro Asp Val Asp Leu
    4910            4915                4920

His Leu Lys Ala Pro Lys Ile Gly Phe Ser Gly Pro Lys Leu Glu
    4925            4930                4935

Gly Gly Glu Val Asp Leu Lys Gly Pro Lys Val Glu Ala Pro Ser
    4940            4945                4950

Leu Asp Val His Met Asp Ser Pro Asp Ile Asn Ile Glu Gly Pro
    4955            4960                4965
```

```
Asp Val Lys Ile Pro Lys Phe Lys Lys Pro Lys Phe Gly Phe Gly
    4970            4975            4980

Ala Lys Ser Pro Lys Ala Asp Ile Lys Ser Pro Ser Leu Asp Val
    4985            4990            4995

Thr Val Pro Glu Ala Glu Leu Asn Leu Glu Thr Pro Glu Ile Ser
    5000            5005            5010

Val Gly Gly Lys Gly Lys Lys Ser Lys Phe Lys Met Pro Lys Ile
    5015            5020            5025

His Met Ser Gly Pro Lys Ile Lys Ala Lys Lys Gln Gly Phe Asp
    5030            5035            5040

Leu Asn Val Pro Gly Gly Glu Ile Asp Ala Ser Leu Lys Ala Pro
    5045            5050            5055

Asp Val Asp Val Asn Ile Ala Gly Pro Asp Ala Ala Leu Lys Val
    5060            5065            5070

Asp Val Lys Ser Pro Lys Thr Lys Lys Thr Met Phe Gly Lys Met
    5075            5080            5085

Tyr Phe Pro Asp Val Glu Phe Asp Ile Lys Ser Pro Lys Phe Lys
    5090            5095            5100

Ala Glu Ala Pro Leu Pro Ser Pro Lys Leu Glu Gly Glu Leu Gln
    5105            5110            5115

Ala Pro Asp Leu Glu Leu Ser Leu Pro Ala Ile His Val Glu Gly
    5120            5125            5130

Leu Asp Ile Lys Ala Lys Ala Pro Lys Val Lys Met Pro Asp Val
    5135            5140            5145

Asp Ile Ser Val Pro Lys Ile Glu Gly Asp Leu Lys Gly Pro Lys
    5150            5155            5160

Val Gln Ala Asn Leu Gly Ala Pro Asp Ile Asn Ile Glu Gly Leu
    5165            5170            5175

Asp Ala Lys Val Lys Thr Pro Ser Phe Gly Ile Ser Ala Pro Gln
    5180            5185            5190

Val Ser Ile Pro Asp Val Asn Val Asn Leu Lys Gly Pro Lys Ile
    5195            5200            5205

Lys Gly Asp Val Pro Ser Val Gly Leu Glu Gly Pro Asp Val Asp
    5210            5215            5220

Leu Gln Gly Pro Glu Ala Lys Ile Lys Phe Pro Lys Phe Ser Met
    5225            5230            5235

Pro Lys Ile Gly Ile Pro Gly Val Lys Met Glu Gly Gly Gly Ala
    5240            5245            5250

Glu Val His Ala Gln Leu Pro Ser Leu Glu Gly Asp Leu Arg Gly
    5255            5260            5265

Pro Asp Val Lys Leu Glu Gly Pro Asp Val Ser Leu Lys Gly Pro
    5270            5275            5280

Gly Val Asp Leu Pro Ser Val Asn Leu Ser Met Pro Lys Val Ser
    5285            5290            5295

Gly Pro Asp Leu Asp Leu Asn Leu Lys Gly Pro Ser Leu Lys Gly
    5300            5305            5310

Asp Leu Asp Ala Ser Val Pro Ser Met Lys Val His Ala Pro Gly
    5315            5320            5325

Leu Asn Leu Ser Gly Val Gly Gly Lys Met Gln Val Gly Gly Asp
    5330            5335            5340

Gly Val Lys Val Pro Gly Ile Asp Ala Thr Thr Lys Leu Asn Val
    5345            5350            5355

Gly Ala Pro Asp Val Thr Leu Arg Gly Pro Ser Leu Gln Gly Asp
```

-continued

```
                    5360                5365                5370
       Leu Ala Val Ser Gly Asp Ile Lys Cys Pro Lys Val Ser Val Gly
               5375                5380                5385
       Ala Pro Asp Leu Ser Leu Glu Ala Ser Glu Gly Ser Ile Lys Leu
               5390                5395                5400
       Pro Lys Met Lys Leu Pro Gln Phe Gly Ile Ser Thr Pro Gly Ser
               5405                5410                5415
       Asp Leu His Val Asn Ala Lys Gly Pro Gln Val Ser Gly Glu Leu
               5420                5425                5430
       Lys Gly Pro Gly Val Asp Val Asn Leu Lys Gly Pro Arg Ile Ser
               5435                5440                5445
       Ala Pro Asn Val Asp Phe Asn Leu Glu Gly Pro Lys Val Lys Gly
               5450                5455                5460
       Ser Leu Gly Ala Thr Gly Glu Ile Lys Gly Pro Thr Val Gly Gly
               5465                5470                5475
       Gly Leu Pro Gly Ile Gly Val Gln Gly Leu Glu Gly Asn Leu Gln
               5480                5485                5490
       Met Pro Gly Ile Lys Ser Ser Gly Cys Asp Val Asn Leu Pro Gly
               5495                5500                5505
       Val Asn Val Lys Leu Pro Thr Gly Gln Ile Ser Gly Pro Glu Ile
               5510                5515                5520
       Lys Gly Gly Leu Lys Gly Ser Glu Val Gly Phe His Gly Ala Ala
               5525                5530                5535
       Pro Asp Ile Ser Val Lys Gly Pro Ala Phe Asn Met Ala Ser Pro
               5540                5545                5550
       Glu Ser Asp Phe Gly Ile Asn Leu Lys Gly Pro Lys Ile Lys Gly
               5555                5560                5565
       Gly Ala Asp Val Ser Gly Gly Val Ser Ala Pro Asp Ile Ser Leu
               5570                5575                5580
       Gly Glu Gly His Leu Ser Val Lys Gly Ser Gly Gly Glu Trp Lys
               5585                5590                5595
       Gly Pro Gln Val Ser Ser Ala Leu Asn Leu Asp Thr Ser Lys Phe
               5600                5605                5610
       Ala Gly Gly Leu His Phe Ser Gly Pro Lys Val Glu Gly Gly Val
               5615                5620                5625
       Lys Gly Gly Gln Ile Gly Leu Gln Ala Pro Gly Leu Ser Val Ser
               5630                5635                5640
       Gly Pro Gln Gly His Leu Glu Ser Gly Ser Gly Lys Val Thr Phe
               5645                5650                5655
       Pro Lys Met Lys Ile Pro Lys Phe Thr Phe Ser Gly Arg Glu Leu
               5660                5665                5670
       Val Gly Arg Glu Met Gly Val Asp Val His Phe Pro Lys Ala Glu
               5675                5680                5685
       Ala Ser Ile Gln Ala Gly Ala Gly Asp Gly Glu Trp Glu Glu Ser
               5690                5695                5700
       Glu Val Lys Leu Lys Lys Ser Lys Ile Lys Met Pro Lys Phe Asn
               5705                5710                5715
       Phe Ser Lys Pro Lys Gly Lys Gly Gly Val Thr Gly Ser Pro Glu
               5720                5725                5730
       Ala Ser Ile Ser Gly Ser Lys Gly Asp Leu Lys Ser Ser Lys Ala
               5735                5740                5745
       Ser Leu Gly Ser Leu Glu Gly Glu Ala Glu Ala Glu Ala Ser Ser
               5750                5755                5760
```

```
Pro Lys Gly Lys Phe Ser Leu Phe Lys Ser Lys Lys Pro Arg His
    5765                5770                5775

Arg Ser Asn Ser Phe Ser Asp Glu Arg Glu Phe Ser Gly Pro Ser
    5780                5785                5790

Thr Pro Thr Gly Thr Leu Glu Phe Glu Gly Gly Glu Val Ser Leu
    5795                5800                5805

Glu Gly Gly Lys Val Lys Gly Lys His Gly Lys Leu Lys Phe Gly
    5810                5815                5820

Thr Phe Gly Gly Leu Gly Ser Lys Ser Lys Gly His Tyr Glu Val
    5825                5830                5835

Thr Gly Ser Asp Asp Glu Thr Gly Lys Leu Gln Gly Ser Gly Val
    5840                5845                5850

Ser Leu Ala Ser Lys Lys Ser Arg Leu Ser Ser Ser Ser Ser Asn
    5855                5860                5865

Asp Ser Gly Asn Lys Val Gly Ile Gln Leu Pro Glu Val Glu Leu
    5870                5875                5880

Ser Val Ser Thr Lys Lys Glu
    5885                5890

<210> SEQ ID NO 55
<211> LENGTH: 339
<212> TYPE: PRT
<213> ORGANISM: Homo sapiens

<400> SEQUENCE: 55

Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Asn Arg Ser
    50                  55                  60

Asn Ala Gln Arg Gln Asp Ile Ala Phe Ala Tyr Gln Arg Arg Thr Lys
65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
    130                 135                 140

Arg Val Tyr Lys Glu Met Tyr Lys Thr Asp Leu Glu Lys Asp Ile Ile
145                 150                 155                 160

Ser Asp Thr Ser Gly Asp Phe Arg Lys Leu Met Val Ala Leu Ala Lys
                165                 170                 175

Gly Arg Arg Ala Glu Asp Gly Ser Val Ile Asp Tyr Glu Leu Ile Asp
            180                 185                 190

Gln Asp Ala Arg Asp Leu Tyr Asp Ala Gly Val Lys Arg Lys Gly Thr
        195                 200                 205

Asp Val Pro Lys Trp Ile Ser Ile Met Thr Glu Arg Ser Val Pro His
    210                 215                 220

Leu Gln Lys Val Phe Asp Arg Tyr Lys Ser Tyr Ser Pro Tyr Asp Met
```

```
                     225                 230                 235                 240
Leu Glu Ser Ile Arg Lys Glu Val Lys Gly Asp Leu Glu Asn Ala Phe
                    245                 250                 255

Leu Asn Leu Val Gln Cys Ile Gln Asn Lys Pro Leu Tyr Phe Ala Asp
                260                 265                 270

Arg Leu Tyr Asp Ser Met Lys Gly Gly Thr Arg Asp Lys Val Leu
            275                 280                 285

Ile Arg Ile Met Val Ser Arg Ser Glu Val Asp Met Leu Lys Ile Arg
        290                 295                 300

Ser Glu Phe Lys Arg Lys Tyr Gly Lys Ser Leu Tyr Tyr Ile Gln
305                 310                 315                 320

Gln Asp Thr Lys Gly Asp Tyr Gln Lys Ala Leu Leu Tyr Leu Cys Gly
                325                 330                 335

Gly Asp Asp

<210> SEQ ID NO 56
<211> LENGTH: 320
<212> TYPE: PRT
<213> ORGANISM: Homo sapiens

<400> SEQUENCE: 56

Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
                20                  25                  30

Thr Asp Glu Glu Ser Ile Leu Thr Leu Leu Thr Ser Arg Ser Asn Ala
            35                  40                  45

Gln Arg Gln Glu Ile Ser Ala Ala Phe Lys Thr Leu Phe Gly Arg Asp
        50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
            100                 105                 110

Ile Ile Ala Ser Arg Thr Pro Glu Glu Leu Arg Ala Ile Lys Gln Val
        115                 120                 125

Tyr Glu Glu Glu Tyr Gly Ser Ser Leu Glu Asp Asp Val Val Gly Asp
    130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
            180                 185                 190

Lys Phe Ile Thr Ile Phe Gly Thr Arg Ser Val Ser His Leu Arg Lys
        195                 200                 205

Val Phe Asp Lys Tyr Met Thr Ile Ser Gly Phe Gln Ile Glu Glu Thr
    210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
```

```
            260                 265                 270
Met Val Ser Arg Ser Glu Ile Asp Leu Phe Asn Ile Arg Lys Glu Phe
            275                 280                 285

Arg Lys Asn Phe Ala Thr Ser Leu Tyr Ser Met Ile Lys Gly Asp Thr
            290                 295                 300

Ser Gly Asp Tyr Lys Lys Ala Leu Leu Leu Leu Cys Gly Glu Asp Asp
305                 310                 315                 320
```

<210> SEQ ID NO 57
<211> LENGTH: 434
<212> TYPE: PRT
<213> ORGANISM: Homo sapiens

<400> SEQUENCE: 57

```
Met Ser Ile Leu Lys Ile His Ala Arg Glu Ile Phe Asp Ser Arg Gly
1               5                   10                  15

Asn Pro Thr Val Glu Val Asp Leu Phe Thr Ser Lys Gly Leu Phe Arg
            20                  25                  30

Ala Ala Val Pro Ser Gly Ala Ser Thr Gly Ile Tyr Glu Ala Leu Glu
            35                  40                  45

Leu Arg Asp Asn Asp Lys Thr Arg Tyr Met Gly Lys Gly Val Ser Lys
50                  55                  60

Ala Val Glu His Ile Asn Lys Thr Ile Ala Pro Ala Leu Val Ser Lys
65                  70                  75                  80

Lys Leu Asn Val Thr Glu Gln Glu Lys Ile Asp Lys Leu Met Ile Glu
            85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
            115                 120                 125

Pro Leu Tyr Arg His Ile Ala Asp Leu Ala Gly Asn Ser Glu Val Ile
            130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ala
            165                 170                 175

Asn Phe Arg Glu Ala Met Arg Ile Gly Ala Glu Val Tyr His Asn Leu
            180                 185                 190

Lys Asn Val Ile Lys Glu Lys Tyr Gly Lys Asp Ala Thr Asn Val Gly
            195                 200                 205

Asp Glu Gly Gly Phe Ala Pro Asn Ile Leu Glu Asn Lys Glu Gly Leu
            210                 215                 220

Glu Leu Leu Lys Thr Ala Ile Gly Lys Ala Gly Tyr Thr Asp Lys Val
225                 230                 235                 240

Val Ile Gly Met Asp Val Ala Ala Ser Glu Phe Phe Arg Ser Gly Lys
            245                 250                 255

Tyr Asp Leu Asp Phe Lys Ser Pro Asp Asp Pro Ser Arg Tyr Ile Ser
            260                 265                 270

Pro Asp Gln Leu Ala Asp Leu Tyr Lys Ser Phe Ile Lys Asp Tyr Pro
            275                 280                 285

Val Val Ser Ile Glu Asp Pro Phe Asp Gln Asp Asp Trp Gly Ala Trp
            290                 295                 300

Gln Lys Phe Thr Ala Ser Ala Gly Ile Gln Val Val Gly Asp Asp Leu
305                 310                 315                 320
```

```
Thr Val Thr Asn Pro Lys Arg Ile Ala Lys Ala Val Asn Glu Lys Ser
            325                 330                 335

Cys Asn Cys Leu Leu Leu Lys Val Asn Gln Ile Gly Ser Val Thr Glu
            340                 345                 350

Ser Leu Gln Ala Cys Lys Leu Ala Gln Ala Asn Gly Trp Gly Val Met
            355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Leu Arg Ile Glu Glu Glu
            405                 410                 415

Leu Gly Ser Lys Ala Lys Phe Ala Gly Arg Asn Phe Arg Asn Pro Leu
            420                 425                 430

Ala Lys

<210> SEQ ID NO 58
<211> LENGTH: 803
<212> TYPE: PRT
<213> ORGANISM: Homo sapiens

<400> SEQUENCE: 58

Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
                20                  25                  30

Glu Asp Leu Gly Lys Ser Arg Glu Gly Ser Arg Thr Asp Asp Glu Val
            35                  40                  45

Val Gln Arg Glu Glu Ala Ile Gln Leu Asp Gly Leu Asn Ala Ser
    50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
            115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
            195                 200                 205

Val Ile Val Thr Ser Lys His Asn Asn Asp Thr Gln His Ile Trp Glu
    210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255
```

```
Asp Tyr Leu Glu Leu Asp Thr Ile Lys Asn Leu Val Lys Lys Tyr Ser
            260                 265                 270

Gln Phe Ile Asn Phe Pro Ile Tyr Val Trp Ser Ser Lys Thr Glu Thr
        275                 280                 285

Val Glu Glu Pro Met Glu Glu Glu Ala Ala Lys Glu Glu Lys Glu
    290                 295                 300

Glu Ser Asp Asp Glu Ala Ala Val Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Gly Val Glu Glu
            340                 345                 350

Asp Glu Tyr Lys Ala Phe Tyr Lys Ser Phe Ser Lys Glu Ser Asp Asp
        355                 360                 365

Pro Met Ala Tyr Ile His Phe Thr Ala Glu Gly Glu Val Thr Phe Lys
    370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
                405                 410                 415

Phe Ile Thr Asp Asp Phe His Asp Met Met Pro Lys Tyr Leu Asn Phe
            420                 425                 430

Val Lys Gly Val Val Asp Ser Asp Asp Leu Pro Leu Asn Val Ser Arg
        435                 440                 445

Glu Thr Leu Gln Gln His Lys Leu Leu Lys Val Ile Arg Lys Lys Leu
    450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
            500                 505                 510

Gln Ser Ser His His Pro Thr Asp Ile Thr Ser Leu Asp Gln Tyr Val
        515                 520                 525

Glu Arg Met Lys Glu Lys Gln Asp Lys Ile Tyr Phe Met Ala Gly Ser
    530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Val Ala
            580                 585                 590

Lys Glu Gly Val Lys Phe Asp Glu Ser Glu Lys Thr Lys Glu Ser Arg
        595                 600                 605

Glu Ala Val Glu Lys Glu Phe Glu Pro Leu Leu Asn Trp Met Lys Asp
    610                 615                 620

Lys Ala Leu Lys Asp Lys Ile Glu Lys Ala Val Val Ser Gln Arg Leu
625                 630                 635                 640

Thr Glu Ser Pro Cys Ala Leu Val Ala Ser Gln Tyr Gly Trp Ser Gly
                645                 650                 655

Asn Met Glu Arg Ile Met Lys Ala Gln Ala Tyr Gln Thr Gly Lys Asp
            660                 665                 670

Ile Ser Thr Asn Tyr Tyr Ala Ser Gln Lys Lys Thr Phe Glu Ile Asn
```

```
                675                 680                 685
Pro Arg His Pro Leu Ile Arg Asp Met Leu Arg Arg Ile Lys Glu Asp
            690                 695                 700

Glu Asp Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
                725                 730                 735

Asp Arg Ile Glu Arg Met Leu Arg Leu Ser Leu Asn Ile Asp Pro Asp
            740                 745                 750

Ala Lys Val Glu Glu Pro Glu Glu Pro Glu Glu Thr Ala Glu
                755                 760                 765

Asp Thr Thr Glu Asp Thr Glu Gln Asp Glu Asp Glu Glu Met Asp Val
            770                 775                 780

Gly Thr Asp Glu Glu Glu Glu Thr Ala Lys Glu Ser Thr Ala Glu Lys
785                 790                 795                 800

Asp Glu Leu

<210> SEQ ID NO 59
<211> LENGTH: 531
<212> TYPE: PRT
<213> ORGANISM: Homo sapiens

<400> SEQUENCE: 59

Met Ser Lys Pro His Ser Glu Ala Gly Thr Ala Phe Ile Gln Thr Gln
1               5                   10                  15

Gln Leu His Ala Ala Met Ala Asp Thr Phe Leu Glu His Met Cys Arg
            20                  25                  30

Leu Asp Ile Asp Ser Pro Pro Ile Thr Ala Arg Asn Thr Gly Ile Ile
        35                  40                  45

Cys Thr Ile Gly Pro Ala Ser Arg Ser Val Glu Thr Leu Lys Glu Met
    50                  55                  60

Ile Lys Ser Gly Met Asn Val Ala Arg Leu Asn Phe Ser His Gly Thr
65                  70                  75                  80

His Glu Tyr His Ala Glu Thr Ile Lys Asn Val Arg Thr Ala Thr Glu
                85                  90                  95

Ser Phe Ala Ser Asp Pro Ile Leu Tyr Arg Pro Val Ala Val Ala Leu
            100                 105                 110

Asp Thr Lys Gly Pro Glu Ile Arg Thr Gly Leu Ile Lys Gly Ser Gly
        115                 120                 125

Thr Ala Glu Val Glu Leu Lys Lys Gly Ala Thr Leu Lys Ile Thr Leu
    130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Glu Val Gly Ser Lys Ile Tyr Val
                165                 170                 175

Asp Asp Gly Leu Ile Ser Leu Gln Val Lys Gln Lys Gly Ala Asp Phe
            180                 185                 190

Leu Val Thr Glu Val Glu Asn Gly Gly Ser Leu Gly Ser Lys Lys Gly
        195                 200                 205

Val Asn Leu Pro Gly Ala Ala Val Asp Leu Pro Ala Val Ser Glu Lys
    210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
```

```
                        245                 250                 255
Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
        275                 280                 285

Gly Ile Met Val Ala Arg Gly Asp Leu Gly Ile Glu Ile Pro Ala Glu
    290                 295                 300

Lys Val Phe Leu Ala Gln Lys Met Met Ile Gly Arg Cys Asn Arg Ala
305                 310                 315                 320

Gly Lys Pro Val Ile Cys Ala Thr Gln Met Leu Glu Ser Met Ile Lys
                325                 330                 335

Lys Pro Arg Pro Thr Arg Ala Glu Gly Ser Asp Val Ala Asn Ala Val
            340                 345                 350

Leu Asp Gly Ala Asp Cys Ile Met Leu Ser Gly Glu Thr Ala Lys Gly
        355                 360                 365

Asp Tyr Pro Leu Glu Ala Val Arg Met Gln His Leu Ile Ala Arg Glu
    370                 375                 380

Ala Glu Ala Ala Ile Tyr His Leu Gln Leu Phe Glu Glu Leu Arg Arg
385                 390                 395                 400

Leu Ala Pro Ile Thr Ser Asp Pro Thr Glu Ala Thr Ala Val Gly Ala
                405                 410                 415

Val Glu Ala Ser Phe Lys Cys Cys Ser Gly Ala Ile Ile Val Leu Thr
            420                 425                 430

Lys Ser Gly Arg Ser Ala His Gln Val Ala Arg Tyr Arg Pro Arg Ala
        435                 440                 445

Pro Ile Ile Ala Val Thr Arg Asn Pro Gln Thr Ala Arg Gln Ala His
    450                 455                 460

Leu Tyr Arg Gly Ile Phe Pro Val Leu Cys Lys Asp Pro Val Gln Glu
465                 470                 475                 480

Ala Trp Ala Glu Asp Val Asp Leu Arg Val Asn Phe Ala Met Asn Val
                485                 490                 495

Gly Lys Ala Arg Gly Phe Phe Lys Lys Gly Asp Val Val Ile Val Leu
            500                 505                 510

Thr Gly Trp Arg Pro Gly Ser Gly Phe Thr Asn Thr Met Arg Val Val
        515                 520                 525

Pro Val Pro
    530

<210> SEQ ID NO 60
<211> LENGTH: 662
<212> TYPE: PRT
<213> ORGANISM: Homo sapiens

<400> SEQUENCE: 60

Met Gly Leu Tyr Arg Ile Arg Val Ser Thr Gly Ala Ser Leu Tyr Ala
1               5                   10                  15

Gly Ser Asn Asn Gln Val Gln Leu Trp Leu Val Gly Gln His Gly Glu
            20                  25                  30

Ala Ala Leu Gly Lys Arg Leu Trp Pro Ala Arg Gly Lys Glu Thr Glu
        35                  40                  45

Leu Lys Val Glu Val Pro Glu Tyr Leu Gly Pro Leu Leu Phe Val Lys
    50                  55                  60

Leu Arg Lys Arg His Leu Leu Lys Asp Asp Ala Trp Phe Cys Asn Trp
65                  70                  75                  80
```

```
Ile Ser Val Gln Gly Pro Gly Ala Gly Asp Glu Val Arg Phe Pro Cys
                85                  90                  95

Tyr Arg Trp Val Glu Gly Asn Gly Val Leu Ser Leu Pro Glu Gly Thr
            100                 105                 110

Gly Arg Thr Val Gly Glu Asp Pro Gln Gly Leu Phe Gln Lys His Arg
            115                 120                 125

Glu Glu Glu Leu Glu Glu Arg Arg Lys Leu Tyr Arg Trp Gly Asn Trp
            130                 135                 140

Lys Asp Gly Leu Ile Leu Asn Met Ala Gly Lys Leu Tyr Asp Leu
145                 150                 155                 160

Pro Val Asp Glu Arg Phe Leu Glu Asp Lys Arg Val Asp Phe Glu Val
                165                 170                 175

Ser Leu Ala Lys Gly Leu Ala Asp Leu Ala Ile Lys Asp Ser Leu Asn
            180                 185                 190

Val Leu Thr Cys Trp Lys Asp Leu Asp Asp Phe Asn Arg Ile Phe Trp
            195                 200                 205

Cys Gly Gln Ser Lys Leu Ala Glu Arg Val Arg Asp Ser Trp Lys Glu
            210                 215                 220

Asp Ala Leu Phe Gly Tyr Gln Phe Leu Asn Gly Ala Asn Pro Val Val
225                 230                 235                 240

Leu Arg Arg Ser Ala His Leu Pro Ala Arg Leu Val Phe Pro Pro Gly
                245                 250                 255

Met Glu Glu Leu Gln Ala Gln Leu Glu Lys Glu Leu Glu Gly Gly Thr
            260                 265                 270

Leu Phe Glu Ala Asp Phe Ser Leu Leu Asp Gly Ile Lys Ala Asn Val
            275                 280                 285

Ile Leu Cys Ser Gln Gln His Leu Ala Ala Pro Leu Val Met Leu Lys
            290                 295                 300

Leu Gln Pro Asp Gly Lys Leu Leu Pro Met Val Ile Gln Leu Gln Leu
305                 310                 315                 320

Pro Arg Thr Gly Ser Pro Pro Pro Leu Phe Leu Pro Thr Asp Pro
                325                 330                 335

Pro Met Ala Trp Leu Leu Ala Lys Cys Trp Val Arg Ser Ser Asp Phe
            340                 345                 350

Gln Leu His Glu Leu Gln Ser His Leu Leu Arg Gly His Leu Met Ala
            355                 360                 365

Glu Val Ile Val Val Ala Thr Met Arg Cys Leu Pro Ser Ile His Pro
            370                 375                 380

Ile Phe Lys Leu Ile Ile Pro His Leu Arg Tyr Thr Leu Glu Ile Asn
385                 390                 395                 400

Val Arg Ala Arg Thr Gly Leu Val Ser Asp Met Gly Ile Phe Asp Gln
                405                 410                 415

Ile Met Ser Thr Gly Gly Gly His Val Gln Leu Leu Lys Gln Ala
            420                 425                 430

Gly Ala Phe Leu Thr Tyr Ser Ser Phe Cys Pro Pro Asp Asp Leu Ala
            435                 440                 445

Asp Arg Gly Leu Leu Gly Val Lys Ser Ser Phe Tyr Ala Gln Asp Ala
450                 455                 460

Leu Arg Leu Trp Glu Ile Ile Tyr Arg Tyr Val Glu Gly Ile Val Ser
465                 470                 475                 480

Leu His Tyr Lys Thr Asp Val Ala Val Lys Asp Asp Pro Glu Leu Gln
                485                 490                 495

Thr Trp Cys Arg Glu Ile Thr Glu Ile Gly Leu Gln Gly Ala Gln Asp
```

-continued

```
                    500                 505                 510
        Arg Gly Phe Pro Val Ser Leu Gln Ala Arg Asp Gln Val Cys His Phe
                    515                 520                 525

Val Thr Met Cys Ile Phe Thr Cys Thr Gly Gln His Ala Ser Val His
                    530                 535                 540

Leu Gly Gln Leu Asp Trp Tyr Ser Trp Val Pro Asn Ala Pro Cys Thr
        545                 550                 555                 560

Met Arg Leu Pro Pro Thr Thr Lys Asp Ala Thr Leu Glu Thr Val
                        565                 570                 575

Met Ala Thr Leu Pro Asn Phe His Gln Ala Ser Leu Gln Met Ser Ile
                    580                 585                 590

Thr Trp Gln Leu Gly Arg Arg Gln Pro Val Met Val Ala Val Gly Gln
                    595                 600                 605

His Glu Glu Glu Tyr Phe Ser Gly Pro Glu Pro Lys Ala Val Leu Lys
                    610                 615                 620

Lys Phe Arg Glu Glu Leu Ala Ala Leu Asp Lys Glu Ile Glu Ile Arg
        625                 630                 635                 640

Asn Ala Lys Leu Asp Met Pro Tyr Glu Tyr Leu Arg Pro Ser Val Val
                        645                 650                 655

Glu Asn Ser Val Ala Ile
                    660
```

<210> SEQ ID NO 61
<211> LENGTH: 165
<212> TYPE: PRT
<213> ORGANISM: Homo sapiens

<400> SEQUENCE: 61

```
        Met Val Asn Pro Thr Val Phe Phe Asp Ile Ala Val Asp Gly Glu Pro
        1               5                   10                  15

Leu Gly Arg Val Ser Phe Glu Leu Phe Ala Asp Lys Val Pro Lys Thr
                    20                  25                  30

Ala Glu Asn Phe Arg Ala Leu Ser Thr Gly Glu Lys Gly Phe Gly Tyr
                    35                  40                  45

Lys Gly Ser Cys Phe His Arg Ile Ile Pro Gly Phe Met Cys Gln Gly
                50                  55                  60

Gly Asp Phe Thr Arg His Asn Gly Thr Gly Lys Ser Ile Tyr Gly
        65                  70                  75                  80

Glu Lys Phe Glu Asp Glu Asn Phe Ile Leu Lys His Thr Gly Pro Gly
                        85                  90                  95

Ile Leu Ser Met Ala Asn Ala Gly Pro Asn Thr Asn Gly Ser Gln Phe
                    100                 105                 110

Phe Ile Cys Thr Ala Lys Thr Glu Trp Leu Asp Gly Lys His Val Val
                    115                 120                 125

Phe Gly Lys Val Lys Glu Gly Met Asn Ile Val Glu Ala Met Glu Arg
                    130                 135                 140

Phe Gly Ser Arg Asn Gly Lys Thr Ser Lys Lys Ile Thr Ile Ala Asp
        145                 150                 155                 160

Cys Gly Gln Leu Glu
                        165
```

<210> SEQ ID NO 62
<211> LENGTH: 184
<212> TYPE: PRT
<213> ORGANISM: Homo sapiens

<400> SEQUENCE: 62

```
Met Val Arg Tyr Ser Leu Asp Pro Glu Asn Pro Thr Lys Ser Cys Lys
1               5                   10                  15

Ser Arg Gly Ser Asn Leu Arg Val His Phe Lys Asn Thr Arg Glu Thr
            20                  25                  30

Ala Gln Ala Ile Lys Gly Met His Ile Arg Lys Ala Thr Lys Tyr Leu
        35                  40                  45

Lys Asp Val Thr Leu Gln Lys Gln Cys Val Pro Phe Arg Arg Tyr Asn
    50                  55                  60

Gly Gly Val Gly Arg Cys Ala Gln Ala Lys Gln Trp Gly Trp Thr Gln
65                  70                  75                  80

Gly Arg Trp Pro Lys Lys Ser Ala Glu Phe Leu Leu His Met Leu Lys
                85                  90                  95

Asn Ala Glu Ser Asn Ala Glu Leu Lys Gly Leu Asp Val Asp Ser Leu
            100                 105                 110

Val Ile Glu His Ile Gln Val Asn Lys Ala Pro Lys Met Arg Arg Arg
        115                 120                 125

Thr Tyr Arg Ala His Gly Arg Ile Asn Pro Tyr Met Ser Ser Pro Cys
    130                 135                 140

His Ile Glu Met Ile Leu Thr Glu Lys Glu Gln Ile Val Pro Lys Pro
145                 150                 155                 160

Glu Glu Glu Val Ala Gln Lys Lys Lys Ile Ser Gln Lys Lys Leu Lys
                165                 170                 175

Lys Gln Lys Leu Met Ala Arg Glu
            180
```

<210> SEQ ID NO 63
<211> LENGTH: 249
<212> TYPE: PRT
<213> ORGANISM: Homo sapiens

<400> SEQUENCE: 63

```
Met Ala Pro Ser Arg Lys Phe Phe Val Gly Gly Asn Trp Lys Met Asn
1               5                   10                  15

Gly Arg Lys Gln Ser Leu Gly Glu Leu Ile Gly Thr Leu Asn Ala Ala
            20                  25                  30

Lys Val Pro Ala Asp Thr Glu Val Val Cys Ala Pro Pro Thr Ala Tyr
        35                  40                  45

Ile Asp Phe Ala Arg Gln Lys Leu Asp Pro Lys Ile Ala Val Ala Ala
    50                  55                  60

Gln Asn Cys Tyr Lys Val Thr Asn Gly Ala Phe Thr Gly Glu Ile Ser
65                  70                  75                  80

Pro Gly Met Ile Lys Asp Cys Gly Ala Thr Trp Val Val Leu Gly His
                85                  90                  95

Ser Glu Arg Arg His Val Phe Gly Glu Ser Asp Glu Leu Ile Gly Gln
            100                 105                 110

Lys Val Ala His Ala Leu Ala Glu Gly Leu Gly Val Ile Ala Cys Ile
        115                 120                 125

Gly Glu Lys Leu Asp Glu Arg Glu Ala Gly Ile Thr Glu Lys Val Val
    130                 135                 140

Phe Glu Gln Thr Lys Val Ile Ala Asp Asn Val Lys Asp Trp Ser Lys
145                 150                 155                 160

Val Val Leu Ala Tyr Glu Pro Val Trp Ala Ile Gly Thr Gly Lys Thr
                165                 170                 175
```

```
Ala Thr Pro Gln Gln Ala Gln Glu Val His Glu Lys Leu Arg Gly Trp
            180                 185                 190

Leu Lys Ser Asn Val Ser Asp Ala Val Ala Gln Ser Thr Arg Ile Ile
        195                 200                 205

Tyr Gly Gly Ser Val Thr Gly Ala Thr Cys Lys Glu Leu Ala Ser Gln
        210                 215                 220

Pro Asp Val Asp Gly Phe Leu Val Gly Gly Ala Ser Leu Lys Pro Glu
225                 230                 235                 240

Phe Val Asp Ile Ile Asn Ala Lys Gln
                245

<210> SEQ ID NO 64
<211> LENGTH: 630
<212> TYPE: PRT
<213> ORGANISM: Homo sapiens

<400> SEQUENCE: 64

Met Glu Leu Gln Pro Pro Glu Ala Ser Ile Ala Val Val Ser Ile Pro
1               5                   10                  15

Arg Gln Leu Pro Gly Ser His Ser Glu Ala Gly Val Gln Gly Leu Ser
            20                  25                  30

Ala Gly Asp Asp Ser Glu Leu Gly Ser His Cys Val Ala Gln Thr Gly
        35                  40                  45

Leu Glu Leu Leu Ala Ser Gly Asp Pro Leu Pro Ser Ala Ser Gln Asn
50                  55                  60

Ala Glu Met Ile Glu Thr Gly Ser Asp Cys Val Thr Gln Ala Gly Leu
65                  70                  75                  80

Gln Leu Leu Ala Ser Ser Asp Pro Pro Ala Leu Ala Ser Lys Asn Ala
                85                  90                  95

Glu Val Thr Gly Thr Met Ser Gln Asp Thr Glu Val Asp Met Lys Glu
            100                 105                 110

Val Glu Leu Asn Glu Leu Glu Pro Glu Lys Gln Pro Met Asn Ala Ala
        115                 120                 125

Ser Gly Ala Ala Met Ser Leu Ala Gly Ala Glu Lys Asn Gly Leu Val
130                 135                 140

Lys Ile Lys Val Ala Glu Asp Glu Ala Glu Ala Ala Ala Ala Ala Lys
145                 150                 155                 160

Phe Thr Gly Leu Ser Lys Glu Glu Leu Leu Lys Val Ala Gly Ser Pro
                165                 170                 175

Gly Trp Val Arg Thr Arg Trp Ala Leu Leu Leu Leu Phe Trp Leu Gly
            180                 185                 190

Trp Leu Gly Met Leu Ala Gly Ala Val Val Ile Ile Val Arg Ala Pro
        195                 200                 205

Arg Cys Arg Glu Leu Pro Ala Gln Lys Trp Trp His Thr Gly Ala Leu
210                 215                 220

Tyr Arg Ile Gly Asp Leu Gln Ala Phe Gln Gly His Gly Ala Gly Asn
225                 230                 235                 240

Leu Ala Gly Leu Lys Gly Arg Leu Asp Tyr Leu Ser Ser Leu Lys Val
                245                 250                 255

Lys Gly Leu Val Leu Gly Pro Ile His Lys Asn Gln Lys Asp Asp Val
            260                 265                 270

Ala Gln Thr Asp Leu Leu Gln Ile Asp Pro Asn Phe Gly Ser Lys Glu
        275                 280                 285

Asp Phe Asp Ser Leu Leu Gln Ser Ala Lys Lys Lys Ser Ile Arg Val
290                 295                 300
```

Ile Leu Asp Leu Thr Pro Asn Tyr Arg Gly Glu Asn Ser Trp Phe Ser
305                 310                 315                 320

Thr Gln Val Asp Thr Val Ala Thr Lys Val Lys Asp Ala Leu Glu Phe
                325                 330                 335

Trp Leu Gln Ala Gly Val Asp Gly Phe Gln Val Arg Asp Ile Glu Asn
            340                 345                 350

Leu Lys Asp Ala Ser Ser Phe Leu Ala Glu Trp Gln Asn Ile Thr Lys
        355                 360                 365

Gly Phe Ser Glu Asp Arg Leu Leu Ile Ala Gly Thr Asn Ser Ser Asp
370                 375                 380

Leu Gln Gln Ile Leu Ser Leu Leu Glu Ser Asn Lys Asp Leu Leu Leu
385                 390                 395                 400

Thr Ser Ser Tyr Leu Ser Asp Ser Gly Ser Thr Gly Glu His Thr Lys
                405                 410                 415

Ser Leu Val Thr Gln Tyr Leu Asn Ala Thr Gly Asn Arg Trp Cys Ser
            420                 425                 430

Trp Ser Leu Ser Gln Ala Arg Leu Leu Thr Ser Phe Leu Pro Ala Gln
        435                 440                 445

Leu Leu Arg Leu Tyr Gln Leu Met Leu Phe Thr Leu Pro Gly Thr Pro
    450                 455                 460

Val Phe Ser Tyr Gly Asp Glu Ile Gly Leu Asp Ala Ala Ala Leu Pro
465                 470                 475                 480

Gly Gln Pro Met Glu Ala Pro Val Met Leu Trp Asp Glu Ser Ser Phe
                485                 490                 495

Pro Asp Ile Pro Gly Ala Val Ser Ala Asn Met Thr Val Lys Gly Gln
            500                 505                 510

Ser Glu Asp Pro Gly Ser Leu Leu Ser Leu Phe Arg Arg Leu Ser Asp
        515                 520                 525

Gln Arg Ser Lys Glu Arg Ser Leu Leu His Gly Asp Phe His Ala Phe
    530                 535                 540

Ser Ala Gly Pro Gly Leu Phe Ser Tyr Ile Arg His Trp Asp Gln Asn
545                 550                 555                 560

Glu Arg Phe Leu Val Val Leu Asn Phe Gly Asp Val Gly Leu Ser Ala
                565                 570                 575

Gly Leu Gln Ala Ser Asp Leu Pro Ala Ser Ala Ser Leu Pro Ala Lys
            580                 585                 590

Ala Asp Leu Leu Leu Ser Thr Gln Pro Gly Arg Glu Glu Gly Ser Pro
        595                 600                 605

Leu Glu Leu Glu Arg Leu Lys Leu Glu Pro His Glu Gly Leu Leu Leu
    610                 615                 620

Arg Phe Pro Tyr Ala Ala
625                 630

<210> SEQ ID NO 65
<211> LENGTH: 532
<212> TYPE: PRT
<213> ORGANISM: Homo sapiens

<400> SEQUENCE: 65

Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
            20                  25                  30

Pro Ser Lys Val Ile Leu Pro Arg Gly Gly Ser Val Leu Val Thr Cys

```
                 35                  40                  45
Ser Thr Ser Cys Asp Gln Pro Lys Leu Leu Gly Ile Glu Thr Pro Leu
         50                  55                  60
Pro Lys Lys Glu Leu Leu Leu Pro Gly Asn Asn Arg Lys Val Tyr Glu
 65                  70                  75                  80
Leu Ser Asn Val Gln Glu Asp Ser Gln Pro Met Cys Tyr Ser Asn Cys
                 85                  90                  95
Pro Asp Gly Gln Ser Thr Ala Lys Thr Phe Leu Thr Val Tyr Trp Thr
                100                 105                 110
Pro Glu Arg Val Glu Leu Ala Pro Leu Pro Ser Trp Gln Pro Val Gly
                115                 120                 125
Lys Asn Leu Thr Leu Arg Cys Gln Val Glu Gly Gly Ala Pro Arg Ala
        130                 135                 140
Asn Leu Thr Val Val Leu Leu Arg Gly Glu Lys Glu Leu Lys Arg Glu
145                 150                 155                 160
Pro Ala Val Gly Glu Pro Ala Glu Val Thr Thr Thr Val Leu Val Arg
                    165                 170                 175
Arg Asp His His Gly Ala Asn Phe Ser Cys Arg Thr Glu Leu Asp Leu
                180                 185                 190
Arg Pro Gln Gly Leu Glu Leu Phe Glu Asn Thr Ser Ala Pro Tyr Gln
            195                 200                 205
Leu Gln Thr Phe Val Leu Pro Ala Thr Pro Pro Gln Leu Val Ser Pro
        210                 215                 220
Arg Val Leu Glu Val Asp Thr Gln Gly Thr Val Val Cys Ser Leu Asp
225                 230                 235                 240
Gly Leu Phe Pro Val Ser Glu Ala Gln Val His Leu Ala Leu Gly Asp
                    245                 250                 255
Gln Arg Leu Asn Pro Thr Val Thr Tyr Gly Asn Asp Ser Phe Ser Ala
                260                 265                 270
Lys Ala Ser Val Ser Val Thr Ala Glu Asp Glu Gly Thr Gln Arg Leu
            275                 280                 285
Thr Cys Ala Val Ile Leu Gly Asn Gln Ser Gln Glu Thr Leu Gln Thr
        290                 295                 300
Val Thr Ile Tyr Ser Phe Pro Ala Pro Asn Val Ile Leu Thr Lys Pro
305                 310                 315                 320
Glu Val Ser Glu Gly Thr Glu Val Thr Val Lys Cys Glu Ala His Pro
                    325                 330                 335
Arg Ala Lys Val Thr Leu Asn Gly Val Pro Ala Gln Pro Leu Gly Pro
                340                 345                 350
Arg Ala Gln Leu Leu Leu Lys Ala Thr Pro Glu Asp Asn Gly Arg Ser
            355                 360                 365
Phe Ser Cys Ser Ala Thr Leu Glu Val Ala Gly Gln Leu Ile His Lys
        370                 375                 380
Asn Gln Thr Arg Glu Leu Arg Val Leu Tyr Gly Pro Arg Leu Asp Glu
385                 390                 395                 400
Arg Asp Cys Pro Gly Asn Trp Thr Trp Pro Glu Asn Ser Gln Gln Thr
                    405                 410                 415
Pro Met Cys Gln Ala Trp Gly Asn Pro Leu Pro Glu Leu Lys Cys Leu
                420                 425                 430
Lys Asp Gly Thr Phe Pro Leu Pro Ile Gly Glu Ser Val Thr Val Thr
            435                 440                 445
Arg Asp Leu Glu Gly Thr Tyr Leu Cys Arg Ala Arg Ser Thr Gln Gly
        450                 455                 460
```

```
Glu Val Thr Arg Lys Val Thr Val Asn Val Leu Ser Pro Arg Tyr Glu
465                 470                 475                 480

Ile Val Ile Ile Thr Val Val Ala Ala Ala Val Ile Met Gly Thr Ala
                485                 490                 495

Gly Leu Ser Thr Tyr Leu Tyr Asn Arg Gln Arg Lys Ile Lys Lys Tyr
            500                 505                 510

Arg Leu Gln Gln Ala Gln Lys Gly Thr Pro Met Lys Pro Asn Thr Gln
            515                 520                 525

Ala Thr Pro Pro
530

<210> SEQ ID NO 66
<211> LENGTH: 491
<212> TYPE: PRT
<213> ORGANISM: Homo sapiens

<400> SEQUENCE: 66

Met Asn Pro Ala Ala Glu Ala Glu Phe Asn Ile Leu Leu Ala Thr Asp
1               5                   10                  15

Ser Tyr Lys Val Thr His Tyr Lys Gln Tyr Pro Pro Asn Thr Ser Lys
            20                  25                  30

Val Tyr Ser Tyr Phe Glu Cys Arg Glu Lys Lys Thr Glu Asn Ser Lys
        35                  40                  45

Leu Arg Lys Val Lys Tyr Glu Glu Thr Val Phe Tyr Gly Leu Gln Tyr
50                  55                  60

Ile Leu Asn Lys Tyr Leu Lys Gly Lys Val Val Thr Lys Glu Lys Ile
65                  70                  75                  80

Gln Glu Ala Lys Asp Val Tyr Lys Glu His Phe Gln Asp Asp Val Phe
                85                  90                  95

Asn Glu Lys Gly Trp Asn Tyr Ile Leu Glu Lys Tyr Asp Gly His Leu
            100                 105                 110

Pro Ile Glu Ile Lys Ala Val Pro Glu Gly Phe Val Ile Pro Arg Gly
        115                 120                 125

Asn Val Leu Phe Thr Val Glu Asn Thr Asp Pro Glu Cys Tyr Trp Leu
130                 135                 140

Thr Asn Trp Ile Glu Thr Ile Leu Val Gln Ser Trp Tyr Pro Ile Thr
145                 150                 155                 160

Val Ala Thr Asn Ser Arg Glu Gln Lys Lys Ile Leu Ala Lys Tyr Leu
                165                 170                 175

Leu Glu Thr Ser Gly Asn Leu Asp Gly Leu Glu Tyr Lys Leu His Asp
            180                 185                 190

Phe Gly Tyr Arg Gly Val Ser Ser Gln Glu Thr Ala Gly Ile Gly Ala
        195                 200                 205

Ser Ala His Leu Val Asn Phe Lys Gly Thr Asp Thr Val Ala Gly Leu
210                 215                 220

Ala Leu Ile Lys Lys Tyr Tyr Gly Thr Lys Asp Pro Val Pro Gly Tyr
225                 230                 235                 240

Ser Val Pro Ala Ala Glu His Ser Thr Ile Thr Ala Trp Gly Lys Asp
                245                 250                 255

His Glu Lys Asp Ala Phe Glu His Ile Val Thr Gln Phe Ser Ser Val
            260                 265                 270

Pro Val Ser Val Val Ser Asp Ser Tyr Asp Ile Tyr Asn Ala Cys Glu
        275                 280                 285

Lys Ile Trp Gly Glu Asp Leu Arg His Leu Ile Val Ser Arg Ser Thr
```

```
                290                 295                 300
Gln Ala Pro Leu Ile Ile Arg Pro Asp Ser Gly Asn Pro Leu Asp Thr
305                 310                 315                 320

Val Leu Lys Val Leu Glu Ile Leu Gly Lys Lys Phe Pro Val Thr Glu
                325                 330                 335

Asn Ser Lys Gly Tyr Lys Leu Leu Pro Pro Tyr Leu Arg Val Ile Gln
                340                 345                 350

Gly Asp Gly Val Asp Ile Asn Thr Leu Gln Glu Ile Val Glu Gly Met
                355                 360                 365

Lys Gln Lys Met Trp Ser Ile Glu Asn Ile Ala Phe Gly Ser Gly Gly
                370                 375                 380

Gly Leu Leu Gln Lys Leu Thr Arg Asp Leu Leu Asn Cys Ser Phe Lys
385                 390                 395                 400

Cys Ser Tyr Val Val Thr Asn Gly Leu Gly Ile Asn Val Phe Lys Asp
                405                 410                 415

Pro Val Ala Asp Pro Asn Lys Arg Ser Lys Gly Arg Leu Ser Leu
                420                 425                 430

His Arg Thr Pro Ala Gly Asn Phe Val Thr Leu Glu Glu Gly Lys Gly
                435                 440                 445

Asp Leu Glu Glu Tyr Gly Gln Asp Leu Leu His Thr Val Phe Lys Asn
                450                 455                 460

Gly Lys Val Thr Lys Ser Tyr Ser Phe Asp Glu Ile Arg Lys Asn Ala
465                 470                 475                 480

Gln Leu Asn Ile Glu Leu Glu Ala Ala His His
                485                 490

<210> SEQ ID NO 67
<211> LENGTH: 465
<212> TYPE: PRT
<213> ORGANISM: Homo sapiens

<400> SEQUENCE: 67

Met Glu Pro Ser Ser Leu Glu Leu Pro Ala Asp Thr Val Gln Arg Ile
1               5                   10                  15

Ala Ala Glu Leu Lys Cys His Pro Thr Asp Glu Arg Val Ala Leu His
                20                  25                  30

Leu Asp Glu Glu Asp Lys Leu Arg His Phe Arg Glu Cys Phe Tyr Ile
            35                  40                  45

Pro Lys Ile Gln Asp Leu Pro Pro Val Asp Leu Ser Leu Val Asn Lys
        50                  55                  60

Asp Glu Asn Ala Ile Tyr Phe Leu Gly Asn Ser Leu Gly Leu Gln Pro
65                  70                  75                  80

Lys Met Val Lys Thr Tyr Leu Glu Glu Leu Asp Lys Trp Ala Lys
                85                  90                  95

Ile Ala Ala Tyr Gly His Glu Val Gly Lys Arg Pro Trp Ile Thr Gly
                100                 105                 110

Asp Glu Ser Ile Val Gly Leu Met Lys Asp Ile Val Gly Ala Asn Glu
            115                 120                 125

Lys Glu Ile Ala Leu Met Asn Ala Leu Thr Val Asn Leu His Leu Leu
        130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175
```

```
Gln Leu His Gly Leu Asn Ile Glu Glu Ser Met Arg Met Ile Lys Pro
            180                 185                 190

Arg Glu Gly Glu Thr Leu Arg Ile Glu Asp Ile Leu Glu Val Ile
        195                 200                 205

Glu Lys Glu Gly Asp Ser Ile Ala Val Ile Leu Phe Ser Gly Val His
    210                 215                 220

Phe Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
            245                 250                 255

Asn Val Glu Leu Tyr Leu His Asp Trp Gly Val Asp Phe Ala Cys Trp
        260                 265                 270

Cys Ser Tyr Lys Tyr Leu Asn Ala Gly Ala Gly Ile Ala Gly Ala
    275                 280                 285

Phe Ile His Glu Lys His Ala His Thr Ile Lys Pro Ala Leu Val Gly
290                 295                 300

Trp Phe Gly His Glu Leu Ser Thr Arg Phe Lys Met Asp Asn Lys Leu
305                 310                 315                 320

Gln Leu Ile Pro Gly Val Cys Gly Phe Arg Ile Ser Asn Pro Pro Ile
            325                 330                 335

Leu Leu Val Cys Ser Leu His Ala Ser Leu Glu Ile Phe Lys Gln Ala
        340                 345                 350

Thr Met Lys Ala Leu Arg Lys Lys Ser Val Leu Leu Thr Gly Tyr Leu
    355                 360                 365

Glu Tyr Leu Ile Lys His Asn Tyr Gly Lys Asp Lys Ala Ala Thr Lys
370                 375                 380

Lys Pro Val Val Asn Ile Ile Thr Pro Ser His Val Glu Glu Arg Gly
385                 390                 395                 400

Cys Gln Leu Thr Ile Thr Phe Ser Val Pro Asn Lys Asp Val Phe Gln
            405                 410                 415

Glu Leu Glu Lys Arg Gly Val Val Cys Asp Lys Arg Asn Pro Asn Gly
        420                 425                 430

Ile Arg Val Ala Pro Val Pro Leu Tyr Asn Ser Phe His Asp Val Tyr
    435                 440                 445

Lys Phe Thr Asn Leu Leu Thr Ser Ile Leu Asp Ser Ala Glu Thr Lys
450                 455                 460

Asn
465

<210> SEQ ID NO 68
<211> LENGTH: 83
<212> TYPE: PRT
<213> ORGANISM: Homo sapiens

<400> SEQUENCE: 68

Met Ser Phe Phe Gln Leu Leu Met Lys Arg Lys Glu Leu Ile Pro Leu
1               5                   10                  15

Val Val Phe Met Thr Val Ala Ala Gly Gly Ala Ser Ser Phe Ala Val
            20                  25                  30

Tyr Ser Leu Trp Lys Thr Asp Val Ile Leu Asp Arg Lys Lys Asn Pro
        35                  40                  45

Glu Pro Trp Glu Thr Val Asp Pro Thr Val Pro Gln Lys Leu Ile Thr
    50                  55                  60

Ile Asn Gln Gln Trp Lys Pro Ile Glu Glu Leu Gln Asn Val Gln Arg
65                  70                  75                  80
```

Val Thr Lys

<210> SEQ ID NO 69
<211> LENGTH: 350
<212> TYPE: PRT
<213> ORGANISM: Homo sapiens

<400> SEQUENCE: 69

Met Glu Pro Lys Arg Ile Arg Glu Gly Tyr Leu Val Lys Lys Gly Ser
1               5                   10                  15

Val Phe Asn Thr Trp Lys Pro Met Trp Val Val Leu Leu Glu Asp Gly
            20                  25                  30

Ile Glu Phe Tyr Lys Lys Lys Ser Asp Asn Ser Pro Lys Gly Met Ile
        35                  40                  45

Pro Leu Lys Gly Ser Thr Leu Thr Ser Pro Cys Gln Asp Phe Gly Lys
    50                  55                  60

Arg Met Phe Val Phe Lys Ile Thr Thr Thr Lys Gln Gln Asp His Phe
65                  70                  75                  80

Phe Gln Ala Ala Phe Leu Glu Glu Arg Asp Ala Trp Val Arg Asp Ile
                85                  90                  95

Lys Lys Ala Ile Lys Cys Ile Glu Gly Gly Gln Lys Phe Ala Arg Lys
            100                 105                 110

Ser Thr Arg Arg Ser Ile Arg Leu Pro Glu Thr Ile Asp Leu Gly Ala
        115                 120                 125

Leu Tyr Leu Ser Met Lys Asp Thr Glu Lys Gly Ile Lys Glu Leu Asn
    130                 135                 140

Leu Glu Lys Asp Lys Lys Ile Phe Asn His Cys Phe Thr Gly Asn Cys
145                 150                 155                 160

Val Ile Asp Trp Leu Val Ser Asn Gln Ser Val Arg Asn Arg Gln Glu
                165                 170                 175

Gly Leu Met Ile Ala Ser Ser Leu Leu Asn Glu Gly Tyr Leu Gln Pro
            180                 185                 190

Ala Gly Asp Met Ser Lys Ser Ala Val Asp Gly Thr Ala Glu Asn Pro
        195                 200                 205

Phe Leu Asp Asn Pro Asp Ala Phe Tyr Tyr Phe Pro Asp Ser Gly Phe
    210                 215                 220

Phe Cys Glu Glu Asn Ser Ser Asp Asp Val Ile Leu Lys Glu Glu
225                 230                 235                 240

Phe Arg Gly Val Ile Ile Lys Gln Gly Cys Leu Leu Lys Gln Gly His
                245                 250                 255

Arg Arg Lys Asn Trp Lys Val Arg Lys Phe Ile Leu Arg Glu Asp Pro
            260                 265                 270

Ala Tyr Leu His Tyr Tyr Asp Pro Ala Gly Ala Glu Asp Pro Leu Gly
        275                 280                 285

Ala Ile His Leu Arg Gly Cys Val Val Thr Ser Val Glu Ser Asn Ser
    290                 295                 300

Asn Gly Arg Lys Ser Glu Glu Glu Asn Leu Phe Glu Ile Ile Thr Ala
305                 310                 315                 320

Asp Glu Val His Tyr Phe Leu Gln Ala Ala Thr Pro Lys Glu Arg Thr
                325                 330                 335

Glu Trp Ile Arg Ala Ile Gln Met Ala Ser Arg Thr Gly Lys
            340                 345                 350

<210> SEQ ID NO 70

<211> LENGTH: 222
<212> TYPE: PRT
<213> ORGANISM: Homo sapiens

<400> SEQUENCE: 70

Met Leu Ser Arg Ala Val Cys Gly Thr Ser Arg Gln Leu Ala Pro Ala
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Lys His His Ala Ala Tyr Val Asn Asn Leu Asn Val
50                  55                  60

Thr Glu Glu Lys Tyr Gln Glu Ala Leu Ala Lys Gly Asp Val Thr Ala
65                  70                  75                  80

Gln Ile Ala Leu Gln Pro Ala Leu Lys Phe Asn Gly Gly Gly His Ile
                85                  90                  95

Asn His Ser Ile Phe Trp Thr Asn Leu Ser Pro Asn Gly Gly Gly Glu
            100                 105                 110

Pro Lys Gly Glu Leu Leu Glu Ala Ile Lys Arg Asp Phe Gly Ser Phe
        115                 120                 125

Asp Lys Phe Lys Glu Lys Leu Thr Ala Ala Ser Val Gly Val Gln Gly
    130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Glu Arg Tyr Met Ala Cys Lys Lys
    210                 215                 220

<210> SEQ ID NO 71
<211> LENGTH: 440
<212> TYPE: PRT
<213> ORGANISM: Homo sapiens

<400> SEQUENCE: 71

Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
            20                  25                  30

Ala Glu Ala Glu Ala Ala Ala Gly Pro Gly Pro Cys Glu Arg Leu Leu
        35                  40                  45

Ser Arg Val Ala Ala Leu Phe Pro Ala Leu Arg Pro Gly Gly Phe Gln
    50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95

Ile Tyr Ile Lys Glu Lys Lys Glu Cys Arg Arg Asp His Arg Pro Pro
            100                 105                 110

Cys Ala Gln Glu Ala Pro Arg Asn Met Val His Pro Asn Val Ile Cys
        115                 120                 125

Asp Gly Cys Asn Gly Pro Val Gly Thr Arg Tyr Lys Cys Ser Val
130                 135                 140

Cys Pro Asp Tyr Asp Leu Cys Ser Val Cys Glu Gly Lys Gly Leu His
145                 150                 155                 160

Arg Gly His Thr Lys Leu Ala Phe Pro Ser Pro Phe Gly His Leu Ser
                165                 170                 175

Glu Gly Phe Ser His Ser Arg Trp Leu Arg Lys Val Lys His Gly His
            180                 185                 190

Phe Gly Trp Pro Gly Trp Glu Met Gly Pro Pro Gly Asn Trp Ser Pro
        195                 200                 205

Arg Pro Pro Arg Ala Gly Glu Ala Arg Pro Gly Pro Thr Ala Glu Ser
210                 215                 220

Ala Ser Gly Pro Ser Glu Asp Pro Ser Val Asn Phe Leu Lys Asn Val
225                 230                 235                 240

Gly Glu Ser Val Ala Ala Leu Ser Pro Leu Gly Ile Glu Val Asp
                245                 250                 255

Ile Asp Val Glu His Gly Gly Lys Arg Ser Arg Leu Thr Pro Val Ser
                260                 265                 270

Pro Glu Ser Ser Ser Thr Glu Glu Lys Ser Ser Ser Gln Pro Ser Ser
            275                 280                 285

Cys Cys Ser Asp Pro Ser Lys Pro Gly Gly Asn Val Glu Gly Ala Thr
290                 295                 300

Gln Ser Leu Ala Glu Gln Met Arg Lys Ile Ala Leu Glu Ser Glu Gly
305                 310                 315                 320

Arg Pro Glu Glu Gln Met Glu Ser Asp Asn Cys Ser Gly Gly Asp Asp
                325                 330                 335

Asp Trp Thr His Leu Ser Ser Lys Glu Val Asp Pro Ser Thr Gly Glu
            340                 345                 350

Leu Gln Ser Leu Gln Met Pro Glu Ser Glu Gly Pro Ser Ser Leu Asp
        355                 360                 365

Pro Ser Gln Glu Gly Pro Thr Gly Leu Lys Glu Ala Ala Leu Tyr Pro
370                 375                 380

His Leu Pro Pro Glu Ala Asp Pro Arg Leu Ile Glu Ser Leu Ser Gln
385                 390                 395                 400

Met Leu Ser Met Gly Phe Ser Asp Glu Gly Gly Trp Leu Thr Arg Leu
                405                 410                 415

Leu Gln Thr Lys Asn Tyr Asp Ile Gly Ala Ala Leu Asp Thr Ile Gln
            420                 425                 430

Tyr Ser Lys His Pro Pro Leu
        435                 440

<210> SEQ ID NO 72
<211> LENGTH: 760
<212> TYPE: PRT
<213> ORGANISM: Homo sapiens

<400> SEQUENCE: 72

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly

```
            50                  55                  60
Ser Ile Cys Tyr Gly Thr Ile Ala Val Ile Val Phe Phe Leu Ile Gly
 65                  70                  75                  80

Phe Met Ile Gly Tyr Leu Gly Tyr Cys Lys Gly Val Glu Pro Lys Thr
                     85                  90                  95

Glu Cys Glu Arg Leu Ala Gly Thr Glu Ser Pro Val Arg Glu Glu Pro
                    100                 105                 110

Gly Glu Asp Phe Pro Ala Ala Arg Arg Leu Tyr Trp Asp Asp Leu Lys
                115                 120                 125

Arg Lys Leu Ser Glu Lys Leu Asp Ser Thr Asp Phe Thr Gly Thr Ile
            130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
                180                 185                 190

Lys Asp Ser Ala Gln Asn Ser Val Ile Ile Val Asp Lys Asn Gly Arg
            195                 200                 205

Leu Val Tyr Leu Val Glu Asn Pro Gly Gly Tyr Val Ala Tyr Ser Lys
            210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
                260                 265                 270

Ser Leu Asn Ala Ile Gly Val Leu Ile Tyr Met Asp Gln Thr Lys Phe
            275                 280                 285

Pro Ile Val Asn Ala Glu Leu Ser Phe Phe Gly His Ala His Leu Gly
            290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
            355                 360                 365

Glu Ser Lys Asn Val Lys Leu Thr Val Ser Asn Val Leu Lys Glu Ile
370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
                420                 425                 430

Phe Ser Asp Met Val Leu Lys Asp Gly Phe Gln Pro Ser Arg Ser Ile
            435                 440                 445

Ile Phe Ala Ser Trp Ser Ala Gly Asp Phe Gly Ser Val Gly Ala Thr
            450                 455                 460

Glu Trp Leu Glu Gly Tyr Leu Ser Ser Leu His Leu Lys Ala Phe Thr
465                 470                 475                 480
```

Tyr Ile Asn Leu Asp Lys Ala Val Leu Gly Thr Ser Asn Phe Lys Val
            485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
            515                 520                 525

Ala Ser Lys Val Glu Lys Leu Thr Leu Asp Asn Ala Ala Phe Pro Phe
            530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
            565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
            595                 600                 605

Leu Asp Tyr Glu Arg Tyr Asn Ser Gln Leu Leu Ser Phe Val Arg Asp
            610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
            645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
            675                 680                 685

Tyr Val Ser Pro Lys Glu Ser Pro Phe Arg His Val Phe Trp Gly Ser
            690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
            725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
            755                 760

<210> SEQ ID NO 73
<211> LENGTH: 105
<212> TYPE: PRT
<213> ORGANISM: Homo sapiens

<400> SEQUENCE: 73

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Ser Glu Lys
            35                  40                  45

Tyr Ser Asn Val Ile Phe Leu Glu Val Asp Val Asp Asp Cys Gln Asp
            50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys

```
                    85                  90                  95

Leu Glu Ala Thr Ile Asn Glu Leu Val
            100                 105

<210> SEQ ID NO 74
<211> LENGTH: 277
<212> TYPE: PRT
<213> ORGANISM: Homo sapiens

<400> SEQUENCE: 74

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275

<210> SEQ ID NO 75
<211> LENGTH: 416
<212> TYPE: PRT
<213> ORGANISM: Homo sapiens

<400> SEQUENCE: 75

Met Ala Ser Ser Gly Ser Ser Pro Arg Pro Ala Pro Asp Glu Asn
1               5                   10                  15

Glu Phe Pro Phe Gly Cys Pro Pro Thr Val Cys Gln Asp Pro Lys Glu
```

-continued

```
                20                  25                  30
Pro Arg Ala Leu Cys Cys Ala Gly Cys Leu Ser Glu Asn Pro Arg Asn
            35                  40                  45
Gly Glu Asp Gln Ile Cys Pro Lys Cys Arg Gly Glu Asp Leu Gln Ser
 50                  55                  60
Ile Ser Pro Gly Ser Arg Leu Arg Thr Gln Glu Lys Ala His Pro Glu
 65                  70                  75                  80
Val Ala Glu Ala Gly Ile Gly Cys Pro Phe Ala Gly Val Gly Cys Ser
                85                  90                  95
Phe Lys Gly Ser Pro Gln Ser Val Gln Glu His Glu Val Thr Ser Gln
            100                 105                 110
Thr Ser His Leu Asn Leu Leu Leu Gly Phe Met Lys Gln Trp Lys Ala
            115                 120                 125
Arg Leu Gly Cys Gly Leu Glu Ser Gly Pro Met Ala Leu Glu Gln Asn
            130                 135                 140
Leu Ser Asp Leu Gln Leu Gln Ala Ala Val Glu Val Ala Gly Asp Leu
145                 150                 155                 160
Glu Val Asp Cys Tyr Arg Ala Pro Cys Ser Glu Ser Gln Glu Glu Leu
                165                 170                 175
Ala Leu Gln His Phe Met Lys Glu Lys Leu Leu Ala Glu Leu Glu Gly
            180                 185                 190
Lys Leu Arg Val Phe Glu Asn Ile Val Ala Val Leu Asn Lys Glu Val
            195                 200                 205
Glu Ala Ser His Leu Ala Leu Ala Thr Ser Ile His Gln Ser Gln Leu
            210                 215                 220
Asp Arg Glu Arg Ile Leu Ser Leu Glu Gln Arg Val Val Glu Leu Gln
225                 230                 235                 240
Gln Thr Leu Ala Gln Lys Asp Gln Ala Leu Gly Lys Leu Glu Gln Ser
                245                 250                 255
Leu Arg Leu Met Glu Glu Ala Ser Phe Asp Gly Thr Phe Leu Trp Lys
            260                 265                 270
Ile Thr Asn Val Thr Arg Arg Cys His Glu Ser Ala Cys Gly Arg Thr
            275                 280                 285
Val Ser Leu Phe Ser Pro Ala Phe Tyr Thr Ala Lys Tyr Gly Tyr Lys
            290                 295                 300
Leu Cys Leu Arg Leu Tyr Leu Asn Gly Asp Gly Thr Gly Lys Arg Thr
305                 310                 315                 320
His Leu Ser Leu Phe Ile Val Ile Met Arg Gly Glu Tyr Asp Ala Leu
                325                 330                 335
Leu Pro Trp Pro Phe Arg Asn Lys Val Thr Phe Met Leu Leu Asp Gln
            340                 345                 350
Asn Asn Arg Glu His Ala Ile Asp Ala Phe Arg Pro Asp Leu Ser Ser
            355                 360                 365
Ala Ser Phe Gln Arg Pro Gln Ser Glu Thr Asn Val Ala Ser Gly Cys
            370                 375                 380
Pro Leu Phe Phe Pro Leu Ser Lys Leu Gln Ser Pro Lys His Ala Tyr
385                 390                 395                 400
Val Lys Asp Asp Thr Met Phe Leu Lys Cys Ile Val Glu Thr Ser Thr
                405                 410                 415
```

<210> SEQ ID NO 76
<211> LENGTH: 606
<212> TYPE: PRT
<213> ORGANISM: Homo sapiens

<400> SEQUENCE: 76

```
Met Pro Tyr Glu Ile Lys Lys Val Phe Ala Ser Leu Pro Gln Val Glu
1               5                   10                  15

Arg Gly Val Ser Lys Ile Ile Gly Gly Asp Pro Lys Gly Asn Asn Phe
            20                  25                  30

Leu Tyr Thr Asn Gly Lys Cys Val Ile Leu Arg Asn Ile Asp Asn Pro
        35                  40                  45

Ala Leu Ala Asp Ile Tyr Thr Glu His Ala His Gln Val Val Ala
    50                  55                  60

Lys Tyr Ala Pro Ser Gly Phe Tyr Ile Ala Ser Gly Asp Val Ser Gly
65                  70                  75                  80

Lys Leu Arg Ile Trp Asp Thr Thr Gln Lys Glu His Leu Leu Lys Tyr
                85                  90                  95

Glu Tyr Gln Pro Phe Ala Gly Lys Ile Lys Asp Ile Ala Trp Thr Glu
            100                 105                 110

Asp Ser Lys Arg Ile Ala Val Val Gly Glu Gly Arg Glu Lys Phe Gly
        115                 120                 125

Ala Val Phe Leu Trp Asp Ser Gly Ser Ser Val Gly Glu Ile Thr Gly
    130                 135                 140

His Asn Lys Val Ile Asn Ser Val Asp Ile Lys Gln Ser Arg Pro Tyr
145                 150                 155                 160

Arg Leu Ala Thr Gly Ser Asp Asp Asn Cys Ala Ala Phe Phe Glu Gly
                165                 170                 175

Pro Pro Phe Lys Phe Lys Phe Thr Ile Gly Asp His Ser Arg Phe Val
            180                 185                 190

Asn Cys Val Arg Phe Ser Pro Asp Gly Asn Arg Phe Ala Thr Ala Ser
        195                 200                 205

Ala Asp Gly Gln Ile Tyr Ile Tyr Asp Gly Lys Thr Gly Glu Lys Val
    210                 215                 220

Cys Ala Leu Gly Gly Ser Lys Ala His Asp Gly Ile Tyr Ala Ile
225                 230                 235                 240

Ser Trp Ser Pro Asp Ser Thr His Leu Leu Ser Ala Ser Gly Asp Lys
                245                 250                 255

Thr Ser Lys Ile Trp Asp Val Ser Val Asn Ser Val Val Ser Thr Phe
            260                 265                 270

Pro Met Gly Ser Thr Val Leu Asp Gln Gln Leu Gly Cys Leu Trp Gln
        275                 280                 285

Lys Asp His Leu Leu Ser Val Ser Leu Ser Gly Tyr Ile Asn Tyr Leu
    290                 295                 300

Asp Arg Asn Asn Pro Ser Lys Pro Leu His Val Ile Lys Gly His Ser
305                 310                 315                 320

Lys Ser Ile Gln Cys Leu Thr Val His Lys Asn Gly Gly Lys Ser Tyr
                325                 330                 335

Ile Tyr Ser Gly Ser His Asp Gly His Ile Asn Tyr Trp Asp Ser Glu
            340                 345                 350

Thr Gly Glu Asn Asp Ser Phe Ala Gly Lys Gly His Thr Asn Gln Val
        355                 360                 365

Ser Arg Met Thr Val Asp Glu Ser Gly Gln Leu Ile Ser Cys Ser Met
    370                 375                 380

Asp Asp Thr Val Arg Tyr Thr Ser Leu Met Leu Arg Asp Tyr Ser Gly
385                 390                 395                 400

Gln Gly Val Val Lys Leu Asp Val Gln Pro Lys Cys Val Ala Val Gly
```

```
                    405                 410                 415
Pro Gly Gly Tyr Ala Val Val Cys Ile Gly Gln Ile Val Leu Leu
                420                 425                 430

Lys Asp Gln Arg Lys Cys Phe Ser Ile Asp Asn Pro Gly Tyr Glu Pro
            435                 440                 445

Glu Val Val Ala Val His Pro Gly Gly Asp Thr Val Ala Ile Gly Gly
        450                 455                 460

Val Asp Gly Asn Val Arg Leu Tyr Ser Ile Leu Gly Thr Thr Leu Lys
465                 470                 475                 480

Asp Glu Gly Lys Leu Leu Glu Ala Lys Gly Pro Val Thr Asp Val Ala
                485                 490                 495

Tyr Ser His Asp Gly Ala Phe Leu Ala Val Cys Asp Ala Ser Lys Val
                500                 505                 510

Val Thr Val Phe Ser Val Ala Asp Gly Tyr Ser Glu Asn Asn Val Phe
            515                 520                 525

Tyr Gly His His Ala Lys Ile Val Cys Leu Ala Trp Ser Pro Asp Asn
        530                 535                 540

Glu His Phe Ala Ser Gly Gly Met Asp Met Met Val Tyr Val Trp Thr
545                 550                 555                 560

Leu Ser Asp Pro Glu Thr Arg Val Lys Ile Gln Asp Ala His Arg Leu
                565                 570                 575

His His Val Ser Ser Leu Ala Trp Leu Asp Glu His Thr Leu Val Thr
            580                 585                 590

Thr Ser His Asp Ala Ser Val Lys Glu Trp Thr Ile Thr Tyr
        595                 600                 605

<210> SEQ ID NO 77
<211> LENGTH: 673
<212> TYPE: PRT
<213> ORGANISM: Homo sapiens

<400> SEQUENCE: 77

Met Ala Lys Pro Ala Gln Gly Ala Lys Tyr Arg Gly Ser Ile His Asp
1               5                   10                  15

Phe Pro Gly Phe Asp Pro Asn Gln Asp Ala Glu Ala Leu Tyr Thr Ala
            20                  25                  30

Met Lys Gly Phe Gly Ser Asp Lys Glu Ala Ile Leu Asp Ile Ile Thr
        35                  40                  45

Ser Arg Ser Asn Arg Gln Arg Gln Glu Val Cys Gln Ser Tyr Lys Ser
    50                  55                  60

Leu Tyr Gly Lys Asp Leu Ile Ala Asp Leu Lys Tyr Glu Leu Thr Gly
65                  70                  75                  80

Lys Phe Glu Arg Leu Ile Val Gly Leu Met Arg Pro Pro Ala Tyr Cys
                85                  90                  95

Asp Ala Lys Glu Ile Lys Asp Ala Ile Ser Gly Ile Gly Thr Asp Glu
            100                 105                 110

Lys Cys Leu Ile Glu Ile Leu Ala Ser Arg Thr Asn Glu Gln Met His
        115                 120                 125

Gln Leu Val Ala Ala Tyr Lys Asp Ala Tyr Glu Arg Asp Leu Glu Ala
    130                 135                 140

Asp Ile Ile Gly Asp Thr Ser Gly His Phe Gln Lys Met Leu Val Val
145                 150                 155                 160

Leu Leu Gln Gly Thr Arg Glu Glu Asp Asp Val Val Ser Glu Asp Leu
                165                 170                 175
```

```
Val Gln Gln Asp Val Gln Asp Leu Tyr Glu Ala Gly Glu Leu Lys Trp
            180                 185                 190

Gly Thr Asp Glu Ala Gln Phe Ile Tyr Ile Leu Gly Asn Arg Ser Lys
            195                 200                 205

Gln His Leu Arg Leu Val Phe Asp Glu Tyr Leu Lys Thr Thr Gly Lys
        210                 215                 220

Pro Ile Glu Ala Ser Ile Arg Gly Glu Leu Ser Gly Asp Phe Glu Lys
225                 230                 235                 240

Leu Met Leu Ala Val Lys Cys Ile Arg Ser Thr Pro Glu Tyr Phe
            245                 250                 255

Ala Glu Arg Leu Phe Lys Ala Met Lys Gly Leu Gly Thr Arg Asp Asn
            260                 265                 270

Thr Leu Ile Arg Ile Met Val Ser Arg Ser Glu Leu Asp Met Leu Asp
            275                 280                 285

Ile Arg Glu Ile Phe Arg Thr Lys Tyr Glu Lys Ser Leu Tyr Ser Met
            290                 295                 300

Ile Lys Asn Asp Thr Ser Gly Glu Tyr Lys Lys Thr Leu Leu Lys Leu
305                 310                 315                 320

Ser Gly Gly Asp Asp Ala Ala Gly Gln Phe Phe Pro Glu Ala Ala
            325                 330                 335

Gln Val Ala Tyr Gln Met Trp Glu Leu Ser Ala Val Ala Arg Val Glu
            340                 345                 350

Leu Lys Gly Thr Val Arg Pro Ala Asn Asp Phe Asn Pro Asp Ala Asp
            355                 360                 365

Ala Lys Ala Leu Arg Lys Ala Met Lys Gly Leu Gly Thr Asp Glu Asp
370                 375                 380

Thr Ile Ile Asp Ile Ile Thr His Arg Ser Asn Val Gln Arg Gln Gln
385                 390                 395                 400

Ile Arg Gln Thr Phe Lys Ser His Phe Gly Arg Asp Leu Met Thr Asp
            405                 410                 415

Leu Lys Ser Glu Ile Ser Gly Asp Leu Ala Arg Leu Ile Leu Gly Leu
            420                 425                 430

Met Met Pro Pro Ala His Tyr Asp Ala Lys Gln Leu Lys Lys Ala Met
            435                 440                 445

Glu Gly Ala Gly Thr Asp Glu Lys Ala Leu Ile Glu Ile Leu Ala Thr
450                 455                 460

Arg Thr Asn Ala Glu Ile Arg Ala Ile Asn Glu Ala Tyr Lys Glu Asp
465                 470                 475                 480

Tyr His Lys Ser Leu Glu Asp Ala Leu Ser Ser Asp Thr Ser Gly His
            485                 490                 495

Phe Arg Arg Ile Leu Ile Ser Leu Ala Thr Gly His Arg Glu Glu Gly
            500                 505                 510

Gly Glu Asn Leu Asp Gln Ala Arg Glu Asp Ala Gln Val Ala Ala Glu
            515                 520                 525

Ile Leu Glu Ile Ala Asp Thr Pro Ser Gly Asp Lys Thr Ser Leu Glu
            530                 535                 540

Thr Arg Phe Met Thr Ile Leu Cys Thr Arg Ser Tyr Pro His Leu Arg
545                 550                 555                 560

Arg Val Phe Gln Glu Phe Ile Lys Met Thr Asn Tyr Asp Val Glu His
            565                 570                 575

Thr Ile Lys Lys Glu Met Ser Gly Asp Val Arg Asp Ala Phe Val Ala
            580                 585                 590

Ile Val Gln Ser Val Lys Asn Lys Pro Leu Phe Phe Ala Asp Lys Leu
```

```
                        595                 600                 605

Tyr Lys Ser Met Lys Gly Ala Gly Thr Asp Glu Lys Thr Leu Thr Arg
        610                 615                 620

Ile Met Val Ser Arg Ser Glu Ile Asp Leu Leu Asn Ile Arg Arg Glu
625                 630                 635                 640

Phe Ile Glu Lys Tyr Asp Lys Ser Leu His Gln Ala Ile Glu Gly Asp
                645                 650                 655

Thr Ser Gly Asp Phe Leu Lys Ala Leu Leu Ala Leu Cys Gly Gly Glu
            660                 665                 670

Asp

<210> SEQ ID NO 78
<211> LENGTH: 462
<212> TYPE: PRT
<213> ORGANISM: Homo sapiens

<400> SEQUENCE: 78

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
    50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
    130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
            180                 185                 190

Ile Ser Gly Trp Asn Gly Asp Asn Met Leu Glu Pro Ser Ala Asn Met
        195                 200                 205

Pro Trp Phe Lys Gly Trp Lys Val Thr Arg Lys Asp Gly Asn Ala Ser
    210                 215                 220

Gly Thr Thr Leu Leu Glu Ala Leu Asp Cys Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Val Leu
            260                 265                 270

Lys Pro Gly Met Val Val Thr Phe Ala Pro Val Asn Val Thr Thr Glu
        275                 280                 285

Val Lys Ser Val Glu Met His His Glu Ala Leu Ser Glu Ala Leu Pro
```

```
            290                 295                 300
Gly Asp Asn Val Gly Phe Lys Val Lys Asn Val Ser Val Lys Asp Val
305                 310                 315                 320

Arg Arg Gly Asn Val Ala Gly Asp Ser Lys Asn Asp Pro Pro Met Glu
                325                 330                 335

Ala Ala Gly Phe Thr Ala Gln Val Ile Ile Leu Asn His Pro Gly Gln
            340                 345                 350

Ile Ser Ala Gly Tyr Ala Pro Val Leu Asp Cys His Met Ala His Ile
        355                 360                 365

Ala Cys Lys Phe Ala Glu Leu Lys Glu Lys Ile Asp Arg Arg Ser Gly
    370                 375                 380

Lys Lys Leu Glu Asp Gly Pro Lys Phe Leu Lys Ser Gly Asp Ala Ala
385                 390                 395                 400

Ile Val Asp Met Val Pro Gly Lys Pro Met Cys Val Glu Ser Phe Ser
                405                 410                 415

Asp Tyr Pro Pro Leu Gly Arg Phe Ala Val Arg Asp Met Arg Gln Thr
            420                 425                 430

Val Ala Val Gly Val Ile Lys Ala Val Asp Lys Lys Ala Ala Gly Ala
        435                 440                 445

Gly Lys Val Thr Lys Ser Ala Gln Lys Ala Gln Lys Ala Lys
    450                 455                 460

<210> SEQ ID NO 79
<211> LENGTH: 248
<212> TYPE: PRT
<213> ORGANISM: Homo sapiens

<400> SEQUENCE: 79

Met Ser Tyr Asp Arg Ala Ile Thr Val Phe Ser Pro Asp Gly His Leu
1               5                   10                  15

Phe Gln Val Glu Tyr Ala Gln Glu Ala Val Lys Lys Gly Ser Thr Ala
                20                  25                  30

Val Gly Val Arg Gly Arg Asp Ile Val Val Leu Gly Val Glu Lys Lys
            35                  40                  45

Ser Val Ala Lys Leu Gln Asp Glu Arg Thr Val Arg Lys Ile Cys Ala
    50                  55                  60

Leu Asp Asp Asn Val Cys Met Ala Phe Ala Gly Leu Thr Ala Asp Ala
65                  70                  75                  80

Arg Ile Val Ile Asn Arg Ala Arg Val Glu Cys Gln Ser His Arg Leu
                85                  90                  95

Thr Val Glu Asp Pro Val Thr Val Glu Tyr Ile Thr Arg Tyr Ile Ala
            100                 105                 110

Ser Leu Lys Gln Arg Tyr Thr Gln Ser Asn Gly Arg Arg Pro Phe Gly
        115                 120                 125

Ile Ser Ala Leu Ile Val Gly Phe Asp Phe Asp Gly Thr Pro Arg Leu
    130                 135                 140

Tyr Gln Thr Asp Pro Ser Gly Thr Tyr His Ala Trp Lys Ala Asn Ala
145                 150                 155                 160

Ile Gly Arg Gly Ala Lys Ser Val Arg Glu Phe Leu Glu Lys Asn Tyr
                165                 170                 175

Thr Asp Glu Ala Ile Glu Thr Asp Asp Leu Thr Ile Lys Leu Val Ile
            180                 185                 190

Lys Ala Leu Leu Glu Val Val Gln Ser Gly Gly Lys Asn Ile Glu Leu
        195                 200                 205
```

Ala Val Met Arg Arg Asp Gln Ser Leu Lys Ile Leu Asn Pro Glu Glu
    210                 215                 220

Ile Glu Lys Tyr Val Ala Glu Ile Glu Lys Lys Glu Glu Asn Glu
225                 230                 235                 240

Lys Lys Lys Gln Lys Lys Ala Ser
                245

<210> SEQ ID NO 80
<211> LENGTH: 483
<212> TYPE: PRT
<213> ORGANISM: Homo sapiens

<400> SEQUENCE: 80

Met Ala Gln Ala Asp Ile Ala Leu Ile Gly Leu Ala Val Met Gly Gln
1               5                   10                  15

Asn Leu Ile Leu Asn Met Asn Asp His Gly Phe Val Val Cys Ala Phe
                20                  25                  30

Asn Arg Thr Val Ser Lys Val Asp Asp Phe Leu Ala Asn Glu Ala Lys
            35                  40                  45

Gly Thr Lys Val Val Gly Ala Gln Ser Leu Lys Glu Met Val Ser Lys
    50                  55                  60

Leu Lys Lys Pro Arg Arg Ile Ile Leu Leu Val Lys Ala Gly Gln Ala
65                  70                  75                  80

Val Asp Asp Phe Ile Glu Lys Leu Val Pro Leu Leu Asp Thr Gly Asp
                85                  90                  95

Ile Ile Ile Asp Gly Gly Asn Ser Glu Tyr Arg Asp Thr Thr Arg Arg
                100                 105                 110

Cys Arg Asp Leu Lys Ala Lys Gly Ile Leu Phe Val Gly Ser Gly Val
            115                 120                 125

Ser Gly Gly Glu Glu Gly Ala Arg Tyr Gly Pro Ser Leu Met Pro Gly
    130                 135                 140

Gly Asn Lys Glu Ala Trp Pro His Ile Lys Thr Ile Phe Gln Gly Ile
145                 150                 155                 160

Ala Ala Lys Val Gly Thr Gly Glu Pro Cys Cys Asp Trp Val Gly Asp
                165                 170                 175

Glu Gly Ala Gly His Phe Val Lys Met Val His Asn Gly Ile Glu Tyr
            180                 185                 190

Gly Asp Met Gln Leu Ile Cys Glu Ala Tyr His Leu Met Lys Asp Val
    195                 200                 205

Leu Gly Met Ala Gln Asp Glu Met Ala Gln Ala Phe Glu Asp Trp Asn
210                 215                 220

Lys Thr Glu Leu Asp Ser Phe Leu Ile Glu Ile Thr Ala Asn Ile Leu
225                 230                 235                 240

Lys Phe Gln Asp Thr Asp Gly Lys His Leu Leu Pro Lys Ile Arg Asp
                245                 250                 255

Ser Ala Gly Gln Lys Gly Thr Gly Lys Trp Thr Ala Ile Ser Ala Leu
            260                 265                 270

Glu Tyr Gly Val Pro Val Thr Leu Ile Gly Glu Ala Val Phe Ala Arg
    275                 280                 285

Cys Leu Ser Ser Leu Lys Asp Glu Arg Ile Gln Ala Ser Lys Lys Leu
290                 295                 300

Lys Gly Pro Gln Lys Phe Gln Phe Asp Gly Asp Lys Lys Ser Phe Leu
305                 310                 315                 320

Glu Asp Ile Arg Lys Ala Leu Tyr Ala Ser Lys Ile Ile Ser Tyr Ala
                325                 330                 335

```
Gln Gly Phe Met Leu Leu Arg Gln Ala Ala Thr Glu Phe Gly Trp Thr
                340                 345                 350
Leu Asn Tyr Gly Gly Ile Ala Leu Met Trp Arg Gly Cys Ile Ile
            355                 360                 365
Arg Ser Val Phe Leu Gly Lys Ile Lys Asp Ala Phe Asp Arg Asn Pro
370                 375                 380
Glu Leu Gln Asn Leu Leu Asp Asp Phe Phe Lys Ser Ala Val Glu
385                 390                 395                 400
Asn Cys Gln Asp Ser Trp Arg Arg Ala Val Ser Thr Gly Val Gln Ala
                405                 410                 415
Gly Ile Pro Met Pro Cys Phe Thr Thr Ala Leu Ser Phe Tyr Asp Gly
                420                 425                 430
Tyr Arg His Glu Met Leu Pro Ala Ser Leu Ile Gln Ala Gln Arg Asp
                435                 440                 445
Tyr Phe Gly Ala His Thr Tyr Glu Leu Leu Ala Lys Pro Gly Gln Phe
                450                 455                 460
Ile His Thr Asn Trp Thr Gly His Gly Gly Thr Val Ser Ser Ser
465                 470                 475                 480
Tyr Asn Ala

<210> SEQ ID NO 81
<211> LENGTH: 87
<212> TYPE: PRT
<213> ORGANISM: Homo sapiens

<400> SEQUENCE: 81

Met Ser Gln Ala Glu Phe Glu Lys Ala Ala Glu Val Arg His Leu
1               5                   10                  15
Lys Thr Lys Pro Ser Asp Glu Glu Met Leu Phe Ile Tyr Gly His Tyr
                20                  25                  30
Lys Gln Ala Thr Val Gly Asp Ile Asn Thr Glu Arg Pro Gly Met Leu
            35                  40                  45
Asp Phe Thr Gly Lys Ala Lys Trp Asp Ala Trp Asn Glu Leu Lys Gly
        50                  55                  60
Thr Ser Lys Glu Asp Ala Met Lys Ala Tyr Ile Asn Lys Val Glu Glu
65                  70                  75                  80
Leu Lys Lys Lys Tyr Gly Ile
                85

<210> SEQ ID NO 82
<211> LENGTH: 911
<212> TYPE: PRT
<213> ORGANISM: Homo sapiens

<400> SEQUENCE: 82

Met Val Asp Tyr His Ala Ala Asn Gln Ser Tyr Gln Tyr Gly Pro Ser
1               5                   10                  15
Ser Ala Gly Asn Gly Ala Gly Gly Gly Ser Met Gly Asp Tyr Met
                20                  25                  30
Ala Gln Glu Asp Asp Trp Asp Arg Asp Leu Leu Leu Asp Pro Ala Trp
            35                  40                  45
Glu Lys Gln Gln Arg Lys Thr Phe Thr Ala Trp Cys Asn Ser His Leu
        50                  55                  60
Arg Lys Ala Gly Thr Gln Ile Glu Asn Ile Asp Glu Asp Phe Arg Asp
65                  70                  75                  80
```

```
Gly Leu Lys Leu Met Leu Leu Leu Glu Val Ile Ser Gly Glu Arg Leu
                 85                  90                  95
Pro Lys Pro Glu Arg Gly Lys Met Arg Val His Lys Ile Asn Asn Val
            100                 105                 110
Asn Lys Ala Leu Asp Phe Ile Ala Ser Lys Gly Val Lys Leu Val Ser
        115                 120                 125
Ile Gly Ala Glu Glu Ile Val Asp Gly Asn Ala Lys Met Thr Leu Gly
    130                 135                 140
Met Ile Trp Thr Ile Ile Leu Arg Phe Ala Ile Gln Asp Ile Ser Val
145                 150                 155                 160
Glu Glu Thr Ser Ala Lys Glu Gly Leu Leu Leu Trp Cys Gln Arg Lys
                165                 170                 175
Thr Ala Pro Tyr Lys Asn Val Asn Val Gln Asn Phe His Ile Ser Trp
            180                 185                 190
Lys Asp Gly Leu Ala Phe Asn Ala Leu Ile His Arg His Arg Pro Glu
        195                 200                 205
Leu Ile Glu Tyr Asp Lys Leu Arg Lys Asp Asp Pro Val Thr Asn Leu
    210                 215                 220
Asn Asn Ala Phe Glu Val Ala Glu Lys Tyr Leu Asp Ile Pro Lys Met
225                 230                 235                 240
Leu Asp Ala Glu Asp Ile Val Asn Thr Ala Arg Pro Asp Glu Lys Ala
                245                 250                 255
Ile Met Thr Tyr Val Ser Ser Phe Tyr His Ala Phe Ser Gly Ala Gln
            260                 265                 270
Lys Ala Glu Thr Ala Ala Asn Arg Ile Cys Lys Val Leu Ala Val Asn
        275                 280                 285
Gln Glu Asn Glu His Leu Met Glu Asp Tyr Glu Lys Leu Ala Ser Asp
    290                 295                 300
Leu Leu Glu Trp Ile Arg Arg Thr Ile Pro Trp Leu Glu Asp Arg Val
305                 310                 315                 320
Pro Gln Lys Thr Ile Gln Glu Met Gln Gln Lys Leu Glu Asp Phe Arg
                325                 330                 335
Asp Tyr Arg Arg Val His Lys Pro Pro Lys Val Gln Glu Lys Cys Gln
            340                 345                 350
Leu Glu Ile Asn Phe Asn Thr Leu Gln Thr Lys Leu Arg Leu Ser Asn
        355                 360                 365
Arg Pro Ala Phe Met Pro Ser Glu Gly Lys Met Val Ser Asp Ile Asn
    370                 375                 380
Asn Gly Trp Gln His Leu Glu Gln Ala Glu Lys Gly Tyr Glu Glu Trp
385                 390                 395                 400
Leu Leu Asn Glu Ile Arg Arg Leu Glu Arg Leu Asp His Leu Ala Glu
                405                 410                 415
Lys Phe Arg Gln Lys Ala Ser Ile His Glu Ala Trp Thr Asp Gly Lys
            420                 425                 430
Glu Ala Met Leu Lys His Arg Asp Tyr Glu Thr Ala Thr Leu Ser Asp
        435                 440                 445
Ile Lys Ala Leu Ile Arg Lys His Glu Ala Phe Glu Ser Asp Leu Ala
    450                 455                 460
Ala His Gln Asp Arg Val Glu Gln Ile Ala Ile Ala Gln Glu Leu
465                 470                 475                 480
Asn Glu Leu Asp Tyr Tyr Asp Ser His Asn Val Asn Thr Arg Cys Gln
                485                 490                 495
Lys Ile Cys Asp Gln Trp Asp Ala Leu Gly Ser Leu Thr His Ser Arg
```

```
                    500                 505                 510
Arg Glu Ala Leu Glu Lys Thr Glu Lys Gln Leu Glu Ala Ile Asp Gln
                515                 520                 525

Leu His Leu Glu Tyr Ala Lys Arg Ala Ala Pro Phe Asn Asn Trp Met
            530                 535                 540

Glu Ser Ala Met Glu Asp Leu Gln Asp Met Phe Ile Val His Thr Ile
545                 550                 555                 560

Glu Glu Ile Glu Gly Leu Ile Ser Ala His Asp Gln Phe Lys Ser Thr
                565                 570                 575

Leu Pro Asp Ala Asp Arg Glu Arg Glu Ala Ile Leu Ala Ile His Lys
            580                 585                 590

Glu Ala Gln Arg Ile Ala Glu Ser Asn His Ile Lys Leu Ser Gly Ser
        595                 600                 605

Asn Pro Tyr Thr Thr Val Thr Pro Gln Ile Ile Asn Ser Lys Trp Glu
        610                 615                 620

Lys Val Gln Gln Leu Val Pro Lys Arg Asp His Ala Leu Leu Glu Glu
625                 630                 635                 640

Gln Ser Lys Gln Gln Ser Asn Glu His Leu Arg Arg Gln Phe Ala Ser
                645                 650                 655

Gln Ala Asn Val Val Gly Pro Trp Ile Gln Thr Lys Met Glu Glu Ile
            660                 665                 670

Gly Arg Ile Ser Ile Glu Met Asn Gly Thr Leu Glu Asp Gln Leu Ser
        675                 680                 685

His Leu Lys Gln Tyr Glu Arg Ser Ile Val Asp Tyr Lys Pro Asn Leu
        690                 695                 700

Asp Leu Leu Glu Gln Gln His Gln Leu Ile Gln Glu Ala Leu Ile Phe
705                 710                 715                 720

Asp Asn Lys His Thr Asn Tyr Thr Met Glu His Ile Arg Val Gly Trp
                725                 730                 735

Glu Gln Leu Leu Thr Thr Ile Ala Arg Thr Ile Asn Glu Val Glu Asn
            740                 745                 750

Gln Ile Leu Thr Arg Asp Ala Lys Gly Ile Ser Gln Glu Gln Met Gln
        755                 760                 765

Glu Phe Arg Ala Ser Phe Asn His Phe Asp Lys Asp His Gly Gly Ala
        770                 775                 780

Leu Gly Pro Glu Glu Phe Lys Ala Cys Leu Ile Ser Leu Gly Tyr Asp
785                 790                 795                 800

Val Glu Asn Asp Arg Gln Gly Glu Ala Glu Phe Asn Arg Ile Met Ser
                805                 810                 815

Leu Val Asp Pro Asn His Ser Gly Leu Val Thr Phe Gln Ala Phe Ile
            820                 825                 830

Asp Phe Met Ser Arg Glu Thr Thr Asp Thr Asp Thr Ala Asp Gln Val
        835                 840                 845

Ile Ala Ser Phe Lys Val Leu Ala Gly Asp Lys Asn Phe Ile Thr Ala
        850                 855                 860

Glu Glu Leu Arg Arg Glu Leu Pro Pro Asp Gln Ala Glu Tyr Cys Ile
865                 870                 875                 880

Ala Arg Met Ala Pro Tyr Gln Gly Pro Asp Ala Val Pro Gly Ala Leu
                885                 890                 895

Asp Tyr Lys Ser Phe Ser Thr Ala Leu Tyr Gly Glu Ser Asp Leu
            900                 905                 910

<210> SEQ ID NO 83
```

```
<211> LENGTH: 505
<212> TYPE: PRT
<213> ORGANISM: Homo sapiens

<400> SEQUENCE: 83

Met Ser Tyr Pro Gly Tyr Pro Pro Pro Gly Gly Tyr Pro Pro Ala
1               5                   10                  15

Ala Pro Gly Gly Pro Trp Gly Ala Ala Tyr Pro Pro Pro
            20                  25                  30

Ser Met Pro Pro Ile Gly Leu Asp Asn Val Ala Thr Tyr Ala Gly Gln
            35                  40                  45

Phe Asn Gln Asp Tyr Leu Ser Gly Met Ala Ala Asn Met Ser Gly Thr
50                      55                  60

Phe Gly Gly Ala Asn Met Pro Asn Leu Tyr Pro Gly Ala Pro Gly Ala
65                  70                  75                  80

Gly Tyr Pro Pro Val Pro Pro Gly Gly Phe Gly Gln Pro Pro Ser Ala
                    85                  90                  95

Gln Gln Pro Val Pro Pro Tyr Gly Met Tyr Pro Pro Gly Gly Asn
                100                 105                 110

Pro Pro Ser Arg Met Pro Ser Tyr Pro Pro Tyr Pro Gly Ala Pro Val
                115                 120                 125

Pro Gly Gln Pro Met Pro Pro Gly Gln Gln Pro Pro Gly Ala Tyr
130                 135                 140

Pro Gly Gln Pro Pro Val Thr Tyr Pro Gly Gln Pro Pro Val Pro Leu
145                 150                 155                 160

Pro Gly Gln Gln Gln Pro Val Pro Ser Tyr Pro Gly Tyr Pro Gly Ser
                    165                 170                 175

Gly Thr Val Thr Pro Ala Val Pro Pro Thr Gln Phe Gly Ser Arg Gly
                180                 185                 190

Thr Ile Thr Asp Ala Pro Gly Phe Asp Pro Leu Arg Asp Ala Glu Val
                195                 200                 205

Leu Arg Lys Ala Met Lys Gly Phe Gly Thr Asp Glu Gln Ala Ile Ile
                210                 215                 220

Asp Cys Leu Gly Ser Arg Ser Asn Lys Gln Arg Gln Gln Ile Leu Leu
225                 230                 235                 240

Ser Phe Lys Thr Ala Tyr Gly Lys Asp Leu Ile Lys Asp Leu Lys Ser
                    245                 250                 255

Glu Leu Ser Gly Asn Phe Glu Lys Thr Ile Leu Ala Leu Met Lys Thr
                260                 265                 270

Pro Val Leu Phe Asp Ile Tyr Glu Ile Lys Glu Ala Ile Lys Gly Val
                275                 280                 285

Gly Thr Asp Glu Ala Cys Leu Ile Glu Ile Leu Ala Ser Arg Ser Asn
                290                 295                 300

Glu His Ile Arg Glu Leu Asn Arg Ala Tyr Lys Ala Glu Phe Lys Lys
305                 310                 315                 320

Thr Leu Glu Glu Ala Ile Arg Ser Asp Thr Ser Gly His Phe Gln Arg
                    325                 330                 335

Leu Leu Ile Ser Leu Ser Gln Gly Asn Arg Asp Glu Ser Thr Asn Val
                340                 345                 350

Asp Met Ser Leu Ala Gln Arg Asp Ala Gln Glu Leu Tyr Ala Ala Gly
                355                 360                 365

Glu Asn Arg Leu Gly Thr Asp Glu Ser Lys Phe Asn Ala Val Leu Cys
                370                 375                 380

Ser Arg Ser Arg Ala His Leu Val Ala Val Phe Asn Glu Tyr Gln Arg
```

```
385                 390                 395                 400
Met Thr Gly Arg Asp Ile Glu Lys Ser Ile Cys Arg Glu Met Ser Gly
                405                 410                 415

Asp Leu Glu Glu Gly Met Leu Ala Val Val Lys Cys Leu Lys Asn Thr
        420                 425                 430

Pro Ala Phe Phe Ala Glu Arg Leu Asn Lys Ala Met Arg Gly Ala Gly
            435                 440                 445

Thr Lys Asp Arg Thr Leu Ile Arg Ile Met Val Ser Arg Ser Glu Thr
450                 455                 460

Asp Leu Leu Asp Ile Arg Ser Glu Tyr Lys Arg Met Tyr Gly Lys Ser
465                 470                 475                 480

Leu Tyr His Asp Ile Ser Gly Asp Thr Ser Gly Asp Tyr Arg Lys Ile
                485                 490                 495

Leu Leu Lys Ile Cys Gly Gly Asn Asp
                500                 505

<210> SEQ ID NO 84
<211> LENGTH: 418
<212> TYPE: PRT
<213> ORGANISM: Homo sapiens

<400> SEQUENCE: 84

Met Ala Gly Arg Leu Pro Ala Cys Val Val Asp Cys Gly Thr Gly Tyr
1               5                   10                  15

Thr Lys Leu Gly Tyr Ala Gly Asn Thr Glu Pro Gln Phe Ile Ile Pro
            20                  25                  30

Ser Cys Ile Ala Ile Lys Glu Ser Ala Lys Val Gly Asp Gln Ala Gln
        35                  40                  45

Arg Arg Val Met Lys Gly Val Asp Asp Leu Asp Phe Phe Ile Gly Asp
    50                  55                  60

Glu Ala Ile Glu Lys Pro Thr Tyr Ala Thr Lys Trp Pro Ile Arg His
65                  70                  75                  80

Gly Ile Val Glu Asp Trp Asp Leu Met Glu Arg Phe Met Glu Gln Val
                85                  90                  95

Ile Phe Lys Tyr Leu Arg Ala Glu Pro Glu Asp His Tyr Phe Leu Leu
            100                 105                 110

Thr Glu Pro Pro Leu Asn Thr Pro Glu Asn Arg Glu Tyr Thr Ala Glu
        115                 120                 125

Ile Met Phe Glu Ser Phe Asn Val Pro Gly Leu Tyr Ile Ala Val Gln
    130                 135                 140

Ala Val Leu Ala Leu Ala Ala Ser Trp Thr Ser Arg Gln Val Gly Glu
145                 150                 155                 160

Arg Thr Leu Thr Gly Thr Val Ile Asp Ser Gly Asp Gly Val Thr His
                165                 170                 175

Val Ile Pro Val Ala Glu Gly Tyr Val Ile Gly Ser Cys Ile Lys His
            180                 185                 190

Ile Pro Ile Ala Gly Arg Asp Ile Thr Tyr Phe Ile Gln Gln Leu Leu
        195                 200                 205

Arg Asp Arg Glu Val Gly Ile Pro Pro Glu Gln Ser Leu Glu Thr Ala
    210                 215                 220

Lys Ala Val Lys Glu Arg Tyr Ser Tyr Val Cys Pro Asp Leu Val Lys
225                 230                 235                 240

Glu Phe Asn Lys Tyr Asp Thr Asp Gly Ser Lys Trp Ile Lys Gln Tyr
                245                 250                 255
```

-continued

```
Thr Gly Ile Asn Ala Ile Ser Lys Lys Glu Phe Ser Ile Asp Val Gly
                260                 265                 270

Tyr Glu Arg Phe Leu Gly Pro Glu Ile Phe His Pro Glu Phe Ala
            275                 280                 285

Asn Pro Asp Phe Thr Gln Pro Ile Ser Glu Val Val Asp Glu Val Ile
290                 295                 300

Gln Asn Cys Pro Ile Asp Val Arg Arg Pro Leu Tyr Lys Asn Ile Val
305                 310                 315                 320

Leu Ser Gly Gly Ser Thr Met Phe Arg Asp Phe Gly Arg Arg Leu Gln
                325                 330                 335

Arg Asp Leu Lys Arg Thr Val Asp Ala Arg Leu Lys Leu Ser Glu Glu
            340                 345                 350

Leu Ser Gly Gly Arg Leu Lys Pro Lys Pro Ile Asp Val Gln Val Ile
            355                 360                 365

Thr His His Met Gln Arg Tyr Ala Val Trp Phe Gly Gly Ser Met Leu
370                 375                 380

Ala Ser Thr Pro Glu Phe Tyr Gln Val Cys His Thr Lys Lys Asp Tyr
385                 390                 395                 400

Glu Glu Ile Gly Pro Ser Ile Cys Arg His Asn Pro Val Phe Gly Val
                405                 410                 415

Met Ser

<210> SEQ ID NO 85
<211> LENGTH: 300
<212> TYPE: PRT
<213> ORGANISM: Homo sapiens

<400> SEQUENCE: 85

Met Ile Leu Leu Glu Val Asn Asn Arg Ile Ile Glu Glu Thr Leu Ala
1               5                   10                  15

Leu Lys Phe Glu Asn Ala Ala Gly Asn Lys Pro Glu Ala Val Glu
            20                  25                  30

Val Thr Phe Ala Asp Phe Asp Gly Val Leu Tyr His Ile Ser Asn Pro
            35                  40                  45

Asn Gly Asp Lys Thr Lys Val Met Val Ser Ile Ser Leu Lys Phe Tyr
50                  55                  60

Lys Glu Leu Gln Ala His Gly Ala Asp Glu Leu Leu Lys Arg Val Tyr
65                  70                  75                  80

Gly Ser Phe Leu Val Asn Pro Glu Ser Gly Tyr Asn Val Ser Leu Leu
                85                  90                  95

Tyr Asp Leu Glu Asn Leu Pro Ala Ser Lys Asp Ser Ile Val His Gln
            100                 105                 110

Ala Gly Met Leu Lys Arg Asn Cys Phe Ala Ser Val Phe Glu Lys Tyr
            115                 120                 125

Phe Gln Phe Gln Glu Glu Gly Lys Glu Gly Glu Asn Arg Ala Val Ile
130                 135                 140

His Tyr Arg Asp Asp Glu Thr Met Tyr Val Glu Ser Lys Lys Asp Arg
145                 150                 155                 160

Val Thr Val Val Phe Ser Thr Val Phe Lys Asp Asp Asp Val Val
            165                 170                 175

Ile Gly Lys Val Phe Met Gln Glu Phe Lys Glu Gly Arg Arg Ala Ser
            180                 185                 190

His Thr Ala Pro Gln Val Leu Phe Ser His Arg Glu Pro Pro Leu Glu
            195                 200                 205
```

```
Leu Lys Asp Thr Asp Ala Ala Val Gly Asp Asn Ile Gly Tyr Ile Thr
    210                 215                 220

Phe Val Leu Phe Pro Arg His Thr Asn Ala Ser Ala Arg Asp Asn Thr
225                 230                 235                 240

Ile Asn Leu Ile His Thr Phe Arg Asp Tyr Leu His Tyr His Ile Lys
                245                 250                 255

Cys Ser Lys Ala Tyr Ile His Thr Arg Met Arg Ala Lys Thr Ser Asp
            260                 265                 270

Phe Leu Lys Val Leu Asn Arg Ala Arg Pro Asp Ala Glu Lys Lys Glu
        275                 280                 285

Met Lys Thr Ile Thr Gly Lys Thr Phe Ser Ser Arg
    290                 295                 300

<210> SEQ ID NO 86
<211> LENGTH: 149
<212> TYPE: PRT
<213> ORGANISM: Homo sapiens

<400> SEQUENCE: 86

Met Ala Asp Gln Leu Thr Glu Glu Gln Ile Ala Glu Phe Lys Glu Ala
1               5                   10                  15

Phe Ser Leu Phe Asp Lys Asp Gly Asp Gly Thr Ile Thr Thr Lys Glu
            20                  25                  30

Leu Gly Thr Val Met Arg Ser Leu Gly Gln Asn Pro Thr Glu Ala Glu
        35                  40                  45

Leu Gln Asp Met Ile Asn Glu Val Asp Ala Asp Gly Asn Gly Thr Ile
    50                  55                  60

Asp Phe Pro Glu Phe Leu Thr Met Met Ala Arg Lys Met Lys Asp Thr
65                  70                  75                  80

Asp Ser Glu Glu Glu Ile Arg Glu Ala Phe Arg Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu
        115                 120                 125

Ala Asp Ile Asp Gly Asp Gly Gln Val Asn Tyr Glu Glu Phe Val Gln
    130                 135                 140

Met Met Thr Ala Lys
145

<210> SEQ ID NO 87
<211> LENGTH: 475
<212> TYPE: PRT
<213> ORGANISM: Homo sapiens

<400> SEQUENCE: 87

Met Ala Asp Met Gln Asn Leu Val Glu Arg Leu Glu Arg Ala Val Gly
1               5                   10                  15

Arg Leu Glu Ala Val Ser His Thr Ser Asp Met His Arg Gly Tyr Ala
            20                  25                  30

Asp Ser Pro Ser Lys Ala Gly Ala Ala Pro Tyr Val Gln Ala Phe Asp
        35                  40                  45

Ser Leu Leu Ala Gly Pro Val Ala Glu Tyr Leu Lys Ile Ser Lys Glu
    50                  55                  60

Ile Gly Gly Asp Val Gln Lys His Ala Glu Met Val His Thr Gly Leu
65                  70                  75                  80
```

```
Lys Leu Glu Arg Ala Leu Leu Val Thr Ala Ser Gln Cys Gln Gln Pro
                85                  90                  95

Ala Glu Asn Lys Leu Ser Asp Leu Leu Ala Pro Ile Ser Glu Gln Ile
            100                 105                 110

Lys Glu Val Ile Thr Phe Arg Glu Lys Asn Arg Gly Ser Lys Leu Phe
        115                 120                 125

Asn His Leu Ser Ala Val Ser Glu Ser Ile Gln Ala Leu Gly Trp Val
    130                 135                 140

Ala Met Ala Pro Lys Pro Gly Pro Tyr Val Lys Glu Met Asn Asp Ala
145                 150                 155                 160

Ala Met Phe Tyr Thr Asn Arg Val Leu Lys Glu Tyr Lys Asp Val Asp
                165                 170                 175

Lys Lys His Val Asp Trp Val Lys Ala Tyr Leu Ser Ile Trp Thr Glu
            180                 185                 190

Leu Gln Ala Tyr Ile Lys Glu Phe His Thr Thr Gly Leu Ala Trp Ser
        195                 200                 205

Lys Thr Gly Pro Val Ala Lys Glu Leu Ser Gly Leu Pro Ser Gly Pro
    210                 215                 220

Ser Ala Gly Ser Cys Pro Pro Pro Pro Cys Pro Pro Pro
225                 230                 235                 240

Pro Val Ser Thr Ile Ser Cys Ser Tyr Glu Ser Ala Ser Arg Ser Ser
                245                 250                 255

Leu Phe Ala Gln Ile Asn Gln Gly Glu Ser Ile Thr His Ala Leu Lys
            260                 265                 270

His Val Ser Asp Asp Met Lys Thr His Lys Asn Pro Ala Leu Lys Ala
    275                 280                 285

Gln Ser Gly Pro Val Arg Ser Gly Pro Lys Pro Phe Ser Ala Pro Lys
    290                 295                 300

Pro Gln Thr Ser Pro Ser Pro Lys Arg Ala Thr Lys Lys Glu Pro Ala
305                 310                 315                 320

Val Leu Glu Leu Glu Gly Lys Lys Trp Arg Val Glu Asn Gln Glu Asn
                325                 330                 335

Val Ser Asn Leu Val Ile Glu Asp Thr Glu Leu Lys Gln Val Ala Tyr
            340                 345                 350

Ile Tyr Lys Cys Val Asn Thr Thr Leu Gln Ile Lys Gly Lys Ile Asn
        355                 360                 365

Ser Ile Thr Val Asp Asn Cys Lys Lys Leu Gly Leu Val Phe Asp Asp
    370                 375                 380

Val Val Gly Ile Val Glu Ile Ile Asn Ser Lys Asp Val Lys Val Gln
385                 390                 395                 400

Val Met Gly Lys Val Pro Thr Ile Ser Ile Asn Lys Thr Asp Gly Cys
                405                 410                 415

His Ala Tyr Leu Ser Lys Asn Ser Leu Asp Cys Glu Ile Val Ser Ala
            420                 425                 430

Lys Ser Ser Glu Met Asn Val Leu Ile Pro Thr Glu Gly Gly Asp Phe
        435                 440                 445

Asn Glu Phe Pro Val Pro Glu Gln Phe Lys Thr Leu Trp Asn Gly Gln
    450                 455                 460

Lys Leu Val Thr Thr Val Thr Glu Ile Ala Gly
465                 470                 475

<210> SEQ ID NO 88
<211> LENGTH: 1675
<212> TYPE: PRT
```

<213> ORGANISM: Homo sapiens

<400> SEQUENCE: 88

```
Met Ala Gln Ile Leu Pro Ile Arg Phe Gln Glu His Leu Gln Leu Gln
1               5                   10                  15

Asn Leu Gly Ile Asn Pro Ala Asn Ile Gly Phe Ser Thr Leu Thr Met
            20                  25                  30

Glu Ser Asp Lys Phe Ile Cys Ile Arg Glu Lys Val Gly Glu Gln Ala
        35                  40                  45

Gln Val Val Ile Ile Asp Met Asn Asp Pro Ser Asn Pro Ile Arg Arg
    50                  55                  60

Pro Ile Ser Ala Asp Ser Ala Ile Met Asn Pro Ala Ser Lys Val Ile
65                  70                  75                  80

Ala Leu Lys Ala Gly Lys Thr Leu Gln Ile Phe Asn Ile Glu Met Lys
                85                  90                  95

Ser Lys Met Lys Ala His Thr Met Thr Asp Asp Val Thr Phe Trp Lys
            100                 105                 110

Trp Ile Ser Leu Asn Thr Val Ala Leu Val Thr Asp Asn Ala Val Tyr
        115                 120                 125

His Trp Ser Met Glu Gly Glu Ser Gln Pro Val Lys Met Phe Asp Arg
    130                 135                 140

His Ser Ser Leu Ala Gly Cys Gln Ile Ile Asn Tyr Arg Thr Asp Ala
145                 150                 155                 160

Lys Gln Lys Trp Leu Leu Leu Thr Gly Ile Ser Ala Gln Gln Asn Arg
                165                 170                 175

Val Val Gly Ala Met Gln Leu Tyr Ser Val Asp Arg Lys Val Ser Gln
            180                 185                 190

Pro Ile Glu Gly His Ala Ala Ser Phe Ala Gln Phe Lys Met Glu Gly
        195                 200                 205

Asn Ala Glu Glu Ser Thr Leu Phe Cys Phe Ala Val Arg Gly Gln Ala
    210                 215                 220

Gly Gly Lys Leu His Ile Ile Glu Val Gly Thr Pro Pro Thr Gly Asn
225                 230                 235                 240

Gln Pro Phe Pro Lys Lys Ala Val Asp Val Phe Phe Pro Pro Glu Ala
                245                 250                 255

Gln Asn Asp Phe Pro Val Ala Met Gln Ile Ser Glu Lys His Asp Val
            260                 265                 270

Val Phe Leu Ile Thr Lys Tyr Gly Tyr Ile His Leu Tyr Asp Leu Glu
        275                 280                 285

Thr Gly Thr Cys Ile Tyr Met Asn Arg Ile Ser Gly Glu Thr Ile Phe
    290                 295                 300

Val Thr Ala Pro His Glu Ala Thr Ala Gly Ile Ile Gly Val Asn Arg
305                 310                 315                 320

Lys Gly Gln Val Leu Ser Val Cys Val Glu Glu Asn Ile Ile Pro
                325                 330                 335

Tyr Ile Thr Asn Val Leu Gln Asn Pro Asp Leu Ala Leu Arg Met Ala
            340                 345                 350

Val Arg Asn Asn Leu Ala Gly Ala Glu Glu Leu Phe Ala Arg Lys Phe
        355                 360                 365

Asn Ala Leu Phe Ala Gln Gly Asn Tyr Ser Glu Ala Ala Lys Val Ala
    370                 375                 380

Ala Asn Ala Pro Lys Gly Ile Leu Arg Thr Pro Asp Thr Ile Arg Arg
385                 390                 395                 400
```

Phe Gln Ser Val Pro Ala Gln Pro Gly Gln Thr Ser Pro Leu Leu Gln
                405                 410                 415

Tyr Phe Gly Ile Leu Leu Asp Gln Gly Gln Leu Asn Lys Tyr Glu Ser
            420                 425                 430

Leu Glu Leu Cys Arg Pro Val Leu Gln Gln Gly Arg Lys Gln Leu Leu
        435                 440                 445

Glu Lys Trp Leu Lys Glu Asp Lys Leu Glu Cys Ser Glu Glu Leu Gly
    450                 455                 460

Asp Leu Val Lys Ser Val Asp Pro Thr Leu Ala Leu Ser Val Tyr Leu
465                 470                 475                 480

Arg Ala Asn Val Pro Asn Lys Val Ile Gln Cys Phe Ala Glu Thr Gly
                485                 490                 495

Gln Val Gln Lys Ile Val Leu Tyr Ala Lys Lys Val Gly Tyr Thr Pro
                500                 505                 510

Asp Trp Ile Phe Leu Leu Arg Asn Val Met Arg Ile Ser Pro Asp Gln
            515                 520                 525

Gly Gln Gln Phe Ala Gln Met Leu Val Gln Asp Glu Glu Pro Leu Ala
    530                 535                 540

Asp Ile Thr Gln Ile Val Asp Val Phe Met Glu Tyr Asn Leu Ile Gln
545                 550                 555                 560

Gln Cys Thr Ala Phe Leu Leu Asp Ala Leu Lys Asn Asn Arg Pro Ser
                565                 570                 575

Glu Gly Pro Leu Gln Thr Arg Leu Leu Glu Met Asn Leu Met His Ala
            580                 585                 590

Pro Gln Val Ala Asp Ala Ile Leu Gly Asn Gln Met Phe Thr His Tyr
    595                 600                 605

Asp Arg Ala His Ile Ala Gln Leu Cys Glu Lys Ala Gly Leu Leu Gln
610                 615                 620

Arg Ala Leu Glu His Phe Thr Asp Leu Tyr Asp Ile Lys Arg Ala Val
625                 630                 635                 640

Val His Thr His Leu Leu Asn Pro Glu Trp Leu Val Asn Tyr Phe Gly
                645                 650                 655

Ser Leu Ser Val Glu Asp Ser Leu Glu Cys Leu Arg Ala Met Leu Ser
            660                 665                 670

Ala Asn Ile Arg Gln Asn Leu Gln Ile Cys Val Gln Val Ala Ser Lys
        675                 680                 685

Tyr His Glu Gln Leu Ser Thr Gln Ser Leu Ile Glu Leu Phe Glu Ser
    690                 695                 700

Phe Lys Ser Phe Glu Gly Leu Phe Tyr Phe Leu Gly Ser Ile Val Asn
705                 710                 715                 720

Phe Ser Gln Asp Pro Asp Val His Phe Lys Tyr Ile Gln Ala Ala Cys
                725                 730                 735

Lys Thr Gly Gln Ile Lys Glu Val Glu Arg Ile Cys Arg Glu Ser Asn
            740                 745                 750

Cys Tyr Asp Pro Glu Arg Val Lys Asn Phe Leu Lys Glu Ala Lys Leu
        755                 760                 765

Thr Asp Gln Leu Pro Leu Ile Ile Val Cys Asp Arg Phe Asp Phe Val
    770                 775                 780

His Asp Leu Val Leu Tyr Leu Tyr Arg Asn Asn Leu Gln Lys Tyr Ile
785                 790                 795                 800

Glu Ile Tyr Val Gln Lys Val Asn Pro Ser Arg Leu Pro Val Val Ile
                805                 810                 815

Gly Gly Leu Leu Asp Val Asp Cys Ser Glu Asp Val Ile Lys Asn Leu

-continued

```
                820             825             830
Ile Leu Val Val Arg Gly Gln Phe Ser Thr Asp Glu Leu Val Ala Glu
                835             840             845
Val Glu Lys Arg Asn Arg Leu Lys Leu Leu Pro Trp Leu Glu Ala
    850             855             860
Arg Ile His Glu Gly Cys Glu Glu Pro Ala Thr His Asn Ala Leu Ala
865             870             875             880
Lys Ile Tyr Ile Asp Ser Asn Asn Pro Glu Arg Phe Leu Arg Glu
                885             890             895
Asn Pro Tyr Tyr Asp Ser Arg Val Val Gly Lys Tyr Cys Glu Lys Arg
                900             905             910
Asp Pro His Leu Ala Cys Val Ala Tyr Glu Arg Gly Gln Cys Asp Leu
                915             920             925
Glu Leu Ile Asn Val Cys Asn Glu Asn Ser Leu Phe Lys Ser Leu Ser
                930             935             940
Arg Tyr Leu Val Arg Arg Lys Asp Pro Glu Leu Trp Gly Ser Val Leu
945             950             955             960
Leu Glu Ser Asn Pro Tyr Arg Arg Pro Leu Ile Asp Gln Val Gln
                965             970             975
Thr Ala Leu Ser Glu Thr Gln Asp Pro Glu Glu Val Ser Val Thr Val
                980             985             990
Lys Ala Phe Met Thr Ala Asp Leu Pro Asn Glu Leu Ile Glu Leu Leu
                995             1000            1005
Glu Lys Ile Val Leu Asp Asn Ser Val Phe Ser Glu His Arg Asn
    1010            1015            1020
Leu Gln Asn Leu Leu Ile Leu Thr Ala Ile Lys Ala Asp Arg Thr
    1025            1030            1035
Arg Val Met Glu Tyr Ile Asn Arg Leu Asp Asn Tyr Asp Ala Pro
    1040            1045            1050
Asp Ile Ala Asn Ile Ala Ile Ser Asn Glu Leu Phe Glu Glu Ala
    1055            1060            1065
Phe Ala Ile Phe Arg Lys Phe Asp Val Asn Thr Ser Ala Val Gln
    1070            1075            1080
Val Leu Ile Glu His Ile Gly Asn Leu Asp Arg Ala Tyr Glu Phe
    1085            1090            1095
Ala Glu Arg Cys Asn Glu Pro Ala Val Trp Ser Gln Leu Ala Lys
    1100            1105            1110
Ala Gln Leu Gln Lys Gly Met Val Lys Glu Ala Ile Asp Ser Tyr
    1115            1120            1125
Ile Lys Ala Asp Asp Pro Ser Ser Tyr Met Glu Val Val Gln Ala
    1130            1135            1140
Ala Asn Thr Ser Gly Asn Trp Glu Glu Leu Val Lys Tyr Leu Gln
    1145            1150            1155
Met Ala Arg Lys Lys Ala Arg Glu Ser Tyr Val Glu Thr Glu Leu
    1160            1165            1170
Ile Phe Ala Leu Ala Lys Thr Asn Arg Leu Ala Glu Leu Glu Glu
    1175            1180            1185
Phe Ile Asn Gly Pro Asn Asn Ala His Ile Gln Gln Val Gly Asp
    1190            1195            1200
Arg Cys Tyr Asp Glu Lys Met Tyr Asp Ala Ala Lys Leu Leu Tyr
    1205            1210            1215
Asn Asn Val Ser Asn Phe Gly Arg Leu Ala Ser Thr Leu Val His
    1220            1225            1230
```

-continued

```
Leu Gly Glu Tyr Gln Ala Ala Val Asp Gly Ala Arg Lys Ala Asn
    1235                1240                1245

Ser Thr Arg Thr Trp Lys Glu Val Cys Phe Ala Cys Val Asp Gly
    1250                1255                1260

Lys Glu Phe Arg Leu Ala Gln Met Cys Gly Leu His Ile Val Val
    1265                1270                1275

His Ala Asp Glu Leu Glu Leu Ile Asn Tyr Tyr Gln Asp Arg
    1280                1285                1290

Gly Tyr Phe Glu Glu Leu Ile Thr Met Leu Glu Ala Ala Leu Gly
    1295                1300                1305

Leu Glu Arg Ala His Met Gly Met Phe Thr Glu Leu Ala Ile Leu
    1310                1315                1320

Tyr Ser Lys Phe Lys Pro Gln Lys Met Arg Glu His Leu Glu Leu
    1325                1330                1335

Phe Trp Ser Arg Val Asn Ile Pro Lys Val Leu Arg Ala Ala Glu
    1340                1345                1350

Gln Ala His Leu Trp Ala Glu Leu Val Phe Leu Tyr Asp Lys Tyr
    1355                1360                1365

Glu Glu Tyr Asp Asn Ala Ile Ile Thr Met Met Asn His Pro Thr
    1370                1375                1380

Asp Ala Trp Lys Glu Gly Gln Phe Lys Asp Ile Ile Thr Lys Val
    1385                1390                1395

Ala Asn Val Glu Leu Tyr Tyr Arg Ala Ile Gln Phe Tyr Leu Glu
    1400                1405                1410

Phe Lys Pro Leu Leu Leu Asn Asp Leu Leu Met Val Leu Ser Pro
    1415                1420                1425

Arg Leu Asp His Thr Arg Ala Val Asn Tyr Phe Ser Lys Val Lys
    1430                1435                1440

Gln Leu Pro Leu Val Lys Pro Tyr Leu Arg Ser Val Gln Asn His
    1445                1450                1455

Asn Asn Lys Ser Val Asn Glu Ser Leu Asn Asn Leu Phe Ile Thr
    1460                1465                1470

Glu Glu Asp Tyr Gln Ala Leu Arg Thr Ser Ile Asp Ala Tyr Asp
    1475                1480                1485

Asn Phe Asp Asn Ile Ser Leu Ala Gln Arg Leu Glu Lys His Glu
    1490                1495                1500

Leu Ile Glu Phe Arg Arg Ile Ala Ala Tyr Leu Phe Lys Gly Asn
    1505                1510                1515

Asn Arg Trp Lys Gln Ser Val Glu Leu Cys Lys Lys Asp Ser Leu
    1520                1525                1530

Tyr Lys Asp Ala Met Gln Tyr Ala Ser Glu Ser Lys Asp Thr Glu
    1535                1540                1545

Leu Ala Glu Glu Leu Leu Gln Trp Phe Leu Gln Glu Glu Lys Arg
    1550                1555                1560

Glu Cys Phe Gly Ala Cys Leu Phe Thr Cys Tyr Asp Leu Leu Arg
    1565                1570                1575

Pro Asp Val Val Leu Glu Thr Ala Trp Arg His Asn Ile Met Asp
    1580                1585                1590

Phe Ala Met Pro Tyr Phe Ile Gln Val Met Lys Glu Tyr Leu Thr
    1595                1600                1605

Lys Val Asp Lys Leu Asp Ala Ser Glu Ser Leu Arg Lys Glu Glu
    1610                1615                1620
```

```
Glu Gln Ala Thr Glu Thr Gln Pro Ile Val Tyr Gly Gln Pro Gln
    1625                1630                1635

Leu Met Leu Thr Ala Gly Pro Ser Val Ala Val Pro Pro Gln Ala
    1640                1645                1650

Pro Phe Gly Tyr Gly Tyr Thr Ala Pro Pro Tyr Gly Gln Pro Gln
    1655                1660                1665

Pro Gly Phe Gly Tyr Ser Met
    1670                1675

<210> SEQ ID NO 89
<211> LENGTH: 166
<212> TYPE: PRT
<213> ORGANISM: Homo sapiens

<400> SEQUENCE: 89

Met Ala Ser Gly Val Ala Val Ser Asp Gly Val Ile Lys Val Phe Asn
1               5                   10                  15

Asp Met Lys Val Arg Lys Ser Ser Thr Pro Glu Glu Val Lys Lys Arg
            20                  25                  30

Lys Lys Ala Val Leu Phe Cys Leu Ser Glu Asp Lys Lys Asn Ile Ile
        35                  40                  45

Leu Glu Glu Gly Lys Glu Ile Leu Val Gly Asp Val Gly Gln Thr Val
    50                  55                  60

Asp Asp Pro Tyr Ala Thr Phe Val Lys Met Leu Pro Asp Lys Asp Cys
65                  70                  75                  80

Arg Tyr Ala Leu Tyr Asp Ala Thr Tyr Glu Thr Lys Glu Ser Lys Lys
                85                  90                  95

Glu Asp Leu Val Phe Ile Phe Trp Ala Pro Glu Ser Ala Pro Leu Lys
            100                 105                 110

Ser Lys Met Ile Tyr Ala Ser Ser Lys Asp Ala Ile Lys Lys Lys Leu
        115                 120                 125

Thr Gly Ile Lys His Glu Leu Gln Ala Asn Cys Tyr Glu Glu Val Lys
    130                 135                 140

Asp Arg Cys Thr Leu Ala Glu Lys Leu Gly Gly Ser Ala Val Ile Ser
145                 150                 155                 160

Leu Glu Gly Lys Pro Leu
                165

<210> SEQ ID NO 90
<211> LENGTH: 129
<212> TYPE: PRT
<213> ORGANISM: Homo sapiens

<400> SEQUENCE: 90

Met Ala Ser Arg Leu Leu Arg Gly Ala Gly Thr Leu Ala Ala Gln Ala
1               5                   10                  15

Leu Arg Ala Arg Gly Pro Ser Gly Ala Ala Ala Met Arg Ser Met Ala
            20                  25                  30

Ser Gly Gly Gly Val Pro Thr Asp Glu Glu Gln Ala Thr Gly Leu Glu
        35                  40                  45

Arg Glu Ile Met Leu Ala Ala Lys Lys Gly Leu Asp Pro Tyr Asn Val
    50                  55                  60

Leu Ala Pro Lys Gly Ala Ser Gly Thr Arg Glu Asp Pro Asn Leu Val
65                  70                  75                  80

Pro Ser Ile Ser Asn Lys Arg Ile Val Gly Cys Ile Cys Glu Glu Asp
                85                  90                  95
```

-continued

```
Asn Thr Ser Val Val Trp Phe Trp Leu His Lys Gly Glu Ala Gln Arg
                100                 105                 110

Cys Pro Arg Cys Gly Ala His Tyr Lys Leu Val Pro Gln Gln Leu Ala
            115                 120                 125

His

<210> SEQ ID NO 91
<211> LENGTH: 98
<212> TYPE: PRT
<213> ORGANISM: Homo sapiens

<400> SEQUENCE: 91

Met Met Cys Gly Ala Pro Ser Ala Thr Gln Pro Ala Thr Ala Glu Thr
1               5                   10                  15

Gln His Ile Ala Asp Gln Val Arg Ser Gln Leu Glu Glu Lys Glu Asn
                20                  25                  30

Lys Lys Phe Pro Val Phe Lys Ala Val Ser Phe Lys Ser Gln Val Val
                35                  40                  45

Ala Gly Thr Asn Tyr Phe Ile Lys Val His Val Gly Asp Glu Asp Phe
            50                  55                  60

Val His Leu Arg Val Phe Gln Ser Leu Pro His Glu Asn Lys Pro Leu
65                  70                  75                  80

Thr Leu Ser Asn Tyr Gln Thr Asn Lys Ala Lys His Asp Glu Leu Thr
                85                  90                  95

Tyr Phe

<210> SEQ ID NO 92
<211> LENGTH: 290
<212> TYPE: PRT
<213> ORGANISM: Homo sapiens

<400> SEQUENCE: 92

Met Ala Ala Leu Arg Val Leu Leu Ser Cys Val Arg Gly Pro Leu Arg
1               5                   10                  15

Pro Pro Val Arg Cys Pro Ala Trp Arg Pro Phe Ala Ser Gly Ala Asn
                20                  25                  30

Phe Glu Tyr Ile Ile Ala Glu Lys Arg Gly Lys Asn Asn Thr Val Gly
            35                  40                  45

Leu Ile Gln Leu Asn Arg Pro Lys Ala Leu Asn Ala Leu Cys Asp Gly
            50                  55                  60

Leu Ile Asp Glu Leu Asn Gln Ala Leu Lys Thr Phe Glu Glu Asp Pro
65                  70                  75                  80

Ala Val Gly Ala Ile Val Leu Thr Gly Gly Asp Lys Ala Phe Ala Ala
                85                  90                  95

Gly Ala Asp Ile Lys Glu Met Gln Asn Leu Ser Phe Gln Asp Cys Tyr
                100                 105                 110

Ser Ser Lys Phe Leu Lys His Trp Asp His Leu Thr Gln Val Lys Lys
            115                 120                 125

Pro Val Ile Ala Ala Val Asn Gly Tyr Ala Phe Gly Gly Gly Cys Glu
        130                 135                 140

Leu Ala Met Met Cys Asp Ile Ile Tyr Ala Gly Glu Lys Ala Gln Phe
145                 150                 155                 160

Ala Gln Pro Glu Ile Leu Ile Gly Thr Ile Pro Gly Ala Gly Gly Thr
                165                 170                 175

Gln Arg Leu Thr Arg Ala Val Gly Lys Ser Leu Ala Met Glu Met Val
                180                 185                 190
```

-continued

Leu Thr Gly Asp Arg Ile Ser Ala Gln Asp Ala Lys Gln Ala Gly Leu
                195                 200                 205

Val Ser Lys Ile Cys Pro Val Glu Thr Leu Val Glu Glu Ala Ile Gln
210                 215                 220

Cys Ala Glu Lys Ile Ala Ser Asn Ser Lys Ile Val Ala Met Ala
225                 230                 235                 240

Lys Glu Ser Val Asn Ala Ala Phe Glu Met Thr Leu Thr Glu Gly Ser
                245                 250                 255

Lys Leu Glu Lys Lys Leu Phe Tyr Ser Thr Phe Ala Thr Asp Asp Arg
                260                 265                 270

Lys Glu Gly Met Thr Ala Phe Val Glu Lys Arg Lys Ala Asn Phe Lys
                275                 280                 285

Asp Gln
    290

<210> SEQ ID NO 93
<211> LENGTH: 462
<212> TYPE: PRT
<213> ORGANISM: Homo sapiens

<400> SEQUENCE: 93

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Ala Glu
            35                  40                  45

Met Gly Lys Gly Ser Phe Lys Tyr Ala Trp Val Leu Asp Lys Leu Lys
50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
            180                 185                 190

Ile Ser Gly Trp Asn Gly Asp Asn Met Leu Glu Pro Ser Ala Asn Met
        195                 200                 205

Pro Trp Phe Lys Gly Trp Lys Val Thr Arg Lys Asp Gly Asn Ala Ser
210                 215                 220

Gly Thr Thr Leu Leu Glu Ala Leu Asp Cys Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Val Leu

-continued

```
               260                 265                 270
Lys Pro Gly Met Val Val Thr Phe Ala Pro Val Asn Val Thr Thr Glu
            275                 280                 285
Val Lys Ser Val Glu Met His His Glu Ala Leu Ser Glu Ala Leu Pro
            290                 295                 300
Gly Asp Asn Val Gly Phe Asn Val Lys Asn Val Ser Val Lys Asp Val
305                 310                 315                 320
Arg Arg Gly Asn Val Ala Gly Asp Ser Lys Asn Asp Pro Pro Met Glu
                325                 330                 335
Ala Ala Gly Phe Thr Ala Gln Val Ile Ile Leu Asn His Pro Gly Gln
            340                 345                 350
Ile Ser Ala Gly Tyr Ala Pro Val Leu Asp Cys His Thr Ala His Ile
            355                 360                 365
Ala Cys Lys Phe Ala Glu Leu Lys Glu Lys Ile Asp Arg Arg Ser Gly
            370                 375                 380
Lys Lys Leu Glu Asp Gly Pro Lys Phe Leu Lys Ser Gly Asp Ala Ala
385                 390                 395                 400
Ile Val Asp Met Val Pro Gly Lys Pro Met Cys Val Glu Ser Phe Ser
                405                 410                 415
Asp Tyr Pro Pro Leu Gly Arg Phe Ala Val Arg Asp Met Arg Gln Thr
            420                 425                 430
Val Ala Val Gly Val Ile Lys Ala Val Asp Lys Ala Ala Gly Ala
            435                 440                 445
Gly Lys Val Thr Lys Ser Ala Gln Lys Ala Gln Lys Ala Lys
    450                 455                 460

<210> SEQ ID NO 94
<211> LENGTH: 338
<212> TYPE: PRT
<213> ORGANISM: Homo sapiens

<400> SEQUENCE: 94

Met Ala Asp Gln Ala Pro Phe Asp Thr Asp Val Asn Thr Leu Thr Arg
1               5                   10                  15
Phe Val Met Glu Glu Gly Arg Lys Ala Arg Gly Thr Gly Glu Leu Thr
                20                  25                  30
Gln Leu Leu Asn Ser Leu Cys Thr Ala Val Lys Ala Ile Ser Ser Ala
            35                  40                  45
Val Arg Lys Ala Gly Ile Ala His Leu Tyr Gly Ile Ala Gly Ser Thr
    50                  55                  60
Asn Val Thr Gly Asp Gln Val Lys Lys Leu Asp Val Leu Ser Asn Asp
65                  70                  75                  80
Leu Val Met Asn Met Leu Lys Ser Ser Phe Ala Thr Cys Val Leu Val
                85                  90                  95
Ser Glu Glu Asp Lys His Ala Ile Ile Val Glu Pro Glu Lys Arg Gly
            100                 105                 110
Lys Tyr Val Val Cys Phe Asp Pro Leu Asp Gly Ser Ser Asn Ile Asp
            115                 120                 125
Cys Leu Val Ser Val Gly Thr Ile Phe Gly Ile Tyr Arg Lys Lys Ser
    130                 135                 140
Thr Asp Glu Pro Ser Glu Lys Asp Ala Leu Gln Pro Gly Arg Asn Leu
145                 150                 155                 160
Val Ala Ala Gly Tyr Ala Leu Tyr Gly Ser Ala Thr Met Leu Val Leu
                165                 170                 175
```

```
Ala Met Asp Cys Gly Val Asn Cys Phe Met Leu Asp Pro Ala Ile Gly
            180                 185                 190

Glu Phe Ile Leu Val Asp Lys Asp Val Lys Ile Lys Lys Gly Lys
        195                 200                 205

Ile Tyr Ser Leu Asn Glu Gly Tyr Ala Arg Asp Phe Asp Pro Ala Val
        210                 215                 220

Thr Glu Tyr Ile Gln Arg Lys Lys Phe Pro Asp Asn Ser Ala Pro
225                 230                 235                 240

Tyr Gly Ala Arg Tyr Val Gly Ser Met Val Ala Asp Val His Arg Thr
                245                 250                 255

Leu Val Tyr Gly Gly Ile Phe Leu Tyr Pro Ala Asn Lys Lys Ser Pro
            260                 265                 270

Asn Gly Lys Leu Arg Leu Leu Tyr Glu Cys Asn Pro Met Ala Tyr Val
        275                 280                 285

Met Glu Lys Ala Gly Gly Met Ala Thr Thr Gly Lys Glu Ala Val Leu
        290                 295                 300

Asp Val Ile Pro Thr Asp Ile His Gln Arg Ala Pro Val Ile Leu Gly
305                 310                 315                 320

Ser Pro Asp Asp Val Leu Glu Phe Leu Lys Val Tyr Glu Lys His Ser
                325                 330                 335

Ala Gln

<210> SEQ ID NO 95
<211> LENGTH: 2647
<212> TYPE: PRT
<213> ORGANISM: Homo sapiens

<400> SEQUENCE: 95

Met Ser Ser Ser His Ser Arg Ala Gly Gln Ser Ala Ala Gly Ala Ala
1               5                   10                  15

Pro Gly Gly Gly Val Asp Thr Arg Asp Ala Glu Met Pro Ala Thr Glu
            20                  25                  30

Lys Asp Leu Ala Glu Asp Ala Pro Trp Lys Lys Ile Gln Gln Asn Thr
        35                  40                  45

Phe Thr Arg Trp Cys Asn Glu His Leu Lys Cys Val Ser Lys Arg Ile
    50                  55                  60

Ala Asn Leu Gln Thr Asp Leu Ser Asp Gly Leu Arg Leu Ile Ala Leu
65                  70                  75                  80

Leu Glu Val Leu Ser Gln Lys Lys Met His Arg Lys His Asn Gln Arg
                85                  90                  95

Pro Thr Phe Arg Gln Met Gln Leu Glu Asn Val Ser Val Ala Leu Glu
            100                 105                 110

Phe Leu Asp Arg Glu Ser Ile Lys Leu Val Ser Ile Asp Ser Lys Ala
        115                 120                 125

Ile Val Asp Gly Asn Leu Lys Leu Ile Leu Gly Leu Ile Trp Thr Leu
    130                 135                 140

Ile Leu His Tyr Ser Ile Ser Met Pro Met Trp Asp Glu Glu Glu Asp
145                 150                 155                 160

Glu Glu Ala Lys Lys Gln Thr Pro Lys Gln Arg Leu Leu Gly Trp Ile
                165                 170                 175

Gln Asn Lys Leu Pro Gln Leu Pro Ile Thr Asn Phe Ser Arg Asp Trp
            180                 185                 190

Gln Ser Gly Arg Ala Leu Gly Ala Leu Val Asp Ser Cys Ala Pro Gly
        195                 200                 205
```

```
Leu Cys Pro Asp Trp Asp Ser Trp Asp Ala Ser Lys Pro Val Thr Asn
    210                 215                 220
Ala Arg Glu Ala Met Gln Gln Ala Asp Asp Trp Leu Gly Ile Pro Gln
225                 230                 235                 240
Val Ile Thr Pro Glu Glu Ile Val Asp Pro Asn Val Asp Glu His Ser
                245                 250                 255
Val Met Thr Tyr Leu Ser Gln Phe Pro Lys Ala Lys Leu Lys Pro Gly
            260                 265                 270
Ala Pro Leu Arg Pro Lys Leu Asn Pro Lys Lys Ala Arg Ala Tyr Gly
        275                 280                 285
Pro Gly Ile Glu Pro Thr Gly Asn Met Val Lys Lys Arg Ala Glu Phe
    290                 295                 300
Thr Val Glu Thr Arg Ser Ala Gly Gln Gly Glu Val Leu Val Tyr Val
305                 310                 315                 320
Glu Asp Pro Ala Gly His Gln Glu Glu Ala Lys Val Thr Ala Asn Asn
                325                 330                 335
Asp Lys Asn Arg Thr Phe Ser Val Trp Tyr Val Pro Glu Val Thr Gly
            340                 345                 350
Thr His Lys Val Thr Val Leu Phe Ala Gly Gln His Ile Ala Lys Ser
        355                 360                 365
Pro Phe Glu Val Tyr Val Asp Lys Ser Gln Gly Asp Ala Ser Lys Val
    370                 375                 380
Thr Ala Gln Gly Pro Gly Leu Glu Pro Ser Gly Asn Ile Ala Asn Lys
385                 390                 395                 400
Thr Thr Tyr Phe Glu Ile Phe Thr Ala Gly Ala Gly Thr Gly Glu Val
                405                 410                 415
Glu Val Val Ile Gln Asp Pro Met Gly Gln Lys Gly Thr Val Glu Pro
            420                 425                 430
Gln Leu Glu Ala Arg Gly Asp Ser Thr Tyr Arg Cys Ser Tyr Gln Pro
        435                 440                 445
Thr Met Glu Gly Val His Thr Val His Val Thr Phe Ala Gly Val Pro
    450                 455                 460
Ile Pro Arg Ser Pro Tyr Thr Val Thr Val Gly Gln Ala Cys Asn Pro
465                 470                 475                 480
Ser Ala Cys Arg Ala Val Gly Arg Gly Leu Gln Pro Lys Gly Val Arg
                485                 490                 495
Val Lys Glu Thr Ala Asp Phe Lys Val Tyr Thr Lys Gly Ala Gly Ser
            500                 505                 510
Gly Glu Leu Lys Val Thr Val Lys Gly Pro Lys Gly Glu Glu Arg Val
        515                 520                 525
Lys Gln Lys Asp Leu Gly Asp Gly Val Tyr Gly Phe Glu Tyr Tyr Pro
    530                 535                 540
Met Val Pro Gly Thr Tyr Ile Val Thr Ile Thr Trp Gly Gly Gln Asn
545                 550                 555                 560
Ile Gly Arg Ser Pro Phe Glu Val Lys Val Gly Thr Glu Cys Gly Asn
                565                 570                 575
Gln Lys Val Arg Ala Trp Gly Pro Gly Leu Glu Gly Gly Val Val Gly
            580                 585                 590
Lys Ser Ala Asp Phe Val Val Glu Ala Ile Gly Asp Asp Val Gly Thr
        595                 600                 605
Leu Gly Phe Ser Val Glu Gly Pro Ser Gln Ala Lys Ile Glu Cys Asp
    610                 615                 620
Asp Lys Gly Asp Gly Ser Cys Asp Val Arg Tyr Trp Pro Gln Glu Ala
```

```
                625                 630                 635                 640
        Gly Glu Tyr Ala Val His Val Leu Cys Asn Ser Glu Asp Ile Arg Leu
                            645                 650                 655
        Ser Pro Phe Met Ala Asp Ile Arg Asp Ala Pro Gln Asp Phe His Pro
                            660                 665                 670
        Asp Arg Val Lys Ala Arg Gly Pro Gly Leu Glu Lys Thr Gly Val Ala
                            675                 680                 685
        Val Asn Lys Pro Ala Glu Phe Thr Val Asp Ala Lys His Gly Gly Lys
                            690                 695                 700
        Ala Pro Leu Arg Val Gln Val Gln Asp Asn Glu Gly Cys Pro Val Glu
        705                 710                 715                 720
        Ala Leu Val Lys Asp Asn Gly Asn Gly Thr Tyr Ser Cys Ser Tyr Val
                            725                 730                 735
        Pro Arg Lys Pro Val Lys His Thr Ala Met Val Ser Trp Gly Gly Val
                            740                 745                 750
        Ser Ile Pro Asn Ser Pro Phe Arg Val Asn Val Gly Ala Gly Ser His
                            755                 760                 765
        Pro Asn Lys Val Lys Val Tyr Gly Pro Gly Val Ala Lys Thr Gly Leu
                            770                 775                 780
        Lys Ala His Glu Pro Thr Tyr Phe Thr Val Asp Cys Ala Glu Ala Gly
        785                 790                 795                 800
        Gln Gly Asp Val Ser Ile Gly Ile Lys Cys Ala Pro Gly Val Val Gly
                            805                 810                 815
        Pro Ala Glu Ala Asp Ile Asp Phe Asp Ile Ile Arg Asn Asp Asn Asp
                            820                 825                 830
        Thr Phe Thr Val Lys Tyr Thr Pro Arg Gly Ala Gly Ser Tyr Thr Ile
                            835                 840                 845
        Met Val Leu Phe Ala Asp Gln Ala Thr Pro Thr Ser Pro Ile Arg Val
                            850                 855                 860
        Lys Val Glu Pro Ser His Asp Ala Ser Lys Val Lys Ala Glu Gly Pro
        865                 870                 875                 880
        Gly Leu Ser Arg Thr Gly Val Glu Leu Gly Lys Pro Thr His Phe Thr
                            885                 890                 895
        Val Asn Ala Lys Ala Ala Gly Lys Gly Lys Leu Asp Val Gln Phe Ser
                            900                 905                 910
        Gly Leu Thr Lys Gly Asp Ala Val Arg Asp Val Asp Ile Ile Asp His
                            915                 920                 925
        His Asp Asn Thr Tyr Thr Val Lys Tyr Thr Pro Val Gln Gln Gly Pro
                            930                 935                 940
        Val Gly Val Asn Val Thr Tyr Gly Gly Asp Pro Ile Pro Lys Ser Pro
        945                 950                 955                 960
        Phe Ser Val Ala Val Ser Pro Ser Leu Asp Leu Ser Lys Ile Lys Val
                            965                 970                 975
        Ser Gly Leu Gly Glu Lys Val Asp Val Gly Lys Asp Gln Glu Phe Thr
                            980                 985                 990
        Val Lys Ser Lys Gly Ala Gly Gly  Gln Gly Lys Val Ala  Ser Lys Ile
                            995                 1000                1005
        Val Gly Pro  Ser Gly Ala Ala  Val Pro Cys Lys Val  Glu Pro Gly
                1010                1015                1020
        Leu Gly  Ala Asp Asn Ser Val  Val Arg Phe Leu Pro  Arg Glu Glu
                1025                1030                1035
        Gly Pro  Tyr Glu Val Glu Val  Thr Tyr Asp Gly Val  Pro Val Pro
                1040                1045                1050
```

-continued

Gly Ser Pro Phe Pro Leu Glu Ala Val Ala Pro Thr Lys Pro Ser
1055            1060                1065

Lys Val Lys Ala Phe Gly Pro Gly Leu Gln Gly Gly Ser Ala Gly
1070            1075                1080

Ser Pro Ala Arg Phe Thr Ile Asp Thr Lys Gly Ala Gly Thr Gly
1085            1090                1095

Gly Leu Gly Leu Thr Val Glu Gly Pro Cys Glu Ala Gln Leu Glu
1100            1105                1110

Cys Leu Asp Asn Gly Asp Gly Thr Cys Ser Val Ser Tyr Val Pro
1115            1120                1125

Thr Glu Pro Gly Asp Tyr Asn Ile Asn Ile Leu Phe Ala Asp Thr
1130            1135                1140

His Ile Pro Gly Ser Pro Phe Lys Ala His Val Val Pro Cys Phe
1145            1150                1155

Asp Ala Ser Lys Val Lys Cys Ser Gly Pro Gly Leu Glu Arg Ala
1160            1165                1170

Thr Ala Gly Glu Val Gly Gln Phe Gln Val Asp Cys Ser Ser Ala
1175            1180                1185

Gly Ser Ala Glu Leu Thr Ile Glu Ile Cys Ser Glu Ala Gly Leu
1190            1195                1200

Pro Ala Glu Val Tyr Ile Gln Asp His Gly Asp Gly Thr His Thr
1205            1210                1215

Ile Thr Tyr Ile Pro Leu Cys Pro Gly Ala Tyr Thr Val Thr Ile
1220            1225                1230

Lys Tyr Gly Gly Gln Pro Val Pro Asn Phe Pro Ser Lys Leu Gln
1235            1240                1245

Val Glu Pro Ala Val Asp Thr Ser Gly Val Gln Cys Tyr Gly Pro
1250            1255                1260

Gly Ile Glu Gly Gln Gly Val Phe Arg Glu Ala Thr Thr Glu Phe
1265            1270                1275

Ser Val Asp Ala Arg Ala Leu Thr Gln Thr Gly Gly Pro His Val
1280            1285                1290

Lys Ala Arg Val Ala Asn Pro Ser Gly Asn Leu Thr Glu Thr Tyr
1295            1300                1305

Val Gln Asp Arg Gly Asp Gly Met Tyr Lys Val Glu Tyr Thr Pro
1310            1315                1320

Tyr Glu Glu Gly Leu His Ser Val Asp Val Thr Tyr Asp Gly Ser
1325            1330                1335

Pro Val Pro Ser Ser Pro Phe Gln Val Pro Val Thr Glu Gly Cys
1340            1345                1350

Asp Pro Ser Arg Val Arg Val His Gly Pro Gly Ile Gln Ser Gly
1355            1360                1365

Thr Thr Asn Lys Pro Asn Lys Phe Thr Val Glu Thr Arg Gly Ala
1370            1375                1380

Gly Thr Gly Gly Leu Gly Leu Ala Val Glu Gly Pro Ser Glu Ala
1385            1390                1395

Lys Met Ser Cys Met Asp Asn Lys Asp Gly Ser Cys Ser Val Glu
1400            1405                1410

Tyr Ile Pro Tyr Glu Ala Gly Thr Tyr Ser Leu Asn Val Thr Tyr
1415            1420                1425

Gly Gly His Gln Val Pro Gly Ser Pro Phe Lys Val Pro Val His
1430            1435                1440

```
Asp Val Thr Asp Ala Ser Lys Val Lys Cys Ser Gly Pro Gly Leu
    1445                1450                1455

Ser Pro Gly Met Val Arg Ala Asn Leu Pro Gln Ser Phe Gln Val
    1460                1465                1470

Asp Thr Ser Lys Ala Gly Val Ala Pro Leu Gln Val Lys Val Gln
    1475                1480                1485

Gly Pro Lys Gly Leu Val Glu Pro Val Asp Val Asp Asn Ala
    1490                1495                1500

Asp Gly Thr Gln Thr Val Asn Tyr Val Pro Ser Arg Glu Gly Pro
    1505                1510                1515

Tyr Ser Ile Ser Val Leu Tyr Gly Asp Glu Val Pro Arg Ser
    1520                1525                1530

Pro Phe Lys Val Lys Val Leu Pro Thr His Asp Ala Ser Lys Val
    1535                1540                1545

Lys Ala Ser Gly Pro Gly Leu Asn Thr Thr Gly Val Pro Ala Ser
    1550                1555                1560

Leu Pro Val Glu Phe Thr Ile Asp Ala Lys Asp Ala Gly Glu Gly
    1565                1570                1575

Leu Leu Ala Val Gln Ile Thr Asp Pro Glu Gly Lys Pro Lys Lys
    1580                1585                1590

Thr His Ile Gln Asp Asn His Asp Gly Thr Tyr Thr Val Ala Tyr
    1595                1600                1605

Val Pro Asp Val Thr Gly Arg Tyr Thr Ile Leu Ile Lys Tyr Gly
    1610                1615                1620

Gly Asp Glu Ile Pro Phe Ser Pro Tyr Arg Val Arg Ala Val Pro
    1625                1630                1635

Thr Gly Asp Ala Ser Lys Cys Thr Val Thr Val Ser Ile Gly Gly
    1640                1645                1650

His Gly Leu Gly Ala Gly Ile Gly Pro Thr Ile Gln Ile Gly Glu
    1655                1660                1665

Glu Thr Val Ile Thr Val Asp Thr Lys Ala Ala Gly Lys Gly Lys
    1670                1675                1680

Val Thr Cys Thr Val Cys Thr Pro Asp Gly Ser Glu Val Asp Val
    1685                1690                1695

Asp Val Val Glu Asn Glu Asp Gly Thr Phe Asp Ile Phe Tyr Thr
    1700                1705                1710

Ala Pro Gln Pro Gly Lys Tyr Val Ile Cys Val Arg Phe Gly Gly
    1715                1720                1725

Glu His Val Pro Asn Ser Pro Phe Gln Val Thr Ala Leu Ala Gly
    1730                1735                1740

Asp Gln Pro Ser Val Gln Pro Pro Leu Arg Ser Gln Gln Leu Ala
    1745                1750                1755

Pro Gln Tyr Thr Tyr Ala Gln Gly Gly Gln Gln Thr Trp Ala Pro
    1760                1765                1770

Glu Arg Pro Leu Val Gly Val Asn Gly Leu Asp Val Thr Ser Leu
    1775                1780                1785

Arg Pro Phe Asp Leu Val Ile Pro Phe Thr Ile Lys Lys Gly Glu
    1790                1795                1800

Ile Thr Gly Glu Val Arg Met Pro Ser Gly Lys Val Ala Gln Pro
    1805                1810                1815

Thr Ile Thr Asp Asn Lys Asp Gly Thr Val Thr Val Arg Tyr Ala
    1820                1825                1830

Pro Ser Glu Ala Gly Leu His Glu Met Asp Ile Arg Tyr Asp Asn
```

-continued

```
                1835                1840                1845

Met His Ile Pro Gly Ser Pro Leu Gln Phe Tyr Val Asp Tyr Val
            1850                1855                1860

Asn Cys Gly His Val Thr Ala Tyr Gly Pro Gly Leu Thr His Gly
            1865                1870                1875

Val Val Asn Lys Pro Ala Thr Phe Thr Val Asn Thr Lys Asp Ala
            1880                1885                1890

Gly Glu Gly Gly Leu Ser Leu Ala Ile Glu Gly Pro Ser Lys Ala
            1895                1900                1905

Glu Ile Ser Cys Thr Asp Asn Gln Asp Gly Thr Cys Ser Val Ser
            1910                1915                1920

Tyr Leu Pro Val Leu Pro Gly Asp Tyr Ser Ile Leu Val Lys Tyr
            1925                1930                1935

Asn Glu Gln His Val Pro Gly Ser Pro Phe Thr Ala Arg Val Thr
            1940                1945                1950

Gly Asp Asp Ser Met Arg Met Ser His Leu Lys Val Gly Ser Ala
            1955                1960                1965

Ala Asp Ile Pro Ile Asn Ile Ser Glu Thr Asp Leu Ser Leu Leu
            1970                1975                1980

Thr Ala Thr Val Val Pro Pro Ser Gly Arg Glu Glu Pro Cys Leu
            1985                1990                1995

Leu Lys Arg Leu Arg Asn Gly His Val Gly Ile Ser Phe Val Pro
            2000                2005                2010

Lys Glu Thr Gly Glu His Leu Val His Val Lys Lys Asn Gly Gln
            2015                2020                2025

His Val Ala Ser Ser Pro Ile Pro Val Val Ile Ser Gln Ser Glu
            2030                2035                2040

Ile Gly Asp Ala Ser Arg Val Arg Val Ser Gly Gln Gly Leu His
            2045                2050                2055

Glu Gly His Thr Phe Glu Pro Ala Glu Phe Ile Ile Asp Thr Arg
            2060                2065                2070

Asp Ala Gly Tyr Gly Gly Leu Ser Leu Ser Ile Glu Gly Pro Ser
            2075                2080                2085

Lys Val Asp Ile Asn Thr Glu Asp Leu Glu Asp Gly Thr Cys Arg
            2090                2095                2100

Val Thr Tyr Cys Pro Thr Glu Pro Gly Asn Tyr Ile Ile Asn Ile
            2105                2110                2115

Lys Phe Ala Asp Gln His Val Pro Gly Ser Pro Phe Ser Val Lys
            2120                2125                2130

Val Thr Gly Glu Gly Arg Val Lys Glu Ser Ile Thr Arg Arg Arg
            2135                2140                2145

Arg Ala Pro Ser Val Ala Asn Val Gly Ser His Cys Asp Leu Ser
            2150                2155                2160

Leu Lys Ile Pro Glu Ile Ser Ile Gln Asp Met Thr Ala Gln Val
            2165                2170                2175

Thr Ser Pro Ser Gly Lys Thr His Glu Ala Glu Ile Val Glu Gly
            2180                2185                2190

Glu Asn His Thr Tyr Cys Ile Arg Phe Val Pro Ala Glu Met Gly
            2195                2200                2205

Thr His Thr Val Ser Val Lys Tyr Lys Gly Gln His Val Pro Gly
            2210                2215                2220

Ser Pro Phe Gln Phe Thr Val Gly Pro Leu Gly Glu Gly Gly Ala
            2225                2230                2235
```

-continued

His Lys Val Arg Ala Gly Gly Pro Gly Leu Glu Arg Ala Glu Ala
2240                2245                2250

Gly Val Pro Ala Glu Phe Ser Ile Trp Thr Arg Glu Ala Gly Ala
2255                2260                2265

Gly Gly Leu Ala Ile Ala Val Glu Gly Pro Ser Lys Ala Glu Ile
2270                2275                2280

Ser Phe Glu Asp Arg Lys Asp Gly Ser Cys Gly Val Ala Tyr Val
2285                2290                2295

Val Gln Glu Pro Gly Asp Tyr Glu Val Ser Val Lys Phe Asn Glu
2300                2305                2310

Glu His Ile Pro Asp Ser Pro Phe Val Val Pro Val Ala Ser Pro
2315                2320                2325

Ser Gly Asp Ala Arg Arg Leu Thr Val Ser Ser Leu Gln Glu Ser
2330                2335                2340

Gly Leu Lys Val Asn Gln Pro Ala Ser Phe Ala Val Ser Leu Asn
2345                2350                2355

Gly Ala Lys Gly Ala Ile Asp Ala Lys Val His Ser Pro Ser Gly
2360                2365                2370

Ala Leu Glu Glu Cys Tyr Val Thr Glu Ile Asp Gln Asp Lys Tyr
2375                2380                2385

Ala Val Arg Phe Ile Pro Arg Glu Asn Gly Val Tyr Leu Ile Asp
2390                2395                2400

Val Lys Phe Asn Gly Thr His Ile Pro Gly Ser Pro Phe Lys Ile
2405                2410                2415

Arg Val Gly Glu Pro Gly His Gly Gly Asp Pro Gly Leu Val Ser
2420                2425                2430

Ala Tyr Gly Ala Gly Leu Glu Gly Gly Val Thr Gly Asn Pro Ala
2435                2440                2445

Glu Phe Val Val Asn Thr Ser Asn Ala Gly Ala Gly Ala Leu Ser
2450                2455                2460

Val Thr Ile Asp Gly Pro Ser Lys Val Lys Met Asp Cys Gln Glu
2465                2470                2475

Cys Pro Glu Gly Tyr Arg Val Thr Tyr Thr Pro Met Ala Pro Gly
2480                2485                2490

Ser Tyr Leu Ile Ser Ile Lys Tyr Gly Gly Pro Tyr His Ile Gly
2495                2500                2505

Gly Ser Pro Phe Lys Ala Lys Val Thr Gly Pro Arg Leu Val Ser
2510                2515                2520

Asn His Ser Leu His Glu Thr Ser Ser Val Phe Val Asp Ser Leu
2525                2530                2535

Thr Lys Ala Thr Cys Ala Pro Gln His Gly Ala Pro Gly Pro Gly
2540                2545                2550

Pro Ala Asp Ala Ser Lys Val Val Ala Lys Gly Leu Gly Leu Ser
2555                2560                2565

Lys Ala Tyr Val Gly Gln Lys Ser Ser Phe Thr Val Asp Cys Ser
2570                2575                2580

Lys Ala Gly Asn Asn Met Leu Leu Val Gly Val His Gly Pro Arg
2585                2590                2595

Thr Pro Cys Glu Glu Ile Leu Val Lys His Val Gly Ser Arg Leu
2600                2605                2610

Tyr Ser Val Ser Tyr Leu Leu Lys Asp Lys Gly Glu Tyr Thr Leu
2615                2620                2625

```
Val Val Lys Trp Gly Asp Glu His Ile Pro Gly Ser Pro Tyr Arg
        2630                2635                2640

Val Val Val Pro
    2645

<210> SEQ ID NO 96
<211> LENGTH: 445
<212> TYPE: PRT
<213> ORGANISM: Homo sapiens

<400> SEQUENCE: 96

Met Asn Glu Glu Tyr Asp Val Ile Val Leu Gly Thr Gly Leu Thr Glu
1               5                   10                  15

Cys Ile Leu Ser Gly Ile Met Ser Val Asn Gly Lys Lys Val Leu His
                20                  25                  30

Met Asp Arg Asn Pro Tyr Tyr Gly Gly Glu Ser Ala Ser Ile Thr Pro
            35                  40                  45

Leu Glu Asp Leu Tyr Lys Arg Phe Lys Ile Pro Gly Ser Pro Pro Glu
    50                  55                  60

Ser Met Gly Arg Gly Arg Asp Trp Asn Val Asp Leu Ile Pro Lys Phe
65                  70                  75                  80

Leu Met Ala Asn Gly Gln Leu Val Lys Met Leu Leu Tyr Thr Glu Val
                85                  90                  95

Thr Arg Tyr Leu Asp Phe Lys Val Thr Glu Gly Ser Phe Val Tyr Lys
            100                 105                 110

Gly Gly Lys Ile Tyr Lys Val Pro Ser Thr Glu Ala Glu Ala Leu Ala
        115                 120                 125

Ser Ser Leu Met Gly Leu Phe Glu Lys Arg Arg Phe Arg Lys Phe Leu
130                 135                 140

Val Tyr Val Ala Asn Phe Asp Glu Lys Asp Pro Arg Thr Phe Glu Gly
145                 150                 155                 160

Ile Asp Pro Lys Lys Thr Thr Met Arg Asp Val Tyr Lys Lys Phe Asp
                165                 170                 175

Leu Gly Gln Asp Val Ile Asp Phe Thr Gly His Ala Leu Ala Leu Tyr
            180                 185                 190

Arg Thr Asp Asp Tyr Leu Asp Gln Pro Cys Tyr Glu Thr Ile Asn Arg
        195                 200                 205

Ile Lys Leu Tyr Ser Glu Ser Leu Ala Arg Tyr Gly Lys Ser Pro Tyr
210                 215                 220

Leu Tyr Pro Leu Tyr Gly Leu Gly Glu Leu Pro Gln Gly Phe Ala Arg
225                 230                 235                 240

Leu Ser Ala Ile Tyr Gly Gly Thr Tyr Met Leu Asn Lys Pro Ile Glu
                245                 250                 255

Glu Ile Ile Val Gln Asn Gly Lys Val Ile Gly Val Lys Ser Glu Gly
            260                 265                 270

Glu Ile Ala Arg Cys Lys Gln Leu Ile Cys Asp Pro Ser Tyr Val Lys
        275                 280                 285

Asp Arg Val Glu Lys Val Gly Gln Val Ile Arg Val Ile Cys Ile Leu
290                 295                 300

Ser His Pro Ile Lys Asn Thr Asn Asp Ala Asn Ser Cys Gln Ile Ile
305                 310                 315                 320

Ile Pro Gln Asn Gln Val Asn Arg Lys Ser Asp Ile Tyr Val Cys Met
                325                 330                 335

Ile Ser Phe Ala His Asn Val Ala Ala Gln Gly Lys Tyr Ile Ala Ile
            340                 345                 350
```

```
Val Ser Thr Thr Val Glu Thr Lys Glu Pro Glu Lys Glu Ile Arg Pro
        355                 360                 365

Ala Leu Glu Leu Leu Glu Pro Ile Glu Gln Lys Phe Val Ser Ile Ser
    370                 375                 380

Asp Leu Leu Val Pro Lys Asp Leu Gly Thr Glu Ser Gln Ile Phe Ile
385                 390                 395                 400

Ser Arg Thr Tyr Asp Ala Thr Thr His Phe Glu Thr Thr Cys Asp Asp
                405                 410                 415

Ile Lys Asn Ile Tyr Lys Arg Met Thr Gly Ser Glu Phe Asp Phe Glu
                420                 425                 430

Glu Met Lys Arg Lys Lys Asn Asp Ile Tyr Gly Glu Asp
        435                 440                 445

<210> SEQ ID NO 97
<211> LENGTH: 354
<212> TYPE: PRT
<213> ORGANISM: Homo sapiens

<400> SEQUENCE: 97

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Ala Gly Tyr Ser Glu Glu
    50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
        115                 120                 125

Arg Leu Trp Lys Asp Ser Gly Val Gln Ala Cys Phe Asn Arg Ser Arg
    130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
    210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Asp Thr Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
```

```
                    275                 280                 285
        Glu Tyr Ala Gly Ser Asn Thr Tyr Glu Glu Ala Ala Tyr Ile Gln
            290                 295                 300

Cys Gln Phe Glu Asp Leu Asn Lys Arg Lys Asp Thr Lys Glu Ile Tyr
        305                 310                 315                 320

Thr His Phe Thr Cys Ala Thr Asp Thr Lys Asn Val Gln Phe Val Phe
                        325                 330                 335

Asp Ala Val Thr Asp Val Ile Ile Lys Asn Asn Leu Lys Asp Cys Gly
                    340                 345                 350

Leu Phe

<210> SEQ ID NO 98
<211> LENGTH: 128
<212> TYPE: PRT
<213> ORGANISM: Homo sapiens

<400> SEQUENCE: 98

Met Ala Gly Gly Lys Ala Gly Lys Asp Ser Gly Lys Ala Lys Ala Lys
        1               5                   10                  15

Ala Val Ser Arg Ser Gln Arg Ala Gly Leu Gln Phe Pro Val Gly Arg
                    20                  25                  30

Ile His Arg His Leu Lys Thr Arg Thr Thr Ser His Gly Arg Val Gly
                35                  40                  45

Ala Thr Ala Ala Val Tyr Ser Ala Ala Ile Leu Glu Tyr Leu Thr Ala
            50                  55                  60

Glu Val Leu Glu Leu Ala Gly Asn Ala Ser Lys Asp Leu Lys Val Lys
        65                  70                  75                  80

Arg Ile Thr Pro Arg His Leu Gln Leu Ala Ile Arg Gly Asp Glu Glu
                        85                  90                  95

Leu Asp Ser Leu Ile Lys Ala Thr Ile Ala Gly Gly Gly Val Ile Pro
                    100                 105                 110

His Ile His Lys Ser Leu Ile Gly Lys Lys Gly Gln Gln Lys Thr Ala
                115                 120                 125

<210> SEQ ID NO 99
<211> LENGTH: 732
<212> TYPE: PRT
<213> ORGANISM: Homo sapiens

<400> SEQUENCE: 99

Met Pro Glu Glu Thr Gln Thr Gln Asp Gln Pro Met Glu Glu Glu Glu
        1               5                   10                  15

Val Glu Thr Phe Ala Phe Gln Ala Glu Ile Ala Gln Leu Met Ser Leu
                    20                  25                  30

Ile Ile Asn Thr Phe Tyr Ser Asn Lys Glu Ile Phe Leu Arg Glu Leu
        35                  40                  45

Ile Ser Asn Ser Ser Asp Ala Leu Asp Lys Ile Arg Tyr Glu Ser Leu
            50                  55                  60

Thr Asp Pro Ser Lys Leu Asp Ser Gly Lys Glu Leu His Ile Asn Leu
        65                  70                  75                  80

Ile Pro Asn Lys Gln Asp Arg Thr Leu Thr Ile Val Asp Thr Gly Ile
                        85                  90                  95

Gly Met Thr Lys Ala Asp Leu Ile Asn Asn Leu Gly Thr Ile Ala Lys
                    100                 105                 110

Ser Gly Thr Lys Ala Phe Met Glu Ala Leu Gln Ala Gly Ala Asp Ile
                115                 120                 125
```

-continued

```
Ser Met Ile Gly Gln Phe Gly Val Gly Phe Tyr Ser Ala Tyr Leu Val
    130                 135                 140
Ala Glu Lys Val Thr Val Ile Thr Lys His Asn Asp Asp Glu Gln Tyr
145                 150                 155                 160
Ala Trp Glu Ser Ser Ala Gly Gly Ser Phe Thr Val Arg Thr Asp Thr
                    165                 170                 175
Gly Glu Pro Met Gly Arg Gly Thr Lys Val Ile Leu His Leu Lys Glu
                180                 185                 190
Asp Gln Thr Glu Tyr Leu Glu Glu Arg Ile Lys Glu Ile Val Lys
            195                 200                 205
Lys His Ser Gln Phe Ile Gly Tyr Pro Ile Thr Leu Phe Val Glu Lys
    210                 215                 220
Glu Arg Asp Lys Glu Val Ser Asp Asp Glu Ala Glu Glu Lys Glu Asp
225                 230                 235                 240
Lys Glu Glu Glu Lys Glu Lys Glu Glu Lys Glu Ser Glu Asp Lys Pro
                245                 250                 255
Glu Ile Glu Asp Val Gly Ser Asp Glu Glu Glu Lys Lys Asp Gly
                260                 265                 270
Asp Lys Lys Lys Lys Lys Ile Lys Glu Lys Tyr Ile Asp Gln Glu
            275                 280                 285
Glu Leu Asn Lys Thr Lys Pro Ile Trp Thr Arg Asn Pro Asp Asp Ile
    290                 295                 300
Thr Asn Glu Glu Tyr Gly Glu Phe Tyr Lys Ser Leu Thr Asn Asp Trp
305                 310                 315                 320
Glu Asp His Leu Ala Val Lys His Phe Ser Val Glu Gly Gln Leu Glu
                325                 330                 335
Phe Arg Ala Leu Leu Phe Val Pro Arg Arg Ala Pro Phe Asp Leu Phe
                340                 345                 350
Glu Asn Arg Lys Lys Lys Asn Asn Ile Lys Leu Tyr Val Arg Arg Val
            355                 360                 365
Phe Ile Met Asp Asn Cys Glu Glu Leu Ile Pro Glu Tyr Leu Asn Phe
    370                 375                 380
Ile Arg Gly Val Val Asp Ser Glu Asp Leu Pro Leu Asn Ile Ser Arg
385                 390                 395                 400
Glu Met Leu Gln Gln Ser Lys Ile Leu Lys Val Ile Arg Lys Asn Leu
                405                 410                 415
Val Lys Lys Cys Leu Glu Leu Phe Thr Glu Leu Ala Glu Asp Lys Glu
                420                 425                 430
Asn Tyr Lys Lys Phe Tyr Glu Gln Phe Ser Lys Asn Ile Lys Leu Gly
            435                 440                 445
Ile His Glu Asp Ser Gln Asn Arg Lys Lys Leu Ser Glu Leu Leu Arg
    450                 455                 460
Tyr Tyr Thr Ser Ala Ser Gly Asp Glu Met Val Ser Leu Lys Asp Tyr
465                 470                 475                 480
Cys Thr Arg Met Lys Glu Asn Gln Lys His Ile Tyr Tyr Ile Thr Gly
                485                 490                 495
Glu Thr Lys Asp Gln Val Ala Asn Ser Ala Phe Val Glu Arg Leu Arg
                500                 505                 510
Lys His Gly Leu Glu Val Ile Tyr Met Ile Glu Pro Ile Asp Glu Tyr
            515                 520                 525
Cys Val Gln Gln Leu Lys Glu Phe Glu Gly Lys Thr Leu Val Ser Val
530                 535                 540
```

```
Thr Lys Glu Gly Leu Glu Leu Pro Glu Asp Glu Glu Lys Lys Lys
545                 550                 555                 560

Gln Glu Glu Lys Lys Thr Lys Phe Glu Asn Leu Cys Lys Ile Met Lys
                565                 570                 575

Asp Ile Leu Glu Lys Lys Val Glu Lys Val Val Ser Asn Arg Leu
            580                 585                 590

Val Thr Ser Pro Cys Cys Ile Val Thr Ser Thr Tyr Gly Trp Thr Ala
                595                 600                 605

Asn Met Glu Arg Ile Met Lys Ala Gln Ala Leu Arg Asp Asn Ser Thr
        610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
                645                 650                 655

Lys Ser Val Lys Asp Leu Val Ile Leu Leu Tyr Glu Thr Ala Leu Leu
            660                 665                 670

Ser Ser Gly Phe Ser Leu Glu Asp Pro Gln Thr His Ala Asn Arg Ile
        675                 680                 685

Tyr Arg Met Ile Lys Leu Gly Leu Gly Ile Asp Glu Asp Pro Thr
690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
                725                 730

<210> SEQ ID NO 100
<211> LENGTH: 379
<212> TYPE: PRT
<213> ORGANISM: Homo sapiens

<400> SEQUENCE: 100

Met Glu Gln Leu Ser Ser Ala Asn Thr Arg Phe Ala Leu Asp Leu Phe
1               5                   10                  15

Leu Ala Leu Ser Glu Asn Asn Pro Ala Gly Asn Ile Phe Ile Ser Pro
            20                  25                  30

Phe Ser Ile Ser Ser Ala Met Ala Met Val Phe Leu Gly Thr Arg Gly
        35                  40                  45

Asn Thr Ala Ala Gln Leu Ser Lys Thr Phe His Phe Asn Thr Val Glu
    50                  55                  60

Glu Val His Ser Arg Phe Gln Ser Leu Asn Ala Asp Ile Asn Lys Arg
65                  70                  75                  80

Gly Ala Ser Tyr Ile Leu Lys Leu Ala Asn Arg Leu Tyr Gly Glu Lys
                85                  90                  95

Thr Tyr Asn Phe Leu Pro Glu Phe Leu Val Ser Thr Gln Lys Thr Tyr
            100                 105                 110

Gly Ala Asp Leu Ala Ser Val Asp Phe Gln His Ala Ser Glu Asp Ala
        115                 120                 125

Arg Lys Thr Ile Asn Gln Trp Val Lys Gly Gln Thr Glu Gly Lys Ile
    130                 135                 140

Pro Glu Leu Leu Ala Ser Gly Met Val Asp Asn Met Thr Lys Leu Val
145                 150                 155                 160

Leu Val Asn Ala Ile Tyr Phe Lys Gly Asn Trp Lys Asp Lys Phe Met
                165                 170                 175

Lys Glu Ala Thr Thr Asn Ala Pro Phe Arg Leu Asn Lys Lys Asp Arg
            180                 185                 190
```

```
Lys Thr Val Lys Met Met Tyr Gln Lys Lys Phe Ala Tyr Gly Tyr
            195                 200                 205

Ile Glu Asp Leu Lys Cys Arg Val Leu Glu Leu Pro Tyr Gln Gly Glu
    210                 215                 220

Glu Leu Ser Met Val Ile Leu Leu Pro Asp Asp Ile Glu Asp Glu Ser
225                 230                 235                 240

Thr Gly Leu Lys Lys Ile Glu Glu Gln Leu Thr Leu Glu Lys Leu His
                245                 250                 255

Glu Trp Thr Lys Pro Glu Asn Leu Asp Phe Ile Glu Val Asn Val Ser
                260                 265                 270

Leu Pro Arg Phe Lys Leu Glu Ser Tyr Thr Leu Asn Ser Asp Leu
            275                 280                 285

Ala Arg Leu Gly Val Gln Asp Leu Phe Asn Ser Ser Lys Ala Asp Leu
    290                 295                 300

Ser Gly Met Ser Gly Ala Arg Asp Ile Phe Ile Ser Lys Ile Val His
305                 310                 315                 320

Lys Ser Phe Val Glu Val Asn Glu Glu Gly Thr Glu Ala Ala Ala Ala
                325                 330                 335

Thr Ala Gly Ile Ala Thr Phe Cys Met Leu Met Pro Glu Glu Asn Phe
            340                 345                 350

Thr Ala Asp His Pro Phe Leu Phe Phe Ile Arg His Asn Ser Ser Gly
            355                 360                 365

Ser Ile Leu Phe Leu Gly Arg Phe Ser Ser Pro
            370                 375

<210> SEQ ID NO 101
<211> LENGTH: 1657
<212> TYPE: PRT
<213> ORGANISM: Homo sapiens

<400> SEQUENCE: 101

Met Ser Ala Ala Asp Glu Val Asp Gly Leu Gly Val Ala Arg Pro His
1               5                   10                  15

Tyr Gly Ser Val Leu Asp Asn Glu Arg Leu Thr Ala Glu Glu Met Asp
            20                  25                  30

Glu Arg Arg Arg Gln Asn Val Ala Tyr Glu Tyr Leu Cys His Leu Glu
        35                  40                  45

Glu Ala Lys Arg Trp Met Glu Ala Cys Leu Gly Glu Asp Leu Pro Pro
    50                  55                  60

Thr Thr Glu Leu Glu Glu Gly Leu Arg Asn Gly Val Tyr Leu Ala Lys
65                  70                  75                  80

Leu Gly Asn Phe Phe Ser Pro Lys Val Val Ser Leu Lys Lys Ile Tyr
                85                  90                  95

Asp Arg Glu Gln Thr Arg Tyr Lys Ala Thr Gly Leu His Phe Arg His
            100                 105                 110

Thr Asp Asn Val Ile Gln Trp Leu Asn Ala Met Asp Glu Ile Gly Leu
        115                 120                 125

Pro Lys Ile Phe Tyr Pro Glu Thr Thr Asp Ile Tyr Asp Arg Lys Asn
    130                 135                 140

Met Pro Arg Cys Ile Tyr Cys Ile His Ala Leu Ser Leu Tyr Leu Phe
145                 150                 155                 160

Lys Leu Gly Leu Ala Pro Gln Ile Gln Asp Leu Tyr Gly Lys Val Asp
                165                 170                 175

Phe Thr Glu Glu Glu Ile Asn Asn Met Lys Thr Glu Leu Glu Lys Tyr
```

-continued

```
                180                 185                 190
Gly Ile Gln Met Pro Ala Phe Ser Lys Ile Gly Gly Ile Leu Ala Asn
            195                 200                 205
Glu Leu Ser Val Asp Glu Ala Ala Leu His Ala Ala Val Ile Ala Ile
        210                 215                 220
Asn Glu Ala Ile Asp Arg Arg Ile Pro Ala Asp Thr Phe Ala Ala Leu
225                 230                 235                 240
Lys Asn Pro Asn Ala Met Leu Val Asn Leu Glu Glu Pro Leu Ala Ser
                245                 250                 255
Thr Tyr Gln Asp Ile Leu Tyr Gln Ala Lys Gln Asp Lys Met Thr Asn
            260                 265                 270
Ala Lys Asn Arg Thr Glu Asn Ser Glu Arg Glu Arg Asp Val Tyr Glu
        275                 280                 285
Glu Leu Leu Thr Gln Ala Glu Ile Gln Gly Asn Ile Asn Lys Val Asn
                290                 295                 300
Thr Phe Ser Ala Leu Ala Asn Ile Asp Leu Ala Leu Glu Gln Gly Asp
305                 310                 315                 320
Ala Leu Ala Leu Phe Arg Ala Leu Gln Ser Pro Ala Leu Gly Leu Arg
                325                 330                 335
Gly Leu Gln Gln Gln Asn Ser Asp Trp Tyr Leu Lys Gln Leu Leu Ser
            340                 345                 350
Asp Lys Gln Gln Lys Arg Gln Ser Gly Gln Thr Asp Pro Leu Gln Lys
        355                 360                 365
Glu Glu Leu Gln Ser Gly Val Asp Ala Ala Asn Ser Ala Ala Gln Gln
        370                 375                 380
Tyr Gln Arg Arg Leu Ala Ala Val Ala Leu Ile Asn Ala Ala Ile Gln
385                 390                 395                 400
Lys Gly Val Ala Glu Lys Thr Val Leu Glu Leu Met Asn Pro Glu Ala
                405                 410                 415
Gln Leu Pro Gln Val Tyr Pro Phe Ala Ala Asp Leu Tyr Gln Lys Glu
            420                 425                 430
Leu Ala Thr Leu Gln Arg Gln Ser Pro Glu His Asn Leu Thr His Pro
        435                 440                 445
Glu Leu Ser Val Ala Val Glu Met Leu Ser Ser Val Ala Leu Ile Asn
        450                 455                 460
Arg Ala Leu Glu Ser Gly Asp Val Asn Thr Val Trp Lys Gln Leu Ser
465                 470                 475                 480
Ser Ser Val Thr Gly Leu Thr Asn Ile Glu Glu Glu Asn Cys Gln Arg
                485                 490                 495
Tyr Leu Asp Glu Leu Met Lys Leu Lys Ala Gln Ala His Ala Glu Asn
            500                 505                 510
Asn Glu Phe Ile Thr Trp Asn Asp Ile Gln Ala Cys Val Asp His Val
        515                 520                 525
Asn Leu Val Val Gln Glu Glu His Glu Arg Ile Leu Ala Ile Gly Leu
        530                 535                 540
Ile Asn Glu Ala Leu Asp Glu Gly Asp Ala Gln Lys Thr Leu Gln Ala
545                 550                 555                 560
Leu Gln Ile Pro Ala Ala Lys Leu Glu Gly Val Leu Ala Glu Val Ala
                565                 570                 575
Gln His Tyr Gln Asp Thr Leu Ile Arg Ala Lys Arg Glu Lys Ala Gln
            580                 585                 590
Glu Ile Gln Asp Glu Ser Ala Val Leu Trp Leu Asp Glu Ile Gln Gly
        595                 600                 605
```

-continued

Gly Ile Trp Gln Ser Asn Lys Asp Thr Gln Glu Ala Gln Lys Phe Ala
    610                 615                 620

Leu Gly Ile Phe Ala Ile Asn Glu Ala Val Glu Ser Gly Asp Val Gly
625                 630                 635                 640

Lys Thr Leu Ser Ala Leu Arg Ser Pro Asp Val Gly Leu Tyr Gly Val
                645                 650                 655

Ile Pro Glu Cys Gly Glu Thr Tyr His Ser Asp Leu Ala Glu Ala Lys
                660                 665                 670

Lys Lys Lys Leu Ala Val Gly Asp Asn Ser Lys Trp Val Lys His
            675                 680                 685

Trp Val Lys Gly Gly Tyr Tyr Tyr His Asn Leu Glu Thr Gln Glu
    690                 695                 700

Gly Gly Trp Asp Glu Pro Pro Asn Phe Val Gln Asn Ser Met Gln Leu
705                 710                 715                 720

Ser Arg Glu Glu Ile Gln Ser Ser Ile Ser Gly Val Thr Ala Ala Tyr
                725                 730                 735

Asn Arg Glu Gln Leu Trp Leu Ala Asn Glu Gly Leu Ile Thr Arg Leu
                740                 745                 750

Gln Ala Arg Cys Arg Gly Tyr Leu Val Arg Gln Glu Phe Arg Ser Arg
            755                 760                 765

Met Asn Phe Leu Lys Lys Gln Ile Pro Ala Ile Thr Cys Ile Gln Ser
770                 775                 780

Gln Trp Arg Gly Tyr Lys Gln Lys Lys Ala Tyr Gln Asp Arg Leu Ala
785                 790                 795                 800

Tyr Leu Arg Ser His Lys Asp Glu Val Val Lys Ile Gln Ser Leu Ala
                805                 810                 815

Arg Met His Gln Ala Arg Lys Arg Tyr Arg Asp Arg Leu Gln Tyr Phe
            820                 825                 830

Arg Asp His Ile Asn Asp Ile Ile Lys Ile Gln Ala Phe Ile Arg Ala
        835                 840                 845

Asn Lys Ala Arg Asp Asp Tyr Lys Thr Leu Ile Asn Ala Glu Asp Pro
    850                 855                 860

Pro Met Val Val Val Arg Lys Phe Val His Leu Leu Asp Gln Ser Asp
865                 870                 875                 880

Gln Asp Phe Gln Glu Glu Leu Asp Leu Met Lys Met Arg Glu Glu Val
                885                 890                 895

Ile Thr Leu Ile Arg Ser Asn Gln Gln Leu Glu Asn Asp Leu Asn Leu
            900                 905                 910

Met Asp Ile Lys Ile Gly Leu Leu Val Lys Asn Lys Ile Thr Leu Gln
        915                 920                 925

Asp Val Val Ser His Ser Lys Lys Leu Thr Lys Lys Asn Lys Glu Gln
    930                 935                 940

Leu Ser Asp Met Met Met Ile Asn Lys Gln Lys Gly Gly Leu Lys Ala
945                 950                 955                 960

Leu Ser Lys Glu Lys Arg Glu Lys Leu Glu Ala Tyr Gln His Leu Phe
                965                 970                 975

Tyr Leu Leu Gln Thr Asn Pro Thr Tyr Leu Ala Lys Leu Ile Phe Gln
            980                 985                 990

Met Pro Gln Asn Lys Ser Thr Lys Phe Met Asp Ser Val Ile Phe Thr
        995                 1000                1005

Leu Tyr Asn Tyr Ala Ser Asn Gln Arg Glu Glu Tyr Leu Leu Leu
    1010                1015                1020

```
Arg Leu Phe Lys Thr Ala Leu Gln Glu Glu Ile Lys Ser Lys Val
    1025            1030                1035

Asp Gln Ile Gln Glu Ile Val Thr Gly Asn Pro Thr Val Ile Lys
    1040            1045                1050

Met Val Val Ser Phe Asn Arg Gly Ala Arg Gly Gln Asn Ala Leu
    1055            1060                1065

Arg Gln Ile Leu Ala Pro Val Val Lys Glu Ile Met Asp Asp Lys
    1070            1075                1080

Ser Leu Asn Ile Lys Thr Asp Pro Val Asp Ile Tyr Lys Ser Trp
    1085            1090                1095

Val Asn Gln Met Glu Ser Gln Thr Gly Glu Ala Ser Lys Leu Pro
    1100            1105                1110

Tyr Asp Val Thr Pro Glu Gln Ala Leu Ala His Glu Glu Val Lys
    1115            1120                1125

Thr Arg Leu Asp Ser Ser Ile Arg Asn Met Arg Ala Val Thr Asp
    1130            1135                1140

Lys Phe Leu Ser Ala Ile Val Ser Ser Val Asp Lys Ile Pro Tyr
    1145            1150                1155

Gly Met Arg Phe Ile Ala Lys Val Leu Lys Asp Ser Leu His Glu
    1160            1165                1170

Lys Phe Pro Asp Ala Gly Glu Asp Glu Leu Leu Lys Ile Ile Gly
    1175            1180                1185

Asn Leu Leu Tyr Tyr Arg Tyr Met Asn Pro Ala Ile Val Ala Pro
    1190            1195                1200

Asp Ala Phe Asp Ile Ile Asp Leu Ser Ala Gly Gly Gln Leu Thr
    1205            1210                1215

Thr Asp Gln Arg Arg Asn Leu Gly Ser Ile Ala Lys Met Leu Gln
    1220            1225                1230

His Ala Ala Ser Asn Lys Met Phe Leu Gly Asp Asn Ala His Leu
    1235            1240                1245

Ser Ile Ile Asn Glu Tyr Leu Ser Gln Ser Tyr Gln Lys Phe Arg
    1250            1255                1260

Arg Phe Phe Gln Thr Ala Cys Asp Val Pro Glu Leu Gln Asp Lys
    1265            1270                1275

Phe Asn Val Asp Glu Tyr Ser Asp Leu Val Thr Leu Thr Lys Pro
    1280            1285                1290

Val Ile Tyr Ile Ser Ile Gly Glu Ile Ile Asn Thr His Thr Leu
    1295            1300                1305

Leu Leu Asp His Gln Asp Ala Ile Ala Pro Glu His Asn Asp Pro
    1310            1315                1320

Ile His Glu Leu Leu Asp Asp Leu Gly Glu Val Pro Thr Ile Glu
    1325            1330                1335

Ser Leu Ile Gly Glu Ser Ser Gly Asn Leu Asn Asp Pro Asn Lys
    1340            1345                1350

Glu Ala Leu Ala Lys Thr Glu Val Ser Leu Thr Leu Thr Asn Lys
    1355            1360                1365

Phe Asp Val Pro Gly Asp Glu Asn Ala Glu Met Asp Ala Arg Thr
    1370            1375                1380

Ile Leu Leu Asn Thr Lys Arg Leu Ile Val Asp Val Ile Arg Phe
    1385            1390                1395

Gln Pro Gly Glu Thr Leu Thr Glu Ile Leu Glu Thr Pro Ala Thr
    1400            1405                1410

Ser Glu Gln Glu Ala Glu His Gln Arg Ala Met Gln Arg Arg Ala
```

```
                        1415                1420                1425

Ile Arg Asp Ala Lys Thr Pro Asp Lys Met Lys Lys Ser Lys Ser
        1430                1435                1440

Val Lys Glu Asp Ser Asn Leu Thr Leu Gln Glu Lys Lys Glu Lys
    1445                1450                1455

Ile Gln Thr Gly Leu Lys Lys Leu Thr Glu Leu Gly Thr Val Asp
    1460                1465                1470

Pro Lys Asn Lys Tyr Gln Glu Leu Ile Asn Asp Ile Ala Arg Asp
    1475                1480                1485

Ile Arg Asn Gln Arg Arg Tyr Arg Gln Arg Arg Lys Ala Glu Leu
    1490                1495                1500

Val Lys Leu Gln Gln Thr Tyr Ala Ala Leu Asn Ser Lys Ala Thr
    1505                1510                1515

Phe Tyr Gly Glu Gln Val Asp Tyr Tyr Lys Ser Tyr Ile Lys Thr
    1520                1525                1530

Cys Leu Asp Asn Leu Ala Ser Lys Gly Lys Val Ser Lys Lys Pro
    1535                1540                1545

Arg Glu Met Lys Gly Lys Lys Ser Lys Lys Ile Ser Leu Lys Tyr
    1550                1555                1560

Thr Ala Ala Arg Leu His Glu Lys Gly Val Leu Leu Glu Ile Glu
    1565                1570                1575

Asp Leu Gln Val Asn Gln Phe Lys Asn Val Ile Phe Glu Ile Ser
    1580                1585                1590

Pro Thr Glu Glu Val Gly Asp Phe Glu Val Lys Ala Lys Phe Met
    1595                1600                1605

Gly Val Gln Met Glu Thr Phe Met Leu His Tyr Gln Asp Leu Leu
    1610                1615                1620

Gln Leu Gln Tyr Glu Gly Val Ala Val Met Lys Leu Phe Asp Arg
    1625                1630                1635

Ala Lys Val Asn Val Asn Leu Leu Ile Phe Leu Leu Asn Lys Lys
    1640                1645                1650

Phe Tyr Gly Lys
    1655

<210> SEQ ID NO 102
<211> LENGTH: 250
<212> TYPE: PRT
<213> ORGANISM: Homo sapiens

<400> SEQUENCE: 102

Met Ala Asp Asn Phe Ser Leu His Asp Ala Leu Ser Gly Ser Gly Asn
1               5                   10                  15

Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr Pro
    50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Thr Gly Ala Tyr Pro Ala Thr Gly Pro Tyr Gly Ala Pro Ala Gly
            100                 105                 110
```

-continued

```
Pro Leu Ile Val Pro Tyr Asn Leu Pro Leu Pro Gly Gly Val Val Pro
            115                 120                 125

Arg Met Leu Ile Thr Ile Leu Gly Thr Val Lys Pro Asn Ala Asn Arg
130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
195                 200                 205

Phe Lys Val Ala Val Asn Asp Ala His Leu Leu Gln Tyr Asn His Arg
210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250

<210> SEQ ID NO 103
<211> LENGTH: 1960
<212> TYPE: PRT
<213> ORGANISM: Homo sapiens

<400> SEQUENCE: 103

Met Ala Gln Gln Ala Ala Asp Lys Tyr Leu Tyr Val Asp Lys Asn Phe
1               5                   10                  15

Ile Asn Asn Pro Leu Ala Gln Ala Asp Trp Ala Ala Lys Lys Leu Val
            20                  25                  30

Trp Val Pro Ser Asp Lys Ser Gly Phe Glu Pro Ala Ser Leu Lys Glu
        35                  40                  45

Glu Val Gly Glu Glu Ala Ile Val Glu Leu Val Glu Asn Gly Lys Lys
    50                  55                  60

Val Lys Val Asn Lys Asp Asp Ile Gln Lys Met Asn Pro Pro Lys Phe
65                  70                  75                  80

Ser Lys Val Glu Asp Met Ala Glu Leu Thr Cys Leu Asn Glu Ala Ser
                85                  90                  95

Val Leu His Asn Leu Lys Glu Arg Tyr Tyr Ser Gly Leu Ile Tyr Thr
            100                 105                 110

Tyr Ser Gly Leu Phe Cys Val Val Ile Asn Pro Tyr Lys Asn Leu Pro
        115                 120                 125

Ile Tyr Ser Glu Glu Ile Val Glu Met Tyr Lys Gly Lys Lys Arg His
    130                 135                 140

Glu Met Pro Pro His Ile Tyr Ala Ile Thr Asp Thr Ala Tyr Arg Ser
145                 150                 155                 160

Met Met Gln Asp Arg Glu Asp Gln Ser Ile Leu Cys Thr Gly Glu Ser
                165                 170                 175

Gly Ala Gly Lys Thr Glu Asn Thr Lys Lys Val Ile Gln Tyr Leu Ala
            180                 185                 190

Tyr Val Ala Ser Ser His Lys Ser Lys Lys Asp Gln Gly Glu Leu Glu
        195                 200                 205

Arg Gln Leu Leu Gln Ala Asn Pro Ile Leu Glu Ala Phe Gly Asn Ala
    210                 215                 220

Lys Thr Val Lys Asn Asp Asn Ser Ser Arg Phe Gly Lys Phe Ile Arg
225                 230                 235                 240
```

-continued

Ile Asn Phe Asp Val Asn Gly Tyr Ile Val Gly Ala Asn Ile Glu Thr
                    245                 250                 255

Tyr Leu Leu Glu Lys Ser Arg Ala Ile Arg Gln Ala Lys Glu Glu Arg
                260                 265                 270

Thr Phe His Ile Phe Tyr Tyr Leu Leu Ser Gly Ala Gly Glu His Leu
            275                 280                 285

Lys Thr Asp Leu Leu Leu Glu Pro Tyr Asn Lys Tyr Arg Phe Leu Ser
        290                 295                 300

Asn Gly His Val Thr Ile Pro Gly Gln Gln Asp Lys Asp Met Phe Gln
305                 310                 315                 320

Glu Thr Met Glu Ala Met Arg Ile Met Gly Ile Pro Glu Glu Glu Gln
                325                 330                 335

Met Gly Leu Leu Arg Val Ile Ser Gly Val Leu Gln Leu Gly Asn Ile
                340                 345                 350

Val Phe Lys Lys Glu Arg Asn Thr Asp Gln Ala Ser Met Pro Asp Asn
                355                 360                 365

Thr Ala Ala Gln Lys Val Ser His Leu Leu Gly Ile Asn Val Thr Asp
        370                 375                 380

Phe Thr Arg Gly Ile Leu Thr Pro Arg Ile Lys Val Gly Arg Asp Tyr
385                 390                 395                 400

Val Gln Lys Ala Gln Thr Lys Glu Gln Ala Asp Phe Ala Ile Glu Ala
                405                 410                 415

Leu Ala Lys Ala Thr Tyr Glu Arg Met Phe Arg Trp Leu Val Leu Arg
                420                 425                 430

Ile Asn Lys Ala Leu Asp Lys Thr Lys Arg Gln Gly Ala Ser Phe Ile
            435                 440                 445

Gly Ile Leu Asp Ile Ala Gly Phe Glu Ile Phe Asp Leu Asn Ser Phe
        450                 455                 460

Glu Gln Leu Cys Ile Asn Tyr Thr Asn Glu Lys Leu Gln Gln Leu Phe
465                 470                 475                 480

Asn His Thr Met Phe Ile Leu Glu Gln Glu Glu Tyr Gln Arg Glu Gly
                485                 490                 495

Ile Glu Trp Asn Phe Ile Asp Phe Gly Leu Asp Leu Gln Pro Cys Ile
                500                 505                 510

Asp Leu Ile Glu Lys Pro Ala Gly Pro Pro Gly Ile Leu Ala Leu Leu
            515                 520                 525

Asp Glu Glu Cys Trp Phe Pro Lys Ala Thr Asp Lys Ser Phe Val Glu
        530                 535                 540

Lys Val Met Gln Glu Gln Gly Thr His Pro Lys Phe Gln Lys Pro Lys
545                 550                 555                 560

Gln Leu Lys Asp Lys Ala Asp Phe Cys Ile Ile His Tyr Ala Gly Lys
                565                 570                 575

Val Asp Tyr Lys Ala Asp Glu Trp Leu Met Lys Asn Met Asp Pro Leu
                580                 585                 590

Asn Asp Asn Ile Ala Thr Leu Leu His Gln Ser Ser Asp Lys Phe Val
            595                 600                 605

Ser Glu Leu Trp Lys Asp Val Asp Arg Ile Ile Gly Leu Asp Gln Val
        610                 615                 620

Ala Gly Met Ser Glu Thr Ala Leu Pro Gly Ala Phe Lys Thr Arg Lys
625                 630                 635                 640

Gly Met Phe Arg Thr Val Gly Gln Leu Tyr Lys Glu Gln Leu Ala Lys
                645                 650                 655

```
Leu Met Ala Thr Leu Arg Asn Thr Asn Pro Asn Phe Val Arg Cys Ile
            660                 665                 670

Ile Pro Asn His Glu Lys Lys Ala Gly Lys Leu Asp Pro His Leu Val
        675                 680                 685

Leu Asp Gln Leu Arg Cys Asn Gly Val Leu Glu Gly Ile Arg Ile Cys
    690                 695                 700

Arg Gln Gly Phe Pro Asn Arg Val Val Phe Gln Glu Phe Arg Gln Arg
705                 710                 715                 720

Tyr Glu Ile Leu Thr Pro Asn Ser Ile Pro Lys Gly Phe Met Asp Gly
                725                 730                 735

Lys Gln Ala Cys Val Leu Met Ile Lys Ala Leu Glu Leu Asp Ser Asn
            740                 745                 750

Leu Tyr Arg Ile Gly Gln Ser Lys Val Phe Phe Arg Ala Gly Val Leu
        755                 760                 765

Ala His Leu Glu Glu Glu Arg Asp Leu Lys Ile Thr Asp Val Ile Ile
    770                 775                 780

Gly Phe Gln Ala Cys Cys Arg Gly Tyr Leu Ala Arg Lys Ala Phe Ala
785                 790                 795                 800

Lys Arg Gln Gln Gln Leu Thr Ala Met Lys Val Leu Gln Arg Asn Cys
                805                 810                 815

Ala Ala Tyr Leu Lys Leu Arg Asn Trp Gln Trp Trp Arg Leu Phe Thr
            820                 825                 830

Lys Val Lys Pro Leu Leu Gln Val Ser Arg Gln Glu Glu Met Met
        835                 840                 845

Ala Lys Glu Glu Glu Leu Val Lys Val Arg Glu Lys Gln Leu Ala Ala
850                 855                 860

Glu Asn Arg Leu Thr Glu Met Glu Thr Leu Gln Ser Gln Leu Met Ala
865                 870                 875                 880

Glu Lys Leu Gln Leu Gln Glu Gln Leu Gln Ala Glu Thr Glu Leu Cys
                885                 890                 895

Ala Glu Ala Glu Glu Leu Arg Ala Arg Leu Thr Ala Lys Lys Gln Glu
            900                 905                 910

Leu Glu Glu Ile Cys His Asp Leu Glu Ala Arg Val Glu Glu Glu Glu
        915                 920                 925

Glu Arg Cys Gln His Leu Gln Ala Glu Lys Lys Lys Met Gln Gln Asn
    930                 935                 940

Ile Gln Glu Leu Glu Glu Gln Leu Glu Glu Glu Glu Ser Ala Arg Gln
945                 950                 955                 960

Lys Leu Gln Leu Glu Lys Val Thr Thr Glu Ala Lys Leu Lys Lys Leu
                965                 970                 975

Glu Glu Glu Gln Ile Ile Leu Glu Asp Gln Asn Cys Lys Leu Ala Lys
            980                 985                 990

Glu Lys Lys Leu Leu Glu Asp Arg Ile Ala Glu Phe Thr Thr Asn Leu
        995                 1000                1005

Thr Glu Glu Glu Glu Lys Ser Lys Ser Leu Ala Lys Leu Lys Asn
    1010                1015                1020

Lys His Glu Ala Met Ile Thr Asp Leu Glu Glu Arg Leu Arg Arg
    1025                1030                1035

Glu Glu Lys Gln Arg Gln Glu Leu Glu Lys Thr Arg Arg Lys Leu
    1040                1045                1050

Glu Gly Asp Ser Thr Asp Leu Ser Asp Gln Ile Ala Glu Leu Gln
    1055                1060                1065

Ala Gln Ile Ala Glu Leu Lys Met Gln Leu Ala Lys Lys Glu Glu
```

-continued

```
              1070                1075                1080

Glu Leu Gln Ala Ala Leu Ala Arg Val Glu Glu Ala Ala Gln
    1085                1090                1095

Lys Asn Met Ala Leu Lys Lys Ile Arg Glu Leu Glu Ser Gln Ile
    1100                1105                1110

Ser Glu Leu Gln Glu Asp Leu Glu Ser Glu Arg Ala Ser Arg Asn
    1115                1120                1125

Lys Ala Glu Lys Gln Lys Arg Asp Leu Gly Glu Glu Leu Glu Ala
    1130                1135                1140

Leu Lys Thr Glu Leu Glu Asp Thr Leu Asp Ser Thr Ala Ala Gln
    1145                1150                1155

Gln Glu Leu Arg Ser Lys Arg Glu Gln Glu Val Asn Ile Leu Lys
    1160                1165                1170

Lys Thr Leu Glu Glu Glu Ala Lys Thr His Glu Ala Gln Ile Gln
    1175                1180                1185

Glu Met Arg Gln Lys His Ser Gln Ala Val Glu Glu Leu Ala Glu
    1190                1195                1200

Gln Leu Glu Gln Thr Lys Arg Val Lys Ala Asn Leu Glu Lys Ala
    1205                1210                1215

Lys Gln Thr Leu Glu Asn Glu Arg Gly Glu Leu Ala Asn Glu Val
    1220                1225                1230

Lys Val Leu Leu Gln Gly Lys Gly Asp Ser Glu His Lys Arg Lys
    1235                1240                1245

Lys Val Glu Ala Gln Leu Gln Glu Leu Gln Val Lys Phe Asn Glu
    1250                1255                1260

Gly Glu Arg Val Arg Thr Glu Leu Ala Asp Lys Val Thr Lys Leu
    1265                1270                1275

Gln Val Glu Leu Asp Asn Val Thr Gly Leu Leu Ser Gln Ser Asp
    1280                1285                1290

Ser Lys Ser Ser Lys Leu Thr Lys Asp Phe Ser Ala Leu Glu Ser
    1295                1300                1305

Gln Leu Gln Asp Thr Gln Glu Leu Leu Gln Glu Glu Asn Arg Gln
    1310                1315                1320

Lys Leu Ser Leu Ser Thr Lys Leu Lys Gln Val Glu Asp Glu Lys
    1325                1330                1335

Asn Ser Phe Arg Glu Gln Leu Glu Glu Glu Glu Glu Ala Lys His
    1340                1345                1350

Asn Leu Glu Lys Gln Ile Ala Thr Leu His Ala Gln Val Ala Asp
    1355                1360                1365

Met Lys Lys Lys Met Glu Asp Ser Val Gly Cys Leu Glu Thr Ala
    1370                1375                1380

Glu Glu Val Lys Arg Lys Leu Gln Lys Asp Leu Glu Gly Leu Ser
    1385                1390                1395

Gln Arg His Glu Glu Lys Val Ala Ala Tyr Asp Lys Leu Glu Lys
    1400                1405                1410

Thr Lys Thr Arg Leu Gln Gln Glu Leu Asp Asp Leu Leu Val Asp
    1415                1420                1425

Leu Asp His Gln Arg Gln Ser Ala Cys Asn Leu Glu Lys Lys Gln
    1430                1435                1440

Lys Lys Phe Asp Gln Leu Leu Ala Glu Glu Lys Thr Ile Ser Ala
    1445                1450                1455

Lys Tyr Ala Glu Glu Arg Asp Arg Ala Glu Ala Glu Ala Arg Glu
    1460                1465                1470
```

```
Lys Glu Thr Lys Ala Leu Ser Leu Ala Arg Ala Leu Glu Glu Ala
1475                1480                1485

Met Glu Gln Lys Ala Glu Leu Glu Arg Leu Asn Lys Gln Phe Arg
1490                1495                1500

Thr Glu Met Glu Asp Leu Met Ser Ser Lys Asp Asp Val Gly Lys
1505                1510                1515

Ser Val His Glu Leu Glu Lys Ser Lys Arg Ala Leu Glu Gln Gln
1520                1525                1530

Val Glu Glu Met Lys Thr Gln Leu Glu Glu Leu Glu Asp Glu Leu
1535                1540                1545

Gln Ala Thr Glu Asp Ala Lys Leu Arg Leu Glu Val Asn Leu Gln
1550                1555                1560

Ala Met Lys Ala Gln Phe Glu Arg Asp Leu Gln Gly Arg Asp Glu
1565                1570                1575

Gln Ser Glu Glu Lys Lys Lys Gln Leu Val Arg Gln Val Arg Glu
1580                1585                1590

Met Glu Ala Glu Leu Glu Asp Glu Arg Lys Gln Arg Ser Met Ala
1595                1600                1605

Val Ala Ala Arg Lys Lys Leu Glu Met Asp Leu Lys Asp Leu Glu
1610                1615                1620

Ala His Ile Asp Ser Ala Asn Lys Asn Arg Asp Glu Ala Ile Lys
1625                1630                1635

Gln Leu Arg Lys Leu Gln Ala Gln Met Lys Asp Cys Met Arg Glu
1640                1645                1650

Leu Asp Asp Thr Arg Ala Ser Arg Glu Glu Ile Leu Ala Gln Ala
1655                1660                1665

Lys Glu Asn Glu Lys Lys Leu Lys Ser Met Glu Ala Glu Met Ile
1670                1675                1680

Gln Leu Gln Glu Glu Leu Ala Ala Ala Glu Arg Ala Lys Arg Gln
1685                1690                1695

Ala Gln Gln Glu Arg Asp Glu Leu Ala Asp Glu Ile Ala Asn Ser
1700                1705                1710

Ser Gly Lys Gly Ala Leu Ala Leu Glu Glu Lys Arg Arg Leu Glu
1715                1720                1725

Ala Arg Ile Ala Gln Leu Glu Glu Glu Leu Glu Glu Glu Gln Gly
1730                1735                1740

Asn Thr Glu Leu Ile Asn Asp Arg Leu Lys Lys Ala Asn Leu Gln
1745                1750                1755

Ile Asp Gln Ile Asn Thr Asp Leu Asn Leu Glu Arg Ser His Ala
1760                1765                1770

Gln Lys Asn Glu Asn Ala Arg Gln Gln Leu Glu Arg Gln Asn Lys
1775                1780                1785

Glu Leu Lys Val Lys Leu Gln Glu Met Glu Gly Thr Val Lys Ser
1790                1795                1800

Lys Tyr Lys Ala Ser Ile Thr Ala Leu Glu Ala Lys Ile Ala Gln
1805                1810                1815

Leu Glu Glu Gln Leu Asp Asn Glu Thr Lys Glu Arg Gln Ala Ala
1820                1825                1830

Cys Lys Gln Val Arg Arg Thr Glu Lys Lys Leu Lys Asp Val Leu
1835                1840                1845

Leu Gln Val Asp Asp Glu Arg Arg Asn Ala Glu Gln Tyr Lys Asp
1850                1855                1860
```

```
Gln Ala Asp Lys Ala Ser Thr Arg Leu Lys Gln Leu Lys Arg Gln
    1865                1870                1875

Leu Glu Glu Ala Glu Glu Ala Gln Arg Ala Asn Ala Ser Arg
1880                1885                1890

Arg Lys Leu Gln Arg Glu Leu Glu Asp Ala Thr Glu Thr Ala Asp
    1895                1900                1905

Ala Met Asn Arg Glu Val Ser Ser Leu Lys Asn Lys Leu Arg Arg
    1910                1915                1920

Gly Asp Leu Pro Phe Val Val Pro Arg Arg Met Ala Arg Lys Gly
    1925                1930                1935

Ala Gly Asp Gly Ser Asp Glu Val Asp Gly Lys Ala Asp Gly
    1940                1945                1950

Ala Glu Ala Lys Pro Ala Glu
    1955            1960

<210> SEQ ID NO 104
<211> LENGTH: 151
<212> TYPE: PRT
<213> ORGANISM: Homo sapiens

<400> SEQUENCE: 104

Met Cys Asp Phe Thr Glu Asp Gln Thr Ala Glu Phe Lys Glu Ala Phe
1               5                   10                  15

Gln Leu Phe Asp Arg Thr Gly Asp Gly Lys Ile Leu Tyr Ser Gln Cys
            20                  25                  30

Gly Asp Val Met Arg Ala Leu Gly Gln Asn Pro Thr Asn Ala Glu Val
        35                  40                  45

Leu Lys Val Leu Gly Asn Pro Lys Ser Asp Glu Met Asn Val Lys Val
    50                  55                  60

Leu Asp Phe Glu His Phe Leu Pro Met Leu Gln Thr Val Ala Lys Asn
65                  70                  75                  80

Lys Asp Gln Gly Thr Tyr Glu Asp Tyr Val Glu Gly Leu Arg Val Phe
                85                  90                  95

Asp Lys Glu Gly Asn Gly Thr Val Met Gly Ala Glu Ile Arg His Val
            100                 105                 110

Leu Val Thr Leu Gly Glu Lys Met Thr Glu Glu Glu Val Glu Met Leu
        115                 120                 125

Val Ala Gly His Glu Asp Ser Asn Gly Cys Ile Asn Tyr Glu Ala Phe
    130                 135                 140

Val Arg His Ile Leu Ser Gly
145                 150

<210> SEQ ID NO 105
<211> LENGTH: 152
<212> TYPE: PRT
<213> ORGANISM: Homo sapiens

<400> SEQUENCE: 105

Met Ala Asn Leu Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Ala Met Lys Phe Leu Arg Ala Ser Glu Glu His Leu
        35                  40                  45

Lys Gln His Tyr Ile Asp Leu Lys Asp Arg Pro Phe Phe Pro Gly Leu
    50                  55                  60
```

```
Val Lys Tyr Met Asn Ser Gly Pro Val Val Ala Met Val Trp Glu Gly
 65                  70                  75                  80

Leu Asn Val Val Lys Thr Gly Arg Val Met Leu Gly Glu Thr Asn Pro
                 85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Lys Ser Ala Glu Lys
        115                 120                 125

Glu Ile Ser Leu Trp Phe Lys Pro Glu Glu Leu Val Asp Tyr Lys Ser
    130                 135                 140

Cys Ala His Asp Trp Val Tyr Glu
145                 150

<210> SEQ ID NO 106
<211> LENGTH: 744
<212> TYPE: PRT
<213> ORGANISM: Homo sapiens

<400> SEQUENCE: 106

Met Ala Gly Arg Ser Met Gln Ala Ala Arg Cys Pro Thr Asp Glu Leu
1               5                   10                  15

Ser Leu Thr Asn Cys Ala Val Val Asn Glu Lys Asp Phe Gln Ser Gly
            20                  25                  30

Gln His Val Ile Val Arg Thr Ser Pro Asn His Arg Tyr Thr Phe Thr
        35                  40                  45

Leu Lys Thr His Pro Ser Val Val Pro Gly Ser Ile Ala Phe Ser Leu
    50                  55                  60

Pro Gln Arg Lys Trp Ala Gly Leu Ser Ile Gly Gln Glu Ile Glu Val
65                  70                  75                  80

Ser Leu Tyr Thr Phe Asp Lys Ala Lys Gln Cys Ile Gly Thr Met Thr
                85                  90                  95

Ile Glu Ile Asp Phe Leu Gln Lys Lys Ser Ile Asp Ser Asn Pro Tyr
            100                 105                 110

Asp Thr Asp Lys Met Ala Ala Glu Phe Ile Gln Gln Phe Asn Asn Gln
        115                 120                 125

Ala Phe Ser Val Gly Gln Gln Leu Val Phe Ser Phe Asn Glu Lys Leu
    130                 135                 140

Phe Gly Leu Leu Val Lys Asp Ile Glu Ala Met Asp Pro Ser Ile Leu
145                 150                 155                 160

Lys Gly Glu Pro Ala Thr Gly Lys Arg Gln Lys Ile Glu Val Gly Leu
                165                 170                 175

Val Val Gly Asn Ser Gln Val Ala Phe Glu Lys Ala Glu Asn Ser Ser
            180                 185                 190

Leu Asn Leu Ile Gly Lys Ala Lys Thr Lys Glu Asn Arg Gln Ser Ile
        195                 200                 205

Ile Asn Pro Asp Trp Asn Phe Glu Lys Met Gly Ile Gly Gly Leu Asp
    210                 215                 220

Lys Glu Phe Ser Asp Ile Phe Arg Arg Ala Phe Ala Ser Arg Val Phe
225                 230                 235                 240

Pro Pro Glu Ile Val Glu Gln Met Gly Cys Lys His Val Lys Gly Ile
                245                 250                 255

Leu Leu Tyr Gly Pro Pro Gly Cys Gly Lys Thr Leu Leu Ala Arg Gln
            260                 265                 270

Ile Gly Lys Met Leu Asn Ala Arg Glu Pro Lys Val Val Asn Gly Pro
    275                 280                 285
```

-continued

```
Glu Ile Leu Asn Lys Tyr Val Gly Glu Ser Glu Ala Asn Ile Arg Lys
    290                 295                 300

Leu Phe Ala Asp Ala Glu Glu Gln Arg Arg Leu Gly Ala Asn Ser
305                 310                 315                 320

Gly Leu His Ile Ile Ile Phe Asp Glu Ile Asp Ala Ile Cys Lys Gln
                    325                 330                 335

Arg Gly Ser Met Ala Gly Ser Thr Gly Val His Asp Thr Val Val Asn
                340                 345                 350

Gln Leu Leu Ser Lys Ile Asp Gly Val Glu Gln Leu Asn Asn Ile Leu
                355                 360                 365

Val Ile Gly Met Thr Asn Arg Pro Asp Leu Ile Asp Glu Ala Leu Leu
    370                 375                 380

Arg Pro Gly Arg Leu Glu Val Lys Met Glu Ile Gly Leu Pro Asp Glu
385                 390                 395                 400

Lys Gly Arg Leu Gln Ile Leu His Ile His Thr Ala Arg Met Arg Gly
                    405                 410                 415

His Gln Leu Leu Ser Ala Asp Val Asp Ile Lys Glu Leu Ala Val Glu
                420                 425                 430

Thr Lys Asn Phe Ser Gly Ala Glu Leu Glu Gly Leu Val Arg Ala Ala
                435                 440                 445

Gln Ser Thr Ala Met Asn Arg His Ile Lys Ala Ser Thr Lys Val Glu
    450                 455                 460

Val Asp Met Glu Lys Ala Glu Ser Leu Gln Val Thr Arg Gly Asp Phe
465                 470                 475                 480

Leu Ala Ser Leu Glu Asn Asp Ile Lys Pro Ala Phe Gly Thr Asn Gln
                    485                 490                 495

Glu Asp Tyr Ala Ser Tyr Ile Met Asn Gly Ile Ile Lys Trp Gly Asp
                500                 505                 510

Pro Val Thr Arg Val Leu Asp Asp Gly Glu Leu Leu Val Gln Gln Thr
                515                 520                 525

Lys Asn Ser Asp Arg Thr Pro Leu Val Ser Val Leu Leu Glu Gly Pro
530                 535                 540

Pro His Ser Gly Lys Thr Ala Leu Ala Ala Lys Ile Ala Glu Glu Ser
545                 550                 555                 560

Asn Phe Pro Phe Ile Lys Ile Cys Ser Pro Asp Lys Met Ile Gly Phe
                    565                 570                 575

Ser Glu Thr Ala Lys Cys Gln Ala Met Lys Lys Ile Phe Asp Asp Ala
                580                 585                 590

Tyr Lys Ser Gln Leu Ser Cys Val Val Asp Ile Glu Arg Leu
                595                 600                 605

Leu Asp Tyr Val Pro Ile Gly Pro Arg Phe Ser Asn Leu Val Leu Gln
    610                 615                 620

Ala Leu Leu Val Leu Lys Lys Ala Pro Pro Gln Gly Arg Lys Leu
625                 630                 635                 640

Leu Ile Ile Gly Thr Thr Ser Arg Lys Asp Val Leu Gln Glu Met Glu
                    645                 650                 655

Met Leu Asn Ala Phe Ser Thr Thr Ile His Val Pro Asn Ile Ala Thr
                660                 665                 670

Gly Glu Gln Leu Leu Glu Ala Leu Glu Leu Leu Gly Asn Phe Lys Asp
                675                 680                 685

Lys Glu Arg Thr Thr Ile Ala Gln Gln Val Lys Gly Lys Lys Val Trp
    690                 695                 700
```

```
Ile Gly Ile Lys Lys Leu Leu Met Leu Ile Glu Met Ser Leu Gln Met
705                 710                 715                 720

Asp Pro Glu Tyr Arg Val Arg Lys Phe Leu Ala Leu Leu Arg Glu Glu
            725                 730                 735

Gly Ala Ser Pro Leu Asp Phe Asp
            740

<210> SEQ ID NO 107
<211> LENGTH: 508
<212> TYPE: PRT
<213> ORGANISM: Homo sapiens

<400> SEQUENCE: 107

Met Leu Arg Arg Ala Leu Leu Cys Leu Ala Val Ala Ala Leu Val Arg
1               5                   10                  15

Ala Asp Ala Pro Glu Glu Glu Asp His Val Leu Val Leu Arg Lys Ser
            20                  25                  30

Asn Phe Ala Glu Ala Leu Ala Ala His Lys Tyr Leu Leu Val Glu Phe
        35                  40                  45

Tyr Ala Pro Trp Cys Gly His Cys Lys Ala Leu Ala Pro Glu Tyr Ala
    50                  55                  60

Lys Ala Ala Gly Lys Leu Lys Ala Glu Gly Ser Glu Ile Arg Leu Ala
65                  70                  75                  80

Lys Val Asp Ala Thr Glu Glu Ser Asp Leu Ala Gln Gln Tyr Gly Val
                85                  90                  95

Arg Gly Tyr Pro Thr Ile Lys Phe Phe Arg Asn Gly Asp Thr Ala Ser
            100                 105                 110

Pro Lys Glu Tyr Thr Ala Gly Arg Glu Ala Asp Asp Ile Val Asn Trp
        115                 120                 125

Leu Lys Lys Arg Thr Gly Pro Ala Ala Thr Thr Leu Pro Asp Gly Ala
130                 135                 140

Ala Ala Glu Ser Leu Val Glu Ser Ser Glu Val Ala Val Ile Gly Phe
145                 150                 155                 160

Phe Lys Asp Val Glu Ser Asp Ser Ala Lys Gln Phe Leu Gln Ala Ala
                165                 170                 175

Glu Ala Ile Asp Asp Ile Pro Phe Gly Ile Thr Ser Asn Ser Asp Val
            180                 185                 190

Phe Ser Lys Tyr Gln Leu Asp Lys Asp Gly Val Val Leu Phe Lys Lys
        195                 200                 205

Phe Asp Glu Gly Arg Asn Asn Phe Glu Gly Glu Val Thr Lys Glu Asn
210                 215                 220

Leu Leu Asp Phe Ile Lys His Asn Gln Leu Pro Leu Val Ile Glu Phe
225                 230                 235                 240

Thr Glu Gln Thr Ala Pro Lys Ile Phe Gly Gly Glu Ile Lys Thr His
                245                 250                 255

Ile Leu Leu Phe Leu Pro Lys Ser Val Ser Asp Tyr Asp Gly Lys Leu
            260                 265                 270

Ser Asn Phe Lys Thr Ala Ala Glu Ser Phe Lys Gly Lys Ile Leu Phe
        275                 280                 285

Ile Phe Ile Asp Ser Asp His Thr Asp Asn Gln Arg Ile Leu Glu Phe
290                 295                 300

Phe Gly Leu Lys Lys Glu Glu Cys Pro Ala Val Arg Leu Ile Thr Leu
305                 310                 315                 320

Glu Glu Glu Met Thr Lys Tyr Lys Pro Glu Ser Glu Glu Leu Thr Ala
                325                 330                 335
```

```
Glu Arg Ile Thr Glu Phe Cys His Arg Phe Leu Glu Gly Lys Ile Lys
            340                 345                 350

Pro His Leu Met Ser Gln Glu Leu Pro Glu Asp Trp Asp Lys Gln Pro
            355                 360                 365

Val Lys Val Leu Val Gly Lys Asn Phe Glu Asp Val Ala Phe Asp Glu
370                 375                 380

Lys Lys Asn Val Phe Val Glu Phe Tyr Ala Pro Trp Cys Gly His Cys
385                 390                 395                 400

Lys Gln Leu Ala Pro Ile Trp Asp Lys Leu Gly Glu Thr Tyr Lys Asp
            405                 410                 415

His Glu Asn Ile Val Ile Ala Lys Met Asp Ser Thr Ala Asn Glu Val
            420                 425                 430

Glu Ala Val Lys Val His Ser Phe Pro Thr Leu Lys Phe Phe Pro Ala
            435                 440                 445

Ser Ala Asp Arg Thr Val Ile Asp Tyr Asn Gly Glu Arg Thr Leu Asp
450                 455                 460

Gly Phe Lys Lys Phe Leu Glu Ser Gly Gly Gln Asp Gly Ala Gly Asp
465                 470                 475                 480

Asp Asp Asp Leu Glu Asp Leu Glu Glu Ala Glu Glu Pro Asp Met Glu
            485                 490                 495

Glu Asp Asp Asp Gln Lys Ala Val Lys Asp Glu Leu
            500                 505

<210> SEQ ID NO 108
<211> LENGTH: 190
<212> TYPE: PRT
<213> ORGANISM: Bos taurus

<400> SEQUENCE: 108

Met Ser Arg Arg Tyr Thr Pro Leu Ala Trp Val Leu Ala Leu Leu
1               5                   10                  15

Gly Leu Gly Ala Ala Gln Asp Cys Gly Ser Ile Val Ser Arg Gly Lys
            20                  25                  30

Trp Gly Ala Leu Ala Ser Lys Cys Ser Gln Arg Leu Arg Gln Pro Val
        35                  40                  45

Arg Tyr Val Val Ser His Thr Ala Gly Ser Val Cys Asn Thr Pro
50                  55                  60

Ala Ser Cys Gln Arg Gln Ala Gln Asn Val Gln Tyr His Val Arg
65                  70                  75                  80

Glu Arg Gly Trp Cys Asp Val Gly Tyr Asn Phe Leu Ile Gly Glu Asp
                85                  90                  95

Gly Leu Val Tyr Glu Gly Arg Gly Trp Asn Thr Leu Gly Ala His Ser
            100                 105                 110

Gly Pro Thr Trp Asn Pro Ile Ala Ile Gly Ile Ser Phe Met Gly Asn
        115                 120                 125

Tyr Met His Arg Val Pro Ala Ser Ala Leu Arg Ala Ala Gln Ser
130                 135                 140

Leu Leu Ala Cys Gly Ala Ala Arg Gly Tyr Leu Thr Pro Asn Tyr Glu
145                 150                 155                 160

Val Lys Gly His Arg Asp Val Gln Gln Thr Leu Ser Pro Gly Asp Glu
                165                 170                 175

Leu Tyr Lys Ile Ile Gln Gln Trp Pro His Tyr Arg Arg Val
            180                 185                 190
```

```
<210> SEQ ID NO 109
<211> LENGTH: 4684
<212> TYPE: PRT
<213> ORGANISM: Homo sapiens

<400> SEQUENCE: 109

Met Val Ala Gly Met Leu Met Pro Arg Asp Gln Leu Arg Ala Ile Tyr
1               5                   10                  15

Glu Val Leu Phe Arg Glu Gly Val Met Val Ala Lys Lys Asp Arg Arg
            20                  25                  30

Pro Arg Ser Leu His Pro His Val Pro Gly Val Thr Asn Leu Gln Val
        35                  40                  45

Met Arg Ala Met Ala Ser Leu Arg Ala Arg Gly Leu Val Arg Glu Thr
    50                  55                  60

Phe Ala Trp Cys His Phe Tyr Trp Tyr Leu Thr Asn Glu Gly Ile Ala
65                  70                  75                  80

His Leu Arg Gln Tyr Leu His Leu Pro Pro Glu Ile Val Pro Ala Ser
                85                  90                  95

Leu Gln Arg Val Arg Arg Pro Val Ala Met Val Met Pro Ala Arg Arg
            100                 105                 110

Thr Pro His Val Gln Ala Val Gln Gly Pro Leu Gly Ser Pro Pro Lys
        115                 120                 125

Arg Gly Pro Leu Pro Thr Glu Glu Gln Arg Val Tyr Arg Arg Lys Glu
    130                 135                 140

Leu Glu Glu Val Ser Pro Glu Thr Pro Val Val Pro Ala Thr Thr Gln
145                 150                 155                 160

Arg Thr Leu Ala Arg Pro Gly Pro Glu Pro Ala Pro Ala Thr Asp Glu
                165                 170                 175

Arg Asp Arg Val Gln Lys Lys Thr Phe Thr Lys Trp Val Asn Lys His
            180                 185                 190

Leu Ile Lys Ala Gln Arg His Ile Ser Asp Leu Tyr Glu Asp Leu Arg
        195                 200                 205

Asp Gly His Asn Leu Ile Ser Leu Leu Glu Val Leu Ser Gly Asp Ser
    210                 215                 220

Leu Pro Arg Glu Lys Gly Arg Met Arg Phe His Lys Leu Gln Asn Val
225                 230                 235                 240

Gln Ile Ala Leu Asp Tyr Leu Arg His Arg Gln Val Lys Leu Val Asn
                245                 250                 255

Ile Arg Asn Asp Asp Ile Ala Asp Gly Asn Pro Lys Leu Thr Leu Gly
            260                 265                 270

Leu Ile Trp Thr Ile Ile Leu His Phe Gln Ile Ser Asp Ile Gln Val
        275                 280                 285

Ser Gly Gln Ser Glu Asp Met Thr Ala Lys Glu Lys Leu Leu Leu Trp
    290                 295                 300

Ser Gln Arg Met Val Glu Gly Tyr Gln Gly Leu Arg Cys Asp Asn Phe
305                 310                 315                 320

Thr Ser Ser Trp Arg Asp Gly Arg Leu Phe Asn Ala Ile Ile His Arg
                325                 330                 335

His Lys Pro Leu Leu Ile Asp Met Asn Lys Val Tyr Arg Gln Thr Asn
            340                 345                 350

Leu Glu Asn Leu Asp Gln Ala Phe Ser Val Ala Glu Arg Asp Leu Gly
        355                 360                 365

Val Thr Arg Leu Leu Asp Pro Glu Asp Val Asp Val Pro Gln Pro Asp
    370                 375                 380
```

```
Glu Lys Ser Ile Ile Thr Tyr Val Ser Ser Leu Tyr Asp Ala Met Pro
385                 390                 395                 400

Arg Val Pro Asp Val Gln Asp Gly Val Arg Ala Asn Glu Leu Gln Leu
            405                 410                 415

Arg Trp Gln Glu Tyr Arg Glu Leu Val Leu Leu Leu Gln Trp Met
        420                 425                 430

Arg His His Thr Ala Ala Phe Glu Glu Arg Arg Phe Pro Ser Ser Phe
        435                 440                 445

Glu Glu Ile Glu Ile Leu Trp Ser Gln Phe Leu Lys Phe Lys Glu Met
450                 455                 460

Glu Leu Pro Ala Lys Glu Ala Asp Lys Asn Arg Ser Lys Gly Ile Tyr
465                 470                 475                 480

Gln Ser Leu Glu Gly Ala Val Gln Ala Gly Gln Leu Lys Val Pro Pro
            485                 490                 495

Gly Tyr His Pro Leu Asp Val Glu Lys Glu Trp Gly Lys Leu His Val
            500                 505                 510

Ala Ile Leu Glu Arg Glu Lys Gln Leu Arg Ser Glu Phe Glu Arg Leu
            515                 520                 525

Glu Cys Leu Gln Arg Ile Val Thr Lys Leu Gln Met Glu Ala Gly Leu
530                 535                 540

Cys Glu Glu Gln Leu Asn Gln Ala Asp Ala Leu Leu Gln Ser Asp Val
545                 550                 555                 560

Arg Leu Leu Ala Ala Gly Lys Val Pro Gln Arg Ala Gly Glu Val Glu
            565                 570                 575

Arg Asp Leu Asp Lys Ala Asp Ser Met Ile Arg Leu Leu Phe Asn Asp
            580                 585                 590

Val Gln Thr Leu Lys Asp Gly Arg His Pro Gln Gly Glu Gln Met Tyr
            595                 600                 605

Arg Arg Val Tyr Arg Leu His Glu Arg Leu Val Ala Ile Arg Thr Glu
            610                 615                 620

Tyr Asn Leu Arg Leu Lys Ala Gly Val Ala Ala Pro Ala Thr Gln Val
625                 630                 635                 640

Ala Gln Val Thr Leu Gln Ser Val Gln Arg Arg Pro Glu Leu Glu Asp
            645                 650                 655

Ser Thr Leu Arg Tyr Leu Gln Asp Leu Leu Ala Trp Val Glu Glu Asn
            660                 665                 670

Gln His Arg Val Asp Gly Ala Glu Trp Gly Val Asp Leu Pro Ser Val
        675                 680                 685

Glu Ala Gln Leu Gly Ser His Arg Gly Leu His Gln Ser Ile Glu Glu
            690                 695                 700

Phe Arg Ala Lys Ile Glu Arg Ala Arg Ser Asp Glu Gly Gln Leu Ser
705                 710                 715                 720

Pro Ala Thr Arg Gly Ala Tyr Arg Asp Cys Leu Gly Arg Leu Asp Leu
            725                 730                 735

Gln Tyr Ala Lys Leu Leu Asn Ser Ser Lys Ala Arg Leu Arg Ser Leu
            740                 745                 750

Glu Ser Leu His Ser Phe Val Ala Ala Thr Lys Glu Leu Met Trp
            755                 760                 765

Leu Asn Glu Lys Glu Glu Glu Val Gly Phe Asp Trp Ser Asp Arg
        770                 775                 780

Asn Thr Asn Met Thr Ala Lys Lys Glu Ser Tyr Ser Ala Leu Met Arg
785                 790                 795                 800

Glu Leu Glu Leu Lys Glu Lys Lys Ile Lys Glu Leu Gln Asn Ala Gly
```

```
                    805                 810                 815
Asp Arg Leu Leu Arg Glu Asp His Pro Ala Arg Pro Thr Val Glu Ser
                820                 825                 830

Phe Gln Ala Ala Leu Gln Thr Gln Trp Ser Trp Met Leu Gln Leu Cys
                835                 840                 845

Cys Cys Ile Glu Ala His Leu Lys Glu Asn Ala Ala Tyr Phe Gln Phe
            850                 855                 860

Phe Ser Asp Val Arg Glu Ala Glu Gly Gln Leu Gln Lys Leu Gln Glu
865                 870                 875                 880

Ala Leu Arg Arg Lys Tyr Ser Cys Asp Arg Ser Ala Thr Val Thr Arg
                885                 890                 895

Leu Glu Asp Leu Leu Gln Asp Ala Gln Asp Glu Lys Glu Gln Leu Asn
                900                 905                 910

Glu Tyr Lys Gly His Leu Ser Gly Leu Ala Lys Arg Ala Lys Ala Val
                915                 920                 925

Val Gln Leu Lys Pro Arg His Pro Ala His Pro Met Arg Gly Arg Leu
            930                 935                 940

Pro Leu Leu Ala Val Cys Asp Tyr Lys Gln Val Glu Val Thr Val His
945                 950                 955                 960

Lys Gly Asp Glu Cys Gln Leu Val Gly Pro Ala Gln Pro Ser His Trp
                965                 970                 975

Lys Val Leu Ser Ser Ser Gly Ser Glu Ala Ala Val Pro Ser Val Cys
                980                 985                 990

Phe Leu Val Pro Pro Pro Asn Gln  Glu Ala Gln Glu Ala  Val Thr Arg
                995                 1000                1005

Leu Glu  Ala Gln His Gln Ala  Leu Val Thr Leu Trp  His Gln Leu
    1010                1015                1020

His Val  Asp Met Lys Ser Leu  Leu Ala Trp Gln Ser  Leu Arg Arg
    1025                1030                1035

Asp Val  Gln Leu Ile Arg Ser  Trp Ser Leu Ala Thr  Phe Arg Thr
    1040                1045                1050

Leu Lys  Pro Glu Glu Gln Arg  Gln Ala Leu His Ser  Leu Glu Leu
    1055                1060                1065

His Tyr  Gln Ala Phe Leu Arg  Asp Ser Gln Asp Ala  Gly Gly Phe
    1070                1075                1080

Gly Pro  Glu Asp Arg Leu Met  Ala Glu Arg Glu Tyr  Gly Ser Cys
    1085                1090                1095

Ser His  His Tyr Gln Gln Leu  Leu Gln Ser Leu Glu  Gln Gly Ala
    1100                1105                1110

Gln Glu  Glu Ser Arg Cys Gln  Arg Cys Ile Ser Glu  Leu Lys Asp
    1115                1120                1125

Ile Arg  Leu Gln Leu Glu Ala  Cys Glu Thr Arg Thr  Val His Arg
    1130                1135                1140

Leu Arg  Leu Pro Leu Asp Lys  Glu Pro Ala Arg Glu  Cys Ala Gln
    1145                1150                1155

Arg Ile  Ala Glu Gln Gln Lys  Ala Gln Ala Glu Val  Glu Gly Leu
    1160                1165                1170

Gly Lys  Gly Val Ala Arg Leu  Ser Ala Glu Ala Glu  Lys Val Leu
    1175                1180                1185

Ala Leu  Pro Glu Pro Ser Pro  Ala Ala Pro Thr Leu  Arg Ser Glu
    1190                1195                1200

Leu Glu  Leu Thr Leu Gly Lys  Leu Glu Gln Val Arg  Ser Leu Ser
    1205                1210                1215
```

-continued

```
Ala Ile Tyr Leu Glu Lys Leu Lys Thr Ile Ser Leu Val Ile Arg
1220                1225                1230

Gly Thr Gln Gly Ala Glu Glu Val Leu Arg Ala His Glu Glu Gln
    1235                1240                1245

Leu Lys Glu Ala Gln Ala Val Pro Ala Thr Leu Pro Glu Leu Glu
1250                1255                1260

Ala Thr Lys Ala Ser Leu Lys Lys Leu Arg Ala Gln Ala Glu Ala
1265                1270                1275

Gln Gln Pro Thr Phe Asp Ala Leu Arg Asp Glu Leu Arg Gly Ala
1280                1285                1290

Gln Glu Val Gly Glu Arg Leu Gln Gln Arg His Gly Glu Arg Asp
    1295                1300                1305

Val Glu Val Glu Arg Trp Arg Glu Arg Val Ala Gln Leu Leu Glu
1310                1315                1320

Arg Trp Gln Ala Val Leu Ala Gln Thr Asp Val Arg Gln Arg Glu
1325                1330                1335

Leu Glu Gln Leu Gly Arg Gln Leu Arg Tyr Tyr Arg Glu Ser Ala
1340                1345                1350

Asp Pro Leu Gly Ala Trp Leu Gln Asp Ala Arg Arg Arg Gln Glu
1355                1360                1365

Gln Ile Gln Ala Met Pro Leu Ala Asp Ser Gln Ala Val Arg Glu
1370                1375                1380

Gln Leu Arg Gln Glu Gln Ala Leu Leu Glu Glu Ile Glu Arg His
1385                1390                1395

Gly Glu Lys Val Glu Glu Cys Gln Arg Phe Ala Lys Gln Tyr Ile
    1400                1405                1410

Asn Ala Ile Lys Asp Tyr Glu Leu Gln Leu Val Thr Tyr Lys Ala
1415                1420                1425

Gln Leu Glu Pro Val Ala Ser Pro Ala Lys Lys Pro Lys Val Gln
1430                1435                1440

Ser Gly Ser Glu Ser Val Ile Gln Glu Tyr Val Asp Leu Arg Thr
1445                1450                1455

His Tyr Ser Glu Leu Thr Thr Leu Thr Ser Gln Tyr Ile Lys Phe
1460                1465                1470

Ile Ser Glu Thr Leu Arg Arg Met Glu Glu Glu Arg Leu Ala
1475                1480                1485

Glu Gln Gln Arg Ala Glu Glu Arg Glu Arg Leu Ala Glu Val Glu
1490                1495                1500

Ala Ala Leu Glu Lys Gln Arg Gln Leu Ala Glu Ala His Ala Gln
1505                1510                1515

Ala Lys Ala Gln Ala Glu Arg Glu Ala Lys Glu Leu Gln Gln Arg
1520                1525                1530

Met Gln Glu Glu Val Val Arg Arg Glu Glu Ala Ala Val Asp Ala
1535                1540                1545

Gln Gln Gln Lys Arg Ser Ile Gln Glu Glu Leu Gln Gln Leu Arg
1550                1555                1560

Gln Ser Ser Glu Ala Glu Ile Gln Ala Lys Ala Arg Gln Ala Glu
1565                1570                1575

Ala Ala Glu Arg Ser Arg Leu Arg Ile Glu Glu Glu Ile Arg Val
1580                1585                1590

Val Arg Leu Gln Leu Glu Ala Thr Glu Arg Gln Arg Gly Gly Ala
1595                1600                1605
```

-continued

```
Glu Gly Glu Leu Gln Ala Leu Arg Ala Arg Ala Glu Glu Ala Glu
    1610                1615                1620
Ala Gln Lys Arg Gln Ala Gln Glu Glu Ala Glu Arg Leu Arg Arg
    1625                1630                1635
Gln Val Gln Asp Glu Ser Gln Arg Lys Arg Gln Ala Glu Val Glu
    1640                1645                1650
Leu Ala Ser Arg Val Lys Ala Glu Ala Glu Ala Arg Glu Lys
    1655                1660                1665
Gln Arg Ala Leu Gln Ala Leu Glu Glu Leu Arg Leu Gln Ala Glu
    1670                1675                1680
Glu Ala Glu Arg Arg Leu Arg Gln Ala Glu Val Glu Arg Ala Arg
    1685                1690                1695
Gln Val Gln Val Ala Leu Glu Thr Ala Gln Arg Ser Ala Glu Ala
    1700                1705                1710
Glu Leu Gln Ser Lys Arg Ala Ser Phe Ala Glu Lys Thr Ala Gln
    1715                1720                1725
Leu Glu Arg Ser Leu Gln Glu Glu His Val Ala Val Ala Gln Leu
    1730                1735                1740
Arg Glu Glu Ala Glu Arg Arg Ala Gln Gln Gln Ala Glu Ala Glu
    1745                1750                1755
Arg Ala Arg Glu Glu Ala Glu Arg Glu Leu Glu Arg Trp Gln Leu
    1760                1765                1770
Lys Ala Asn Glu Ala Leu Arg Leu Arg Leu Gln Ala Glu Glu Val
    1775                1780                1785
Ala Gln Gln Lys Ser Leu Ala Gln Ala Glu Ala Glu Lys Gln Lys
    1790                1795                1800
Glu Glu Ala Glu Arg Glu Ala Arg Arg Arg Gly Lys Ala Glu Glu
    1805                1810                1815
Gln Ala Val Arg Gln Arg Glu Leu Ala Glu Gln Glu Leu Glu Lys
    1820                1825                1830
Gln Arg Gln Leu Ala Glu Gly Thr Ala Gln Gln Arg Leu Ala Ala
    1835                1840                1845
Glu Gln Glu Leu Ile Arg Leu Arg Ala Glu Thr Glu Gln Gly Glu
    1850                1855                1860
Gln Gln Arg Gln Leu Leu Glu Glu Leu Ala Arg Leu Gln Arg
    1865                1870                1875
Glu Ala Ala Ala Thr Gln Lys Arg Gln Glu Leu Glu Ala Glu
    1880                1885                1890
Leu Ala Lys Val Arg Ala Glu Met Glu Val Leu Leu Ala Ser Lys
    1895                1900                1905
Ala Arg Ala Glu Glu Glu Ser Arg Ser Thr Ser Glu Lys Ser Lys
    1910                1915                1920
Gln Arg Leu Glu Ala Glu Ala Gly Arg Phe Arg Glu Leu Ala Glu
    1925                1930                1935
Glu Ala Ala Arg Leu Arg Ala Leu Ala Glu Glu Ala Lys Arg Gln
    1940                1945                1950
Arg Gln Leu Ala Glu Glu Asp Ala Ala Arg Gln Arg Ala Glu Ala
    1955                1960                1965
Glu Arg Val Leu Ala Glu Lys Leu Ala Ala Ile Gly Glu Ala Thr
    1970                1975                1980
Arg Leu Lys Thr Glu Ala Glu Ile Ala Leu Lys Glu Lys Glu Ala
    1985                1990                1995
Glu Asn Glu Arg Leu Arg Arg Leu Ala Glu Asp Glu Ala Phe Gln
```

-continued

```
                2000                2005                2010
Arg Arg Arg Leu Glu Glu Gln Ala Ala Gln His Lys Ala Asp Ile
            2015                2020                2025
Glu Glu Arg Leu Ala Gln Leu Arg Lys Ala Ser Asp Ser Glu Leu
            2030                2035                2040
Glu Arg Gln Lys Gly Leu Val Glu Asp Thr Leu Arg Gln Arg Arg
            2045                2050                2055
Gln Val Glu Glu Glu Ile Leu Ala Leu Lys Ala Ser Phe Glu Lys
            2060                2065                2070
Ala Ala Ala Gly Lys Ala Glu Leu Glu Leu Glu Leu Gly Arg Ile
            2075                2080                2085
Arg Ser Asn Ala Glu Asp Thr Leu Arg Ser Lys Glu Gln Ala Glu
            2090                2095                2100
Leu Glu Ala Ala Arg Gln Arg Gln Leu Ala Ala Glu Glu Glu Arg
            2105                2110                2115
Arg Arg Arg Glu Ala Glu Glu Arg Val Gln Lys Ser Leu Ala Ala
            2120                2125                2130
Glu Glu Glu Ala Ala Arg Gln Arg Lys Ala Ala Leu Glu Glu Val
            2135                2140                2145
Glu Arg Leu Lys Ala Lys Val Glu Glu Ala Arg Arg Leu Arg Glu
            2150                2155                2160
Arg Ala Glu Gln Glu Ser Ala Arg Gln Leu Gln Leu Ala Gln Glu
            2165                2170                2175
Ala Ala Gln Lys Arg Leu Gln Ala Glu Glu Lys Ala His Ala Phe
            2180                2185                2190
Ala Val Gln Gln Lys Glu Gln Glu Leu Gln Gln Thr Leu Gln Gln
            2195                2200                2205
Glu Gln Ser Val Leu Asp Gln Leu Arg Gly Glu Ala Glu Ala Ala
            2210                2215                2220
Arg Arg Ala Ala Glu Glu Ala Glu Glu Ala Arg Val Gln Ala Glu
            2225                2230                2235
Arg Glu Ala Ala Gln Ser Arg Arg Gln Val Glu Glu Ala Glu Arg
            2240                2245                2250
Leu Lys Gln Ser Ala Glu Glu Gln Ala Gln Ala Arg Ala Gln Ala
            2255                2260                2265
Gln Ala Ala Ala Glu Lys Leu Arg Lys Glu Ala Glu Gln Glu Ala
            2270                2275                2280
Ala Arg Arg Ala Gln Ala Glu Gln Ala Ala Leu Arg Gln Lys Gln
            2285                2290                2295
Ala Ala Asp Ala Glu Met Glu Lys His Lys Lys Phe Ala Glu Gln
            2300                2305                2310
Thr Leu Arg Gln Lys Ala Gln Val Glu Gln Glu Leu Thr Thr Leu
            2315                2320                2325
Arg Leu Gln Leu Glu Glu Thr Asp His Gln Lys Asn Leu Leu Asp
            2330                2335                2340
Glu Glu Leu Gln Arg Leu Lys Ala Glu Ala Thr Glu Ala Ala Arg
            2345                2350                2355
Gln Arg Ser Gln Val Glu Glu Glu Leu Phe Ser Val Arg Val Gln
            2360                2365                2370
Met Glu Glu Leu Ser Lys Leu Lys Ala Arg Ile Glu Ala Glu Asn
            2375                2380                2385
Arg Ala Leu Ile Leu Arg Asp Lys Asp Asn Thr Gln Arg Phe Leu
            2390                2395                2400
```

```
Gln Glu Glu Ala Glu Lys Met Lys Gln Val Ala Glu Glu Ala Ala
2405                2410                2415

Arg Leu Ser Val Ala Ala Gln Glu Ala Ala Arg Leu Arg Gln Leu
2420                2425                2430

Ala Glu Glu Asp Leu Ala Gln Gln Arg Ala Leu Ala Glu Lys Met
2435                2440                2445

Leu Lys Glu Lys Met Gln Ala Val Gln Glu Ala Thr Arg Leu Lys
2450                2455                2460

Ala Glu Ala Glu Leu Leu Gln Gln Gln Lys Glu Leu Ala Gln Glu
2465                2470                2475

Gln Ala Arg Arg Leu Gln Glu Asp Lys Glu Gln Met Ala Gln Gln
2480                2485                2490

Leu Ala Glu Glu Thr Gln Gly Phe Gln Arg Thr Leu Glu Ala Glu
2495                2500                2505

Arg Gln Arg Gln Leu Glu Met Ser Ala Glu Ala Glu Arg Leu Lys
2510                2515                2520

Leu Arg Val Ala Glu Met Ser Arg Ala Gln Ala Arg Ala Glu Glu
2525                2530                2535

Asp Ala Gln Arg Phe Arg Lys Gln Ala Glu Glu Ile Gly Glu Lys
2540                2545                2550

Leu His Arg Thr Glu Leu Ala Thr Gln Glu Lys Val Thr Leu Val
2555                2560                2565

Gln Thr Leu Glu Ile Gln Arg Gln Gln Ser Asp His Asp Ala Glu
2570                2575                2580

Arg Leu Arg Glu Ala Ile Ala Glu Leu Glu Arg Glu Lys Glu Lys
2585                2590                2595

Leu Gln Gln Glu Ala Lys Leu Leu Gln Leu Lys Ser Glu Glu Met
2600                2605                2610

Gln Thr Val Gln Gln Glu Gln Leu Leu Gln Glu Thr Gln Ala Leu
2615                2620                2625

Gln Gln Ser Phe Leu Ser Glu Lys Asp Ser Leu Leu Gln Arg Glu
2630                2635                2640

Arg Phe Ile Glu Gln Glu Lys Ala Lys Leu Glu Gln Leu Phe Gln
2645                2650                2655

Asp Glu Val Ala Lys Ala Gln Gln Leu Arg Glu Glu Gln Gln Arg
2660                2665                2670

Gln Gln Gln Gln Met Glu Gln Glu Arg Gln Arg Leu Val Ala Ser
2675                2680                2685

Met Glu Glu Ala Arg Arg Arg Gln His Glu Ala Glu Glu Gly Val
2690                2695                2700

Arg Arg Lys Gln Glu Glu Leu Gln Gln Leu Glu Gln Gln Arg Arg
2705                2710                2715

Gln Gln Glu Glu Leu Leu Ala Glu Glu Asn Gln Arg Leu Arg Glu
2720                2725                2730

Gln Leu Gln Leu Leu Glu Glu Gln His Arg Ala Ala Leu Ala His
2735                2740                2745

Ser Glu Glu Val Thr Ala Ser Gln Val Ala Ala Thr Lys Thr Leu
2750                2755                2760

Pro Asn Gly Arg Asp Ala Leu Asp Gly Pro Ala Ala Glu Ala Glu
2765                2770                2775

Pro Glu His Ser Phe Asp Gly Leu Arg Arg Lys Val Ser Ala Gln
2780                2785                2790
```

-continued

```
Arg Leu Gln Glu Ala Gly Ile Leu Ser Ala Glu Glu Leu Gln Arg
2795                2800                2805

Leu Ala Gln Gly His Thr Thr Val Asp Glu Leu Ala Arg Arg Glu
2810                2815                2820

Asp Val Arg His Tyr Leu Gln Gly Arg Ser Ser Ile Ala Gly Leu
2825                2830                2835

Leu Leu Lys Ala Thr Asn Glu Lys Leu Ser Val Tyr Ala Ala Leu
2840                2845                2850

Gln Arg Gln Leu Leu Ser Pro Gly Thr Ala Leu Ile Leu Leu Glu
2855                2860                2865

Ala Gln Ala Ala Ser Gly Phe Leu Leu Asp Pro Val Arg Asn Arg
2870                2875                2880

Arg Leu Thr Val Asn Glu Ala Val Lys Glu Gly Val Val Gly Pro
2885                2890                2895

Glu Leu His His Lys Leu Leu Ser Ala Glu Arg Ala Val Thr Gly
2900                2905                2910

Tyr Lys Asp Pro Tyr Thr Gly Gln Gln Ile Ser Leu Phe Gln Ala
2915                2920                2925

Met Gln Lys Gly Leu Ile Val Arg Glu His Gly Ile Arg Leu Leu
2930                2935                2940

Glu Ala Gln Ile Ala Thr Gly Gly Val Ile Asp Pro Val His Ser
2945                2950                2955

His Arg Val Pro Val Asp Val Ala Tyr Arg Arg Gly Tyr Phe Asp
2960                2965                2970

Glu Glu Met Asn Arg Val Leu Ala Asp Pro Ser Asp Asp Thr Lys
2975                2980                2985

Gly Phe Phe Asp Pro Asn Thr His Glu Asn Leu Thr Tyr Leu Gln
2990                2995                3000

Leu Leu Glu Arg Cys Val Glu Asp Pro Glu Thr Gly Leu Cys Leu
3005                3010                3015

Leu Pro Leu Thr Asp Lys Ala Ala Lys Gly Gly Glu Leu Val Tyr
3020                3025                3030

Thr Asp Ser Glu Ala Arg Asp Val Phe Glu Lys Ala Thr Val Ser
3035                3040                3045

Ala Pro Phe Gly Lys Phe Gln Gly Lys Thr Val Thr Ile Trp Glu
3050                3055                3060

Ile Ile Asn Ser Glu Tyr Phe Thr Ala Glu Gln Arg Arg Asp Leu
3065                3070                3075

Leu Arg Gln Phe Arg Thr Gly Arg Ile Thr Val Glu Lys Ile Ile
3080                3085                3090

Lys Ile Ile Ile Thr Val Val Glu Glu Gln Glu Gln Lys Gly Arg
3095                3100                3105

Leu Cys Phe Glu Gly Leu Arg Ser Leu Val Pro Ala Ala Glu Leu
3110                3115                3120

Leu Glu Ser Arg Val Ile Asp Arg Glu Leu Tyr Gln Gln Leu Gln
3125                3130                3135

Arg Gly Glu Arg Ser Val Arg Asp Val Ala Glu Val Asp Thr Val
3140                3145                3150

Arg Arg Ala Leu Arg Gly Ala Asn Val Ile Ala Gly Val Trp Leu
3155                3160                3165

Glu Glu Ala Gly Gln Lys Leu Ser Ile Tyr Asn Ala Leu Lys Lys
3170                3175                3180

Asp Leu Leu Pro Ser Asp Met Ala Val Ala Leu Leu Glu Ala Gln
```

-continued

```
            3185              3190              3195

Ala Gly Thr Gly His Ile Ile Asp Pro Ala Thr Ser Ala Arg Leu
    3200              3205              3210

Thr Val Asp Glu Ala Val Arg Ala Gly Leu Val Gly Pro Glu Phe
    3215              3220              3225

His Glu Lys Leu Leu Ser Ala Glu Lys Ala Val Thr Gly Tyr Arg
    3230              3235              3240

Asp Pro Tyr Thr Gly Gln Ser Val Ser Leu Phe Gln Ala Leu Lys
    3245              3250              3255

Lys Gly Leu Ile Pro Arg Glu Gln Gly Leu Arg Leu Leu Asp Ala
    3260              3265              3270

Gln Leu Ser Thr Gly Gly Ile Val Asp Pro Ser Lys Ser His Arg
    3275              3280              3285

Val Pro Leu Asp Val Ala Cys Ala Arg Gly Cys Leu Asp Glu Glu
    3290              3295              3300

Thr Ser Arg Ala Leu Ser Ala Pro Arg Ala Asp Ala Lys Ala Tyr
    3305              3310              3315

Ser Asp Pro Ser Thr Gly Glu Pro Ala Thr Tyr Gly Glu Leu Gln
    3320              3325              3330

Gln Arg Cys Arg Pro Asp Gln Leu Thr Gly Leu Ser Leu Leu Pro
    3335              3340              3345

Leu Ser Glu Lys Ala Ala Arg Ala Arg Gln Glu Glu Leu Tyr Ser
    3350              3355              3360

Glu Leu Gln Ala Arg Glu Thr Phe Glu Lys Thr Pro Val Glu Val
    3365              3370              3375

Pro Val Gly Gly Phe Lys Gly Arg Thr Val Thr Val Trp Glu Leu
    3380              3385              3390

Ile Ser Ser Glu Tyr Phe Thr Ala Glu Gln Arg Gln Glu Leu Leu
    3395              3400              3405

Arg Gln Phe Arg Thr Gly Lys Val Thr Val Glu Lys Val Ile Lys
    3410              3415              3420

Ile Leu Ile Thr Ile Val Glu Glu Val Glu Thr Leu Arg Gln Glu
    3425              3430              3435

Arg Leu Ser Phe Ser Gly Leu Arg Ala Pro Val Pro Ala Ser Glu
    3440              3445              3450

Leu Leu Ala Ser Gly Val Leu Ser Arg Ala Gln Phe Glu Gln Leu
    3455              3460              3465

Lys Asp Gly Lys Thr Thr Val Lys Asp Leu Ser Glu Leu Gly Ser
    3470              3475              3480

Val Arg Thr Leu Leu Gln Gly Ser Gly Cys Leu Ala Gly Ile Tyr
    3485              3490              3495

Leu Glu Asp Thr Lys Glu Lys Val Ser Ile Tyr Glu Ala Met Arg
    3500              3505              3510

Arg Gly Leu Leu Arg Ala Thr Thr Ala Ala Leu Leu Glu Ala
    3515              3520              3525

Gln Ala Ala Thr Gly Phe Leu Val Asp Pro Val Arg Asn Gln Arg
    3530              3535              3540

Leu Tyr Val His Glu Ala Val Lys Ala Gly Val Val Gly Pro Glu
    3545              3550              3555

Leu His Glu Gln Leu Leu Ser Ala Glu Lys Ala Val Thr Gly Tyr
    3560              3565              3570

Arg Asp Pro Tyr Ser Gly Ser Thr Ile Ser Leu Phe Gln Ala Met
    3575              3580              3585
```

-continued

```
Gln Lys Gly Leu Val Leu Arg Gln His Gly Ile Arg Leu Leu Glu
    3590                3595                3600

Ala Gln Ile Ala Thr Gly Gly Ile Ile Asp Pro Val His Ser His
    3605                3610                3615

Arg Val Pro Val Asp Val Ala Tyr Gln Arg Gly Tyr Phe Ser Glu
    3620                3625                3630

Glu Met Asn Arg Val Leu Ala Asp Pro Ser Asp Thr Lys Gly
    3635                3640                3645

Phe Phe Asp Pro Asn Thr His Glu Asn Leu Thr Tyr Arg Gln Leu
    3650                3655                3660

Leu Glu Arg Cys Val Glu Asp Pro Glu Thr Gly Leu Arg Leu Leu
    3665                3670                3675

Pro Leu Lys Gly Ala Glu Lys Ala Glu Val Val Glu Thr Thr Gln
    3680                3685                3690

Val Tyr Thr Glu Glu Thr Arg Arg Ala Phe Glu Glu Thr Gln
    3695                3700                3705

Ile Asp Ile Pro Gly Gly Gly Ser His Gly Gly Ser Thr Met Ser
    3710                3715                3720

Leu Trp Glu Val Met Gln Ser Asp Leu Ile Pro Glu Glu Gln Arg
    3725                3730                3735

Ala Gln Leu Met Ala Asp Phe Gln Ala Gly Arg Val Thr Lys Glu
    3740                3745                3750

Arg Met Ile Ile Ile Ile Glu Ile Ile Glu Lys Thr Glu Ile
    3755                3760                3765

Ile Arg Gln Gln Gly Leu Ala Ser Tyr Asp Tyr Val Arg Arg Arg
    3770                3775                3780

Leu Thr Ala Glu Asp Leu Phe Glu Ala Arg Ile Ile Ser Leu Glu
    3785                3790                3795

Thr Tyr Asn Leu Leu Arg Glu Gly Thr Arg Ser Leu Arg Glu Ala
    3800                3805                3810

Leu Glu Ala Glu Ser Ala Trp Cys Tyr Leu Tyr Gly Thr Gly Ser
    3815                3820                3825

Val Ala Gly Val Tyr Leu Pro Gly Ser Arg Gln Thr Leu Ser Ile
    3830                3835                3840

Tyr Gln Ala Leu Lys Lys Gly Leu Leu Ser Ala Glu Val Ala Arg
    3845                3850                3855

Leu Leu Leu Glu Ala Gln Ala Ala Thr Gly Phe Leu Leu Asp Pro
    3860                3865                3870

Val Lys Gly Glu Arg Leu Thr Val Asp Glu Ala Val Arg Lys Gly
    3875                3880                3885

Leu Val Gly Pro Glu Leu His Asp Arg Leu Leu Ser Ala Glu Arg
    3890                3895                3900

Ala Val Thr Gly Tyr Arg Asp Pro Tyr Thr Glu Gln Thr Ile Ser
    3905                3910                3915

Leu Phe Gln Ala Met Lys Lys Glu Leu Ile Pro Thr Glu Glu Ala
    3920                3925                3930

Leu Arg Leu Leu Asp Ala Gln Leu Ala Thr Gly Gly Ile Val Asp
    3935                3940                3945

Pro Arg Leu Gly Phe His Leu Pro Leu Glu Val Ala Tyr Gln Arg
    3950                3955                3960

Gly Tyr Leu Asn Lys Asp Thr His Asp Gln Leu Ser Glu Pro Ser
    3965                3970                3975
```

| | | | | | | | | | | | |
|---|---|---|---|---|---|---|---|---|---|---|---|
|Glu|Val|Arg|Ser|Tyr|Val|Asp|Pro|Ser|Thr|Asp|Glu|Arg|Leu|Ser|
| |3980| | | |3985| | | |3990| | | | | |

Tyr Thr Gln Leu Leu Arg Arg Cys Arg Arg Asp Asp Gly Thr Gly
    3995            4000            4005

Gln Leu Leu Leu Pro Leu Ser Asp Ala Arg Lys Leu Thr Phe Arg
    4010            4015            4020

Gly Leu Arg Lys Gln Ile Thr Met Glu Glu Leu Val Arg Ser Gln
    4025            4030            4035

Val Met Asp Glu Ala Thr Ala Leu Gln Leu Arg Glu Gly Leu Thr
    4040            4045            4050

Ser Ile Glu Glu Val Thr Lys Asn Leu Gln Lys Phe Leu Glu Gly
    4055            4060            4065

Thr Ser Cys Ile Ala Gly Val Phe Val Asp Ala Thr Lys Glu Arg
    4070            4075            4080

Leu Ser Val Tyr Gln Ala Met Lys Lys Gly Ile Ile Arg Pro Gly
    4085            4090            4095

Thr Ala Phe Glu Leu Leu Glu Ala Gln Ala Ala Thr Gly Tyr Val
    4100            4105            4110

Ile Asp Pro Ile Lys Gly Leu Lys Leu Thr Val Glu Glu Ala Val
    4115            4120            4125

Arg Met Gly Ile Val Gly Pro Glu Phe Lys Asp Lys Leu Leu Ser
    4130            4135            4140

Ala Glu Arg Ala Val Thr Gly Tyr Lys Asp Pro Tyr Ser Gly Lys
    4145            4150            4155

Leu Ile Ser Leu Phe Gln Ala Met Lys Lys Gly Leu Ile Leu Lys
    4160            4165            4170

Asp His Gly Ile Arg Leu Leu Glu Ala Gln Ile Ala Thr Gly Gly
    4175            4180            4185

Ile Ile Asp Pro Glu Glu Ser His Arg Leu Pro Val Glu Val Ala
    4190            4195            4200

Tyr Lys Arg Gly Leu Phe Asp Glu Glu Met Asn Glu Ile Leu Thr
    4205            4210            4215

Asp Pro Ser Asp Asp Thr Lys Gly Phe Phe Asp Pro Asn Thr Glu
    4220            4225            4230

Glu Asn Leu Thr Tyr Leu Gln Leu Met Glu Arg Cys Ile Thr Asp
    4235            4240            4245

Pro Gln Thr Gly Leu Cys Leu Leu Pro Leu Lys Glu Lys Lys Arg
    4250            4255            4260

Glu Arg Lys Thr Ser Ser Lys Ser Ser Val Arg Lys Arg Arg Val
    4265            4270            4275

Val Ile Val Asp Pro Glu Thr Gly Lys Glu Met Ser Val Tyr Glu
    4280            4285            4290

Ala Tyr Arg Lys Gly Leu Ile Asp His Gln Thr Tyr Leu Glu Leu
    4295            4300            4305

Ser Glu Gln Glu Cys Glu Trp Glu Glu Ile Thr Ile Ser Ser Ser
    4310            4315            4320

Asp Gly Val Val Lys Ser Met Ile Ile Asp Arg Arg Ser Gly Arg
    4325            4330            4335

Gln Tyr Asp Ile Asp Asp Ala Ile Ala Lys Asn Leu Ile Asp Arg
    4340            4345            4350

Ser Ala Leu Asp Gln Tyr Arg Ala Gly Thr Leu Ser Ile Thr Glu
    4355            4360            4365

Phe Ala Asp Met Leu Ser Gly Asn Ala Gly Gly Phe Arg Ser Arg

```
            4370                4375                4380
Ser  Ser  Ser  Val  Gly  Ser  Ser  Ser  Tyr  Pro  Ile  Ser  Pro  Ala
     4385                4390                4395

Val  Ser  Arg  Thr  Gln  Leu  Ala  Ser  Trp  Ser  Asp  Pro  Thr  Glu  Glu
     4400                4405                4410

Thr  Gly  Pro  Val  Ala  Gly  Ile  Leu  Asp  Thr  Glu  Thr  Leu  Glu  Lys
     4415                4420                4425

Val  Ser  Ile  Thr  Glu  Ala  Met  His  Arg  Asn  Leu  Val  Asp  Asn  Ile
     4430                4435                4440

Thr  Gly  Gln  Arg  Leu  Leu  Glu  Ala  Gln  Ala  Cys  Thr  Gly  Gly  Ile
     4445                4450                4455

Ile  Asp  Pro  Ser  Thr  Gly  Glu  Arg  Phe  Pro  Val  Thr  Asp  Ala  Val
     4460                4465                4470

Asn  Lys  Gly  Leu  Val  Asp  Lys  Ile  Met  Val  Asp  Arg  Ile  Asn  Leu
     4475                4480                4485

Ala  Gln  Lys  Ala  Phe  Cys  Gly  Phe  Glu  Asp  Pro  Arg  Thr  Lys  Thr
     4490                4495                4500

Lys  Met  Ser  Ala  Ala  Gln  Ala  Leu  Lys  Lys  Gly  Trp  Leu  Tyr  Tyr
     4505                4510                4515

Glu  Ala  Gly  Gln  Arg  Phe  Leu  Glu  Val  Gln  Tyr  Leu  Thr  Gly  Gly
     4520                4525                4530

Leu  Ile  Glu  Pro  Asp  Thr  Pro  Gly  Arg  Val  Pro  Leu  Asp  Glu  Ala
     4535                4540                4545

Leu  Gln  Arg  Gly  Thr  Val  Asp  Ala  Arg  Thr  Ala  Gln  Lys  Leu  Arg
     4550                4555                4560

Asp  Val  Gly  Ala  Tyr  Ser  Lys  Tyr  Leu  Thr  Cys  Pro  Lys  Thr  Lys
     4565                4570                4575

Leu  Lys  Ile  Ser  Tyr  Lys  Asp  Ala  Leu  Asp  Arg  Ser  Met  Val  Glu
     4580                4585                4590

Glu  Gly  Thr  Gly  Leu  Arg  Leu  Leu  Glu  Ala  Ala  Ala  Gln  Ser  Thr
     4595                4600                4605

Lys  Gly  Tyr  Tyr  Ser  Pro  Tyr  Ser  Val  Ser  Gly  Ser  Gly  Ser  Thr
     4610                4615                4620

Ala  Gly  Ser  Arg  Thr  Gly  Ser  Arg  Thr  Gly  Ser  Arg  Ala  Gly  Ser
     4625                4630                4635

Arg  Arg  Gly  Ser  Phe  Asp  Ala  Thr  Gly  Ser  Gly  Phe  Ser  Met  Thr
     4640                4645                4650

Phe  Ser  Ser  Ser  Ser  Tyr  Ser  Ser  Ser  Gly  Tyr  Gly  Arg  Arg  Tyr
     4655                4660                4665

Ala  Ser  Gly  Ser  Ser  Ala  Ser  Leu  Gly  Gly  Pro  Glu  Ser  Ala  Val
     4670                4675                4680

Ala
```

<210> SEQ ID NO 110
<211> LENGTH: 627
<212> TYPE: PRT
<213> ORGANISM: Homo sapiens

<400> SEQUENCE: 110

```
Met  Ala  Arg  Gly  Ser  Val  Ser  Asp  Glu  Glu  Met  Met  Glu  Leu  Arg  Glu
 1                 5                  10                 15

Ala  Phe  Ala  Lys  Val  Asp  Thr  Asp  Gly  Asn  Gly  Tyr  Ile  Ser  Phe  Asn
              20                  25                  30

Glu  Leu  Asn  Asp  Leu  Phe  Lys  Ala  Ala  Cys  Leu  Pro  Leu  Pro  Gly  Tyr
```

-continued

```
                35                  40                  45
Arg Val Arg Glu Ile Thr Glu Asn Leu Met Ala Thr Gly Asp Leu Asp
 50                  55                  60
Gln Asp Gly Arg Ile Ser Phe Asp Glu Phe Ile Lys Ile Phe His Gly
65                  70                  75                  80
Leu Lys Ser Thr Asp Val Ala Lys Thr Phe Arg Lys Ala Ile Asn Lys
                85                  90                  95
Lys Glu Gly Ile Cys Ala Ile Gly Gly Thr Ser Glu Gln Ser Ser Val
                100                 105                 110
Gly Thr Gln His Ser Tyr Ser Glu Glu Glu Lys Tyr Ala Phe Val Asn
                115                 120                 125
Trp Ile Asn Lys Ala Leu Glu Asn Asp Pro Asp Cys Arg His Val Ile
                130                 135                 140
Pro Met Asn Pro Asn Thr Asn Asp Leu Phe Asn Ala Val Gly Asp Gly
145                 150                 155                 160
Ile Val Leu Cys Lys Met Ile Asn Leu Ser Val Pro Asp Thr Ile Asp
                165                 170                 175
Glu Arg Thr Ile Asn Lys Lys Lys Leu Thr Pro Phe Thr Ile Gln Glu
                180                 185                 190
Asn Leu Asn Leu Ala Leu Asn Ser Ala Ser Ala Ile Gly Cys His Val
                195                 200                 205
Val Asn Ile Gly Ala Glu Asp Leu Lys Glu Gly Lys Pro Tyr Leu Val
                210                 215                 220
Leu Gly Leu Leu Trp Gln Val Ile Lys Ile Gly Leu Phe Ala Asp Ile
225                 230                 235                 240
Glu Leu Ser Arg Asn Glu Ala Leu Ile Ala Leu Leu Arg Glu Gly Glu
                245                 250                 255
Ser Leu Glu Asp Leu Met Lys Leu Ser Pro Glu Glu Leu Leu Leu Arg
                260                 265                 270
Trp Ala Asn Tyr His Leu Glu Asn Ala Gly Cys Asn Lys Ile Gly Asn
                275                 280                 285
Phe Ser Thr Asp Ile Lys Asp Ser Lys Ala Tyr Tyr His Leu Leu Glu
                290                 295                 300
Gln Val Ala Pro Lys Gly Asp Glu Glu Gly Val Pro Ala Val Val Ile
305                 310                 315                 320
Asp Met Ser Gly Leu Arg Glu Lys Asp Asp Ile Gln Arg Ala Glu Cys
                325                 330                 335
Met Leu Gln Gln Ala Glu Arg Leu Gly Cys Arg Gln Phe Val Thr Ala
                340                 345                 350
Thr Asp Val Val Arg Gly Asn Pro Lys Leu Asn Leu Ala Phe Ile Ala
                355                 360                 365
Asn Leu Phe Asn Arg Tyr Pro Ala Leu His Lys Pro Glu Asn Gln Asp
                370                 375                 380
Ile Asp Trp Gly Ala Leu Glu Gly Glu Thr Arg Glu Glu Arg Thr Phe
385                 390                 395                 400
Arg Asn Trp Met Asn Ser Leu Gly Val Asn Pro Arg Val Asn His Leu
                405                 410                 415
Tyr Ser Asp Leu Ser Asp Ala Leu Val Ile Phe Gln Leu Tyr Glu Lys
                420                 425                 430
Ile Lys Val Pro Val Asp Trp Asn Arg Val Asn Lys Pro Pro Tyr Pro
                435                 440                 445
Lys Leu Gly Gly Asn Met Lys Lys Leu Glu Asn Cys Asn Tyr Ala Val
                450                 455                 460
```

```
Glu Leu Gly Lys Asn Gln Ala Lys Phe Ser Leu Val Gly Ile Gly Gly
465                 470                 475                 480

Gln Asp Leu Asn Glu Gly Asn Arg Thr Leu Thr Ala Leu Ile Trp
                485                 490                 495

Gln Leu Met Arg Arg Tyr Thr Leu Asn Ile Leu Glu Glu Ile Gly Gly
                500                 505                 510

Gly Gln Lys Val Asn Asp Asp Ile Ile Val Asn Trp Val Asn Glu Thr
            515                 520                 525

Leu Arg Glu Ala Lys Lys Ser Ser Ile Ser Ser Phe Lys Asp Pro
530                 535                 540

Lys Ile Ser Thr Ser Leu Pro Val Leu Asp Leu Ile Asp Ala Ile Gln
545                 550                 555                 560

Pro Gly Ser Ile Asn Tyr Asp Leu Leu Lys Thr Glu Asn Leu Asn Asp
                565                 570                 575

Asp Glu Lys Leu Asn Asn Ala Lys Tyr Ala Ile Ser Met Ala Arg Lys
                580                 585                 590

Ile Gly Ala Arg Val Tyr Ala Leu Pro Glu Asp Leu Val Glu Val Asn
                595                 600                 605

Pro Lys Met Val Met Thr Val Phe Ala Cys Leu Met Gly Lys Gly Met
    610                 615                 620

Lys Arg Val
625

<210> SEQ ID NO 111
<211> LENGTH: 541
<212> TYPE: PRT
<213> ORGANISM: Homo sapiens

<400> SEQUENCE: 111

Met Ala Ser Met Gly Thr Leu Ala Phe Asp Glu Tyr Gly Arg Pro Phe
1               5                   10                  15

Leu Ile Ile Lys Asp Gln Asp Arg Lys Ser Arg Leu Met Gly Leu Glu
                20                  25                  30

Ala Leu Lys Ser His Ile Met Ala Ala Lys Ala Val Ala Asn Thr Met
                35                  40                  45

Arg Thr Ser Leu Gly Pro Asn Gly Leu Asp Lys Met Met Val Asp Lys
            50                  55                  60

Asp Gly Asp Val Thr Val Thr Asn Asp Gly Ala Thr Ile Leu Ser Met
65                  70                  75                  80

Met Asp Val Asp His Gln Ile Ala Lys Leu Met Val Glu Leu Ser Lys
                85                  90                  95

Ser Gln Asp Asp Glu Ile Gly Asp Gly Thr Thr Gly Val Val Val Leu
                100                 105                 110

Ala Gly Ala Leu Leu Glu Glu Ala Glu Gln Leu Leu Asp Arg Gly Ile
            115                 120                 125

His Pro Ile Arg Ile Ala Asp Gly Tyr Glu Gln Ala Ala Arg Val Ala
            130                 135                 140

Ile Glu His Leu Asp Lys Ile Ser Asp Ser Val Leu Val Asp Ile Lys
145                 150                 155                 160

Asp Thr Glu Pro Leu Ile Gln Thr Ala Lys Thr Thr Leu Gly Ser Lys
                165                 170                 175

Val Val Asn Ser Cys His Arg Gln Met Ala Glu Ile Ala Val Asn Ala
                180                 185                 190

Val Leu Thr Val Ala Asp Met Glu Arg Arg Asp Val Asp Phe Glu Leu
```

```
            195                 200                 205
Ile Lys Val Glu Gly Lys Val Gly Arg Leu Glu Asp Thr Lys Leu
210                 215                 220

Ile Lys Gly Val Ile Val Asp Lys Asp Phe Ser His Pro Gln Met Pro
225                 230                 235                 240

Lys Lys Val Glu Asp Ala Lys Ile Ala Ile Leu Thr Cys Pro Phe Glu
                245                 250                 255

Pro Pro Lys Pro Lys Thr Lys His Lys Leu Asp Val Thr Ser Val Glu
            260                 265                 270

Asp Tyr Lys Ala Leu Gln Lys Tyr Glu Lys Glu Lys Phe Glu Glu Met
        275                 280                 285

Ile Gln Gln Ile Lys Glu Thr Gly Ala Asn Leu Ala Ile Cys Gln Trp
290                 295                 300

Gly Phe Asp Asp Glu Ala Asn His Leu Leu Leu Gln Asn Asn Leu Pro
305                 310                 315                 320

Ala Val Arg Trp Val Gly Gly Pro Glu Ile Glu Leu Ile Ala Ile Ala
                325                 330                 335

Thr Gly Gly Arg Ile Val Pro Arg Phe Ser Glu Leu Thr Ala Glu Lys
            340                 345                 350

Leu Gly Phe Ala Gly Leu Val Gln Glu Ile Ser Phe Gly Thr Thr Lys
        355                 360                 365

Asp Lys Met Leu Val Ile Glu Gln Cys Lys Asn Ser Arg Ala Val Thr
370                 375                 380

Ile Phe Ile Arg Gly Gly Asn Lys Met Ile Ile Glu Glu Ala Lys Arg
385                 390                 395                 400

Ser Leu His Asp Ala Leu Cys Val Ile Arg Asn Leu Ile Arg Asp Asn
                405                 410                 415

Arg Val Val Tyr Gly Gly Gly Ala Ala Glu Ile Ser Cys Ala Leu Ala
            420                 425                 430

Val Ser Gln Glu Ala Asp Lys Cys Pro Thr Leu Glu Gln Tyr Ala Met
        435                 440                 445

Arg Ala Phe Ala Asp Ala Leu Glu Val Ile Pro Met Ala Leu Ser Glu
450                 455                 460

Asn Ser Gly Met Asn Pro Ile Gln Thr Met Thr Glu Val Arg Ala Arg
465                 470                 475                 480

Gln Val Lys Glu Met Asn Pro Ala Leu Gly Ile Asp Cys Leu His Lys
                485                 490                 495

Gly Thr Asn Asp Met Lys Gln Gln His Val Ile Glu Thr Leu Ile Gly
            500                 505                 510

Lys Lys Gln Gln Ile Ser Leu Ala Thr Gln Met Val Arg Met Ile Leu
        515                 520                 525

Lys Ile Asp Asp Ile Arg Lys Pro Gly Glu Ser Glu Glu
530                 535                 540

<210> SEQ ID NO 112
<211> LENGTH: 623
<212> TYPE: PRT
<213> ORGANISM: Homo sapiens

<400> SEQUENCE: 112

Met Glu Ser Tyr His Lys Pro Asp Gln Gln Lys Leu Gln Ala Leu Lys
1               5                   10                  15

Asp Thr Ala Asn Arg Leu Arg Ile Ser Ser Ile Gln Ala Thr Thr Ala
            20                  25                  30
```

-continued

```
Ala Gly Ser Gly His Pro Thr Ser Cys Cys Ser Ala Ala Glu Ile Met
             35                  40                  45
Ala Val Leu Phe Phe His Thr Met Arg Tyr Lys Ser Gln Asp Pro Arg
 50                  55                  60
Asn Pro His Asn Asp Arg Phe Val Leu Ser Lys Gly His Ala Ala Pro
 65                  70                  75                  80
Ile Leu Tyr Ala Val Trp Ala Glu Ala Gly Phe Leu Ala Glu Ala Glu
             85                  90                  95
Leu Leu Asn Leu Arg Lys Ile Ser Ser Asp Leu Asp Gly His Pro Val
            100                 105                 110
Pro Lys Gln Ala Phe Thr Asp Val Ala Thr Gly Ser Leu Gly Gln Gly
            115                 120                 125
Leu Gly Ala Ala Cys Gly Met Ala Tyr Thr Gly Lys Tyr Phe Asp Lys
130                 135                 140
Ala Ser Tyr Arg Val Tyr Cys Leu Leu Gly Asp Gly Glu Leu Ser Glu
145                 150                 155                 160
Gly Ser Val Trp Glu Ala Met Ala Phe Ala Ser Ile Tyr Lys Leu Asp
                165                 170                 175
Asn Leu Val Ala Ile Leu Asp Ile Asn Arg Leu Gly Gln Ser Asp Pro
            180                 185                 190
Ala Pro Leu Gln His Gln Met Asp Ile Tyr Gln Lys Arg Cys Glu Ala
            195                 200                 205
Phe Gly Trp His Ala Ile Ile Val Asp Gly His Ser Val Glu Glu Leu
            210                 215                 220
Cys Lys Ala Phe Gly Gln Ala Lys His Gln Pro Thr Ala Ile Ile Ala
225                 230                 235                 240
Lys Thr Phe Lys Gly Arg Gly Ile Thr Gly Val Glu Asp Lys Glu Ser
                245                 250                 255
Trp His Gly Lys Pro Leu Pro Lys Asn Met Ala Glu Gln Ile Ile Gln
            260                 265                 270
Glu Ile Tyr Ser Gln Ile Gln Ser Lys Lys Ile Leu Ala Thr Pro
            275                 280                 285
Pro Gln Glu Asp Ala Pro Ser Val Asp Ile Ala Asn Ile Arg Met Pro
            290                 295                 300
Ser Leu Pro Ser Tyr Lys Val Gly Asp Lys Ile Ala Thr Arg Lys Ala
305                 310                 315                 320
Tyr Gly Gln Ala Leu Ala Lys Leu Gly His Ala Ser Asp Arg Ile Ile
                325                 330                 335
Ala Leu Asp Gly Asp Thr Lys Asn Ser Thr Phe Ser Glu Ile Phe Lys
            340                 345                 350
Lys Glu His Pro Asp Arg Phe Ile Glu Cys Tyr Ile Ala Glu Gln Asn
            355                 360                 365
Met Val Ser Ile Ala Val Gly Cys Ala Thr Arg Asn Arg Thr Val Pro
            370                 375                 380
Phe Cys Ser Thr Phe Ala Ala Phe Phe Thr Arg Ala Phe Asp Gln Ile
385                 390                 395                 400
Arg Met Ala Ala Ile Ser Glu Ser Asn Ile Asn Leu Cys Gly Ser His
                405                 410                 415
Cys Gly Val Ser Ile Gly Glu Asp Gly Pro Ser Gln Met Ala Leu Glu
            420                 425                 430
Asp Leu Ala Met Phe Arg Ser Val Pro Thr Ser Thr Val Phe Tyr Pro
            435                 440                 445
Ser Asp Gly Val Ala Thr Glu Lys Ala Val Glu Leu Ala Ala Asn Thr
```

```
              450                 455                 460
    Lys Gly Ile Cys Phe Ile Arg Thr Ser Arg Pro Glu Asn Ala Ile Ile
    465                 470                 475                 480

Tyr Asn Asn Asn Glu Asp Phe Gln Val Gly Gln Ala Lys Val Val Leu
                        485                 490                 495

Lys Ser Lys Asp Asp Gln Val Thr Val Ile Gly Ala Gly Val Thr Leu
                    500                 505                 510

His Glu Ala Leu Ala Ala Glu Leu Leu Lys Lys Glu Lys Ile Asn
                515                 520                 525

Ile Arg Val Leu Asp Pro Phe Thr Ile Lys Pro Leu Asp Arg Lys Leu
            530                 535                 540

Ile Leu Asp Ser Ala Arg Ala Thr Lys Gly Arg Ile Leu Thr Val Glu
    545                 550                 555                 560

Asp His Tyr Tyr Glu Gly Gly Ile Gly Glu Ala Val Ser Ser Ala Val
                        565                 570                 575

Val Gly Glu Pro Gly Ile Thr Val Thr His Leu Ala Val Asn Arg Val
                    580                 585                 590

Pro Arg Ser Gly Lys Pro Ala Glu Leu Leu Lys Met Phe Gly Ile Asp
                595                 600                 605

Arg Asp Ala Ile Ala Gln Ala Val Arg Gly Leu Ile Thr Lys Ala
            610                 615                 620

<210> SEQ ID NO 113
<211> LENGTH: 2541
<212> TYPE: PRT
<213> ORGANISM: Homo sapiens

<400> SEQUENCE: 113

Met Val Ala Leu Ser Leu Lys Ile Ser Ile Gly Asn Val Val Lys Thr
1               5                   10                  15

Met Gln Phe Glu Pro Ser Thr Met Val Tyr Asp Ala Cys Arg Ile Ile
                20                  25                  30

Arg Glu Arg Ile Pro Glu Ala Pro Ala Gly Pro Pro Ser Asp Phe Gly
            35                  40                  45

Leu Phe Leu Ser Asp Asp Pro Lys Lys Gly Ile Trp Leu Glu Ala
        50                  55                  60

Gly Lys Ala Leu Asp Tyr Tyr Met Leu Arg Asn Gly Asp Thr Met Glu
65                  70                  75                  80

Tyr Arg Lys Lys Gln Arg Pro Leu Lys Ile Arg Met Leu Asp Gly Thr
                85                  90                  95

Val Lys Thr Ile Met Val Asp Asp Ser Lys Thr Val Thr Asp Met Leu
            100                 105                 110

Met Thr Ile Cys Ala Arg Ile Gly Ile Thr Asn His Asp Glu Tyr Ser
        115                 120                 125

Leu Val Arg Glu Leu Met Glu Glu Lys Lys Glu Glu Ile Thr Gly Thr
    130                 135                 140

Leu Arg Lys Asp Lys Thr Leu Leu Arg Asp Glu Lys Lys Met Glu Lys
145                 150                 155                 160

Leu Lys Gln Lys Leu His Thr Asp Asp Glu Leu Asn Trp Leu Asp His
                165                 170                 175

Gly Arg Thr Leu Arg Glu Gln Gly Val Glu Glu His Glu Thr Leu Leu
            180                 185                 190

Leu Arg Arg Lys Phe Phe Tyr Ser Asp Gln Asn Val Asp Ser Arg Asp
        195                 200                 205
```

-continued

```
Pro Val Gln Leu Asn Leu Leu Tyr Val Gln Ala Arg Asp Asp Ile Leu
    210                 215                 220
Asn Gly Ser His Pro Val Ser Phe Asp Lys Ala Cys Glu Phe Ala Gly
225                 230                 235                 240
Phe Gln Cys Gln Ile Gln Phe Gly Pro His Asn Glu Gln Lys His Lys
                245                 250                 255
Ala Gly Phe Leu Asp Leu Lys Asp Phe Leu Pro Lys Glu Tyr Val Lys
                260                 265                 270
Gln Lys Gly Glu Arg Lys Ile Phe Gln Ala His Lys Asn Cys Gly Gln
            275                 280                 285
Met Ser Glu Ile Glu Ala Lys Val Arg Tyr Val Lys Leu Ala Arg Ser
    290                 295                 300
Leu Lys Thr Tyr Gly Val Ser Phe Phe Leu Val Lys Glu Lys Met Lys
305                 310                 315                 320
Gly Lys Asn Lys Leu Val Pro Arg Leu Leu Gly Ile Thr Lys Glu Cys
                325                 330                 335
Val Met Arg Val Asp Glu Lys Thr Lys Glu Val Ile Gln Glu Trp Asn
                340                 345                 350
Leu Thr Asn Ile Lys Arg Trp Ala Ala Ser Pro Lys Ser Phe Thr Leu
            355                 360                 365
Asp Phe Gly Asp Tyr Gln Asp Gly Tyr Tyr Ser Val Gln Thr Thr Glu
    370                 375                 380
Gly Glu Gln Ile Ala Gln Leu Ile Ala Gly Tyr Ile Asp Ile Ile Leu
385                 390                 395                 400
Lys Lys Lys Lys Ser Lys Asp His Phe Gly Leu Glu Gly Asp Glu Glu
                405                 410                 415
Ser Thr Met Leu Glu Asp Ser Val Ser Pro Lys Lys Ser Thr Val Leu
                420                 425                 430
Gln Gln Gln Tyr Asn Arg Val Gly Lys Val Glu His Gly Ser Val Ala
            435                 440                 445
Leu Pro Ala Ile Met Arg Ser Gly Ala Ser Gly Pro Glu Asn Phe Gln
    450                 455                 460
Val Gly Ser Met Pro Pro Ala Gln Gln Gln Ile Thr Ser Gly Gln Met
465                 470                 475                 480
His Arg Gly His Met Pro Pro Leu Thr Ser Ala Gln Gln Ala Leu Thr
                485                 490                 495
Gly Thr Ile Asn Ser Ser Met Gln Ala Val Gln Ala Ala Gln Ala Thr
                500                 505                 510
Leu Asp Asp Phe Asp Thr Leu Pro Pro Leu Gly Gln Asp Ala Ala Ser
            515                 520                 525
Lys Ala Trp Arg Lys Asn Lys Met Asp Glu Ser Lys His Glu Ile His
    530                 535                 540
Ser Gln Val Asp Ala Ile Thr Ala Gly Thr Ala Ser Val Val Asn Leu
545                 550                 555                 560
Thr Ala Gly Asp Pro Ala Glu Thr Asp Tyr Thr Ala Val Gly Cys Ala
                565                 570                 575
Val Thr Thr Ile Ser Ser Asn Leu Thr Glu Met Ser Arg Gly Val Lys
                580                 585                 590
Leu Leu Ala Ala Leu Leu Glu Asp Glu Gly Gly Ser Gly Arg Pro Leu
            595                 600                 605
Leu Gln Ala Ala Lys Gly Leu Ala Gly Ala Val Ser Glu Leu Leu Arg
    610                 615                 620
Ser Ala Gln Pro Ala Ser Ala Glu Pro Arg Gln Asn Leu Leu Gln Ala
```

-continued

```
            625                 630                 635                 640

Ala Gly Asn Val Gly Gln Ala Ser Gly Glu Leu Leu Gln Gln Ile Gly
                    645                 650                 655

Glu Ser Asp Thr Asp Pro His Phe Gln Asp Ala Leu Met Gln Leu Ala
                    660                 665                 670

Lys Ala Val Ala Ser Ala Ala Ala Leu Val Leu Lys Ala Lys Ser
                    675                 680                 685

Val Ala Gln Arg Thr Glu Asp Ser Gly Leu Gln Thr Gln Val Ile Ala
    690                 695                 700

Ala Ala Thr Gln Cys Ala Leu Ser Thr Ser Gln Leu Val Ala Cys Thr
705                 710                 715                 720

Lys Val Val Ala Pro Thr Ile Ser Ser Pro Val Cys Gln Glu Gln Leu
                    725                 730                 735

Val Glu Ala Gly Arg Leu Val Ala Lys Ala Val Glu Gly Cys Val Ser
                    740                 745                 750

Ala Ser Gln Ala Ala Thr Glu Asp Gly Gln Leu Leu Arg Gly Val Gly
                    755                 760                 765

Ala Ala Ala Thr Ala Val Thr Gln Ala Leu Asn Glu Leu Leu Gln His
        770                 775                 780

Val Lys Ala His Ala Thr Gly Ala Gly Pro Ala Gly Arg Tyr Asp Gln
785                 790                 795                 800

Ala Thr Asp Thr Ile Leu Thr Val Thr Glu Asn Ile Phe Ser Ser Met
                    805                 810                 815

Gly Asp Ala Gly Glu Met Val Arg Gln Ala Arg Ile Leu Ala Gln Ala
                    820                 825                 830

Thr Ser Asp Leu Val Asn Ala Ile Lys Ala Asp Ala Glu Gly Glu Ser
        835                 840                 845

Asp Leu Glu Asn Ser Arg Lys Leu Leu Ser Ala Ala Lys Ile Leu Ala
    850                 855                 860

Asp Ala Thr Ala Lys Met Val Glu Ala Ala Lys Gly Ala Ala Ala His
865                 870                 875                 880

Pro Asp Ser Glu Glu Gln Gln Gln Arg Leu Arg Glu Ala Ala Glu Gly
                    885                 890                 895

Leu Arg Met Ala Thr Asn Ala Ala Gln Asn Ala Ile Lys Lys Lys
                    900                 905                 910

Leu Val Gln Arg Leu Glu His Ala Ala Lys Gln Ala Ala Ser Ala
            915                 920                 925

Thr Gln Thr Ile Ala Ala Gln His Ala Ala Ser Thr Pro Lys Ala
    930                 935                 940

Ser Ala Gly Pro Gln Pro Leu Leu Val Gln Ser Cys Lys Ala Val Ala
945                 950                 955                 960

Glu Gln Ile Pro Leu Leu Val Gln Gly Val Arg Gly Ser Gln Ala Gln
                    965                 970                 975

Pro Asp Ser Pro Ser Ala Gln Leu Ala Leu Ile Ala Ala Ser Gln Ser
                    980                 985                 990

Phe Leu Gln Pro Gly Gly Lys Met  Val Ala Ala Lys  Ala Ser Val
            995                 1000                1005

Pro Thr  Ile Gln Asp Gln Ala  Ser Ala Met Gln Leu  Ser Gln Cys
    1010                1015                1020

Ala Lys  Asn Leu Gly Thr Ala  Leu Ala Glu Leu Arg  Thr Ala Ala
        1025                1030                1035

Gln Lys  Ala Gln Glu Ala Cys  Gly Pro Leu Glu Met  Asp Ser Ala
        1040                1045                1050
```

```
Leu Ser Val Val Gln Asn Leu Glu Lys Asp Leu Gln Glu Val Lys
    1055            1060                1065

Ala Ala Ala Arg Asp Gly Lys Leu Lys Pro Leu Pro Gly Glu Thr
    1070            1075                1080

Met Glu Lys Cys Thr Gln Asp Leu Gly Asn Ser Thr Lys Ala Val
    1085            1090                1095

Ser Ser Ala Ile Ala Gln Leu Leu Gly Glu Val Ala Gln Gly Asn
    1100            1105                1110

Glu Asn Tyr Ala Gly Ile Ala Ala Arg Asp Val Ala Gly Gly Leu
    1115            1120                1125

Arg Ser Leu Ala Gln Ala Ala Arg Gly Val Ala Ala Leu Thr Ser
    1130            1135                1140

Asp Pro Ala Val Gln Ala Ile Val Leu Asp Thr Ala Ser Asp Val
    1145            1150                1155

Leu Asp Lys Ala Ser Ser Leu Ile Glu Glu Ala Lys Lys Ala Ala
    1160            1165                1170

Gly His Pro Gly Asp Pro Glu Ser Gln Gln Arg Leu Ala Gln Val
    1175            1180                1185

Ala Lys Ala Val Thr Gln Ala Leu Asn Arg Cys Val Ser Cys Leu
    1190            1195                1200

Pro Gly Gln Arg Asp Val Asp Asn Ala Leu Arg Ala Val Gly Asp
    1205            1210                1215

Ala Ser Lys Arg Leu Leu Ser Asp Ser Leu Pro Pro Ser Thr Gly
    1220            1225                1230

Thr Phe Gln Glu Ala Gln Ser Arg Leu Asn Glu Ala Ala Ala Gly
    1235            1240                1245

Leu Asn Gln Ala Ala Thr Glu Leu Val Gln Ala Ser Arg Gly Thr
    1250            1255                1260

Pro Gln Asp Leu Ala Arg Ala Ser Gly Arg Phe Gly Gln Asp Phe
    1265            1270                1275

Ser Thr Phe Leu Glu Ala Gly Val Glu Met Ala Gly Gln Ala Pro
    1280            1285                1290

Ser Gln Glu Asp Arg Ala Gln Val Val Ser Asn Leu Lys Gly Ile
    1295            1300                1305

Ser Met Ser Ser Ser Lys Leu Leu Leu Ala Ala Lys Ala Leu Ser
    1310            1315                1320

Thr Asp Pro Ala Ala Pro Asn Leu Lys Ser Gln Leu Ala Ala Ala
    1325            1330                1335

Ala Arg Ala Val Thr Asp Ser Ile Asn Gln Leu Ile Thr Met Cys
    1340            1345                1350

Thr Gln Gln Ala Pro Gly Gln Lys Glu Cys Asp Asn Ala Leu Arg
    1355            1360                1365

Glu Leu Glu Thr Val Arg Glu Leu Leu Glu Asn Pro Val Gln Pro
    1370            1375                1380

Ile Asn Asp Met Ser Tyr Phe Gly Cys Leu Asp Ser Val Met Glu
    1385            1390                1395

Asn Ser Lys Val Leu Gly Glu Ala Met Thr Gly Ile Ser Gln Asn
    1400            1405                1410

Ala Lys Asn Gly Asn Leu Pro Glu Phe Gly Asp Ala Ile Ser Thr
    1415            1420                1425

Ala Ser Lys Ala Leu Cys Gly Phe Thr Glu Ala Ala Ala Gln Ala
    1430            1435                1440
```

```
Ala Tyr Leu Val Gly Val Ser Asp Pro Asn Ser Gln Ala Gly Gln
1445                1450                1455

Gln Gly Leu Val Glu Pro Thr Gln Phe Ala Arg Ala Asn Gln Ala
1460                1465                1470

Ile Gln Met Ala Cys Gln Ser Leu Gly Glu Pro Gly Cys Thr Gln
1475                1480                1485

Ala Gln Val Leu Ser Ala Ala Thr Ile Val Ala Lys His Thr Ser
1490                1495                1500

Ala Leu Cys Asn Ser Cys Arg Leu Ala Ser Ala Arg Thr Thr Asn
1505                1510                1515

Pro Thr Ala Lys Arg Gln Phe Val Gln Ser Ala Lys Glu Val Ala
1520                1525                1530

Asn Ser Thr Ala Asn Leu Val Lys Thr Ile Lys Ala Leu Asp Gly
1535                1540                1545

Ala Phe Thr Glu Glu Asn Arg Ala Gln Cys Arg Ala Ala Thr Ala
1550                1555                1560

Pro Leu Leu Glu Ala Val Asp Asn Leu Ser Ala Phe Ala Ser Asn
1565                1570                1575

Pro Glu Phe Ser Ser Ile Pro Ala Gln Ile Ser Pro Glu Gly Arg
1580                1585                1590

Ala Ala Met Glu Pro Ile Val Ile Ser Ala Lys Thr Met Leu Glu
1595                1600                1605

Ser Ala Gly Gly Leu Ile Gln Thr Ala Arg Ala Leu Ala Val Asn
1610                1615                1620

Pro Arg Asp Pro Pro Ser Trp Ser Val Leu Ala Gly His Ser Arg
1625                1630                1635

Thr Val Ser Asp Ser Ile Lys Lys Leu Ile Thr Ser Met Arg Asp
1640                1645                1650

Lys Ala Pro Gly Gln Leu Glu Cys Glu Thr Ala Ile Ala Ala Leu
1655                1660                1665

Asn Ser Cys Leu Arg Asp Leu Asp Gln Ala Ser Leu Ala Ala Val
1670                1675                1680

Ser Gln Gln Leu Ala Pro Arg Glu Gly Ile Ser Gln Glu Ala Leu
1685                1690                1695

His Thr Gln Met Leu Thr Ala Val Gln Glu Ile Ser His Leu Ile
1700                1705                1710

Glu Pro Leu Ala Asn Ala Ala Arg Ala Glu Ala Ser Gln Leu Gly
1715                1720                1725

His Lys Val Ser Gln Met Ala Gln Tyr Phe Glu Pro Leu Thr Leu
1730                1735                1740

Ala Ala Val Gly Ala Ala Ser Lys Thr Leu Ser His Pro Gln Gln
1745                1750                1755

Met Ala Leu Leu Asp Gln Thr Lys Thr Leu Ala Glu Ser Ala Leu
1760                1765                1770

Gln Leu Leu Tyr Thr Ala Lys Glu Ala Gly Gly Asn Pro Lys Gln
1775                1780                1785

Ala Ala His Thr Gln Glu Ala Leu Glu Glu Ala Val Gln Met Met
1790                1795                1800

Thr Glu Ala Val Glu Asp Leu Thr Thr Thr Leu Asn Glu Ala Ala
1805                1810                1815

Ser Ala Ala Gly Val Val Gly Gly Met Val Asp Ser Ile Thr Gln
1820                1825                1830

Ala Ile Asn Gln Leu Asp Glu Gly Pro Met Gly Glu Pro Glu Gly
```

-continued

```
            1835                1840                1845
Ser Phe Val Asp Tyr Gln Thr Thr Met Val Arg Thr Ala Lys Ala
    1850                1855                1860
Ile Ala Val Thr Val Gln Glu Met Val Thr Lys Ser Asn Thr Ser
    1865                1870                1875
Pro Glu Glu Leu Gly Pro Leu Ala Asn Gln Leu Thr Ser Asp Tyr
    1880                1885                1890
Gly Arg Leu Ala Ser Glu Ala Lys Pro Ala Ala Val Ala Ala Glu
    1895                1900                1905
Asn Glu Glu Ile Gly Ser His Ile Lys His Arg Val Gln Glu Leu
    1910                1915                1920
Gly His Gly Cys Ala Ala Leu Val Thr Lys Ala Gly Ala Leu Gln
    1925                1930                1935
Cys Ser Pro Ser Asp Ala Tyr Thr Lys Lys Glu Leu Ile Glu Cys
    1940                1945                1950
Ala Arg Arg Val Ser Glu Lys Val Ser His Val Leu Ala Ala Leu
    1955                1960                1965
Gln Ala Gly Asn Arg Gly Thr Gln Ala Cys Ile Thr Ala Ala Ser
    1970                1975                1980
Ala Val Ser Gly Ile Ile Ala Asp Leu Asp Thr Thr Ile Met Phe
    1985                1990                1995
Ala Thr Ala Gly Thr Leu Asn Arg Glu Gly Thr Glu Thr Phe Ala
    2000                2005                2010
Asp His Arg Glu Gly Ile Leu Lys Thr Ala Lys Val Leu Val Glu
    2015                2020                2025
Asp Thr Lys Val Leu Val Gln Asn Ala Ala Gly Ser Gln Glu Lys
    2030                2035                2040
Leu Ala Gln Ala Ala Gln Ser Ser Val Ala Thr Ile Thr Arg Leu
    2045                2050                2055
Ala Asp Val Val Lys Leu Gly Ala Ala Ser Leu Gly Ala Glu Asp
    2060                2065                2070
Pro Glu Thr Gln Val Val Leu Ile Asn Ala Val Lys Asp Val Ala
    2075                2080                2085
Lys Ala Leu Gly Asp Leu Ile Ser Ala Thr Lys Ala Ala Ala Gly
    2090                2095                2100
Lys Val Gly Asp Asp Pro Ala Val Trp Gln Leu Lys Asn Ser Ala
    2105                2110                2115
Lys Val Met Val Thr Asn Val Thr Ser Leu Leu Lys Thr Val Lys
    2120                2125                2130
Ala Val Glu Asp Glu Ala Thr Lys Gly Thr Arg Ala Leu Glu Ala
    2135                2140                2145
Thr Thr Glu His Ile Arg Gln Glu Leu Ala Val Phe Cys Ser Pro
    2150                2155                2160
Glu Pro Pro Ala Lys Thr Ser Thr Pro Glu Asp Phe Ile Arg Met
    2165                2170                2175
Thr Lys Gly Ile Thr Met Ala Thr Ala Lys Ala Val Ala Ala Gly
    2180                2185                2190
Asn Ser Cys Arg Gln Glu Asp Val Ile Ala Thr Ala Asn Leu Ser
    2195                2200                2205
Arg Arg Ala Ile Ala Asp Met Leu Arg Ala Cys Lys Glu Ala Ala
    2210                2215                2220
Tyr His Pro Glu Val Ala Pro Asp Val Arg Leu Arg Ala Leu His
    2225                2230                2235
```

Tyr Gly Arg Glu Cys Ala Asn Gly Tyr Leu Glu Leu Leu Asp His
2240                2245                2250

Val Leu Leu Thr Leu Gln Lys Pro Ser Pro Glu Leu Lys Gln Gln
    2255                2260                2265

Leu Thr Gly His Ser Lys Arg Val Ala Gly Ser Val Thr Glu Leu
    2270                2275                2280

Ile Gln Ala Ala Glu Ala Met Lys Gly Thr Glu Trp Val Asp Pro
    2285                2290                2295

Glu Asp Pro Thr Val Ile Ala Glu Asn Glu Leu Leu Gly Ala Ala
    2300                2305                2310

Ala Ala Ile Glu Ala Ala Lys Lys Leu Glu Gln Leu Lys Pro
    2315                2320                2325

Arg Ala Lys Pro Lys Glu Ala Asp Glu Ser Leu Asn Phe Glu Glu
    2330                2335                2340

Gln Ile Leu Glu Ala Ala Lys Ser Ile Ala Ala Ala Thr Ser Ala
    2345                2350                2355

Leu Val Lys Ala Ala Ser Ala Ala Gln Arg Glu Leu Val Ala Gln
    2360                2365                2370

Gly Lys Val Gly Ala Ile Pro Ala Asn Ala Leu Asp Asp Gly Gln
    2375                2380                2385

Trp Ser Gln Gly Leu Ile Ser Ala Ala Arg Met Val Ala Ala Ala
    2390                2395                2400

Thr Asn Asn Leu Cys Glu Ala Ala Asn Ala Ala Val Gln Gly His
    2405                2410                2415

Ala Ser Gln Glu Lys Leu Ile Ser Ser Ala Lys Gln Val Ala Ala
    2420                2425                2430

Ser Thr Ala Gln Leu Leu Val Ala Cys Lys Val Lys Ala Asp Gln
    2435                2440                2445

Asp Ser Glu Ala Met Lys Arg Leu Gln Ala Ala Gly Asn Ala Val
    2450                2455                2460

Lys Arg Ala Ser Asp Asn Leu Val Lys Ala Ala Gln Lys Ala Ala
    2465                2470                2475

Ala Phe Glu Glu Gln Glu Asn Glu Thr Val Val Val Lys Glu Lys
    2480                2485                2490

Met Val Gly Gly Ile Ala Gln Ile Ile Ala Ala Gln Glu Glu Met
    2495                2500                2505

Leu Arg Lys Glu Arg Glu Leu Glu Glu Ala Arg Lys Lys Leu Ala
    2510                2515                2520

Gln Ile Arg Gln Gln Gln Tyr Lys Phe Leu Pro Ser Glu Leu Arg
    2525                2530                2535

Asp Glu His
    2540

<210> SEQ ID NO 114
<211> LENGTH: 482
<212> TYPE: PRT
<213> ORGANISM: Homo sapiens

<400> SEQUENCE: 114

Met Ala Ala Leu Met Thr Pro Gly Thr Gly Ala Pro Ala Pro Gly
1               5                   10                  15

Asp Phe Ser Gly Glu Gly Ser Gln Gly Leu Pro Asp Pro Ser Pro Glu
                20                  25                  30

Pro Lys Gln Leu Pro Glu Leu Ile Arg Met Lys Arg Asp Gly Gly Arg

```
                35                  40                  45
Leu Ser Glu Ala Asp Ile Arg Gly Phe Val Ala Ala Val Val Asn Gly
 50                  55                  60

Ser Ala Gln Gly Ala Gln Ile Gly Ala Met Leu Met Ala Ile Arg Leu
 65                  70                  75                  80

Arg Gly Met Asp Leu Glu Thr Ser Val Leu Thr Gln Ala Leu Ala
                 85                  90                  95

Gln Ser Gly Gln Gln Leu Glu Trp Pro Glu Ala Trp Arg Gln Gln Leu
                100                 105                 110

Val Asp Lys His Ser Thr Gly Val Gly Asp Lys Val Ser Leu Val
                115                 120                 125

Leu Ala Pro Ala Leu Ala Ala Cys Gly Cys Lys Val Pro Met Ile Ser
            130                 135                 140

Gly Arg Gly Leu Gly His Thr Gly Gly Thr Leu Asp Lys Leu Glu Ser
145                 150                 155                 160

Ile Pro Gly Phe Asn Val Ile Gln Ser Pro Glu Gln Met Gln Val Leu
                165                 170                 175

Leu Asp Gln Ala Gly Cys Cys Ile Val Gly Gln Ser Glu Gln Leu Val
                180                 185                 190

Pro Ala Asp Gly Ile Leu Tyr Ala Ala Arg Asp Val Thr Ala Thr Val
                195                 200                 205

Asp Ser Leu Pro Leu Ile Thr Ala Ser Ile Leu Ser Lys Lys Leu Val
210                 215                 220

Glu Gly Leu Ser Ala Leu Val Val Asp Val Lys Phe Gly Gly Ala Ala
225                 230                 235                 240

Val Phe Pro Asn Gln Glu Gln Ala Arg Glu Leu Ala Lys Thr Leu Val
                245                 250                 255

Gly Val Gly Ala Ser Leu Gly Leu Arg Val Ala Ala Leu Thr Ala
                260                 265                 270

Met Asp Lys Pro Leu Gly Arg Cys Val Gly His Ala Leu Glu Val Glu
                275                 280                 285

Glu Ala Leu Leu Cys Met Asp Gly Ala Gly Pro Pro Asp Leu Arg Asp
                290                 295                 300

Leu Val Thr Thr Leu Gly Gly Ala Leu Leu Trp Leu Ser Gly His Ala
305                 310                 315                 320

Gly Thr Gln Ala Gln Gly Ala Ala Arg Val Ala Ala Leu Asp Asp
                325                 330                 335

Gly Ser Ala Leu Gly Arg Phe Glu Arg Met Leu Ala Ala Gln Gly Val
                340                 345                 350

Asp Pro Gly Leu Ala Arg Ala Leu Cys Ser Gly Ser Pro Ala Glu Arg
                355                 360                 365

Arg Gln Leu Leu Pro Arg Ala Arg Glu Gln Glu Leu Leu Ala Pro
                370                 375                 380

Ala Asp Gly Thr Val Glu Leu Val Arg Ala Leu Pro Leu Ala Leu Val
385                 390                 395                 400

Leu His Glu Leu Gly Ala Gly Arg Ser Arg Ala Gly Glu Pro Leu Arg
                405                 410                 415

Leu Gly Val Gly Ala Glu Leu Leu Val Asp Val Gly Gln Arg Leu Arg
                420                 425                 430

Arg Gly Thr Pro Trp Leu Arg Val His Arg Asp Gly Pro Ala Leu Ser
                435                 440                 445

Gly Pro Gln Ser Arg Ala Leu Gln Glu Ala Leu Val Leu Ser Asp Arg
450                 455                 460
```

```
Ala Pro Phe Ala Ala Pro Ser Pro Phe Ala Glu Leu Val Leu Pro Pro
465                 470                 475                 480

Gln Gln
```

<210> SEQ ID NO 115
<211> LENGTH: 617
<212> TYPE: PRT
<213> ORGANISM: Homo sapiens

<400> SEQUENCE: 115

```
Met Asp Phe Ser Lys Leu Pro Lys Ile Leu Asp Glu Asp Lys Glu Ser
1               5                   10                  15

Thr Phe Gly Tyr Val His Gly Val Ser Gly Pro Val Val Thr Ala Cys
                20                  25                  30

Asp Met Ala Gly Ala Ala Met Tyr Glu Leu Val Arg Val Gly His Ser
            35                  40                  45

Glu Leu Val Gly Glu Ile Ile Arg Leu Glu Gly Asp Met Ala Thr Ile
        50                  55                  60

Gln Val Tyr Glu Glu Thr Ser Gly Val Ser Val Gly Asp Pro Val Leu
65                  70                  75                  80

Arg Thr Gly Lys Pro Leu Ser Val Glu Leu Gly Pro Gly Ile Met Gly
                85                  90                  95

Ala Ile Phe Asp Gly Ile Gln Arg Pro Leu Ser Asp Ile Ser Ser Gln
                100                 105                 110

Thr Gln Ser Ile Tyr Ile Pro Arg Gly Val Asn Val Ser Ala Leu Ser
            115                 120                 125

Arg Asp Ile Lys Trp Asp Phe Thr Pro Cys Lys Asn Leu Arg Val Gly
        130                 135                 140

Ser His Ile Thr Gly Gly Asp Ile Tyr Gly Ile Val Ser Glu Asn Ser
145                 150                 155                 160

Leu Ile Lys His Lys Ile Met Leu Pro Pro Arg Asn Arg Gly Thr Val
                165                 170                 175

Thr Tyr Ile Ala Pro Pro Gly Asn Tyr Asp Thr Ser Asp Val Val Leu
                180                 185                 190

Glu Leu Glu Phe Glu Gly Val Lys Glu Lys Phe Thr Met Val Gln Val
            195                 200                 205

Trp Pro Val Arg Gln Val Arg Pro Val Thr Glu Lys Leu Pro Ala Asn
        210                 215                 220

His Pro Leu Leu Thr Gly Gln Arg Val Leu Asp Ala Leu Phe Pro Cys
225                 230                 235                 240

Val Gln Gly Gly Thr Thr Ala Ile Pro Gly Ala Phe Gly Cys Gly Lys
                245                 250                 255

Thr Val Ile Ser Gln Ser Leu Ser Lys Tyr Ser Asn Ser Asp Val Ile
                260                 265                 270

Ile Tyr Val Gly Cys Gly Glu Arg Gly Asn Glu Met Ser Glu Val Leu
            275                 280                 285

Arg Asp Phe Pro Glu Leu Thr Met Glu Val Asp Gly Lys Val Glu Ser
        290                 295                 300

Ile Met Lys Arg Thr Ala Leu Val Ala Asn Thr Ser Asn Met Pro Val
305                 310                 315                 320

Ala Ala Arg Glu Ala Ser Ile Tyr Thr Gly Ile Thr Leu Ser Glu Tyr
                325                 330                 335

Phe Arg Asp Met Gly Tyr His Val Ser Met Met Ala Asp Ser Thr Ser
                340                 345                 350
```

```
Arg Trp Ala Glu Ala Leu Arg Glu Ile Ser Gly Arg Leu Ala Glu Met
        355                 360                 365

Pro Ala Asp Ser Gly Tyr Pro Ala Tyr Leu Gly Ala Arg Leu Ala Ser
        370                 375                 380

Phe Tyr Glu Arg Ala Gly Arg Val Lys Cys Leu Gly Asn Pro Glu Arg
385                 390                 395                 400

Glu Gly Ser Val Ser Ile Val Gly Ala Val Ser Pro Pro Gly Gly Asp
                405                 410                 415

Phe Ser Asp Pro Val Thr Ser Ala Thr Leu Gly Ile Val Gln Val Phe
                420                 425                 430

Trp Gly Leu Asp Lys Lys Leu Ala Gln Arg Lys His Phe Pro Ser Val
            435                 440                 445

Asn Trp Leu Ile Ser Tyr Ser Lys Tyr Met Arg Ala Leu Asp Glu Tyr
        450                 455                 460

Tyr Asp Lys His Phe Thr Glu Phe Val Pro Leu Arg Thr Lys Ala Lys
465                 470                 475                 480

Glu Ile Leu Gln Glu Glu Asp Leu Ala Glu Ile Val Gln Leu Val
                485                 490                 495

Gly Lys Ala Ser Leu Ala Glu Thr Asp Lys Ile Thr Leu Glu Val Ala
                500                 505                 510

Lys Leu Ile Lys Asp Asp Phe Leu Gln Gln Asn Gly Tyr Thr Pro Tyr
            515                 520                 525

Asp Arg Phe Cys Pro Phe Tyr Lys Thr Val Gly Met Leu Ser Asn Met
        530                 535                 540

Ile Ala Phe Tyr Asp Met Ala Arg Arg Ala Val Glu Thr Thr Ala Gln
545                 550                 555                 560

Ser Asp Asn Lys Ile Thr Trp Ser Ile Ile Arg Glu His Met Gly Asp
                565                 570                 575

Ile Leu Tyr Lys Leu Ser Ser Met Lys Phe Lys Asp Pro Leu Lys Asp
                580                 585                 590

Gly Glu Ala Lys Ile Lys Ser Asp Tyr Ala Gln Leu Leu Glu Asp Met
            595                 600                 605

Gln Asn Ala Phe Arg Ser Leu Glu Asp
        610                 615
```

METHODS FOR IDENTIFYING DENDRITIC CELL SUBSETS, FOR DETERMINING IF A PATIENT IS DEVELOPING A REGULATORY OR AN EFFECTOR IMMUNE RESPONSE, AND FOR DETERMINING RESPONSE TO IMMUNOTHERAPY

The present invention concerns methods for determining if a dendritic cell belongs to a tolerogenic dendritic cell subset or to an effector dendritic cell subset, methods for determining if a patient undergoing immunotherapy, and/or who has been administered with a vaccine, is developing an immune response oriented either towards a regulatory T cell response or towards an effector T cell response, and methods of determining response to immunotherapy.

BACKGROUND OF THE INVENTION

Dendritic cells (hereinafter abbreviated as "DCs") are specialized antigen presenting cells that integrate a variety of incoming signals to orchestrate adaptive immune responses.

These cells have peculiar and opposite abilities, and therefore can be distinguished in two major and differently specialized subpopulations: on the one hand the effector proinflammatory DCs (also called proinflammatory DCs) and on the other hand the tolerogenic DCs (also called regulatory or DCreg).

The effector DCs, when activated, are crucial for the presentation of peptides and proteins to T and B lymphocytes and are widely recognized as professional antigen-presenting cells (APC), thanks to their ability to prime naïve T cells.

This subpopulation is involved in responses against infectious pathogens and tumors. Depending on the type of pathogen or antigen encountered and the profile of costimulatory molecules engaged, effector DCs have the capacity to induce different polarizations of T helper lymphocytes, that is to drive the development of Th1, Th2 or Th17 effector CD4+ T cells.

The effector DC subpopulation can be divided into at least three distinct cell subsets regarding the helper T cells they are able to prime: DC1 cell subset which drives the development of Th1 cells (cells producing type 1 cytokines IFN-γ and IL-2), DC2 cell subset which drives the development of Th2 cells (cells producing type 2 cytokines IL-4, IL-5 and IL-13), and DC17 cell subset which drives the development of Th17 cells (cells producing IL-17).

In contrast, tolerogenic DCs mediate the suppression of antigen (Ag)-specific immune responses via the induction of regulatory (also called suppressive) CD4+ T cells, T-cell anergy and clonal deletion of T-cells. Tolerogenic DCs are thus critically involved in promoting and maintaining clinical and/or immunological tolerance, as well as regulating excessive and undesired immune responses. Regulatory T cells exert immuno-suppressive functions which are crucial to contain autoimmunity, chronic inflammation, but also to promote allogenic stem cell engraftment and to mediate tolerance to solid tissue allografts (see the review article by Gregori. S, Tissue Antigens, 77: 89-99, 2011). Further, regulatory/tolerogenic DCs have been shown to suppress inflammatory response to inhaled allergens (Swiecki and Colonna, Eur. J. Immunol., 40:2094-2098, 2010; Kuipers, Vaccine, 23(37):4577-4588, 2005; Lambrecht, Allergy, 60(3): 271-282, 2005).

Therefore, bidirectional interactions between DCs and T cells initiate either effector or tolerogenic responses, which are crucial to establish appropriate defense mechanisms, while precluding uncontrolled inflammation and immune response.

However, since different Th-specific polarization are involved in immune responses against tumors, pathogens, allergens and in autoimmunity or graft rejection, inappropriate T helper lymphocyte polarization can be detrimental. For instance, failure of regulatory T cells function has been implicated in the development of many autoimmune diseases (Roncarolo et al., Nat. Rev. Immunol., 7:585-598, 2007). Further, when DCs initiate a tolerogenic response as opposed to an effector response in case of infectious diseases or tumors, regulatory T cells can contribute to immune escape of pathogens or tumor cells. Conversely, when DCs initiate an effector response rather than a tolerogenic response, autoimmune reactions, chronic inflammation or allergenic responses are observed.

Concerning the desensitization, a broadly accepted paradigm to explain the clinical efficacy of allergen-specific immunotherapy is a modulation of CD4+ T cell functions characterized by a shift from Th2 toward regulatory T cell responses. In this regard, the capacity of DCs to initiate and orient such effector or regulatory T cell responses suggests that those cells may contribute to both allergic inflammation and its resolution. For example, there is a growing body of evidence that DCs play a role in allergic sensitization through their capacity to induce and maintain allergen-specific Th2 responses (Lambrecht, Allergy, 60(3): 271-282, 2005). In contrast, tolerogenic DCs have been detected in the oral mucosa, and as such, appear to be essential in contributing to tolerance induction following sublingual immunotherapy.

Nowadays, there is a great interest in distinguishing these polarized DCs (i.e. effector DC subsets which drive the development of Th1, Th2 or Th17 effector CD4+ T, respectively termed DC1, DC2, DC17, and tolerogenic DC subsets which drive the development of suppressive/regulatory CD4+ T cells, induction of T-cell anergy and clonal deletion of T-cells) to assess the orientation of antigen-specific adaptive immune responses, and to monitor the efficacy of immunotherapy protocols.

DESCRIPTION OF THE INVENTION

The Inventors herein identified novel biomarkers to distinguish DC polarization, these biomarkers could be used to follow immunotherapy/vaccination protocols, in particular allergen-specific immunotherapy.

Specifically, with evidence that monocyte-derived DCs accessible in the blood express functionally relevant markers associated with various differentiation patterns, as showed by Cheong, C. et al. (Cell, 143: 416-429, 2010), the inventors focused on those cells to investigate early orientations of adaptive immune responses.

Hence, the inventors, after having developed in vitro various subsets of effector and tolerogenic human DCs, compared the whole cell proteomes of these different subsets using two complementary quantitative proteomic strategies, i.e. differential gel electrophoresis (DiGE) and label-free mass spectrometry techniques.

The inventors identified various marker proteins for effector dendritic cell subsets (in particular for DC1, DC17), as well as for tolerogenic dendritic cells.

They have also demonstrated that marker proteins are indicative of the type of response to a treatment, in particular that overexpression of C1Q (Complement C1q) and/or STAB1 (Stabilin-1) is associated with tolerogenic DCs and thus indicative of clinical responses induced by allergen-specific immunotherapy. Indeed, the expression of such tolerogenic DC markers was increased in PBMCs from grass pollen allergic patients exhibiting successful clinical responses during sublingual immunotherapy, as opposed to nonresponders or to patients treated with the placebo where the expression globally declined.

In its broadest aspect, the invention relates to the use of any one or more of the marker proteins, or of the mRNA of these proteins, disclosed in Tables 1.A, 1.B, 1.D, 1.E and 2.A to F, for determining if a dendritic cell belongs to a tolerogenic dendritic cell subset or to a effector dendritic cell subset, and for determining if a patient under immunotherapy and/or vaccinated is developing an immune response oriented either towards a regulatory T cell response or towards an effector T cell response. In another embodiment, the marker is used to determine the efficacy of immunotherapeutic treatment/vaccination (i.e. to distinguish between therapy responder and nonresponder patients).

Therefore, a first aspect of the invention provides an in vitro method of determining the dendritic cell subset, the method comprising detection of a marker protein listed in Tables 1.A, 1.B, 1.D, 1.E and 2.A to F, or an mRNA thereof. In a preferred embodiment, the at least one marker protein (or an mRNAs thereof) is preferably selected from the group consisting of:

C1Q (subunit A, B and/or C, respectively SEQ ID Nos; 45, 46, 47), CATC (SEQ ID NO: 48), MRC1 (SEQ ID NO: 50), STAB1 (SEQ ID NO: 51), TPP1 (SEQ ID NO: 5) (biomarkers overexpressed by tolerogenic DCs and underexpressed by effector DCs, recited in Tables 1A and 2A);

TFR1 (also known as CD71) (SEQ ID NO: 72), NMES1 (SEQ ID NO: 68), TRAF1 (SEQ ID NO: 75), FSCN1 (SEQ ID NO: 23), IRF4 (SEQ ID NO: 35), Lamin-A/C (SEQ ID No 32) (biomarkers overexpressed by both effector DCs DC1 and DC17, recited in Tables 1D and/or 2D);

ITAM (also called CD11b) (SEQ ID NO: 15) (biomarker underexpressed by both effector DCs DC1 and DC17, recited in Tables 1B and 2B);

MX1 (SEQ ID NO: 41/42) (biomarker overexpressed by DC1 subset, recited in Tables 1E and 2E);

PGRP1 (bovine sequence recited in SEQ ID NO: 108) (biomarker overexpressed by DC17 subset, recited in Table 2F).

In a second aspect, the in vitro method is for determining if a dendritic cell belongs to a tolerogenic dendritic cell subset or to an effector dendritic cell subset, which method comprises determining the level of expression by the dendritic cell to be tested of at least one marker protein selected from the group consisting of proteins listed in Tables 1.A, 1.B, 1.D, 1.E and 2.A to F, or an mRNA thereof.

In a preferred embodiment, the at least one marker protein (or an mRNAs thereof) is preferably selected from the group consisting of:

C1Q (subunit A, B and/or C, respectively SEQ ID Nos; 45, 46, 47), CATC (SEQ ID NO: 48), MRC1 (SEQ ID NO: 50), STAB1 (SEQ ID NO: 51), TPP1 (SEQ ID NO: 5) (biomarkers overexpressed by tolerogenic DCs and underexpressed by effector DCs, recited in Tables 1A and 2A);

TFR1 (also known as CD71) (SEQ ID NO: 72), NMES1 (SEQ ID NO: 68), TRAF1 (SEQ ID NO: 75), FSCN1 (SEQ ID NO: 23), IRF4 (SEQ ID NO: 35) Lamin-A/C (SEQ ID No 32) (biomarkers overexpressed by both effector DCs DC1 and DC17, recited in Tables 1D and/or 2D);

ITAM (also called CD11b) (SEQ ID NO: 15) (biomarker underexpressed by both effector DCs DC1 and DC17, recited in Tables 1B and 2B);

MX1 (SEQ ID NO: 41/42) (biomarker overexpressed by DC1 subset, recited in Tables 1E and 2E);

PGRP1 (bovine sequence recited in SEQ ID NO: 108) (biomarker overexpressed by DC17 subset, recited in Table 2F).

In another embodiment, the method is for determining if the dendritic cell belongs to the effector dendritic cell "DC1" subset (i.e. effector DCs which drive the development of Th1 CD4+ T cells). In this embodiment, the level of expression of at least one marker protein selected from the group consisting of proteins listed in Tables 1.E and 2.E, more preferably at least MX1 (SEQ ID NO: 41/42), or an mRNA thereof, is determined.

In another preferred embodiment, the method is for determining if the dendritic cell belongs to the effector dendritic cell "DC17" subset (i.e. effector DCs which drive the development of Th17 CD4+ T cells). In this embodiment, the level of expression of at least one marker protein selected from the group consisting of the proteins listed in Tables 2.C and 2.F, more preferably PGRP1 (bovine sequence recited in SEQ ID NO: 108), or an mRNA thereof, is determined.

In another preferred embodiment, the method is for determining if the dendritic cell belongs to a tolerogenic dendritic cell subset, and the level of expression of at least one marker protein selected from the group consisting of the proteins listed in Tables 1.A and 2.A, or an mRNA thereof, is determined. In a more preferred embodiment, the at least one marker protein selected from the group consisting of the proteins listed in Tables 1.A and 2.A, or an mRNA thereof, is selected from the group consisting of C1Q (subunit A, B and/or C, respectively SEQ ID Nos; 45, 46, 47), CATC (SEQ ID NO: 48), MRC1 (SEQ ID NO: 50), STAB1 (SEQ ID NO: 51), TPP1 (SEQ ID NO: 5). Advantageously, the marker proteins are at least C1Q (subunit A, B and/or C) and/or STAB1.

In a further preferred embodiment, the method comprises the steps of:

a) determining the level of expression of at least one marker protein selected from the group consisting of proteins listed in Tables 1 A, 1.B, 1.D, 1.E and 2 A to F, or an mRNA thereof;

b) comparing said level of expression with that of a control standard or a control sample;

c) based on the comparison with the control, identifying to which subset of dendritic cell belongs the dendritic cell to be tested.

When the control sample consists of immature dendritic cells, step c) comprises:

identifying the dendritic cell overexpressing at least one marker protein selected from the group consisting of proteins listed in Tables 1.A and 2.A, or an mRNA thereof, more preferably at least one marker protein selected from the group consisting of C1Q (subunit A, B and/or C, respectively SEQ ID Nos; 45, 46, 47), CATC (SEQ ID NO: 48), MRC1 (SEQ ID NO: 50), STAB1 (SEQ ID NO: 51), TPP1 (SEQ ID NO: 5) advantageously at least C1Q (subunit A, B and/or C) and/or STAB1, or an mRNA thereof, as belonging to a tolerogenic dendritic cell subset;

identifying the dendritic cell:
  underexpressing at least one marker protein selected from the group consisting of proteins listed in Tables 1.A, 1.B, 2.B, 2.C, more preferably at least one marker protein selected from the group consisting of C1Q (subunit A, B and/or C, respectively SEQ ID Nos; 45, 46, 47), CATC (SEQ ID NO: 48), MRC1 (SEQ ID NO: 50), STAB1 (SEQ ID NO: 51), TPP1 (SEQ ID NO: 5) and ITAM (SEQ ID NO: 15), or an mRNA thereof; and/or
  overexpressing at least one marker protein selected from the group consisting of proteins listed in Tables 1.D, 1.E, 2.D, 2.E, 2.F, more preferably at least one marker protein selected from the group consisting of TFR1 (also known as CD71) (SEQ ID NO: 72), NMES1 (SEQ ID NO: 68), TRAF1 (SEQ ID NO: 75), FSCN1 (SEQ ID NO: 23), IRF4 (SEQ ID NO: 35), MX1 (SEQ ID NO: 41/42), Lamin-A/C (SEQ ID No 32), and PGRP1 (bovine sequence recited in SEQ ID NO: 108), or an mRNA thereof;
as belonging to an effector dendritic cell subset.

Further, when the control sample consists of immature dendritic cells which have not been polarized towards tolerogenic or effector subsets, a dendritic cell overexpressing at least one marker protein selected from the group consisting of proteins listed in Tables 1.E and 2.E, more preferably at least MX1 (SEQ ID NO: 41/42), or an mRNA thereof, is identified as belonging to the effector dendritic cell "DC1" subset.

A dendritic cell underexpressing, by comparison with the level of expression of a control sample consisting of immature dendritic cells, at least one marker protein, selected from the group consisting of proteins listed in Table 2.C, and/or overexpressing at least one marker protein, selected from the group consisting of the proteins listed in Table 2.F, more preferably PGRP1 (bovine sequence recited in SEQ ID NO: 108), or an mRNA thereof, is identified as belonging to the effector dendritic cell "DC17" subset.

In a third aspect of the invention, the in vitro method is for determining if a patient is developing an immune response oriented either towards a regulatory T cell response or towards an effector T cell response, which method comprises determining the level of expression of at least one marker protein selected from the group consisting of proteins listed in Tables 1 A, 1.B, 1.D, 1.E and 2 A to F, or an mRNA thereof, in a biological sample from the patient. In a preferred embodiment, the at least one marker protein (or an mRNAs thereof) is preferably selected from the group consisting of:
  C1Q (subunit A, B and/or C, respectively SEQ ID Nos; 45, 46, 47), CATC (SEQ ID NO: 48), MRC1 (SEQ ID NO: 50), STAB1 (SEQ ID NO: 51), TPP1 (SEQ ID NO: 5) (biomarkers overexpressed by tolerogenic DCs and underexpressed by effector DCs, recited in Tables 1A and 2A);
  TFR1 (also known as CD71) (SEQ ID NO: 72), NMES1 (SEQ ID NO: 68), TRAF1 (SEQ ID NO: 75), FSCN1 (SEQ ID NO: 23), IRF4 (SEQ ID NO: 35), Lamin-A/C (SEQ ID No 32) (biomarkers overexpressed by both effector DCs DC1 and DC17, recited in Tables 1D and/or 2D);
  ITAM (also called CD11b) (SEQ ID NO: 15) (biomarker underexpressed by both effector DCs DC1 and DC17, recited in Tables 1B and 2B);
  MX1 (SEQ ID NO: 41/42) (biomarker overexpressed by DC1 subset, recited in Tables 1E and 2E);
  PGRP1 (bovine sequence recited in SEQ ID NO: 108) (biomarker overexpressed by DC17 subset, recited in Table 2F).

In the third aspect of the invention, the patient may be a patient suffering from a disease, for instance an infectious disease, a tumor, an autoimmune disease, an allergy, or a patient who has been grafted. Further, the patient may be treated or not against said disease or against graft rejection.

In a preferred embodiment, the patient is undergoing immunotherapy and/or has been administered with a vaccine.

If the method is carried out on a sample obtained from a non treated patient, it will allow assessing which type of T cell response the patient suffering from a disease is developing.

Preferably, the method comprises the steps of:
  a) determining in a biological sample from the patient the level of expression of at least one marker protein selected from the group consisting of proteins listed in Tables 1 A, 1.B, 1.D, 1.E and 2 A to F, or an mRNA thereof;
  b) comparing said level of expression with a control standard or a control sample;
  c) based on the comparison with the control, indentifying if the patient develops an immune response oriented either towards a regulatory T cell response or towards an effector T cell response, in particular Th1, Th2 or Th17 response.

When the patient is not treated, the control may consist of immature dendritic cells which have not been polarized towards tolerogenic or effector subsets. Alternatively, the control may be a biological sample from a healthy patient of the same nature than that of the biological sample to be tested (e.g. peripheral blood when the biological sample to be tested is peripheral blood, etc).

When the patient is treated, the control may consist of a sample which had been obtained before the beginning of the treatment, said biological sample being of the same nature than that of the biological sample to be tested.

Whatever the type of patients (i.e. treated or not treated), when the above recited controls are used, step c) is as follows:
  identifying that the patient is developing an immune response oriented towards a regulatory T cell response when the level of expression of at least one marker protein selected from the group consisting of proteins listed in Tables 1.A and 2.A, more preferably at least one marker protein is selected from the group consisting of C1Q (subunit A, B and/or C, respectively SEQ ID Nos; 45, 46, 47), CATC (SEQ ID NO: 48), MRC1 (SEQ ID NO: 50), STAB1 (SEQ ID NO: 51), TPP1 (SEQ ID NO: 5); advantageously the marker proteins are at least C1Q (subunit A, B and/or C) and/or STAB1, or an mRNA thereof, is higher than that of the control;
  identifying that the patient is developing an immune response oriented towards an effector T cell response when:
    the level of expression of at least one marker protein selected from the group consisting of proteins listed in Tables 1.A, 1.B, 2.B, 2.C, more preferably at least one marker protein selected from the group consisting of C1Q (subunit A, B and/or C, respectively SEQ ID Nos; 45, 46, 47), CATC (SEQ ID NO: 48), MRC1 (SEQ ID NO: 50), STAB1 (SEQ ID NO: 51), TPP1 (SEQ ID NO: 5), and ITAM (SEQ ID NO: 15), or an mRNA thereof, is lower than the one of the control; and/or
    the level of expression of at least one marker protein selected from the group consisting of proteins listed in Tables 1.D, 1.E, 2.D, 2.E, 2.F, more preferably at least one marker protein selected from the group consisting of TFR1 (also known as CD71) (SEQ ID NO: 72), NMES1 (SEQ ID NO: 68), TRAF1 (SEQ ID NO: 75), FSCN1 (SEQ ID NO: 23), IRF4 (SEQ ID NO: 35), MX1 (SEQ ID NO: 41/42), Lamin-A/C (SEQ ID No 32) and PGRP1 (bovine sequence recited in SEQ ID NO: 108), or an mRNA thereof, is higher than that of the control.

Further, when the patient is identified as developing an immune response oriented towards an effector T cell response, the type of effector response (in particular Th1 and Th17 response) can be easily assessed by determining the level of expression of the marker proteins by the different effector dendritic cell subsets since it is known that DC1 cell subset drives the development of Th1 cells (cells producing type 1 cytokines IFN-γ and IL-2) and DC17 cell subset drives the development of Th17 cells (cells producing IL-17).

If at least one marker protein selected from the group consisting of proteins listed in Tables 1.E and 2.E, more preferably at least MX1 (SEQ ID NO: 41/42), or an mRNA thereof, is overexpressed in the biological sample from the patient, the effector response is a Th1 response.

On the other hand, if at least one marker protein selected from the group consisting of the proteins listed in Table 2.F, more preferably PGRP1 (bovine sequence recited in SEQ ID NO: 108), or an mRNA thereof, is overexpressed in the biological sample from the patient, the effector response is a Th17 response.

In an embodiment, the patient is undergoing immunotherapy and/or has been administered with a vaccine aiming to induce an immune response against an infectious disease or a tumor. In this embodiment, the level of expression of at least one marker protein selected from the group consisting of proteins listed in Tables 1.A, 1.B, 2.B, 2.C and Tables 1.D, 1.E, 2.D, 2.E, 2.F, or an mRNA thereof, is determined, and wherein (i) a level of expression of at least one marker protein selected from the group consisting of proteins listed in Tables 1.D, 1.E, 2.D, 2.E, 2.F, more preferably at least one marker protein selected from the group consisting of TFR1 (also known as CD71) (SEQ ID NO: 72), NMES1 (SEQ ID NO: 68), TRAF1 (SEQ ID NO: 75), FSCN1 (SEQ ID NO: 23), IRF4 (SEQ ID NO: 35), MX1 (SEQ ID NO: 41/42), Lamin-A/C (SEQ ID No 32) and PGRP1 (bovine sequence recited in SEQ ID NO: 108), or an mRNA thereof, which is higher than the level of expression of the control, and/or (ii) a level of expression of at least one marker protein listed in Tables 1.A, 1.B, 2.B, 2.C, more preferably at least one marker protein selected from the group consisting of C1Q (subunit A, B and/or C, respectively SEQ ID Nos; 45, 46, 47), CATC (SEQ ID NO: 48), MRC1 (SEQ ID NO: 50), STAB1 (SEQ ID NO: 51), TPP1 (SEQ ID NO: 5), and ITAM (SEQ ID NO: 15), or an mRNA thereof, which is lower than the level of expression of the control, indicates that the immune response is oriented towards an effector T cell response, and also identifies the patient as likely to be a responder to the immunotherapy and/or vaccine. In this embodiment, the control preferably consists of a sample which had been harvested before the beginning of the treatment, said biological sample being of the same nature than that of the biological sample to be tested.

In another embodiment, the patient is undergoing an immunotherapy and/or has been administered with a vaccine aiming to treat an autoimmune disease or an allergy. In this embodiment, the level of expression of at least one marker protein selected from the group consisting of proteins listed in Tables 1.A and 2.A, or an mRNA thereof, is determined, and wherein a level of expression of at least one of these marker proteins, more preferably at least one marker protein selected from the group consisting of C1Q (subunit A, B and/or C, respectively SEQ ID Nos; 45, 46, 47), CATC (SEQ ID NO: 48), MRC1 (SEQ ID NO: 50), STAB1 (SEQ ID NO: 51), TPP1 (SEQ ID NO: 5), advantageously at least C1Q (subunit A, B and/or C) and/or STAB1, or an mRNA thereof, which is higher than the level of expression of the control indicates that the immune response is oriented towards a regulator T cell response, and also identifies the patient as likely to be a responder to the immunotherapy and/or vaccine. In this embodiment, the control preferably consists of a sample which had been harvested before the beginning of the treatment, said biological sample being of the same nature than that of the biological sample to be tested.

In a particularly preferred embodiment, the patient is undergoing an immunotherapy that aims to treat an allergy, preferably the immunotherapy is a desensitization therapy, the immunotherapy aims to (i) reduce the immune response against the allergen(s) which trigger(s) the allergy and/or (ii) manifestation of clinical symptoms of allergy. A level of expression of at least one of the marker protein selected from the group consisting of proteins listed in Tables 1.A and 2.A, or an mRNA thereof, which is higher than the level of expression of the control (a biological sample harvested before the beginning of the treatment of the same nature than that of the biological sample to be tested) indicates that the immune response is oriented towards a regulatory T cell response, and also identifies the patient as likely to be a responder to the immunotherapy and/or vaccine. Advantageously, the level of expression of at least one of C1Q (subunit A, B and/or C) (SEQ ID Nos: 45, 46 and 47) and STAB-1 (SEQ ID NO: 51), or an mRNA thereof, is determined, and a level of expression of anyone of the subunit A, B and/or C of C1Q, and/or STAB1, or an mRNA thereof, which is higher than the level of expression of the control indicates that the immune response is oriented towards a regulatory T cell response and also identifies the patient as likely to be a responder to the desensitization therapy (i.e. the immune response against the allergen(s) which trigger(s) the allergy and/or (ii) the manifestation of clinical symptoms of allergy are reduced).

The invention further discloses kits that are useful in the above methods.

Accordingly, a fourth aspect of the invention relates to a kit for determining if a dendritic cell belongs to a tolerogenic dendritic cell subset or to an effector dendritic cell subset comprising:

a) means for determining the level of expression of at least one marker protein listed in Tables 1 A, 1.B, 1.D, 1.E and 2 A to F, or an mRNA thereof; and b) optionally, instructions for the use of said kit in determining if a dendritic cell belongs to a tolerogenic dendritic cell subset or to an effector dendritic cell subset.

A fifth aspect of the invention also relates to a kit for determining if a patient is developing an immune response oriented either towards a regulatory T cell response or towards an effector T cell response, which kit comprises:

a) means for determining the level of expression of at least one marker protein listed in Tables 1 A, 1.B, 1.D, 1.E and 2 A to F, or an mRNA thereof; and b) optionally, instructions for the use of said kit in determining if the immune response is oriented towards a regulatory T cell response or towards an effector T cell response.

For the fourth and fifth aspects of the invention, the kit comprises preferably the means for determining the level of expression of at least one, and by order of preference at least 2, 3, 4, 5, 6, 7, 8, 9, 10, 11, 12, 13, 14, 15, 16 or 17, marker protein(s) (or (an) mRNA(s) thereof) selected from the group consisting of:

C1Q (subunit A, B and/or C, respectively SEQ ID Nos; 45, 46, 47), CATC (SEQ ID NO: 48), MRC1 (SEQ ID NO: 50), STAB1 (SEQ ID NO: 51), TPP1 (SEQ ID NO: 5) (biomarkers overexpressed by tolerogenic DCs and underexpressed by effector DCs, recited in Tables 1A and 2A);

TFR1 (also known as CD71) (SEQ ID NO: 72), NMES1 (SEQ ID NO: 68), TRAF1 (SEQ ID NO: 75), FSCN1 (SEQ ID NO: 23), IRF4 (SEQ ID NO: 35), Lamin-A/C (SEQ ID No 32) (biomarkers overexpressed by both effector DCs DC1 and DC17, recited in Tables 1D and/or 2D);

ITAM (also called CD11b) (SEQ ID NO: 15) (biomarker underexpressed by both effector DCs DC1 and DC17, recited in Tables 1B and 2B);

MX1 (SEQ ID NO: 41/42) (biomarker overexpressed by DC1 subset, recited in Tables 1E and 2E);

PGRP1 (bovine sequence recited in SEQ ID NO: 108) (biomarker overexpressed by DC17 subset, recited in Table 2F).

A sixth aspect of the invention concerns a kit for determining if a patient is responding to an immunotherapy which aims to treat an allergy, which kit comprises:

a) means for determining the level of expression of at least one of C1Q (subunit A, B and/or C) (SEQ ID Nos: 45, 46 and 47) and/or STAB1 (SEQ ID NO: 51), or an mRNA thereof; and b) optionally, instructions for the use of said kit in determining if the patient is responding to the immunotherapy.

Advantageously, the kit further comprises means for determining the level of expression of at least one other protein listed in Tables 1.A, and 2.A, or an mRNA thereof.

Optionally, the kits of the fourth, fifth and sixth aspects of the invention may further comprise means for measuring the expression level of some housekeeping genes.

In a preferred embodiment, the kits according to the invention comprises, in addition to the means for determining the level of expression of at least the recited marker protein(s), or for determining the expression of an mRNA thereof, a control sample comprising a known amount of the marker protein(s) to be measured.

The kits according to the fourth aspect of the invention may further comprise:

i. a standard control curve showing a relationship between concentration of the marker proteins in a sample and the probable subset to which the dendritic cell to be tested belongs (i.e. tolerogenic dendritic cell subset or effector dendritic cell subset); outcome (short life-expectancy, metastases development, relapse . . . );

ii. a control sample indicative of the expression level of the marker protein(s) to be measured in an immature dendritic cell.

The kits according to the fifth aspect of the invention may further comprise:

i. a standard control curve showing a relationship between concentration of the marker proteins in a biological sample and the probable development of a T cell response oriented towards a regulatory T cell response or towards an effector T cell response;

ii. a control sample indicative of the expression level of the marker protein(s) to be measured in a biological sample of the same nature from an healthy patient.

The kits according to the sixth aspect of the invention may further comprise:

i. a standard control curve showing a relationship between concentration of the marker protein(s) C1Q and/or STAB1 in a biological sample and the probable outcome of the allergy (responder or non-responder patient);

ii. a control sample indicative of the expression level of the marker protein(s) to be measured in a biological sample of the same nature from a responder patient, and/or a control sample indicative of the expression level of the marker protein(s) to be measured in a biological sample of the same nature from a non-responder patient.

Means for determining the expression level of the marker proteins, or the mRNA thereof, which are listed in Tables 1.A, 1.B, 1.D, 1.E and 2.A to F are well-known in the art. They include, e.g. reagents allowing the detection of mRNA by real-time quantitative-PCR, such as primers specific for the marker proteins to be measured. When the kit comprises means for real-time quantitative-PCR mRNA detection, the kit may further comprise a second reagent, labeled with a detectable compound, which binds to mRNA synthesized during the PCR, such as e.g. SYBER GREEN reagents or TaqMan reagents.

Means for determining the expression level of the marker proteins may also include antibodies specifically binding to the marker proteins to be measured. Such means can be labeled with detectable compound such as fluorophores or radioactive compounds. For example, the probe or the antibody specifically binding to the marker proteins may be labeled with a detectable compound. Alternatively, when the kit comprises an antibody, the kit may further comprise a secondary antibody, labeled with a detectable compound, which binds to an unlabelled antibody specifically binding to the marker protein(s) to be measured.

The means for measuring the expression level of the marker proteins may also include reagents such as e.g. reaction, hybridization and/or washing buffers. The means may be present, e.g., in vials or microtiter plates, or be attached to a solid support such as a microarray as can be the case for primers and probes.

A seventh aspect of the invention relates to an in vitro method for screening for compounds which are suitable for polarizing a dendritic cell towards a tolerogenic dendritic cell subset or towards an effector dendritic cell subset, which method comprises the steps of:

a) providing a test compound;

b) bringing immature dendritic cells into contact with the test compound;

c) determining the level of expression by the dendritic cell of at least one marker protein listed in Tables 1.A, 1.B, 1.D, 1.E and 2.A to F, or an mRNA thereof;

wherein, when the control consists of immature dendritic cells:

(i) the determination that dendritic cells contacted with the test compound express at least one marker protein listed in Tables 1.A and 2.A, more preferably at least one marker protein selected from the group consisting of C1Q (subunit A, B and/or C, respectively SEQ ID Nos; 45, 46, 47), CATC (SEQ ID NO: 48), MRC1 (SEQ ID NO: 50), STAB1 (SEQ ID NO: 51), TPP1 (SEQ ID NO: 5), advantageously at least C1Q (subunit A, B and/or C) and/or STAB1, or an mRNA thereof, at a level higher than the level of a control sample consisting of immature dendritic cells which has not been contacted with the test compound indicates that said test compound is suitable for polarizing a dendritic cell towards a tolerogenic dendritic cell subset; whereas (ii) the determination that dendritic cells into contact with the test compound express at least one marker protein listed in Tables 1.A, 1.B, 2.B, 2.C, more preferably at least one marker protein selected from the group consisting of C1Q (subunit A, B and/or C, respectively SEQ ID Nos; 45, 46, 47), CATC (SEQ ID NO: 48), MRC1 (SEQ ID NO: 50), STAB1 (SEQ ID NO: 51), TPP1 (SEQ ID NO: 5), and ITAM (SEQ ID NO: 15), or an mRNA thereof, at a lower level than the level of a control sample consisting of immature dendritic cells which has not been contacted with the test compound, and/or express at least one marker protein or listed in Tables 1.D, 1.E, 2.D, 2.E, 2.F, more preferably at least one marker protein selected from the group consisting of TFR1 (also known as CD71) (SEQ ID NO: 72), NMES1 (SEQ ID NO: 68), TRAF1 (SEQ ID NO: 75), FSCN1 (SEQ ID NO: 23), IRF4 (SEQ ID NO: 35), MX1 (SEQ ID NO: 41/42), Lamin-A/C (SEQ ID No 32) and PGRP1 (bovine sequence recited in SEQ ID NO: 108), or an mRNA thereof, at a higher level than the level of a control sample consisting of immature dendritic cells which have not been contacted with the test compound, indicates that said test compound is suitable for polarizing a dendritic cell towards an effector dendritic cell subset.

Marker Proteins

The term 'marker protein' includes all isoforms of said proteins. Thus, for the marker proteins described above, the term 'marker protein' includes the polypeptide having the amino acid sequences disclosed herein and all isoforms thereof. 'Isoform' refers to all alternative forms of a protein, for example amino-acid substituted forms, alternatively spliced versions and post-translationally modified forms such as glycoforms. Post-translationally modified isoforms may include acetylated, formylated, lipoylated, myristoylated, palmitoylated, alkylated, methylated, amidated, glycosylated, hyrdroxylated, nitrosylated, phosphorylated, sulphated, polysialylated and sialylated forms. Isoforms include naturally occurring variants, allelic variants, SNPs (single nucleotide polymorphisms), alternative splice variants and truncated or secreted forms of the protein. Alternatively spliced and truncated mRNAs encoding the marker proteins may also be detected.

Detection of the 'level of expression' of a marker protein may refer to the level of expression of any individual isoform of said protein; the collective level of expression of selected isoforms of said protein; or the total level of expression of said protein including the reference sequence and all isoforms.

In one embodiment, the marker proteins have the sequence corresponding to the Uni-Prot/Swiss-Prot accession number recited in Tables 1 and 2.
In some embodiments, the methods of the invention involve detection of a single marker protein or protein isoform of the proteins listed in Tables 1.A, 1.B, 1.D, 1.E and 2.A to F, or an mRNA thereof. In other embodiments, more than one protein or protein isoform listed in Tables 1 A, 1.B, 1.D, 1.E and 2 A to F, or an mRNA thereof, is detected, for example at least 2, 3, 4, 5, 6, 7, 8, 9, 10, 11, 12, 13, 14, 15, 16, 17, 18, 19, 20, 21, 22, 23, 24, 25, 26, 27, 28, 29 or at least 30 proteins or protein isoforms, or the mRNAs thereof.

In certain embodiment, a set of biomarkers comprising at least C1Q (subunit A, B and/or C) and/or STAB1 is used.

Complement C1q (C1Q) is involved in serum complement system. In human, it is composed of 18 polypeptide chains: six A-subunits (UniProt/Swiss-Prot accession number C1QA_HUMAN, 245 amino acids long), six B-subunits (UniProt/Swiss-Prot accession number C1QB_HUMAN, 253 amino acids long), and six C-subunits (UniProt/Swiss-Prot accession number C1QCA_HUMAN, 245 amino acids). C1Q associates with the proenzymes C1r and C1s in the molar ratio of 1:2:2. to yield C1, the first component of the serum complement system.

Stabilin1 (STAB1) is a single-pass type I membrane protein, 2570 residues long in human (precursor form). It acts as a scavenger receptor for acetylated low density lipoprotein. Binds to both Gram-positive and Gram-negative bacteria and may play a role in defense against bacterial infection. Two isoforms have been identified in human.

An increase or decrease in the level of expression of a protein isoform, or an mRNA thereof, may be detected in a biological sample compared to a control, as detailed below. The fold change in the patient sample compared to the control may be at least 1.2, at least 1.4, at least 1.6, at least 1.8, at least 2, at least 2.2, at least 2.4, at least 2.6, at least 2.8, at least 3, at least 3.5, at least 4, at least 4.5, at least 5, at least 6, at least 7 or at least 8-fold.

As used throughout the present specification, any reference to the "marker proteins" of the Tables 1 and 2 is meant to encompass any naturally occurring isoform of the marker proteins naturally encoded by human, but also their homologous and orthologous counterpart of other animals. The patient is preferably a mammal, such as a rodent, a feline, an equine, a bovine, an ovine, a canine or a primate, and is preferably a human, in particular a child, a woman, a man.

Depending on the origin of sample to be tested (e.g. a rodent, a feline, an equine, a bovine, an ovine, a canine or a primate . . . ), the person skilled in the art will easily determine which are the sequences of the markers to be detected by consulting the commonly known sequence databases and will therefore choose the means suitable for detecting these markers.

For instance, when the patient is a human, the term "marker proteins" is intended to mean any naturally occurring isoform of the marker proteins naturally encoded by human genome, including the protein having an amino acid sequence corresponding to the sequences of accession number listed in Tables 1 and 2, human equivalents of the non_human sequences listed in Tables 1 and 2 allelic variants thereof and splice variants thereof.

Biological Sample

The biological sample may be, without limitation, blood (e.g. peripheral blood, PBMCs), plasma, serum, mucosal (e.g. nasal secretion, saliva), bronchoalveolar cerebrospinal fluid or urine. It may as well be tissues, most particularly from mucosal surfaces. In some embodiments, said biological sample contains antigen-presenting cells (i.e. monocytes, macrophages and/or dendritic cells), more preferably dendritic cells. However, it is not necessary for the sample to contain antigen-presenting cells, as the marker protein may be secreted and may be detected in body fluids or tissues which do not contain the antigen-presenting cells themselves.

The biological sample is preferably taken before the commencement of therapy or before the planned commencement of therapy. The sample may also be taken after the commencement of therapy, for example after one round of therapy is completed in order to decide whether to proceed to further rounds. In particular, where the method comprises monitoring of a patient undergoing immunotherapy, samples taken before the commencement of therapy, during therapy and/or at the end of therapy may be required.

In all aspect of the invention relating to allergy, the biological sample is preferably peripheral blood or PBMCs, nasal secretion, saliva or bronchoalveolar fluid.

Control

The expression of the marker proteins by dendritic cells to be tested, or where appropriate in a patient biological sample, may be compared with a control standard value and/or or with the expression of said marker in a control sample as explained above, for instance a control sample of the same nature.

A standard value may be obtained by, for example, detecting the level of expression in a given subset of dendritic cells (e.g. immature dendritic cells, effector or tolerogenic dendritic cells) or in a given group of subjects (for instance healthy subjects, patients developing an immune response oriented towards a regulatory T cell response or towards an effector T cell response, patients previously identified as a responder to a treatment, or patients previously identified as a non-responder to a treatment) and obtaining an average or median figure.

The control sample may consist of immature dendritic cells. In the context of the invention, the term "immature dendritic cells" is intended to mean that the dendritic cells are not activated and have not been polarized towards tolerogenic or effector subsets. Immature dendritic cells may be obtained from monocytes sorted out from peripheral blood (e.g. from PBMCs) by method well known from the one skilled in the art. Such methods are for instance disclosed in Sallusto and Lanzavecchia, J Exp Med, 179:1109-1118,1994, and in the examples of the present application. Other sources of DCs include plasmacytoid DCs (from blood, PBMCs, tissues) dermal DCs and langerhans cells (from skin or mucosal tissues).

As will be clear to the skilled person, the nature of the comparison of the dendritic cell to be tested, or where appropriate in a patient biological sample to be tested, with the control and the conclusions drawn will depend on the nature of the control.

For instance, where the marker protein is disclosed herein as a protein overexpressed in the tolerogenic dendritic cell subset and the control is based on immature dendritic cells or an effector dendritic cell subset, a value the same as or similar to, or lower than, the control may be indicative that the dendritic cell to be tested does not belong to a tolerogenic dendritic cell subset, whereas a value higher than the control may be indicative that the dendritic cell to be tested belongs to a tolerogenic dendritic cell subset. Conversely, where the control is based on tolerogenic dendritic cells, a value the same as or similar to, or higher than, the control may be indicative that the dendritic cell to be tested belongs to a tolerogenic dendritic cell subset, whereas a value lower than the control may be indicative that the dendritic cell to be tested does not belong to a tolerogenic dendritic cell subset.

Similarly, where the marker protein is disclosed herein as a protein overexpressed in an effector dendritic cell subset and the control is based on immature dendritic cells or a tolerogenic dendritic cell subset, a value the same as or similar to, or lower than, the control may be indicative that the dendritic cell to be tested does not belong to an effector dendritic cell subset, whereas a value higher than the control may be indicative that the dendritic cell to be tested belongs to an effector dendritic cell subset. Conversely, where the control is based on effector dendritic cells, a value the same as or similar to, or higher than, the control may be indicative that the dendritic cell to be tested belongs to an effector dendritic cell subset, whereas a value lower than the control may be indicative that the dendritic cell to be tested does not belong to an effector dendritic cell subset.

Similarly, where the marker protein is disclosed herein as a protein underexpressed in an effector dendritic cell subset and the control is based on immature dendritic cells or a tolerogenic dendritic cell subset, a value the same as or similar to, or higher than, the control may be indicative that the dendritic cell to be tested does not belong to an effector dendritic cell subset, whereas a value lower than the control may be indicative that the dendritic cell to be tested belongs to an effector dendritic cell subset. Conversely, where the control is based on effector dendritic cells, a value the same as or similar to, or lower than, the control may be indicative that the dendritic cell to be tested belongs to an effector dendritic cell subset, whereas a value higher than the control may be indicative that the dendritic cell to be tested does not belong to an effector dendritic cell subset.

The same type of reasoning applies to determine if a patient is developing an immune response oriented either towards a regulatory T cell response or towards an effector T cell response.

For instance, concerning the embodiments wherein the patient has not been treated, as exemplified above the control may be immature dendritic cells which have not been polarized towards tolerogenic or effector subsets, or a biological sample from a healthy patient of the same nature than that of the biological sample to be tested. The control may also be effector dendritic cells, tolerogenic dendritic cells, biological sample of a patient who is developing a regulatory T cell response, biological sample of a patient who is developing an effector T cell response. On the basis of a reasoning similar to that above in relation to the determination of to which dendritic cell subset belongs the DCs to be tested, depending on the type of control the person skilled in the art will be able to determine if a patient is developing an immune response oriented either towards a regulatory T cell response or towards an effector T cell response.

Regarding the embodiments wherein the patient has been treated, as exemplified above the control may be a biological sample from a patient or group of patients of the same nature as that of the biological sample to be tested, which sample has been obtained before the treatment begins (see the third aspect of the invention). Preferably, the control is a pre-treatment sample taken from the patient undergoing treatment. The control may also be effector dendritic cells, tolerogenic dendritic cells, a biological sample from a patient who is developing a regulatory T cell response, a biological sample from a patient who is developing an effector T cell response. Further, when one wishes to determine if the patient will likely be a responder or a non-responder to a treatment, the control may be a biological sample from a healthy patient, a biological sample from a patient previously identified as a responder to the treatment, a biological sample from a patient previously identified as a non-responder to the treatment (biological samples of the same nature than that of the biological sample to be tested and, where the sample is a patient sample, obtained before the beginning of treatment).

Where the marker protein is disclosed herein as a protein overexpressed in responder subjects and the control is based on a non-responder subject or group of such subjects, a value the same as or similar to, or lower than, the control may be indicative of non-responsiveness to therapy, whereas a value higher than the control may be indicative of responsiveness to therapy. Conversely, where the control is based on a responder subject or group of such subjects, a value the same as or similar to, or higher than, the control may be indicative of responsiveness to therapy, whereas a value lower than the control may be indicative of non-responsiveness to therapy. Where the control is based on an average or median value obtained from a random group of subjects, a value higher than the control may be indicative of responsiveness to therapy. Preferably, the method is intended to monitor patients during therapy to establish whether they are responding to therapy, an increase or decrease in marker protein expression during therapy is indicative of responsiveness to treatment.

Similarly, where the marker protein is disclosed herein as a protein underexpressed in responder subjects and the control is based on a non-responder subject or group of such subjects, a value the same as or similar to, or higher than, the control may be indicative of non-responsiveness to therapy, whereas a value lower than the control may be indicative of responsiveness to therapy. Where the control is based on a responder subject or group of such subjects, a value the same as or similar to, or lower than, the control may be indicative of responsiveness to therapy, whereas a value higher than the control may be indicative of non-responsiveness to therapy. Where the control is based on an average or median value obtained from a random group of subjects, a value lower than the control may be indicative of responsiveness to therapy. Where the method is intended to monitor patients during therapy to establish whether they are responding to therapy, a reduction in marker protein expression during therapy is indicative of responsiveness to treatment.

In the context of the present invention, the term "overexpression" and "overexpress" is intended to mean that the level of expression of given protein marker, or an mRNA thereof, is higher than that of the control. On the other hand, the term "underexpression" and "underexpress" is intended to mean that the level of expression of given protein marker, or an mRNA thereof, is lower than that of the control.

Detection of Marker Proteins/Determination of the Level of Expression of Markers Proteins The level of expression of the marker protein may be determined by gel electrophoresis (SDS-PAGE), in particular one and two-dimensional gel electrophoresis (1D-, 2D-PAGE), carried out on the sample or a protein-containing extract thereof. 2D-PAGE is a well established technique in which proteins are first separated in one dimension by isoelectric focusing and further separated by SDS-PAGE along a second dimension. Protein expression may be analyzed by visualization of labeled proteins, or by western blotting (i.e. using a monoclonal or polyclonal antibody). Protein quantitation by 2D-PAGE is usually carried out by 2D-DiGE, in which proteins from a control sample and the test sample are labeled with different dyes. The dyes are of similar mass and identical charge so the labeled proteins migrate to the same position on the gel, allowing quantitation to be carried out within a single gel.

Protein expression may also be determined by mass spectrometry assays (LC-MS or LC-MS/MS). Qualitative and quantitative mass spectrometric techniques are known and used in the art. To this aim, target peptides specific for marker proteins are selected and quantified based on calibration curves established with synthetic peptides labeled with stable isotopes. Enzymatic digests, spiked with a defined amount of isotope labeled target peptides, are analyzed by liquid chromatography coupled with mass spectrometry. The ratio between labeled and non-labeled target peptides is measured to assess target peptide concentrations and therefore protein marker concentration.

Expression may also be determined using an antibody which binds to the protein, for example a monoclonal or polyclonal antibody, an antibody variant or fragments such as a single chain antibody, a diabody, a minibody, a single chain Fv fragment (sc(Fv)), a Sc(Fv)$_2$ antibody, a Fab fragment or a F(ab')$_2$ fragment, a V$_H$H antibody or a single domain antibody. The antibody may be mono-, bi-, tri- or multivalent. The antibody may be immobilized on a solid support. Antibodies may be used to determine protein expression in a range of immunological assays including competitive and non-competitive assay systems using techniques such as western blotting, immunohistochemistry/immunofluorescence (i.e protein detection on fixed cells or tissues), radioimmunoassay such as RIA (radio-linked immunoassay), ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, e.g. FIA (fluorescence-linked immunoassay), chemiluminescence immunoassays, ECLIA (electrochemiluminescence immunoassay) and protein A immunoassays. Such assays are routine and well known to the person skilled in the art.

Expression may alternatively be determined using a protein-specific aptamer. An aptamer is a short peptide capable of specifically binding to a specific protein sequence, consisting of a variable peptide loop attached at both ends to a protein scaffold. Methods for making protein aptamers are well known in the art, the most commonly used method being the yeast two-hybrid system. Such aptamers may preferably be labeled in order to allow the detection of a protein-ligand interaction. A nanotechnology-based assay could also be used.

Detection of mRNA of the Marker Proteins/Determination of the Level of Expression of mRNA of the Markers Proteins The level of expression of mRNAs may be determined by real-time quantitative RT-PCR, using primers specific for the marker proteins to be measured. This method allows the detection of mRNA in a biological sample by generating cDNA by reverse transcription using at least one primer; amplifying the cDNA so produced using gene specific polynucleotides as sense and antisense primers and detecting the presence of the amplified cDNA by methods well known to the person skilled in the art. This include cDNA amplification with specific predesigned primers using SYBR GREEN or Taqman reagents.

Therapeutic Applications

"Therapy", "therapeutic", "treatment" or "treating" include reducing, alleviating or inhibiting or eliminating the symptoms of diseases (e.g. infectious diseases, tumors, autoimmune diseases) or of pathological conditions (e.g. allergy and graft rejection), as well as treatment intended to reduce, alleviate, inhibit or eliminate said symptoms. These terms may include preventive treatment which is intended to, or has the effect of, reducing, alleviating, inhibiting or eliminate future symptoms. They may also include treatment of ongoing symptoms.

By "a tumor" is meant any type of cancerous (malignant) tumor.

The malignant tumor may be for instance carcinomas, adenocarcinomas, sarcomas, malignant melanomas, mesotheliomas, blastomas. The carcinoma or adenocarcinoma may for example correspond to a bladder, a colon, a kidney, an ovary, a prostate, a lung, an uterus, a breast or a prostate carcinoma or adenocarcinoma. The blastoma may for example correspond to a neuroblastoma, a glioblastoma or a retinoblastoma. The cancer is preferably selected from the group consisting of prostate cancer (e.g. prostate adenocarcinoma), lung cancer (e.g. squamous cellular carcinoma), breast cancer (e.g. infiltrated ductal carcinoma), ovary cancer (e.g. serous papillary carcinoma), uterus cancer (squamous cellular carcinoma), brain cancer (e.g. astrocytoma), colon cancer (e.g. colon adenocarcinoma), colorectal cancer, rectal cancer (e.g. rectal adenocarcinoma), cancer of the striated muscle (e.g. rhabdomyosarcoma), thyroid cancer, testicular cancer. In a most preferred embodiment, the cancer is selected from the group consisting of lung cancer, prostate cancer, ovary cancer, uterus cancer, brain cancer, colon cancer, colorectal cancer, rectal cancer and cancer of the striated muscle, bladder cancer, liver cancer, kidney cancer, thyroid cancer.

By "infectious disease", also known as contagious disease or transmissible disease, is meant any disease which is due to a biological agent which can be spread from one subject to another. The biological agents may be viruses, bacteria, fungi, protozoa and multicellular parasites.

"Autoimmune disease" is a condition that occurs when the immune system mistakenly attacks and destroys healthy body tissue. Examples of autoimmune (or autoimmune-related) disorders include Addison's disease, Celiac disease-sprue (gluten-sensitive enteropathy), Dermatomyositis, Graves disease, Hashimoto's thyroiditis, Multiple sclerosis, Myasthenia gravis, Pernicious anemia, Reactive arthritis, Rheumatoid arthritis, Sjogren syndrome, Systemic lupus erythematosus and Type I diabetes.

"Graft rejection" is the rejection of the graft (organs, tissues or cells) by the recipient The rejection may be based on both cell-mediated and antibody-mediated immunity directed against cells of the graft. The graft may be for instance a xenograft (i.e. tissue that is transplanted from one species to another) or an allograft (i.e. a graft of tissue obtained from a donor genetically different from, though of the same species as the recipient).

"Allergy" is a condition characterized by production of allergen-specific IgE in response to a specific allergen, usually a protein. Clinical manifestations and symptoms of allergy may include nasal congestion, nasal pruritis, ocular pruritis, tearing, rhinorrhoea, sinusitis, rhinitis, sneezing, wheezing, conjunctivitis, dermal itching, dermatitis, skin irritation and asthma.

An 'allergen' is a substance, usually a protein, which elicits the production of IgE antibodies in predisposed individuals. Allergens may include pollen allergens (such as tree, herb, weed and grass pollen allergens), insect allergens (such as inhalant, saliva and venom allergens, e.g. cockroach, midge and house dust mite allergens and hymenoptera venom allergens), animal hair and dander allergens (from e.g. dog, cat, horse, rat, mouse, rabbit) and food allergens. In a preferred embodiment, the patient has grass pollen allergy and the immunotherapy uses grass pollen allergen.

For instance, a protein allergen may be selected from the group consisting of a protein allergen of the genus *Dermatophagoides*; a protein allergen of the genus *Felis*; a protein allergen of the genus *Ambrosia*; a protein allergen of the genus *Lolium*; a protein allergen of the genus *Cryptomeria*; a protein allergen of the genus *Alternaria*; a protein allergen of the genus Alder, a protein allergen of the genus *Betula*; a protein allergen of the genus *Blomia*; a protein allergen of the genus *Quercus*; a protein allergen of the genus *Olea*; a protein allergen of the genus *Artemisia*; a protein allergen of the genus *Plantago*; a protein allergen of the genus *Parietaria*; a protein allergen of the genus Canine; a protein allergen of the genus *Blattella*; a protein allergen of the genus *Apis*; a protein allergen of the genus *Cupressus*; a protein allergen of the genus *Thuya*; a protein allergen of the genus *Chamaecyparis*; a protein allergen of the genus *Periplaneta*; a protein allergen of the genus *Agropyron*; a protein allergen of the genus *Secale*; a protein allergen of the genus *Triticum*; a protein allergen of the genus *Cynorhodon*; a protein allergen of the genus *Juniperus*; a protein allergen of the genus *Dactylis*; a protein allergen of the genus *Festuca*; a protein allergen of the genus *Poa*; a protein allergen of the genus *Lolium*; a protein allergen of the genus *Avena*; a protein allergen of the genus *Holcus*; a protein allergen of the genus *Anthoxanthum*; a protein allergen of the genus *Arrhenatherum*; a protein allergen of the genus *Agrostis*; a protein allergen of the genus *Phleum*; a protein allergen of the genus *Phalaris*; a protein allergen of the genus *Paspalum*; and a protein allergen of the genus *Sorghum*.

Examples of various known protein allergens derived from some of the above-identified genus include: *Betula* (*verrucosa*) Bet v I; Bet v II; *Blomia* Blo 1 1; Blo t III; Blo t V; Blo t XII; *Cynorhodon* Cyn d I; *Dermatophagoides* (*pteronyssinus* or *farinae*) Der p I; Der p II; Der p III; Der p VII; Der f I; Der f II; Der f III; Der f VII; *Felis* (*domesticus*) Fel d I; *Ambrosia* (*artemiisfolia*) Amb a 1.1; Amb a 1.2; Amb a 1.3; Amb a 1.4; Amb a II; *Lollium* (*perenne*) Lol p I; Lot p II; Lol p III; Lot p IV; Lol p IX (Lol p V or Lol p Ib); *Cryptomeria* (*japonica*) Cry j I; Cry j II; *Canis* (*familiaris*) Can f I; Can f II; *Juniperus* (*sabinoides* or *virginiana*) Jun s I; Jun v I; *Juniperus* (*ashei*) Jun a I; Jun a II; *Dactylis* (*glomerata*) Dae g I; Dae g V; *Poa* (*pratensis*) Poa p I; PhI p I; PhI p V; PhI p VI and *Sorghum* (*halepensis*) Sor h I.

"Immunotherapy" is intended to mean a treatment of disease by inducing, enhancing, or suppressing an immune response by administration of substances (e.g. allergens, immunomodulators such as granulocyte colony-stimulating factor (G-CSF), interferons, imiquimod, cellular membrane fractions from bacteria, cytokines/interleukins (e.g. IL-2, IL-7, IL-12), various chemokines) or cells (for instance lymphocytes, macrophages, dendritic cells, natural killer cells (NK Cell), cytotoxic T lymphocytes.

"Vaccine" refers to a pharmaceutical composition comprising an antigen and optionally an adjuvant to stimulate the immune system of an individual to develop adaptive immunity to said antigen. The antigen may for instance be biological agents (for example a viruses, bacteria, fungi, protozoa and multicellular parasites) or a peptide therefrom, or a tumoral antigen.

Vaccines can be prophylactic (e.g. to prevent or ameliorate the effects of a future infection by the pathogen biological agent), or therapeutic (e.g. vaccines against cancer).

The substance used in immunotherapy and the vaccine may be administered via a parenteral route, such as subcutaneously or intravenously, for example via injection, or via alternative routes such as intranasal, skin immunisation e.g. transdermal, intralymphatic administration or mucosal (administration on mucosal surfaces, e.g. a sublingual, oral, buccal, ocular, rectal, urinal, vaginal, pulmonary or otolar surface.

In relation to allergy, immunotherapy may for example consist of administering an allergen to a patient with the aim of reducing current or future immune response, such as an IgE response, and/or manifestation of clinical symptoms of allergy. Immunotherapy is conventionally carried out by administering repeatedly a monodose or incremental doses of an allergen to a patient in need thereof, thereby resulting in an adaptive immune response of the patient who becomes desensitised to the allergen. Immunotherapy may comprise administration of allergen to a mucosal surface, optionally a sublingual, oral, buccal, ocular, rectal, urinal, vaginal, pulmonary or otolar surface. In particular, immunotherapy may be sublingual immunotherapy. Alternatively, immunotherapy may comprise administration via a parenteral route, such as subcutaneously or intravenously, for example via injection, or via alternative routes such as intranasal, skin immunisation e.g. transdermal, or intralymphatic administration.

The allergen used for immunotherapy may be a single allergenic substance or a mixture of such substances, for example a mixture of proteins. It may be a partially or fully purified extract, such as a pollen extract, a recombinant protein, a hypoallergen or peptide derived therefrom. For example, where the immunotherapy is used to treat grass pollen allergy, the allergen administered for immunotherapy may be a grass pollen extract from pollen of one or several genera of grasses, such as *Dactylis, Poa, Lolium, Anthoxanthum* and *Phleum* genera. The allergen may also be an allergoid, i.e. a chemically modified form of a naturally occurring allergen which has been chemically modified (for example by aldehydation). The allergen may be administered in conjunction with an adjuvant.

"Response" of a patient to treatment indicates that the patient manifests a reduction in the clinical symptoms. Clinical symptoms may be assessed over the course of treatment, i.e. symptoms before treatment may be compared to symptoms during and after treatment. Alternatively, a reduction in symptoms may be determined by comparison to a baseline level established before treatment. Concerning allergy, this approach is particularly useful where, for example, immunotherapy is carried out in patients not currently experiencing symptoms, as may be the case for seasonal grass pollen allergy sufferers, who may be treated before the pollen season. Symptoms may be assessed by standard methods, such as patient self-assessment or record of the amount of medication required. The degree of a patient's response to treatment may be assessed by measuring the degree of reduction of severity in symptoms, for example as described in the experimental section below. A 'responder' subject as defined herein is a subject who responds to immunotherapy with an improvement in clinical symptoms, preferably a statistically significant improvement as compared to patients receiving placebo or no treatment. Preferably, a responder subject will demonstrate an improvement in clinical symptoms which is greater than the average or median improvement seen in a random sample of subjects. A 'non-responder' subject is a subject who does not manifest any improvement in clinical symptoms following immunotherapy, or who demonstrates a non-statistically significant improvement in symptoms, or who demonstrates an improvement in clinical symptoms which is less than the average or median improvement seen in a random sample of subjects. For example, where the allergy is grass pollen allergy, improvement in clinical symptoms may be detected by a reduction in the frequency or severity of nasal congestion, nasal pruritis, ocular pruritis, tearing, rhinorrhoea, sinusitis, rhinitis, sneezing, wheezing and/or conjunctivitis.

"Patient" includes any individual who is a candidate for immunotherapy or vaccine, including individuals not currently undergoing therapy.

Concerning allergy, in most cases, the patient will be an individual who has, or has had at any time in the past, clinical symptoms of allergy and/or sensitization to an allergen and/or an allergen-specific IgE response, or an individual at risk of developing such symptoms. Sensitisation to an allergen may be assessed by detecting IgE directed against allergen(s) from this source in the serum of the patient or by skin testing with a preparation containing the corresponding allergen(s). The allergen may without limitation include any of the allergens disclosed herein, in particular a grass pollen allergen.

Table 1: Proteins identified through the 2D-DIGE approach with a FDR p-value≤0.05.

Max. fold represents the ratio of the average volumes of the highest vs. lowest conditions.

TABLE 1 A

| | Protein denomination | Accession number | Protein name | SEQ ID NO | Max. fold |
|---|---|---|---|---|---|
| Proteins upregulated in DEX-DCs and downregulated in LPS-DCs and PGN-DCs | OSTF1_HUMAN | Q92882 | Osteoclast stimulating factor 1 | 1 | 2.80 |
| | EF2_HUMAN | P13639 | Elongation factor 2 | 2 | 1.80 |
| | F13A_HUMAN | P00488 | Coagulation factor XIII A chain | 3 | 1.50 |
| | ANXA1_HUMAN | P04083 | Annexin A1 | 4 | 1.40 |
| | TPP1_HUMAN | O14773 | Tripeptidyl-peptidase 1 | 5 | 1.30 |
| | CLIC2_HUMAN | O15247 | Chloride intracellular channel protein 2 | 6 | 1.30 |
| | GPX1_HUMAN | P07203 | Glutathione peroxidase 1 | 7 | 1.20 |
| | IMDH2_HUMAN | P12268 | Inosine-5' monophosphate dehydrogenase 2 | 8 | 1.20 |
| | GBB2_HUMAN | P62879 | Guanin nucleotide-binding protein G(I)/G(S)/G(T) subunit beta 2 | 9 | 1.20 |
| | GBB1_HUMAN | P62873 | Guanin nucleotide-binding protein G(I)/G(S)/G(T) subunit beta 1 | 10 | |
| | IF4A3_HUMAN | P38919 | Eukaryotic initiation factor 4A-III | 11 | 1.20 |

TABLE 1 B

| | Protein denomination | Accession number | Protein name | SEQ ID NO | Max. fold |
|---|---|---|---|---|---|
| Proteins downregulated in LPS-DCs and PGN-DCs | COF1_HUMAN | P23528 | Cofilin-1 | 12 | 2.70 |
| | MK14_HUMAN | Q16539 | Mitogen-activated protein kinase 14 | 13 | 1.60 |
| | SAMH1_HUMAN | Q9Y3Z3 | SAM domain and HD domain-containing protein 1 | 14 | 1.50 |
| | ITAM_HUMAN | P11215 | Integrin alpha-M (CD11b) | 15 | 1.40 |
| | VIME_HUMAN | P08670 | Vimentin | 16 | 1.30 |
| | RHG01_HUMAN | Q07960 | Rho GTPase-activating protein1 | 17 | 1.20 |

TABLE 1 C

| | Protein denomination | Accession number | Protein name | SEQ ID NO | Max. fold |
|---|---|---|---|---|---|
| protein regulated in DEX, LPS and PGN-DCs | FKBP5_HUMAN | Q13451 | Peptidyl-prolyl cis-trans isomerase FKBP5 | 18 | 1.70 |

TABLE 1 D

| | Protein denomination | Accession number | Protein name | SEQ ID NO | Max. fold |
|---|---|---|---|---|---|
| Proteins upregulated in LPS-DCs and PGN-DCs | 2B11_HUMAN | P04229 | HLA class II histocompatibilité antigen DRB-1-1 beta chain | 19 | 2.7 |
| | 2B1G_HUMAN | Q29974 | HLA class II histocompatibility antigen, DRB1-16 beta chain | 20 | |
| | H4_Human | P62805 | Histone H4 | 21 | 2.4 |
| | HSPB1_HUMAN | P04792 | Heat shock protein beta 1 | 22 | 2.4 |
| | FSCN1_HUMAN | Q16658 | Fascin | 23 | 2.3 |
| | EHD1_HUMAN | Q9H4M9 | EH domain-containing protein 1 | 24 | 2.1 |
| | GFPT1_HUMAN | Q06210 | Glucosamine-fructose-6-phosphate aminotransferase 1 | 25 | 1.7 |
| | FABPH_HUMAN | P05413 | Fatty acid binding protein, heart ou FABP3 | 26 | 1.7 |
| | HCK_HUMAN | P08631 | Tyrosine-protein kinase HCK | 27 | 1.6 |
| | DC1L1_HUMAN | Q9Y6G9 | Cytoplasmic dynein 1 light intermediate chain 1 | 28 | 1.6 |
| | MOES_HUMAN | P26038 | Moesin | 29 | 1.5 |
| | gi|47419918 | 47419918 | Tryptophanyl-tRNA synthetase cytoplasmic isoform b | 30 | 1.5 |
| | UFL1_HUMAN | O94874 | E3 UFM1-protein ligase 1 | 31 | 1.4 |
| | LMNA_HUMAN | P02545 | Lamin-A/C | 32 | 1.4 |
| | SYWC_HUMAN | P23381 | Tryptophanyl-tRNA synthetase cytoplasmic | 33 | 1.3 |
| | gi|493066 | 493066 | Glycyl-tRNA synthetase | 34 | 1.3 |
| | IRF4_HUMAN | Q15306 | Interferon regulatory factor 4 | 35 | 1.3 |

TABLE 1 D-continued

| Protein denomination | Accession number | Protein name | SEQ ID NO | Max. fold |
|---|---|---|---|---|
| VINC_HUMAN | P18206 | Vinculin | 36 | 1.2 |
| gi\|780808 | 780808 | p21-activated protein kinase | 37 | 1.2 |
| MOL1A_HUMAN | Q7L9L4 | MPS one binder kinase activator like 1A | 38 | 1.2 |
| PP1B_HUMAN | P62140 | Serine/threonine protein phosphatase PP1-beta catalytic subunit | 39 | 1.2 |
| ENOA_HUMAN | P06733 | Alpha-enolase | 40 | 1.2 |

TABLE 1 E

| | Protein denomination | Accession number | Protein name | SEQ ID NO | Max. fold |
|---|---|---|---|---|---|
| Proteins upregulated in LPS-DCs | gi\|5410451 | 5410451 | Interferon-induced protein p78 or Interferon-induced GTP-binding protein Mx1 | 41 | 10.4 |
| | gi\|188901 | 188901 | Interferon-induced Mx protein or Interferon-induced GTP-binding protein Mx1 | 42 | 4 |
| | CASP7_HUMAN | P55210 | Caspase-7 | 43 | 1.7 |
| | PSME2_HUMAN | Q9UL46 | Proteasome activator complex subunit 2 | 44 | 1.2 |

Table 2: Proteins identified through the label-free MS approach with a FDR p-value<0.01. (Proteins identified with two or more peptides are included in this table)
Max. fold represents the ratio of the average volumes of the highest vs. lowest conditions.

TABLE 2 A

| | Identification data | | | | Quantification data | | | | |
|---|---|---|---|---|---|---|---|---|---|
| | Protein | | | | | Average normalized abundance | | | |
| | denomination | Accession number | Protein name | SEQ ID NO | Max. fold | Ctrl-DCs | LPS-DCs | DEX-DCs | PGN-DCs |
| Proteins upregulated in DEX-DCs | ANXA_1 HUMAN | P04083 | Annexin A1 | 4 | 2.2 | 3704 | 3798 | 4354 | 2011 |
| | | | | | 1.6 | 12517 | 14568 | 15378 | 9741 |
| | | | | | 1.6 | 10689 | 8718 | 13646 | 13301 |
| | | | | | 1.5 | 2449 | 1990 | 3013 | 2980 |
| | C1QA_HUMAN | P02745 | Complement C1q subcomponent subunit A | 45 | — | — | — | — | — |
| | C1QB_HUMAN | P02746 | Complement C1q subcomponent subunit A | 46 | 1.6 | 7474 | 6593 | 10221 | 8449 |
| | | | | | 3.6 | 1617 | 1092 | 3965 | 1379 |
| | C1QC_HUMAN | P02747 | Complement C1q subcomponent subunit C | 47 | 3.7 | 2380 | 1158 | 4308 | 1536 |
| | | | | | 2.7 | 2790 | 1759 | 4812 | 1828 |
| | | | | | 2.3 | 1570 | 1031 | 2406 | 1529 |
| | | | | | 5.0 | 1342 | 543 | 2725 | 687 |
| | CATC_HUMAN | P53634 | Dipeptidyl peptidase 1 | 48 | 2.6 | 7502 | 6021 | 9396 | 3657 |
| | | | | | 1.9 | 11690 | 8807 | 14732 | 7926 |
| | | | | | 2.2697 | 11220 | 11320 | 15459 | 6811 |
| | F13A_HUMAN | P00488 | Coagulation factor XIII A chain | 3 | 1.7 | 1971 | 2140 | 2262 | 1339 |
| | | | | | 1.8 | 5225 | 3779 | 6244 | 3546 |
| | CLIC2_ | O15247 | Chloride | 6 | 2.1 | 3143 | 2980 | 3857 | 1794 |

TABLE 2 A-continued

| | Identification data | | | | Quantification data | | | |
|---|---|---|---|---|---|---|---|---|
| | Protein | | | | Average normalized abundance | | | |
| | Protein denomination | Accession number | Protein name | SEQ ID NO | Max. fold | Ctrl-DCs | LPS-DCs | DEX-DCs | PGN-DCs |
| | HUMAN | | intracellular channel protein 2 | | 1.5 | 4231 | 3661 | 4306 | 5511 |
| | FKBP5_HUMAN | Q13451 | Peptidyl-prolyl cis-trans isomerase FKBP5 | 49 | 1.6 | 2312 | 2935 | 3640 | 2531 |
| | | | | | 1.7 | 3106 | 3004 | 5224 | 4552 |
| | | | | | 1.6 | 2696 | 2594 | 4046 | 3529 |
| | MRC1_HUMAN | P22897 | Macrophage mannose receptor 1 | 50 | 2.0 | 5903 | 5085 | 6814 | 3380 |
| | | | | | 1.9 | 5812 | 4925 | 6954 | 3623 |
| | | | | | 1.6 | 2955 | 2477 | 3197 | 4056 |
| | | | | | 2.1 | 3515 | 2641 | 5337 | 2561 |
| | | | | | 1.9 | 4212 | 3284 | 5181 | 2678 |
| | STAB1_HUMAN | Q9NY15 | Stabilin-1 | 51 | 1.6 | 2351 | 2076 | 2394 | 1519 |
| | | | | | 3.1 | 1497 | 698 | 2159 | 958 |
| | | | | | 1.9 | 3290 | 2208 | 4172 | 2409 |
| | | | | | 2.8 | 3198 | 1627 | 4503 | 1961 |

TABLE 2 B

| | Identification data | | | | Quantification data | | | |
|---|---|---|---|---|---|---|---|---|
| | Protein denomination | Accession number | Protein name | SEQ ID NO | Max. fold | Average normalized abundance | | | |
| downregulated in LPS_DCs and PGN-DCs | CYTC_HUMAN | P01034 | Cystatin-C | 52 | 2.4 | 9896 | 4615 | 7747 | 4130 |
| | | | | | 1.7 | 8638 | 4977 | 6610 | 6399 |
| | | | | | 2.6 | 7814 | 3029 | 5925 | 4231 |
| | GELS_HUMAN | P06396 | Gelsolin precursor | 53 | 1.6 | 6824 | 6357 | 6735 | 10105 |
| | | | | | 1.9 | 5384 | 6460 | 5372 | 5326 |
| | ITAM_HUMAN | P11215 | Integrin alpha-M | 15 | 1.6 | 4013 | 3163 | 3832 | 2442 |

TABLE 2 C

| | Identification data | | | | Quantification data | | | |
|---|---|---|---|---|---|---|---|---|
| | Protein denomination | Accession number | Protein name | SEQ ID NO | Max. fold | Average normalized abundance | | | |
| Proteins downregulated in PGN-DCs | AHNK_HUMAN | Q09666 | Neuroblast differentiation-associated protein AHNAK | 54 | 1.6 | 2567 | 2515 | 2629 | 1610 |
| | | | | | 1.8 | 3089 | 2871 | 3047 | 1734 |
| | ANXA2_HUMAN | P07355 | Annexin A2 | 55 | 1.9 | 15012 | 16344 | 14692 | 8508 |
| | | | | | 2.7 | 6551 | 7172 | 6385 | 2694 |
| | | | | | 2.7 | 15123 | 14124 | 15099 | 38660 |
| | | | | | 1.7 | 36362 | 36743 | 35236 | 60496 |
| | ANXA5_HUMAN | P08758 | Annexin A5 | 56 | 2.0 | 17023 | 18183 | 16940 | 9102 |
| | | | | | 1.8 | 11213 | 10552 | 11135 | 18740 |
| | ENOA_HUMAN | P06733 | Alpha-enolase-Homo sapiens (Human) | 57 | 1.7 | 2355 | 2632 | 2384 | 1516 |
| | | | | | 1.5 | 11376 | 12725 | 11939 | 8482 |
| | | | | | 1.7 | 9053 | 10739 | 9334 | 6441 |
| | | | | | 2.5 | 852 | 2122 | 930 | 1090 |
| | ENPL_HUMAN | P14625 | Endoplasmin | 58 | 1.5 | 3024 | 3283 | 2784 | 2141 |
| | | | | | 1.6 | 14655 | 15149 | 14275 | 9251 |
| | KPYM_HUMAN | P14618 | Pyruvate kinase isozymes M1/M2 | 59 | 1.6 | 4840 | 5088 | 4933 | 3221 |
| | | | | | 1.7 | 88255 | 65132 | 79819 | 113607 |
| | | | | | 2.7 | 50825 | 64042 | 54639 | 23540 |
| | | | | | 1.7 | 14316 | 15813 | 13706 | 9310 |
| | LOX15_HUMAN | P16050 | Arachidonate 15-lipoxygenase | 60 | 1.9 | 14475 | 13698 | 13685 | 7723 |
| | | | | | 2.4 | 3002 | 3452 | 2981 | 1442 |
| | | | | | 1.9 | 16095 | 14500 | 14656 | 26859 |
| | | | | | 1.7 | 4943 | 5230 | 4148 | 3052 |

TABLE 2 C-continued

| Identification data | | | SEQ ID NO | Quantification data | | | | |
|---|---|---|---|---|---|---|---|---|
| Protein denomination | Accession number | Protein name | | Max. fold | Average normalized abundance | | | |
| PPIA_HUMAN | P62937 | Peptidyl-prolyl cis-trans isomerase A | 61 | 1.7 | 17897 | 20499 | 18929 | 11953 |
| | | | | 1.5 | 14389 | 15483 | 14751 | 10133 |
| RL17_HUMAN | P18621 | 60S ribosomal protein L17 | 62 | 2.4 | 2053 | 2187 | 2171 | 919 |
| | | | | 1.8 | 9608 | 12208 | 11055 | 6614 |
| TPIS_HUMAN | P60174 | Triosephosphate isomerase | 63 | 1.8 | 8019 | 7514 | 8238 | 4642 |
| | | | | 1.8 | 5463 | 5933 | 5788 | 3250 |
| | | | | 1.8 | 12456 | 10795 | 12344 | 19374 |
| VIME_HUMAN | P08670 | Vimentin | 16 | 1.8 | 2681 | 3037 | 2885 | 1659 |
| | | | | 1.8 | 29904 | 32923 | 30758 | 18143 |
| | | | | 1.8 | 10970 | 9574 | 10119 | 16791 |
| | | | | 2.4 | 1963 | 2997 | 3661 | 1555 |
| | | | | 3.0 | 4034 | 5669 | 3578 | 1912 |
| | | | | 2.5 | 75084 | 68014 | 71654 | 171573 |
| | | | | 2.7 | 9454 | 7092 | 9330 | 18883 |

TABLE 2 D

| | Identification data | | | SEQ ID NO | Quantification data | | | | |
|---|---|---|---|---|---|---|---|---|---|
| | Protein denomination | Accession number | Protein name | | Max. fold | Average normalized abundance | | | |
| Proteins upregulated in LPS-DCs and PGN_DCs | 4F2_HUMAN | P08195 | 4F2 cell-surface antigen heavy chain | 64 | 3.2 | 1995 | 2584 | 1584 | 5011 |
| | | | | | 1.9 | 12354 | 15099 | 9853 | 19010 |
| | | | | | 3.2 | 772 | 902 | 742 | 2345 |
| | | | | | 2.1 | 2202 | 3316 | 1797 | 3757 |
| | | | | | 2.5 | 1172 | 1606 | 992 | 2494 |
| | FSCN1_HUMAN | Q16658 | Fascin | 23 | 2.9 | 5272 | 12192 | 4268 | 9920 |
| | | | | | 3.2 | 5270 | 13501 | 4172 | 12927 |
| | | | | | 3.8 | 14077 | 43171 | 11509 | 34373 |
| | | | | | 2.9 | 2193 | 4564 | 1864 | 5420 |
| | | | | | 3.7 | 1457 | 4827 | 1297 | 2691 |
| | | | | | 3.0 | 1277 | 2967 | 1015 | 3039 |
| | | | | | 2.3 | 1686 | 3669 | 1582 | 2883 |
| | | | | | 2.5 | 3769 | 8074 | 3263 | 7013 |
| | | | | | 2.6 | 11477 | 26754 | 10218 | 25086 |
| | ICAM1_HUMAN | P05362 | Intercellular adhesion molecule 1 | 65 | 2.2 | 2034 | 3073 | 1611 | 3474 |
| | | | | | 2.2 | 1923 | 3181 | 1669 | 3685 |
| | | | | | 1.6 | 2443 | 3615 | 2201 | 3591 |
| | | | | | 4.5 | 712 | 1451 | 459 | 2047 |
| | NAMPT_HUMAN | P43490 | Nicotinamide phosphoribosyl-transferase | 66 | 2.4 | 1108 | 2306 | 1146 | 2659 |
| | | | | | 2.2 | 3132 | 6743 | 3159 | 6311 |
| | | | | | 2.2 | 10385 | 22063 | 10021 | 19083 |
| | | | | | 2.3 | 1595 | 3727 | 1618 | 3501 |
| | | | | | 3.0 | 1117 | 3243 | 1076 | 1860 |
| | KYNU_HUMAN | Q16719 | Kynureninase | 67 | 1.8 | 5499 | 9648 | 5472 | 8408 |
| | | | | | 1.7 | 1985 | 3298 | 1907 | 2875 |
| | NMES1_HUMAN | Q9C002 | Normal mucosa of esophagus-specific gene 1 protein | 68 | 4.2 | 3296 | 12391 | 2947 | 10587 |
| | | | | | 2.6 | 2542 | 5287 | 2380 | 6293 |
| | PLEK_HUMAN | P08567 | Pleckstrin | 69 | 1.6 | 6202 | 7374 | 5583 | 8952 |
| | | | | | 1.8 | 4865 | 5383 | 4404 | 8014 |
| | SODM_HUMAN | P04179 | Superoxide dismutase [Mn], mitochondrial | 70 | 3.1 | 1688 | 5243 | 1720 | 2998 |
| | | | | | 2.6 | 3540 | 9075 | 3831 | 7881 |
| | | | | | 3.0 | 2416 | 7274 | 2509 | 4560 |
| | | | | | 2.3 | 8143 | 18609 | 8426 | 13174 |
| | | | | | 3.0 | 3217 | 9671 | 3414 | 6175 |
| | SQSTM_HUMAN | Q13501 | Sequestosome-1 | 71 | 3.0 | 1446 | 2612 | 1340 | 4003 |
| | | | | | 3.3 | 2448 | 3825 | 2411 | 7969 |
| | TFR1_HUMAN | P02786 | Transferrin receptor protein 1 | 72 | 3.3 | 831 | 1655 | 706 | 2330 |
| | | | | | 2.9 | 1317 | 2671 | 1195 | 3406 |
| | THIO_HUMAN | P10599 | Thioredoxin | 73 | 2.3 | 2293 | 5159 | 2276 | 3532 |
| | | | | | 2.5 | 5734 | 13178 | 6045 | 5240 |
| | | | | | 2.1 | 10809 | 21593 | 10467 | 20805 |
| | | | | | 2.4 | 30419 | 69901 | 29547 | 50103 |
| | | | | | 2.3 | 101297 | 224091 | 103322 | 228649 |
| | | | | | 2.6 | 48549 | 118886 | 46574 | 117462 |

TABLE 2 D-continued

| Identification data | | | | Quantification data | | | | |
|---|---|---|---|---|---|---|---|---|
| Protein denomination | Accession number | Protein name | SEQ ID NO | Max. fold | Average normalized abundance | | | |
| TNR5_HUMAN | P25942 | Tumor necrosis factor receptor superfamily member 5 | 74 | 3.1 4.3 5.8 | 5447 5861 834 | 10298 12674 1816 | 3752 3587 431 | 11645 15265 2516 |
| TRAF1_HUMAN | Q13077 | TNF receptor-associated factor 1 | 75 | 3.7 4.8 | 1818 2328 | 4985 9905 | 1732 2223 | 6495 10621 |
| WDR1_HUMAN | O75083 | WD repeat-containing protein 1 | 76 | 1.6 1.6 | 2734 2553 | 2750 2394 | 2581 2605 | 1747 3843 |

TABLE 2 E

| | Identification data | | | | Quantification data | | | | |
|---|---|---|---|---|---|---|---|---|---|
| | Protein denomination | Accession number | Protein name | SEQ ID NO | Max. fold | Average normalized abundance | | | |
| Proteins upregulated in LPS-DCs | ANXA6_HUMAN | P08133 | Annexin A6 | 77 | 1.5 1.6 | 3787 1988 | 3652 2562 | 3594 2084 | 2467 1608 |
| | EF1A3_HUMAN | Q5VTE0 | Putative elongation factor 1-alpha-like 3 | 78 | 1.9 1.7 2.4 | 67654 49861 4234 | 69590 52072 4116 | 63692 48138 4145 | 121609 81980 9686 |
| | MX1_HUMAN | P20591 | Interferon-induced GTP-binding protein Mx1 | 41/42 | 3.5 | 1244 | 4136 | 1192 | 1198 |
| | PSA7_HUMAN | O14818 | Proteasome subunit alpha type-7 | 79 | 1.5 1.5 | 3424 2203 | 3013 2612 | 3617 2212 | 4544 1693 |

TABLE 2 F

| | Identification data | | | | Quantification data | | | | |
|---|---|---|---|---|---|---|---|---|---|
| | Protein denomination | Accession number | Protein name | SEQ ID NO | Max fold | Average normalized abundance | | | |
| Proteins upregulated in PGN-DCs | 6PGD_HUMAN | P52209 | 6-phosphogluconate dehydrogenase, decarboxylating | 80 | 1.6 1.7 | 7835 8080 | 7137 8587 | 7616 8579 | 11625 13947 |
| | ACBP_HUMAN | P07108 | Acyl-CoA-binding protein | 81 | 2.1 1.5 | 12747 21984 | 13940 21707 | 12757 21195 | 6564 31805 |
| | ACTN4_HUMAN | O43707 | Alpha-actinin-4 | 82 | 2.4 1.6 | 2497 2829 | 2295 2951 | 2406 2737 | 5406 4340 |
| | ANX11_HUMAN | P50995 | Annexin A11 | 83 | 1.9 1.7 1.5 | 29177 25413 2783 | 28473 23614 2429 | 30290 26068 2938 | 16267 41108 3724 |
| | ARP3_HUMAN | P61158 | Actin-related protein 3 | 84 | 2.0 1.7 | 10799 5713 | 8498 5402 | 10123 5595 | 17278 9284 |
| | ARPC2_HUMAN | O15144 | Actin-related protein 2/3 complex subunit 2 | 85 | 1.9 2.7 2.2 | 8144 2497 2120 | 7600 2208 2096 | 7669 2481 2113 | 14592 5972 4670 |
| | CALM_HUMAN | P62158 | Calmodulin | 86 | 1.7 1.6 3.4 2.0 | 19131 27338 1950 1391 | 18507 24856 1647 1018 | 20170 28457 1540 1527 | 12032 40690 5173 2081 |
| | CAP1_HUMAN | Q01518 | Adenylyl cyclase-associated protein 1 | 87 | 2.2 1.6 | 2453 5612 | 1914 5082 | 2147 5398 | 4261 7997 |
| | CLH1_HUMAN | Q00610 | Clathrin heavy chain 1 | 88 | 2.0 1.5 | 2646 2071 | 2409 1815 | 2683 2052 | 4770 2731 |

TABLE 2 F-continued

| | Identification data | | | Quantification data | | | | |
|---|---|---|---|---|---|---|---|---|
| Protein denomination | Accession number | Protein name | SEQ ID NO | Max fold | Average normalized abundance | | | |
| COF1_HUMAN | P23528 | Cofilin-1 | 89 | 1.6 | 28916 | 29249 | 29655 | 18615 |
| | | | | 2.2 | 2888 | 3028 | 2876 | 1358 |
| | | | | 2.4 | 14082 | 13247 | 13903 | 31963 |
| COX5B_HUMAN | P10606 | Cytochrome c oxidase subunit 5B, mitochondrial | 90 | 1.8 | 2269 | 2263 | 2478 | 1385 |
| | | | | 2.5 | 2647 | 2120 | 2694 | 5286 |
| CYTB_HUMAN | P04080 | Cystalin-B | 91 | 1.6 | 4050 | 4392 | 4316 | 2750 |
| | | | | 1.9 | 47731 | 43797 | 47260 | 81174 |
| ECHM_HUMAN | P30084 | Enoyl-CoA hydratase, mitochondrial | 92 | 1.7 | 5282 | 4105 | 5561 | 3213 |
| | | | | 4.1 | 1390 | 976 | 1389 | 3957 |
| EF1A1_HUMAN | P68104 | Elongation factor 1-alpha 1 | 93 | 1.9 | 44018 | 49843 | 43272 | 26910 |
| | | | | 1.6 | 9984 | 12310 | 9823 | 7657 |
| | | | | 2.2 | 19725 | 23516 | 18225 | 10533 |
| | | | | 1.8 | 4207 | 4434 | 2788 | 4953 |
| F16P1_HUMAN | P09467 | Fructose-1,6-bisphosphatase 1 | 94 | 1.9 | 3474 | 3117 | 3355 | 6021 |
| | | | | 1.9 | 2955 | 2762 | 3025 | 5129 |
| FLNA_HUMAN | P21333 | Filamin-A | 95 | 2.8 | 3767 | 3152 | 3658 | 1361 |
| | | | | 1.8 | 4386 | 4693 | 4177 | 2678 |
| | | | | 1.7 | 3116 | 3220 | 2964 | 1920 |
| | | | | 1.6 | 1482 | 1350 | 1521 | 2204 |
| | | | | 2.1 | 10372 | 7891 | 9894 | 16647 |
| | | | | 2.3 | 4111 | 3596 | 4065 | 8390 |
| | | | | 1.8 | 2763 | 2649 | 2675 | 4794 |
| | | | | 2.5 | 1314 | 1057 | 1268 | 2625 |
| | | | | 2.2 | 2367 | 2040 | 2150 | 4456 |
| | | | | 1.7 | 10756 | 9626 | 10527 | 16365 |
| GDIB_HUMAN | P50395 | Rab GDP dissociation inhibitor beta | 96 | 1.8 | 3088 | 2702 | 3031 | 4767 |
| | | | | 1.8 | 29167 | 27659 | 27971 | 33420 |
| | | | | 1.9 | 1330 | 1122 | 1245 | 2159 |
| GNAI1_HUMAN | P63096 | Guanine nucteotide-binding protein G(i) subunit alpha-1 | 97 | 1.8 | 7841 | 7275 | 8117 | 13432 |
| | | | | 2.0 | 3280 | 2893 | 3390 | 5829 |
| H2AV_HUMAN | Q71UI9 | Histone H2A.V | 98 | 2.1 | 8760 | 7334 | 9216 | 15245 |
| | | | | 2.5 | 2328 | 3610 | 3327 | 1444 |
| H4_HUMAN | P62805 | Histone H4 | 21 | 1.6 | 9501 | 10197 | 10167 | 6530 |
| | | | | 3.0 | 44202 | 28398 | 44775 | 85837 |
| | | | | 2.7 | 13431 | 12607 | 14756 | 34129 |
| | | | | 1.9 | 3762 | 3287 | 3887 | 6319 |
| HS90A_HUMAN | P07900 | Heat shock protein HSP 90-alpha | 99 | 1.6 | 3179 | 2640 | 3037 | 4306 |
| | | | | 2.9 | 1240 | 1083 | 1109 | 3161 |
| ILEU_HUMAN | P30740 | Leukocyte elastase inhibitor | 100 | 1.6 | 15255 | 16333 | 16589 | 10496 |
| | | | | 1.8 | 9134 | 9256 | 9906 | 16632 |
| IQGA1_HUMAN | P46940 | Ras GTPase-activating-like protein IQGAP1 | 101 | 2.5 | 1506 | 1102 | 1510 | 2739 |
| | | | | 2.1 | 1585 | 2095 | 1701 | 1012 |
| | | | | 1.6 | 2925 | 2636 | 2910 | 4129 |
| | | | | 1.7 | 2150 | 1978 | 2318 | 3300 |
| LEG3_HUMAN | P17931 | Galectin-3 | 102 | 1.8 | 24791 | 21077 | 23155 | 38156 |
| | | | | 1.5 | 4219 | 3860 | 3980 | 5830 |
| LMNA_HUMAN | P02545 | Lamin-A/C | 32 | 2.1 | 1207 | 1193 | 1192 | 2484 |
| | | | | 2.1 | 1961 | 1899 | 1972 | 3937 |
| MYH9_HUMAN | P35579 | Myosin-9 | 103 | 1.6 | 13802 | 12193 | 13718 | 19168 |
| | | | | 1.9 | 2342 | 1780 | 2016 | 3410 |
| | | | | 1.8 | 2829 | 3314 | 2792 | 1856 |
| | | | | 1.5 | 3223 | 3506 | 2963 | 2329 |
| | | | | 1.5 | 3899 | 3633 | 3854 | 5593 |
| | | | | 2.1 | 4215 | 3497 | 3959 | 7451 |
| | | | | 2.0 | 3957 | 3759 | 4102 | 7534 |
| | | | | 2.6 | 6062 | 8037 | 6107 | 3050 |
| | | | | 2.0 | 3650 | 3065 | 3513 | 6124 |
| | | | | 1.6 | 3997 | 5113 | 4218 | 6414 |
| | | | | 1.8 | 1426 | 1200 | 1492 | 2176 |
| | | | | 1.9 | 1761 | 1416 | 1955 | 2658 |
| MYL6_HUMAN | P60660 | Myosin light polypeptide 6 | 104 | 2.0 | 21271 | 24544 | 20606 | 18109 |
| | | | | 2.2 | 2846 | 2685 | 2787 | 5834 |
| NDKB_HUMAN | P22392 | Nucleoside diphosphate kinase B | 105 | 2.1 | 4231 | 3605 | 3903 | 7740 |
| | | | | 2.2 | 2548 | 2287 | 2577 | 5053 |
| NSF_ | P46459 | Vesicle-fusing | 106 | 1.7 | 3280 | 2971 | 3268 | 4976 |

TABLE 2 F-continued

| Identification data | | | | Quantification data | | | | |
|---|---|---|---|---|---|---|---|---|
| Protein denomination | Accession number | Protein name | SEQ ID NO | Max fold | Average normalized abundance | | | |
| HUMAN | | ATPase | | 1.7 | 1491 | 1454 | 1486 | 2442 |
| PDIA1_ HUMAN | P07237 | Protein disulfide-isomerase | 107 | 2.1 | 3666 | 3482 | 3215 | 6621 |
| | | | | 3.4 | 3132 | 2300 | 2705 | 7867 |
| *PGRP1_ BOVIN | Q8SPP7 | *Peptidoglycan recognition protein 1 OS = Bos indicus | 108 | 91.8 | 129 | 130 | 129 | 11807 |
| PLEC_ HUMAN | Q15149 | Plectin | 109 | 1.8 | 3420 | 3204 | 3209 | 5755 |
| | | | | 1.5 | 2759 | 2586 | 2821 | 3965 |
| PLSL_ HUMAN | P13796 | Plastin-2 | 110 | 1.6 | 6023 | 7292 | 5858 | 4563 |
| | | | | 1.7 | 9257 | 8937 | 8816 | 15216 |
| SYWC_ HUMAN | P23381 | Tryptophanyl-tRNA synthetase, cytoplasmic | 33 | 1.7 | 2480 | 3179 | 2399 | 1909 |
| | | | | 1.5 | 2688 | 3704 | 2447 | 2505 |
| | | | | 2.2 | 1195 | 1355 | 1185 | 2649 |
| TCPE_ HUMAN | P48643 | T-comptex protein 1 subunit epsilon | 111 | 1.5 | 1600 | 1588 | 1619 | 2383 |
| | | | | 1.5 | 2604 | 2511 | 2612 | 3887 |
| TKT_ HUMAN | P29401 | Transketolase | 112 | 1.8 | 5398 | 5362 | 5995 | 3381 |
| | | | | 2.1 | 6464 | 5853 | 7224 | 12506 |
| TLN1_ HUMAN | Q9Y490 | Talin-1 | 113 | 1.8 | 5380 | 4564 | 5162 | 8101 |
| | | | | 2.0 | 1392 | 1238 | 1324 | 2452 |
| | | | | 1.7 | 6109 | 5101 | 6034 | 8428 |
| TYPH_ HUMAN | P19971 | Thymidine phosphorylase | 114 | 3.0 | 3598 | 8066 | 4725 | 2708 |
| | | | | 3.0 | 3288 | 3614 | 2814 | 8569 |
| | | | | 2.2 | 4122 | 8395 | 5466 | 3873 |
| VATA_ HUMAN | P38606 | V-type proton ATPase catalytic subunit A | 115 | 1.6 | 2526 | 2345 | 2379 | 1622 |
| | | | | 1.8 | 4121 | 3746 | 4025 | 6649 |

TABLE 3

| Type of proteins | Identification Method | Protein denomination | Protein Name | Fold increase in mRNA (DEX-DCs vs. Ctrl-DCs) | Go annotation function (nextprot) | Involvement in effector immunity/tolerance |
|---|---|---|---|---|---|---|
| Proteins upregulated and validated in tolerogenic DCs | 2D-DiGE | GPX1_ HUMAN | Glutathione peroxidase 1 | 4.7 | Oxidoreduction | GPX1-KO mice → symptoms and pathology of inflammatory bowel disease |
| | | IMDH2_ HUMAN | Inosine-5' monophosphate dehydrogenase 2 | 4.2 | Oxidoreduction GMP/purine biosynthesis | Induction after glucocorticoid and mycophenolate mofetil treatment |
| | | OSTF1_ HUMAN | Osteoclast stimulating factor 1 | 2.7 | Signal transduction, ossification | Unknown |
| | | TPP1_ HUMAN | Tripeptidyl-peptidase 1 | 2.9 | Serine protease, lysosomal hydrolase | Correlation with colorectal carcinoma progression and metastasis |
| | 2D-DiGE and label free MS | ANXA1_ HUMAN | Annexin A1 | 3.9 | Signal transduction | Inhibition of inflammatory mediators generation<br>Higher levels in healthy buccal tissues when compared with inflammatory exudates from the periodontal tissue<br>ANXA1-KO mice → exacerbation of arthritis<br>ANXA1 auto-antibodies in patients with inflammatory disorders like rheumatoid arthritis, systemic and cutaneous lupus erythematosus |
| | | CLIC2_ HUMAN | Chloride intracellular channel protein 2 | 4.6 | Ion channel, ion transport | Unknown |
| | | F13A_ HUMAN | Coagulation factor XIII A chain | 6.2 | Coagulation factor | Intracellular expression in dermal DCs<br>Local consumption and/or loss of Factor XIII within the inflamed tissue during acute episodes of inflammatory bowel diseases<br>Human deficiency is associated with impaired wound healing |
| | | FKBP5_ HUMAN | Peptidyl-prolyl cis-trans isomerase | 14.9 | Chaperone | Induction after glucocorticoid treatment |

TABLE 3-continued

| Type of proteins | Identification Method | Protein denomination | Protein Name | Fold increase in mRNA (DEX-DCs vs. Ctrl-DCs) | Go annotation function (nextprot) | Involvement in effector immunity/tolerance |
|---|---|---|---|---|---|---|
| | Label free MS | C1QB_HUMAN | Complement C1q subcomponent subunit B | 12.4 | Complement subunits, innate immunity, signal transduction | Component of the classical complement pathway. Binds to immune complexes to elicit microbial killing and enhance phagocytosis |
| | | C1QC_HUMAN | Complement C1q subcomponent subunit C | 6.7 | | Treatment of moDCs with C1q induces tolerogenic DCs secreting IL-10, capable to phagocytose apoptotic cells Human deficiency leads to the development of lupus-like autoimmune disease. Deficient patients are at greater risks of spontaneous miscarriages or preterm birth Importance during the early stage of pregnancy |
| | | CATC_HUMAN | Dipeptidyl peptidase 1 | 4.1 | Thiol protease, hydrolase, activation of F13A | Overexpression in adenocarcinomas when compared to the normal gastric mucosa Human deficiency is associated with the Papillon-Lefèvre syndrome characterized by severe early-onset periodontitis (gingival inflammation and loss of connective tissues supporting the teeth) |
| | | MRC1_HUMAN | Macrophage mannose receptor 1 | 4.7 | Endocytosis, phogocytosis of glycoproteins | Mediate allergen uptake by DCs Ligation by tumoral mucins on tumor associated macrophages induces an immunosuppressive profile Crosslinking on moDCs induces anergic suppressive/requlatory DCs |
| | | STAB1_HUMAN | Stabilin-1 | 11.7 | Receptor of acetylated LDL, inflammatory response | Induction after glucocorticoid treatment Expression by alternatively activated macrophages in the placenta and in tissues during wound healing Silencing in placental leukocytes increased the secretion of the pro-inflammatory cytokine TNF-□ Presence of CD11b⁺ F4/80⁺ STAB-1⁺ macrophages in malignant tumors |
| Proteins upregulated and validated in efffector DCs | 2D-DiGE | IRF4_HUMAN | Interferon regulatory factor 4 | 2.3/1.1 | Transcription activator | Induction during DCs differentiation and maturation IRF4-KO mice → resistant to experimental autoimmune encephalomyelitis induction, no development of Th17 cells Controls Th2 mediated immune responses in vitro and in vivo |
| | 2D-DiGE and label free MS | MX1_HUMAN | Interferon-induced GTP-binding protein | 8.7/−2.2 | Antiviral defense | Antiviral activity against RNA viruses Induction in human DCs after LPS stimulation |
| | | FSCN1_HUMAN | Fascin | 7.9/4.5 | Cytoskeleton organization Cell motility | Induction in DCs upon maturation, crucial in the development of dendrites Role during the formation of immunological synapses |
| | Label free MS | CD71/TFRC_HUMAN | Transferrin receptor protein 1 | 4.2/3.7 | Endocytosis, Host-virus interaction, iron homeostasis | Specific upregulation on moDCs after incubation with inflammatory cytokines or maturating agents (Pasquier, Lepelletier et al. 2004) Strong CD71 expression in macrophage from human tonsils after chronic inflammation Expressed by alveolar monocytes/macrophages in patients with allergic asthma or pulmonary sarcoidosis |
| | | NMES1_HUMAN | Normal mucosa of esophagus-specific gene 1 protein | 15.3/14.5 | unknown | Downregulation in human esophageal squamous cell carcinoma |
| | | PGRP1_BOVIN | Peptidoglycan receognition protein 1 | 1/91.5 | Innate immunity, antibiotic, antimicrobial | Pattern receptor that binds murein peptidoglycans of Gram-positive bacteria and has bactericidal activity |
| | | TRAF1_HUMAN | TNF receptor-associated factor 1 | 8.9/10.0 | TNF receptor signaling pathway. Regulation of Apoptosis | Adapter molecule that regulated the activation of NF-κB and JNK TRAF1-KO mice → Impaired goblet cell hyperplasia, eosinophilic inflammation and airway hyperreponsivenes in a model of asthma Expression required in resident lung DCs for the development of asthma. |

All the sequences with the accession numbers given in the application are those present in the recited database at the date of filing. All documents referred to herein are hereby incorporated by reference in their entirety.

The present invention will be further illustrated by the additional description and drawings which follow, which refer to examples illustrating the characterization of markers of dendritic cell subsets, and their role in assessing the clinical response of patients undergoing anti-allergy immunotherapy. It should be understood however that these examples are given only by way of illustration of the invention and do not constitute in any way a limitation thereof.

Figure 1:
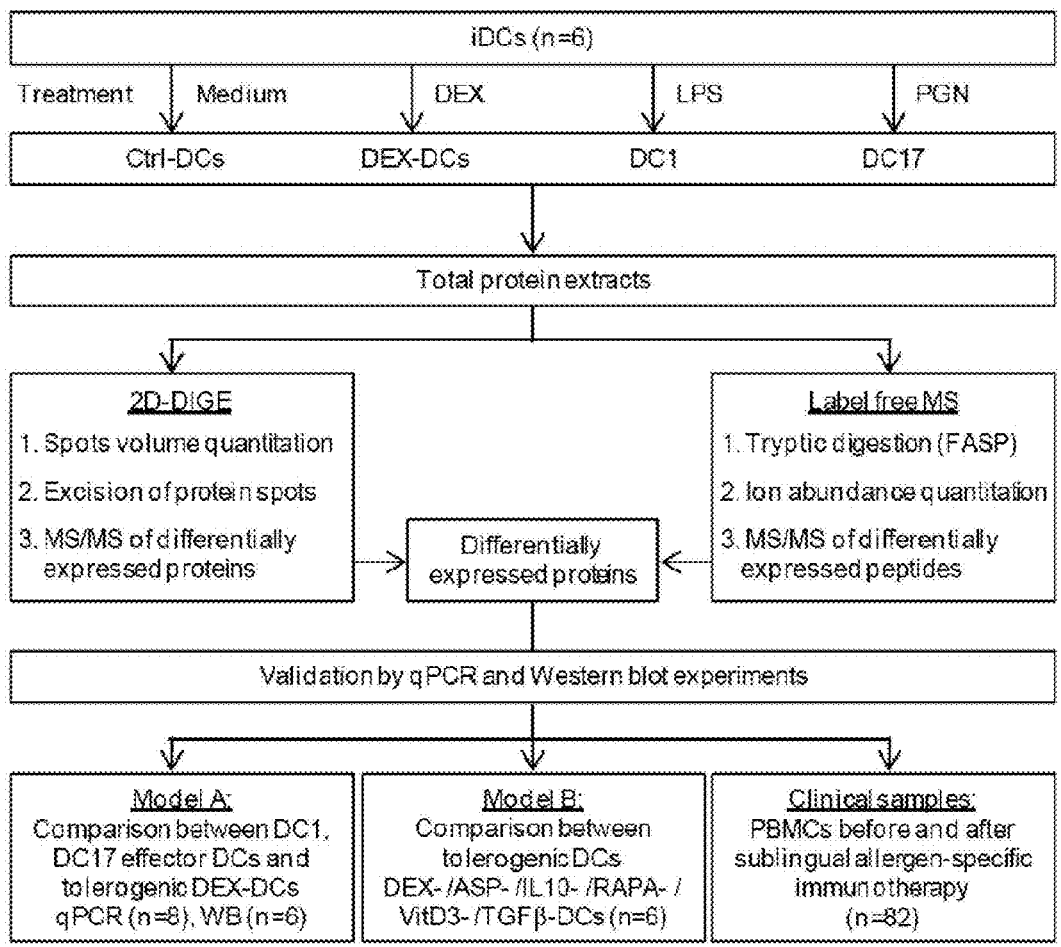
FIG. 1 is a schematic outline of the study methodology. Total proteins were extracted from treated DCs (Ctrl-, LPS-, DEX- and PGN-DCs) and subjected to either 2D-DIGE or label-free MS quantitation (FASP, Filter Aided Sample Preparation; Wisniewski et al. Nat. Methods, 6.

359-362, 2009). Differentially expressed protein spots or peptides were then identified after MS/MS analysis. Candidate markers of tolerogenic DCs were validated by western blotting (WB) and/or qPCR in Ctrl-, LPS-, DEX- and PGN-DCs (model A), in 6 distinct tolerogenic DC types (model B) and in clinical samples (PBMCs) obtained from allergic patients undergoing allergen-specific immunotherapy. In model A, WB were performed from whole cell lysates used in proteomics experiments and additional treated DC samples were collected from 8 donors for qPCR validation. In model B, DC samples were used for both WB and qPCR validations. In the clinical study, PBMCs (n=328) were collected from 82 patients before and after immunotherapy and ex vivo restimulated or not with grass-pollen allergen extract.

FIG. 2 illustrates the results of an in vitro treatment of DCs with LPS, PGN or DEX. It shows that treatment of DCs with LPS, PGN or DEX induced pro-inflammatory (DC1, DC17) and tolerogenic DCs respectively.

Monocytes were isolated from PBMCs by negative selection and cultured 6 days in the presence of IL-4 and GM-CSF to generated moDCs. Cells were treated with either LPS (1 µg/ml), PGN (10 µg/ml) or DEX (1 µg/ml) for 24 h.

(A) Cell surface phenotype was assessed by flow cytometry after staining with Abs against CD80, CD83, CD86, ILT2, ILT3 and ILT4 (dashed line: isotype control, plain line: Ctrl-DCs, filled in grey: treated-DCs).

(B) Tolerogenic genes expression (GILZ, IDO, RALDH1 and RALDH2) was assessed by qPCR analysis.

(C) Cytokine production was analyzed by ELISA or CBA (IL-1b, IL-6, IL-8, IL-10, IL-12p70, IL-23 and TNF-a).

(D/E) DCs were cocultured with naïve CD4+ T cells during 5 days and polarization cytokines were analyzed by qPCR or CBA (IFN-g, IL-4, IL-9, IL-10, IL-13, IL-17A). A representative donor out of four is presented in A, whereas mean±SEM values of 4 independent donors are presented in B to E.

FIG. 3 illustrates the markers of tolerogenic DCs identified by 2D-DIGE.

Proteins were considered significantly differentially expressed in DEX-DCs with a FDR p-values≤0.05 and at least a 1.2-fold change in volume (see Table 1).

(A) Representative Cy2 image obtained from a 2DDIGE gel with localization of differentially overexpressed protein spots. Whole cell extracts were fractionated using narrow range pH gradient gels (pI range of 5.3 to 6.5, 1 pH unit/24 cm) in the first dimension and a 11% SDS PAGE in the second dimension. Protein spots marked with an arrow are upregulated in DEX-DCs and described in suppl. Table 1.

(B/C) Western blot analyses of target proteins in Ctrl-, LPS-, DEX- and PGN-DCs. Two representative donors are presented in B whereas mean±SEM of 6 independent experiments are presented in C. *p-value≤0.05, **p-value≤0.01 were considered significant (Wilcoxon test). β-actin was used as loading control.

(D) Validation of tolerogenic genes at the mRNA level by qPCR. Data are expressed as relative amounts of mRNA in treated DCs in comparison with Ctrl-DCs. Data are normalized to amounts of β-actin and shown as mean±SEM.

FIG. 4 illustrates differentially-expressed inflammatory proteins identified by proteomic approaches.

Proteins significantly upregulated in effector DCs detected with 2D-DIGE (FDR p-value≤0.05 and at least a 1.2 fold change, see also Table 1) and label-free MS (FDR p-value≤0.01 and at least a 1.5 fold change, Table 2).

(A) Cy2 image obtained from a 2D-DIGE gel, with localization of differentially expressed protein spots. Whole cell extracts were fractionated using narrow range pH gradient gels (pI range of 5.3 to 6.5, 1 pH unit/24 cm) in the first dimension and a 11% SDS PAGE in the second dimension. Protein spots marked with an arrow are upregulated in LPS- and/or PGN-DCs and described in Table 1.

(B/C) Western blot analysis of target proteins in Ctrl-, LPS-, DEX- and PGN-DCs. Two representative donors are presented in B whereas mean±SEM of 6 independent experiments are presented in C. *p-value≤0.05, **p-value≤0.01 were considered significant (Wilcoxon test). β-actin was used as loading control.

(D) Validation of pro-inflammatory genes at the mRNA level by qPCR. Data are expressed as relative amounts of mRNA in treated DCs in comparison with Ctrl-DCs. Data are normalized to amounts of β-actin and shown as mean±SEM.

Figure 5:
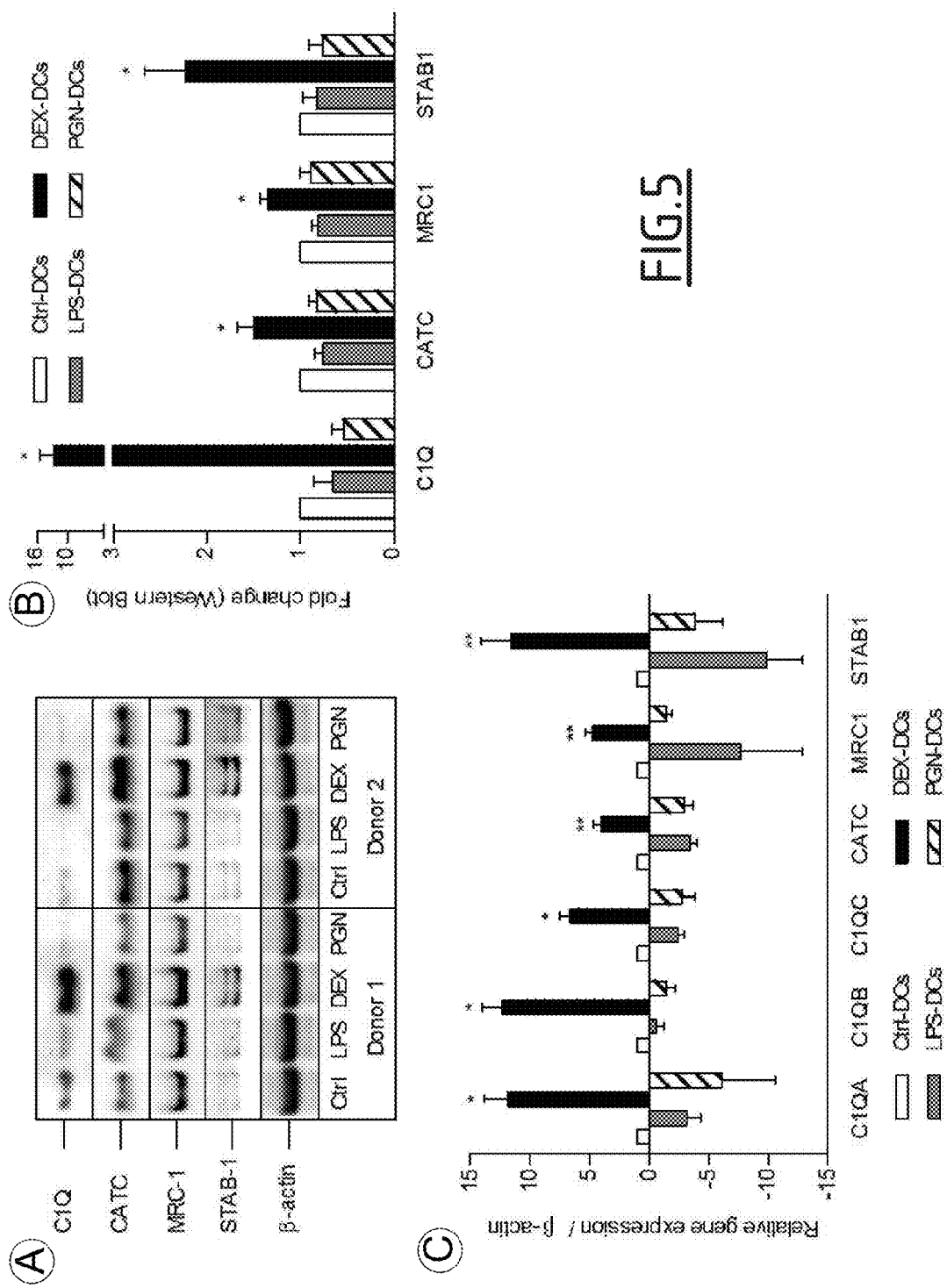

FIG. 5 illustrates markers of regulatory DCs identified by label-free MS.

(A/B) Western blot analysis of upregulated proteins in DEX-DCs with a FDR p-value≤0.01 and at least a 1.5-fold change in abundance (see also Table 2). Two representative donors are presented in D whereas mean±SEM of 6 independent experiments are presented in E. *p-value≤0.05, **p-value≤0.01 were considered significant (Wilcoxon test). β-actin was used as loading control.

(C) Validation of tolerogenic genes at the mRNA level by qPCR. Data are expressed as relative amounts of mRNA in treated DCs in comparison with Ctrl-DCs. Data are normalized to amounts of β-actin and shown as mean±SEM.

FIG. 6 illustrates the characterization of new in vitro models of tolerogenic DCs.

DEX-DCs were used as a control and compared to ASP-DCs (24 h treatment), DEX, IL-10, RAPA, VitD3 or TGFb-DCs generated after treatment with pharmacological or biological agents during the differentiation step [IL-10 (10 ng/ml), TGFb (20 ng/ml), Rapamycin (10 nM), 1,25 dihydroxy-vitamin D3 (10 nM)].

(A) Cell surface phenotype was assessed by flow cytometry after staining with Abs against CD11c, CD14, ILT2, ILT3 and ILT4.

(B) Percentage of inhibition of LPS-induced expression of costimulatory molecules in differentially treated DCs.

(C) Inhibition of LPS-induced cytokine secretion in differentially treated DCs. 100% represents a complete inhibition of the expression/secretion of the molecule. A representative donor out of four is presented in A, whereas mean±SEM values of 6 independent donors are presented in B and C.

FIG. 7 illustrates the validation of candidate markers in different models of tolerogenic DCs.

(A/B) Western blot analysis of target proteins in treated DCs. Two representative donors are presented in A whereas mean±SEM of 6 independent experiments are presented in B. *p-value≤0.05, **pvalue≤0.01 were considered significant (Wilcoxon test). GAPDH was used as loading control.

(C/D) Validation of tolerogenic genes at the mRNA level by qPCR. Data are expressed as relative amounts of mRNA in treated DCs in comparison with Ctrl-DCs. Data are normalized to amounts of GAPDH and shown as mean±SEM (n=6).

FIG. 8 illustrates mRNA expression of C1QA, C1QB, C1QC and STAB1 in PBMCs from 82 patients correlates with the clinical efficacy of allergen-specific immunotherapy.

(A) mRNA expression of C1QA, C1QB, C1QC and STAB1 in unrestimulated PBMCs from 82 patients in the active group in comparison to the placebo group or in responders (% ARTSS≥43.9) versus non responders (% ARTSS<43.9) (Mann-Whitney test). Data are expressed as relative amounts of mRNA in PBMCs after treatment in comparison with PBMCs before immunotherapy. Data are normalized to amounts of b-actin and shown as a mean±SEM for each group.

(B) Correlation of mRNA expression of each individual patient with clinical improvement (% ARTSS) in the active and placebo group. R represents the Spearman correlation coefficient. 1 represents a perfect correlation, whereas a score between 0 and 1 indicates that the two variables increase or decrease together. (AR: active responders, ANR: active non responders, PR: placebo responders, PNR: placebo non responders).

EXAMPLE 1

Materials and Methods

Monocyte-derived DC Polarization

Human PBMCs were separated out of buffy coats obtained from healthy volunteers (Etablissement Francais du Sang, Rungis, France) by centrifugation over a Ficoll-Paque plus gradient (PAA, Les Mureaux, France). Monocytes were purified through negative selection with the untouched human monocyte kit (Dynal, Invitrogen, Cergy Pontoise, France). To generate monocyte-derived DCs, 5 to 8.107 cells were cultured at 37° C., 5% $CO_2$ in RPMI medium with stable glutamine supplemented with 10 µg/ml gentamycin, 50 µM 2-ME, 1% non essential amino acids (all from Invitrogen) and 10% fetal calf serum (Gentaur, Brussels, Belgium) in presence of human rGM-CSF and rIL-4 (Gentaur), using 250 and 100 ng/ml concentrations, respectively. After 6 days, a pure population of DCs was obtained, with more than 95% of $CD14^-$ $CD11c^+$ cells detected by flow cytometry using a FC500 cytometer and the CXP analysis software (Beckman Coulter, Villepinte, France) or Flowjo software (TreeStar, Olten, Switzerland). Up to 107 DCs were plated in presence of either medium, dexamethasone, (DEX, 1 µg/ml [2.5 µM], Sigma-Aldrich, Saint-Quentin Fallavier, France), highly purified lipopolysaccharide (LPS) from *Escherichia coli* (1 µg/ml, InvivoGen, Toulouse, France), or peptidoglycan from *Staphylococcus aureus* (PGN, 10 µg/ml, InvivoGen) for 24 h at 37° C. and 5% $CO_2$ (Model A, FIG. 1). For tolerogenic DCs models (Model B, FIG. 1), cells were cultured for 24 h with either DEX or proteases from *Aspergillus oryzae* (ASP, 20 µg/ml, Sigma-Aldrich) as described elsewhere (see Zimmer, A. et al. J. Immunol. 186: 3966-3976, 2011) or incubated during the differentiation step with either DEX, IL-10 (10 ng/ml, R&D Systems, Lille, France), TGFb (20 ng/ml, R&D Systems), Rapamycin (10 nM, Sigma-Aldrich) or 1,25 dihydroxy-vitamin D3 (10 nM, Sigma-Aldrich). Drugs were added to cultures at day 1, with fresh medium provided every other day. To monitor a potential anti-inflammatory effect, treated DCs were stimulated with LPS (1 µg/ml) during 24 h.

Characterization of Effector and Regulatory DCs

For immuno-fluorescence staining, cells were harvested, washed in PBS and incubated for 20 min at 4° C. with the following mAbs: FITC anti-CD14, FITC anti-CD80, PE anti-CD86, PC5 anti-CD83 (Beckman coulter), FITC anti-ILT2, PE anti-ILT4, PC5 anti-ILT3 (R&D systems) or PE-CD11c (Miltenyi Biotec, Paris, France). Cells were stained with corresponding isotype-matched control mAbs and analyzed by flow cytometry.

Cytokine measurement was performed in supernatants using the cytometric bead array technology or ELISA kits. IFN-g, IL-1b, IL-6, IL-8, IL-9, IL-10, IL-12p70, IL-13, IL-23, IL-17A and TNF-α were measured using the human inflammatory CBA kit or CBA flex sets (BD Biosciences, Le Pont de Claix, France) and analyzed by flow cytometry according to the manufacturer's instructions using a FACS Array instrument and the FCAP Software (BD Biosciences). IL-23 concentration was measured with an ELISA kit (Ebiosciences, Paris, France) as per the manufacturer's instructions.

DC/T coculture experiments were performed as described elsewhere (see Zimmer, A. et al. J. Immunol. 186: 3966-3976, 2011). Briefly, treated DCs were cultured with allogeneic naive CD4+ T cells at a 1:10 DCs/T ratio for 5 days. Naive CD4+ T cells were isolated from PBMCs by negative selection using the MACS naïve CD4 isolation kit II (Miltenyi Biotec), following the manufacturer's instructions. Such naive T cells were confirmed to be >95% pure based upon CD3, CD4, and CD45RA expression evaluated by flow cytometry.

Supernatants were analyzed for cytokine release as described above.

Differential Gel Electrophoresis Analysis of DC Subtypes

Polarized DCs were washed 3 times with cold PBS and cell pellets were lysed in buffer A containing 8.3 M urea, 2 M thiourea, 4% CHAPS, 50 mM DTT and 24 mM spermine (all obtained from Sigma-Aldrich). After centrifugation (16 000 g, 1 h, 20° C.), supernatants were recovered and stored at −80° C. Proteins were then quantified using a Bradford assay (Biorad, Marnes La Coquette, France) and fractionated over a 4-12% gradient precast gel (NuPAGE, Invitrogen) to control protein quality.

For 2D-DIGE analysis, 100 µg of proteins were precipitated using the PerfectFocus kit from GBiosciences, resuspended in DIGE labeling buffer containing 8.3 M Urea, 2 M Thiourea, 4% CHAPS and 30 mM Tris pH 8.8, labeled with Cy2/3/5 dyes (CyDye DIGE Fluors, GE Healthcare, Velizy, France) and separated on 24 cm Immobiline pH 5.3-6.5 Drystrip gels by isoelectrofocusing (IEF) using the Ettan IPGphor system (GE Healthcare). For analytical and preparative experiments, IEF was done for a total of 132 and 145 kVh, respectively. Strips were then equilibrated in reduction and alkylation buffers (containing 6 M Urea, 50 mM Tris pH 8.8, 30% glycerol, 2% SDS and either 1% DTT or 5% iodoacetamide) before loading onto 11% SDS-polyacrylamide gels for separation according to molecular mass using an Ettan DALT Six Electrophoresis System (GE Healthcare). DIGE gels were scanned using an Ettan DIGE Imager (GE Healthcare) according to the manufacturer's instructions. Differentially expressed spots were determined by image analysis with SameSpots software (Non linear Dynamics, Newcastle, England) and selected for automatic spot picking (FDR p-value≤05 and fold change≥1.2). Principal component analysis (PCA) and dendrogram plots were also carried out using SameSpots software. The relative nearness of samples in the PCA plot indicates similarity, whereas large distances between samples indicate dissimilarity in protein abundance. The correlation analysis (dendrogram plot) was performed on log normalized protein abundance levels. Proteins were then clustered according to how closely correlated they were.

Preparative gels stained with SYPRO Ruby (Invitrogen) were used for automatic spot picking (using an EXQuest spot cutter, Biorad) of differentially expressed protein spots.

Gel plugs were then washed with 200 µl of 100 mM NH$_4$HCO$_3$/50% acetonitrile (ACN) for 45 min at 37° C. and then dehydrated in ACN. Each spot was digested with trypsin (10 ng/µl of 40 mM NH4HCO3/10% ACN, Sigma-Aldrich) at 37° C. overnight and subsequently 6 µl of ACN was added to the mixture prior to ultrasonication for 45 min at 30° C. NanoLC-MS/MS analysis was accomplished using the Ultimate 3000 RS nano LC system (Dionex, Voisins le Bretonneux, France) coupled to an ESI-Qq-TOF MS (Maxis 3G) from Bruker Daltonics (Wissembourg, France). H2O/ACN/FA (100/0/0.1 volume ratios, respectively) was used as solvent A and H$_2$O/ACN/FA (20/80/0.1 volume ratios, respectively) as solvent B. Tryptic peptides diluted in 0.1% FA were injected and trapped on an Acclaim PepMap100 (100 µm×2 cm, C$_{18}$, 5 µm, 100 Å, Dionex) with a flow rate of 12 µl/min (2% ACN, 0.1% FA). Separation was performed using an Acclaim PepMap RSLC (75 µm×15 cm, C$_{18}$, 2 µm, 100 Å, Dionex) with a flow rate of 450 nl/min and a linear gradient (5-45% B for 45 min, 45-95% B for 1 min and 95% B for 15 min). Database search was carried out using an in-house Mascot server (Matrix Science, version 2.3) against the Swiss-Prot and NCBInr databases. Data were searched against the *Homo sapiens* or mammalian databases with precursor mass tolerance of 15 ppm and fragment mass deviation of 0.05 Da. The search included cysteine carbamidomethylation as a fixed modification and methionine oxidation as a variable modification. Up to two missed cleavages were allowed for protease digestion. All identifications were based on the sequencing of more than one peptide and only proteins with a Mascot score with 0.05 were considered for identification. Protein scores were derived from individual ions scores.

Label Free MS Analysis of DC Subtypes

Label-free MS of digested total protein lysates (solubilized in buffer A as described above), was conducted to compare proteomes of control, effector and regulatory DC subsets. Briefly, a common ultrafiltration device was used for detergent removal (CHAPS) to enable subsequent proteome analysis (Filter-aided sample preparation, FASP). 100 µg of proteins were mixed with urea-containing buffers in the filter unit (Amicon Ultra-0.5 ml, Ultracel-10 kDa Membrane, Millipore, Molsheim, France), reduced with 20 mM DTT, alkylated with 50 mM iodoacetamide, digested with Lys-C (37° C., 5 h, ratio 1/50, Sigma-Aldrich) and then with trypsin (37° C., overnight, ratio 1/50). After digestion, peptides were desalted using RPC18 Dynal magnetic beads (Invitrogen), acidified with FA and 1.5 to 2 µg of tryptic peptides were analyzed by nanoLC-MS or nanoLC-MS/MS.

NanoLC-MS analysis was accomplished using the Ultimate 3000 RS nano LC system (Dionex) coupled to an ESI-Qq-TOF MS (Maxis 3G) from Bruker Daltonics. H2O/ACN/FA (100/0/0.15 volume ratios respectively) was used as solvent A and H2O/ACN/FA (20/80/0.15 volume ratios respectively) as solvent B. 1.5 to 2 µg of tryptic peptides were injected (36 µl±3 µl) and trapped for 10 min on an Acclaim PepMap100 (100 µm×2 cm, C$_{18}$, 5 µm, 100 Å, Dionex) with a flow rate of 12 µl/min (2% ACN, 0.15% FA). Separation was then performed using an Acclaim PepMap RSLC (75 µm×50 cm, C$_{18}$, 2 µm, 100 Å, Dionex) with a flow rate of 270 nl/min, two linear gradient segments (5-25% B for 180 min, 25-45% B for 50 min) and holding at 95% B for a further 10 min before returning to 5% B for 20 min. In MS mode, full scan MS spectra were acquired from m/z 280 to 1500 (1 MS spectrum of 0.8 s) during 270 min. Ion intensities recorded in LC-MS data were analyzed using Progenesis LC-MS v3.1 software (Non Linear Dynamics) to provide reliable measurements of peptide (feature) abundance across samples. Internal calibration was performed by enabling the lock mass option in MS mode (minimum intensity>200 and mass±0.015 Da). Parameters used for peptide detection were peptide intensity>300, peptide abundance>2000 and 2$^+$≤peptide charge≤6$^+$. Data were then normalized by the "normalize to all features" method and comparison between the four groups (obtained from Ctrl-, LPS-, DEX- and PGN-DCs respectively) was performed to choose which peptides were statistically differentially represented (FDR p-value≤0.01 and fold change≥1.5). PCA and dendrogram plots were also carried out□ using Progenesis LC-MS software. Targeted nanoLC-MS/MS were accomplished by means of an inclusion mass list in the MS instrument method. Inclusion lists were generated from differentially expressed peptides and imported into MS acquisition software (mass±0.02 Da and retention time±3 min). LCMS/MS data were analyzed using an in-house Mascot server (Matrix Science, version 2.3) against the UniProt/Swiss-Prot database, taxonomy *Homo sapiens* or mammalia, assuming tryptic or semi-tryptic digestion. Identification parameters were identical to those described for 2D-DIGE analysis. Peptide identifications were accepted if established with a greater than 95% probability, as specified by Mascot software. For accurate mass measurements, the lock mass option was enabled in MS and MS/MS mode. Both m/z 299.2945 (methylstearate, Sigma-Aldrich) and m/z 1221.9906 ions (Chip cube high mass reference, Agilent, Massy, France) generated in the electrospray process from ambient air were used for internal recalibration.

Western Blot Analysis

NuPAGE-Western blotting was carried out according to standard procedures (NuPAGE technical guide, Invitrogen). Samples were separated on 4 to 12% MES, 3 to 8% Tris acetate or 10 to 20% Tris glycine NuPAGE, depending upon the molecular mass of target proteins. The following primary antibodies were used for immunoblotting analyses: anti-ANXA1 (Cat. no. 3299, 1/1000), anti-GAPDH (Cat. no. 14C10, 1/1000), anti-GPX1 (Cat. no. 3286, 1/1000), anti-IRF4 (Cat. no. 4964, 1/1000) and anti-TRAF1 (45D3, 1/1000) from Cell Signaling Technology (Danvers, Mass.), anti-β-actin (Cat. no. MS-1295, 1/2000) and anti-Factor XIIIA (Cat. no. RB-1464, 1/1000) from Neomarkers (Labvision, Cheshire, England), anti-FKBP5 (Cat. no. H00002289-MO2, 1/250) and anti-MX1 (Cat. no. H00004599-B01P, 1/500) from Abnova (Taipei, Taiwan), anti-CD71 (Cat. no. TA307375, 1/1000) from Origene (Rockville, Md.), anti-CATC (Cat. no. sc-74590, 1/500), anti-NMES1 (Cat. no. sc-138479, 1/500) and anti-STAB1 (Cat. no. sc-98788, 1/500) from Santa Cruz (Santa Cruz, Calif.), anti-MRC1 (Cat. no. 18704-1-AP, 1/1000) from Proteintech group (Manchester, England), anti-C1Q (Cat. no. ab71089, 1/1000) from Abcam (Paris, France). The rabbit polyclonal serum raised against GILZ was previously described (see Asselin-Labat, et al. Blood, 104: 215-223, 2004). Peroxidase-conjugated goat anti-mouse and anti-rabbit secondary antibodies were both obtained from Jackson Immunoresearch Laboratories (Sufflok, England), and the chemiluminescence detection kit was from Pierce (SuperSignal West Pico Chemiluminescent Substrate, Fisher Scientific, Illkirch, France). Western blot signals were acquired with a CCD camera (Fusion FX7, Vilber-Lourmat, Marnes La Vallée, France) and band volume was quantified using the Bio-1D software (Vilber-Lourmat). β-actin or GAPDH were used as loading controls.

RNA Isolation and Quantitative Real-time PCR Analysis

Total RNA was extracted from treated DCs or PBMCs using RNeasy mini kits (Qiagen, Courtaboeuf, France) and cDNAs were obtained using TaqMan reverse transcription reagents (Applied Biosystems, Les Ulis, France) as per the manufacturer's instructions. Messenger RNA expression was evaluated by quantitative PCR on a 7900HT real-time PCR system (Applied Biosystems) with predesigned Taqman gene expression assays and reagents, according to the manufacturer's instructions. Expression of the following genes was assessed in DCs or PBMCs: GILZ (Hs00608272_m1), IDO (Hs00158032_m1), RALDH-1 (Hs00167445_m1), RALDH-2 (Hs00180254_m1), ANXA1 (Hs00167549_m1), CLIC2 (Hs01574555_m)1, FKBP5 (Hs01561001_m1), F13A (Hs00173388_m1), GPX1 (Hs00829989_gH), IMDH2 (Hs00168418_m1), OSF1 (Hs00273458_m1), TPP1 (Hs00166099_m1), C1QA (Hs00381122_m1), C1QB (Hs00608019_m1), C1QC (Hs00757779_m1), CATB (Hs00947433_m1), CATC (Hs00175188_m1), STAB1 (Hs01109068_m1), MRC1 (Hs00267207_m1), CD71 (Hs00951083_m1), FSCN1 (Hs00979631_g1), IRF4 (Hs01056533_m1), MX1 (Hs00895608_m1), NMES1 (Hs00260902_m1), TRAF1 (Hs01090170_m1). Expression of the following genes was assessed in T cells: IFNg (Hs00989291_m1), IL-4 (Hs00174122_m1), IL-10 (Hs00961622_m1) and IL-17A (Hs00174383_m1). Data were interpreted for each target gene in comparison with endogenous β-actin (Hs99999903_m1) or GAPDH (Hs03929097_g1) as controls. The relative amount of target genes in each sample was calculated in comparison with the calibrator sample using the ΔΔCt The magnitude of gene induction was calculated using the formula $2^{-\Delta\Delta Ct}=2^{(-\Delta Ct} $ for stimulated cells$-\Delta Ct$ for unstimulated cells).

Statistical Analysis

Data are expressed as mean±SEM. Statistical differences between groups were assessed using the Wilcoxon test. Treatments were compared to controls and p-values≤00.05 or 0.01 were considered as significant. Statistical and graphical analyses were performed using the Prism 5 software (GraphPad, La Jolla, Calif.). Significant differences in protein expression changes were determined in the 2D-DIGE analysis using an FDR (False Discovery Rate) adjusted p-value (or FDR p-value) threshold of 0.05 (http://www.nonlinear.com/support/progenesis/samespots/faq/pq-values.aspx#qvalues). In label-free MS experiments, a FDR p-value with a threshold of 0.01 was used to determine significant changes in peptide abundance. A fold change filter of 1.2 (2D-DIGE) or 1.5 (label-free MS) was selected to target proteins with a level of differential expression readily detectable using western blotting.

Clinical Samples from VO56.07A Pollen Chamber Study

The design and protocol of the allergen specific immunotherapy study were described in Horak F et al. (J. Allergy Clin. Immunol. 124: 471-477, 2009). This clinical trial assessed the efficacy and onset of action of grass-pollen tablets administered sublingually under controlled allergen exposure conditions provided in a challenge chamber. Briefly, eligible patients were men and women between 18 and 50 years old with a documented history of moderate-to-severe seasonal grass pollen-related allergic rhinoconjunctivitis for at least the previous two years. Patients were selected for inclusion based upon a positive specific skin prick test response (wheal diameter>3 mm) to a 5-grass pollen extract (Stallergenes SA) as well as a specific serum IgE level of at least 0.70 kU/I for timothy grass (assessed with the UniCAP system, Phadia, Uppsala, Sweden). In addition, patients had a confirmed symptomatic reaction to an allergen challenge test at baseline (i.e. before the administration of any treatment), defined as a rhinoconjunctivitis total symptom score (RTSS) encompassing sneezing, runny nose, itchy nose, nasal congestion, watery eyes, and itchy eyes. The study was a randomized, doubleblind, parallel-group, placebo-controlled, single-center trial, conducted outside of the pollen season. After an initial screening visit, 82 eligible patients were randomized 1:1 to receive either a grass pollen or placebo tablet via the sublingual route. Challenges were performed before treatment and after 1 week and 1, 2, and 4 months of treatment. The investigational product was a 5-grass-pollen SLIT tablet (orchard, meadow, perennial rye, sweet vernal, and timothy grasses; Stallergenes SA) taken once daily before eating or drinking and, preferably, at the same time of the day throughout the 4-month treatment period (see Moingeon et al., Int. Arch. Allergy Immunol. 146: 338-342, 2008). Whole blood was collected before and after 4 months of treatment for serum measurements and cellular assays. PBMCs were purified from blood samples and frozen. At the end of the study, PBMCs were thawed and maintained for 24 h in culture and subsequently restimulated or not with a grass-pollen allergen extract (300 IR, Stallergenes, SA) for further 24 h. Cultured PBMCs were washed and used for RNA isolation and PCR analysis as described above. All samples were coded and processed in a blind manner by the operators.

Since patients were challenged before treatment (at visit 2), it was possible to evaluate individual clinical responses by calculating the percentage improvement of Average Rhinoconjunctivitis Total Symptom Score (ARTSS) between the baseline (challenge at V2) and after the challenge at the end of treatment (Visit 7 after 4 months): (ARTSS at V2−ARTSS at V7)/ARTSS at V2×100.

To analyze potential links between changes in immunological parameters and clinical responses, the median of percentages of improvement of ARTSS in the active group corresponding to at least a 43.9% decrease of ARTSS after treatment was considered as a threshold. Subjects with an ARTSS improvement greater than or equal to the threshold were considered as responders and those lower than the threshold as non-responders. Immunological results were described using summary statistics for 4 subgroups including active responders: AR, active non-responders: ANR, placebo responders: PR and placebo non-responders: PNR. Results were expressed as individual plots for patients from the 4 subgroups.

EXAMPLE 2

Results

Establishment of Effector (DC1 and DC17) and Tolerogenic Human DCs

After an initial screening of approximately 40 biological and pharmacological agents, three molecules capable of inducing either effector or tolerogenic DCs from immature monocyte derived DCs were selected. The bacterial LPS was the most potent inducer of effector DC1 (i.e. DCs supporting the differentiation of CD4+ Th1 cells) whereas the peptidoglycan (PGN) from the *Staphylococcus aureus* wall was the best inducer of DC17 (i.e. DCs capable to elicit CD4+ Th17 cells). As shown in FIG. 2A, these treated DCs, termed LPS-DCs and PGN-DCs respectively, upregulated the expression of costimulatory (i.e. CD80, CD83, CD86) but not inhibitory molecules, with the exception of ILT4 which was induced by LPS treatment. Such treated-DCs upregulated IDO gene expression and secreted high amounts of IL-6 and IL-8 (FIGS. 2B and C). LPS-DCs also secreted IL-12p70 and TNF-α, in contrast to PGN-DCs which rather produced IL-β and IL-23 (FIG. 2C). Importantly, cocultures with naïve CD4+ T cells confirmed a distinct DC1 and DC17 polarization respectively, in that incubation with LPS-DCs induced IFN-g secretion in T cells at day 5 whereas IL-17A gene expression was enhanced in PGN-DCs/CD4+ T cells cocultures (FIGS. 2D and E). As previously reported by the inventors, treatment of DCs with DEX led to the generation of tolerogenic DCs, upregulating the expression of ILT2 and ILT4 and tolerogenic genes like GILZ, IDO or RALDH1 (FIGS. 2A and B). CD4+ T cells cocultured with DEX-DCs upregulated IL-10 (FIGS. 2D and E). Although not shown, it was confirmed that these cells are bona fide regulatory T cells (Tr1), since they are Foxp3- and exhibit a suppressive activity in third party experiments (Zimmer et al., J. Immunol., 186: 3966-3976, 2011). Altogether, these cellular assays performed on samples from 4 healthy donors unambiguously confirmed that effector DC1, DC17 and tolerogenic (i.e. regulatory) DCs can be obtained from human moDCs under such in vitro cell-culture conditions.

Identification of Molecular Markers for Effector and Tolerogenic Human DCs by 2D-DIGE Potential differences in protein expression between control (Ctrl-DCs), LPS-, DEX- and PGN-DCs generated from 6 independent donors were subsequently investigated (FIG. 1). To this aim, 2D-DIGE for quantitative comparison of DC proteomes was first relied upon. Whole cell extracts were fractionated by 2D gel electrophoresis using narrow range pH gradient gels (with pI ranging from 5.3 to 6.5, 1 pH unit/24 cm) in the first dimension to increase the depth of the analysis in comparison with broad range gradients (data not shown). A pooled standard encompassing the 24 samples and labeled with the Cy2 fluorescent dye was used to normalize differences between gels and experiments. In those analyses, a total of 1250 protein spots could be precisely quantified in human DCs, using high resolution "ultra-zoom" 2D gels, as shown in a representative 2D pattern (FIG. 3A). Out of these 1250 spots, 52 were differentially expressed under at least one condition, with a FDR p-value≤0.05 and at least a 1.2-fold change in volume. As shown in Table 1, 48 spots (92.3%) were identified by mass spectrometry after in-gel trypsin digestion, corresponding to 40 non-redundant proteins. Seventeen proteins were found to be dysregulated in tolerogenic DCs, when compared with Ctrl-, LPS- or PGN-DCs (Table 1A and B). In contrast, the expression levels of 23 proteins were modified in LPS- and/or PGN-DCs in comparison to Ctrl- or DEX-DCs (Table 1C-E). Identified proteins were further clustered based upon similar expression profiles. Three proteins, including MX1, were specifically upregulated in LPS-DCs whereas 20 were upregulated in both DC1 and DC17 effector cells (e.g. FSCN1, HLA class II and IRF4). Six proteins were rather downregulated in LPS and PGN-DCs (e.g. ITAM/CD11b) whereas the FKBP5 protein was upregulated in all 3 effector and regulatory conditions. Remarkably, 8 proteins were specifically overexpressed in DEX-DCs (i.e. ANXA1, CLIC2, FKBP5, F13A, GPX1, IMDH2, OSF1, TPP1, Table 1 and FIG. 3). To further validate the previous findings, some candidate markers for effector or tolerogenic DCs were selected and their expression levels by western blotting using commercially available antibodies were directly assessed. Moreover, additional samples from treated DCs were collected from 8 donors to assess marker gene expression by qPCR.

Representative proteomic and gene expression data are shown in FIG. 4 for selected candidate markers of effector DCs (i.e. FSCN1, IRF4 and MX1). Whereas FSCN1 and IRF4 genes showed higher levels of expression in both effector conditions, MX1 was only strongly overexpressed in LPS-DCs (e.g. with mRNA levels increased by 10-fold) when compared with Ctrl-, DEX- and PGN-DCs (FIG. 4B-D). Downregulation of the expression of ITAM/CD11 b in DC1 and DC17 conditions was also confirmed by western blotting analysis and flow cytometry (data not shown). Among the 8 potential markers of regulatory DCs, 4 were confirmed at the protein level (i.e. ANXA1, FKBP5, F13A and GPX1). Specifically, western blotting analyses indicated a significantly higher level of ANXA1, as well as an induction of FKBP5 in DEX-DCs (by 1.4- and 2.6-fold, respectively) when compared with Ctrl-DCs. F13A and GPX1 exhibited a slight increase in DEX-DCs in comparison Ctrl-DCs (p-values≤0.1, FIGS. 3B and C). Due to the non-availability or poor affinity of antibodies to either CLIC2, IMDH2, OSF1 or TPP1, the latter proteins could not be assessed as markers by immunoblotting. Nonetheless, all such candidate markers were validated at the mRNA level (FIG. 3D). In this respect, up to a 15-fold increase in FKBP5 and F13A gene expression was observed in DEX-DCs relative to Ctrl-DCs with a concomitant decrease under effector conditions. The known function of each potential marker of regulatory DCs in immunity/tolerance is summarized in Table 3. Collectively, data indicate that high expression levels of ANXA1, CLIC2, FKBP5, F13A, GPX1, IMDH2, OSF1 and TPP1 represent a valid molecular signature of tolerogenic DEX-DCs.

Identification of Molecular Markers for Effector and Tolerogenic Human DCs by Label-free MS Whereas 2D-DIGE can resolve protein species with different pIs or molecular masses, this approach overlooks proteins with extreme pIs and molecular weights, as well as highly hydrophobic proteins. Thus, label free MS-based approaches to overcome these limitations were initiated and protein expression profiles between Ctrl-, LPS-, DEX- and PGN-DCs further compared (FIGS. 1 and 5). Following enzymatic digestion, peptide analyses were performed using nano liquid chromatography mass spectrometry (nanoLC-MS). For in-depth analysis of complex mixtures such as whole DC lysates, an ultra high pressure LC was used, with an extended column length of 50 cm to increase both chromatographic resolution, reproducibility and peptide quantitation. An analysis of DC peptides in 270 min gradient was performed, resulting in the detection of 33500 isotope patterns (i.e. features characterized by a retention time and a mass over charge (m/z) ratio) which were further quantified using the Progenesis LC-MS software. The high LC reproducibility and very high mass accuracy achieved in the analysis of the high resolution MS data enabled a comparison of ion abundances between different runs. Up to 945 features were significantly detected as differentially expressed in at least one condition (with FDR p-value≤0.01 and fold≥1.5). A higher abundance of the m/z 865.70 molecular ion in DEX-DCs compared with Ctrl-, LPS- and PGN-DCs (with an abundance of 16300 vs. 8700, 5800 and 6095, respectively) has been found. Differentially regulated peptides were subsequently fragmented in MS/MS mode, leading to the identification of proteins further matched to sequence databases. Among the 945 differentially expressed features, 354 of them (37.5%) were identified representing a total of 190 non-redundant proteins 1 peptide, data not shown). The difficulty to interpret some of the MS/MS spectra was likely due to signal interference caused by co-eluting components, the presence of post-translationally modified peptides (e.g. glycopeptides), unknown peptide sequences and further, the relatively low-intensity of some ion precursors. To increase the stringency and accuracy of protein quantitation, only proteins identified with two or more peptides were included in the final analysis, representing a total of 77 differentially expressed proteins. Sixty eight proteins were significantly dysregulated in effector DCs whereas 9 proteins were specifically upregulated in tolerogenic DCs. Such data are summarized in Table 2 with specific details on peptide/protein identification. Included in this list were two proteins (ITAM/CD11b and MX1, 1 peptide) previously shown to be upregulated in effector DCs, as well as PGRP1 (1 peptide), also known as "peptidoglycan recognition protein", exhibiting a >90-fold increase in the PGN condition. Proteins were clustered based on abundance within each DC conditions. One cluster comprising 50 proteins was shown to be specifically up or downregulated in PGN-DCs (Table 2C and F) whereas four proteins were highly expressed in LPS-DCs (i.e. ANXA6, EF1A1, MX1 and PSA7, Table 2E). MX1 overexpresssion in LPS-DCs was also confirmed by proteomic DIGE analysis. Upregulation of 14 proteins (e.g. FSCN1, ICAM1, NMES1, TRAF1 and TFR1/CD71) and downregulation of 3 other proteins (CYTC, GELS and ITAM) were observed in both DC1 and DC17 cells (Table 2B). Interestingly, the two proteomics approaches confirmed the upregulation of FSCN1 and downregulation of ITAM/CD11b in effector DCs. Some proteins previously shown by others to be elevated in effector DCs (see Ferreira et al., Proteomics Clin. Appl., 2: 1349-1360, 2008; Watarai et al., Proteomics, 5: 4001-4011, 2005) were confirmed in the present study (e.g. ICAM1 and TRAF1). Furthermore, label free MS experiments revealed 9 proteins consistently increased in tolerogenic DEX-DCs when compared with Ctrl-, LPS- and PGN-DCs (Table 2A). In this regard, 4 of those proteins (ANXA1, CLIC2, F13A and FKBP5) had been identified in the DIGE analysis described above whereas the other 5 proteins (C1QB, C1QC, CATC, MRC1 and STAB1) were only detected and shown to be upregulated in DEX-DCs when using the LC-MS approach. Among those, the analysis of C1QC specific peptides revealed up to a 5-fold increase in tolerogenic DEX-DCs. Next, validation experiments for candidate markers identified by label-free MS using both western blotting and qPCR were performed. Based on those analyses, three markers for effector DCs (CD71, NMES 1 and TRAF1) with confirmed upregulation in both LPS- and PGN-DCs when compared with either Ctrl or DEX-DCs (FIG. 1) were selected. Importantly, western blotting analyses confirmed significantly higher levels of C1Q, CATC, MRC1 and STAB1 in regulatory DEX-DCs (by 12-, 1.5-, 1.4- and 2.2-fold, respectively, FIGS. 5A and B). Moreover, as shown in FIG. 5C, C1Q (including subunits A, B and C), CATC, MRC1 and STAB1 mRNA levels were significantly elevated in DEX-DCs, with up to a 12-fold increase in C1QA, C1QB and STAB1 gene expression when compared with Ctrl-DCs. The function of each of these potential markers of tolerogenic DEX-DCs in effector immunity/tolerance is summarized in Table 3. Altogether, these data demonstrate that C1QA, C1QB, C1QC, CATC, MRC1 and STAB1 are valid candidate markers of regulatory DCs induced by DEX.

Assessment of Candidate Marker Expression in Distinct Subtypes of Tolerogenic DCs.

Further, the expression of the most promising candidate markers in various types of regulatory DCs obtained from moDCs under distinct cell culture conditions was investigated. To generate tolerogenic DCs, monocyte-derived iDCs were treated with proteases from *Aspergillus oryzae* during 24 h (as described by Zimmer, A. et al. J. Immunol. 186: 3966-3976, 2011) or cultured monocytes during the differentiation step with either DEX, IL-10, Rapamycin, 1,25 dihydrovitamin D3 or TGFb during 7 days, as reported by others (Monti et al., Transplantation, 75: 137-145, 2003; Steinbrink et al., Blood, 99: 2468-2476, 2002; Van Kooten, C. & Gelderman, K. A., Methods Mol. Biol., 677: 149-159, 2011; Penna et al., J. Immunol., 178: 145-153, 2007; Ohtani et al., Immunology, 126: 485-499, 2009). Staining with CD11c, CD14, ILT2, ILT3 and ILT4 antibodies allowed us to discriminate those various tolerogenic DCs based on surface phenotype (FIG. 6A). More specifically, ASP-DCs exhibit a $CD11c^{low}$ phenotype in contrast to all other DC types, which are rather $CD11c^{high}$. CD14 expression clusters DCs in 3 groups since $DEX_{24h}$ (24 h treatment) and TGFb-DCs are $CD14^{neg}$ cells, whereas VitD3 and Rapa-DCs are $CD14^{med}$ and $DEX_{diff}$ (treatment during the differentiation step) and IL-10-DCs are $CD14^{high}$. $DEX_{24h}$ and TGFb-DCs can be further distinguished as $ILT2^{low}$ and $ILT2^{med}$ cells, respectively. Rapa-DCs and VitD3-DCs differ in that they are $ILT3^{low}$ and $ILT3^{high}$, respectively. Lastly, DEXdiff-DCs are ILT4med whereas IL-10-DCs are ILT4high. To confirm the antiinflammatory profile of such generated DCs, they were stimulated with LPS during 24 h and assessed the expression of costimulatory molecules and cytokine secretion. As shown in FIG. 6B, all tolerogenic DC subtypes had a blunted LPS-induced upregulation of costimulatory molecules. LPS induced cytokine secretion was also inhibited in all regulatory DC types. Only in VitD3-DCs was IL-6, IL-8 and TNF-α secretion left uninhibited after LPS stimulation (FIG. 6C).

The expression of candidate markers identified through quantitative proteomic studies (listed in Table 3 and Tables 1 and 2) and from the literature (GILZ, IDO, RALDH1 and RALDH2) was assessed in the six types of tolerogenic DCs, by qPCR as well as western blotting based on the availability of antibodies. Representative data are shown in FIG. 7. Specifically, 5 subgroups of candidate markers for regulatory DCs were defined. ANXA1, CATC and GILZ were expressed in all models and thus can be considered as pan-regulatory DC markers. CATC protein overexpression was for instance detected in all conditions except in Rapa-DCs, whereas CATC gene induction was detected in both $DEX_{24h/diff}$, IL-10 and Rapa-DCs. Surprisingly, the upregulation of ANXA1, C1Q, CATC and GPX1 in Rapa-DCs was more easily seen at the mRNA level, possibly due to differences in terms of kinetics of gene induction for such markers. ANXA1, CATC and GILZ were the only proteins upregulated in TGFb-DCs, highlighting the phenotypic heterogeneity of tolerogenic DCs. A second group of markers encompass C1Q and TPP1, associated with most tolerogenic DCs, with the exception of ASP- and TGFb-DCs. The experiments indicated that $DEX_{24h}$-DCs are quite similar to $DEX_{diff}$-DCs, with the latter exhibiting higher amounts of tolerogenic markers. A third group comprising CLIC2, FKBP5, GPX1 and IMDH2 proteins were upregulated in $DEX_{24h/diff}$ and Rapa-DCs. These markers may represent a family of immunosuppressant-induced proteins. Furthermore, F13A, MRC1 and STAB1 proteins were consistently and jointly upregulated in IL-10-DCs and $DEX_{24h/diff}$-DCs. Lastly, the overexpression of IDO, RALDH1 and RALDH2 proteins were restricted to $ASP_{24h}$- and $DEX_{24h/diff}$-DCs in agreement with the previous report (see Zimmer, A. et al. J. Immunol. 186: 3966-3976, 2011). Collectively, data i) establish unambiguously a substantial phenotypic heterogeneity among known tolerogenic DCs, ii) highlight the broad relevance of ANXA1, C1Q, CATC, GILZ, STAB1 and TPP1 molecules as shared regulatory DC markers.

Assessment of Markers for Effector/Tolerogenic DCs in PBMCs from Patients Undergoing Allergen-specific Immunotherapy.

The present inventors hypothesized that markers of effector and regulatory DCs might be useful to investigate immune changes induced in allergic patients during allergen-specific immunotherapy (such as a Th2 to Th1/Treg transition) with thus, a potential shift from effector to tolerogenic DCs. In this context, they relied upon blood samples collected during a placebo-controlled clinical study conducted in an allergen challenge chamber to evaluate a candidate allergy vaccine. Specifically, they assessed the mRNA expression of candidate markers in PBMCs from grass pollen allergic patients undergoing sublingual immunotherapy with grass-pollen tablets as described in "Materials and Methods". To this aim, since PBMCs contain less than 0.5-1% DCs, they first selected candidate markers based on their previous patterns of expression in distinct regulatory DC models (FIG. 7), but also on gene expression data reported in the literature in various blood cell populations (BioGPS resource, data not shown). The latter step was critical in order to eliminate genes significantly expressed by either T, B, NK, endothelial or polynuclear cells. As a result, they selected 15 candidate marker genes for further studies. ANXA1, CATC, GILZ were selected because they represent pan-regulatory DC markers, even if they are ubiquitously expressed among different blood cell populations. For instance, CATC is expressed in both B cells, DCs, myeloid and NK cells and monocytes. In contrast, C1QC, CLIC2, F13A, IDO, MRC1 and RALDH1 expression was only slightly observed in PBMCs and STAB1 expression levels were significant only in DCs, myeloid cells and monocytes. With the same rationale, five markers (CD71, FSCN1, MX1, NMES1 and TRAF1) were chosen to monitor changes in effector DCs populations. These markers were assessed in 80 PBMC samples (i.e. PBMCs cultured ex vivo before and after treatment, with or without restimulation with grass-pollen allergen) from 20 clinical patients belonging to each of the following group: active responders (AR, n=6), active non-responders (ANR, n=6), placebo responders (PR, n=4) and placebo non responders (PNR, n=4).

ANXA1, CATC, F13A, GILZ, IDO, MRC1, RALDH1 and CLIC2, identified as markers of tolerogenic DCs, did not exhibit any significant variations in their patterns of expression in PBMCs, when comparing patients in placebo or active groups, or clinical responders and non responders, respectively (data not shown). Likewise, no significant changes in effector DCs markers were detected at a group level in either unrestimulated or restimulated PBMCs, although some individual patients showed a concomitant upregulation of all effector genes (data not shown). A considerable increase in the expression of C1Q (subunits A, B and C) and STAB1, two markers of regulatory DCs, was detected in PBMCs restimulated or not with the grass-pollen extract in the active group in comparison to the placebo group. To confirm those findings, mRNA levels were assessed for these 4 genes in the entire cohort of the clinical study (i.e. 62 additional patients corresponding to 248 PBMCs samples). 4 effector genes (CD71-FSCN1-MX1-TRAF1) were also assessed in these patients, as controls.

These experiments confirmed a statistically significant upregulation of C1Q and STAB1 in the active group when compared to the placebo group in either unrestimulated PBMCs (FIG. 8A) or restimulated PBMCs (data not shown). Even more interestingly, C1QA, C1QB and C1QC were specifically upregulated in the group of patients with a confirmed clinical response to the treatment (column "AR") in contrast to non responders (column "ANR") where these genes were rather downregulated. STAB1 was also confirmed as induced in AR in comparison to other groups where it was rather downregulated (FIG. 8A). C1Q and STAB1 mRNA expression was plotted against the clinical efficacy score (% ARTSS) and a significant correlation between the two variables could be established for C1Q subunits and STAB1 (Pearson correlation of 0.41, p=0.009 for C1QA and 0.32, p=0.037 for STAB1) (FIG. 8B). No differences were detected in mRNA expression of effectors genes between groups (data not shown) and no correlation could be established with clinical efficacy (data not shown) for these genes indicating that the clinical efficacy of allergen-specific immunotherapy does not correlate with significant changes in effector DCs markers.

Collectively, these data describe two potential markers of tolerance associated with short-term efficacy of allergen-specific immunotherapy, namely C1Q and STAB1.

Altogether, the present inventors discovered novel markers specific of polarized effector or regulatory DCs, some of which can be easily detected in human PBMCs. Importantly, the induction of C1Q and STAB1, two markers expressed by various types of regulatory DCs, correlates with clinical efficacy of allergen-specific immunotherapy. Such an identification of candidate biomarkers for short-term efficacy provides new avenues for the clinical follow-up of patients and the development of new vaccine candidates based on allergenic extracts.

---

The invention claimed is:

1. A method for treating a patient suffering from allergy to an allergen and undergoing allergen immunotherapy, which method comprises:
   a) administering an effective amount of an allergen immunotherapy to a patient suffering from allergy to said allergen;
   b) determining the level of expression, by dendritic cells, of at least STAB1, or an mRNA thereof, in a biological sample from the patient treated with allergen immunotherapy, said biological sample containing dendritic cells;
   c) comparing said level of expression with that of a control and
   d) based on the comparison with the control, identifying if the immune response developed by the patient is oriented either towards a tolerogenic dendritic cell response or towards an effector dendritic cell response, wherein the control either consists of (i) immature dendritic cells which have not been polarized towards tolerogenic or effector subsets, or where appropriate consists of (ii) a biological sample from the patient obtained before said patient undergoes allergen immunotherapy, said biological sample containing dendritic cells, and wherein step d) is as follows:
   identifying that the patient is developing an immune response oriented towards a tolerogenic dendritic cell response when the level of expression, by dendritic cells, of at least STAB1, or an mRNA thereof, is higher than that of the control, and then proceeding with administering further rounds of the same allergen immunotherapy to the patient; and/or
   identifying that the patient is developing an immune response oriented towards an effector dendritic cell response when the level of expression, by dendritic cells, of at least STAB1, or an mRNA thereof, is lower than that of the control, and then stopping the allergen immunotherapy to the patient.

2. The method according to claim 1, wherein the allergen immunotherapy treats an allergy, wherein the level of expression, by dendritic cells, of at least STAB1, or an mRNA thereof, is determined, and wherein a level of expression of at least this marker protein, or an mRNA thereof, which is higher than the level of expression of the control indicates that the immune response is oriented towards a tolerogenic dendritic cell response, and also identifies the patient as likely to be a responder to the allergen immunotherapy.

3. The method according to claim 2, wherein the allergen immunotherapy which treats an allergy is a desensitization therapy, wherein the level of expression, by dendritic cells, of at least STAB1, or an mRNA thereof, is determined, and wherein a level of expression of STAB1, or an mRNA thereof, which is higher than the level of expression of the control indicates that the immune response is oriented towards a tolerogenic dendritic cell response and also identifies the patient as likely to be a responder to the desensitization therapy.

4. A method for treating a patient suffering from allergy to an allergen and undergoing allergen immunotherapy, comprising:
   a) administering an effective amount of an allergen immunotherapy to a patient suffering from allergy to said allergen,
   b) determining the level of expression, by dendritic cells, of at least STAB 1, or an mRNA thereof, in a biological sample from the patient treated with allergen immunotherapy, said biological sample containing dendritic cells,
   c) comparing said level of expression with that of a control, wherein said control consists of (i) immature dendritic cells which have not been polarized towards tolerogenic or effector subsets, or where appropriate consists of (ii) a biological sample from the patient obtained before said patient underwent allergen immunotherapy, said biological sample containing dendritic cells;
   d) based on the comparison with the control,
   identifying that the patient is developing an immune response oriented towards a tolerogenic dendritic cell response when the level of expression, by dendritic cells, of at least STAB1, or an mRNA thereof, is higher than that of the control, and then proceeding with administering further rounds of the same allergen immunotherapy to the patient; and/or
   identifying that the patient is developing an immune response oriented towards an effector dendritic cell response when the level of expression, by dendritic cells, of at least STAB1, or an mRNA thereof, is lower than that of the control, and then stopping the allergen immunotherapy to the patient.

* * * * *